(12) United States Patent
Lu et al.

(10) Patent No.: US 10,676,753 B2
(45) Date of Patent: Jun. 9, 2020

(54) CONSTRUCTS AND METHOD OF USE FOR RICE GLUATAMATE RECEPTOR-LIKE GENES

(71) Applicant: PIONEER OVERSEAS CORPORATION

(72) Inventors: Guihua Lu, Beijing (CN); Yang Gao, Beijing (CN); Junhua Liu, Beijing (CN); Guanfan Mao, Beijing (CN); Changgui Wang, Beijing (CN); Wei Wang, Beijing (CN); Xiping Wang, Beijing (CN)

(73) Assignee: PIONEER OVERSEAS CORPORATION, Johnston, IA (US)

( * ) Notice: Subject to any disclaimer, the term of this patent is extended or adjusted under 35 U.S.C. 154(b) by 187 days.

(21) Appl. No.: 15/307,260

(22) PCT Filed: Jun. 19, 2015

(86) PCT No.: PCT/CN2015/081953
§ 371 (c)(1),
(2) Date: Oct. 27, 2016

(87) PCT Pub. No.: WO2015/192805
PCT Pub. Date: Dec. 23, 2015

(65) Prior Publication Data
US 2017/0088853 A1    Mar. 30, 2017

(30) Foreign Application Priority Data

Jun. 20, 2014   (WO) ................ PCT/CN2014/080386

(51) Int. Cl.
*C12N 15/82* (2006.01)
*C07K 14/415* (2006.01)

(52) U.S. Cl.
CPC ........ *C12N 15/8273* (2013.01); *C07K 14/415* (2013.01); *C12N 15/8261* (2013.01)

(58) Field of Classification Search
None
See application file for complete search history.

(56) References Cited

U.S. PATENT DOCUMENTS

2006/0123505 A1* 6/2006 Kikuchi ............... C07K 14/415
                                                800/278

FOREIGN PATENT DOCUMENTS

CN          103503777 A        1/2014

OTHER PUBLICATIONS

Ni et al. (Rice 9.1 (2016): 9). (Year: 2016).*
Kumar et al. (Annual review of physiology 75 (2013):313-337). (Year: 2013).*
Schmidt et al. (AoB Plants 2012 (2012). (Year: 2012).*
GenBank Accession AK065496, dated Dec. 4, 2008. (Year: 2008).*
Osakabe et al. (Journal of Biological Chemistry (2010): jbc-M109). (Year: 2010).*
Lu, Guihua et al. "Application ofT-DNA activation tagging to identify glutamate receptor-like genes that enhance drought tolerance in plants" Plant Cell Rep, vol. vol. 33, Mar. 29, 2014 (Mar. 29, 2014), pp. 617-631.
Tanaka, T. et al. ""Os09g0429400 [*Oryza sativa* Japonica Group]" retrieved from NCBI Database accession No. NP_001063234.2" Database Genbank, Jun. 8, 2010 (Jun. 8, 2010) (Sequence not provided).
Tanaka, T. et al. ""Os02g0117500 [*Oryza sativa* Japonica Group]" retrieved from NCBI Database accession No. NP_001045687.1" Database Genbank, Jun. 8, 2010 (Jun. 8, 2010) (Sequence not provided).
Sasaki, T. et al. ""Avr9/Cf-9 rapidly elicited protein-like [*Oryza sativa* Japonica Group]" retrieved from NCBI Database accession No. BAD35802.1" Database Genbank, Feb. 16, 2008 (Feb. 16, 2008) (Sequence not provided).
Sasaki, T. et al. "Avr9/Cf-9 rapidly elicited protein-like [*Oryza sativa* Japonica Group]" retrieved from NCBI Database accession No. BAD35799.1 Database Genbank, Feb. 16, 2008 (Feb. 16, 2008) (Sequence not provided).
Yu, J. et al. ""hypothetical protein OsJ_20410 [*Oryza sativa* Japonica Group]" retrieved from NCBI Database accession No. EEE65241.1" Database Genbank, Feb. 5, 2009 (Feb. 5, 2009) (Sequence not provided).
Sasaki, T. et al. ""glutamate receptor, ionotropic kainate 5 precursor-like protein [*Oryza sativa* Japonica Group]" retrieved from NCBI Database accession No. BAD45662.1" Database Genbank, Feb. 16, 2008 (Feb. 16, 2008) (Sequence not provided).
Kikuchi, S. et al. ""unnamed protein product [*Oryza sativa* Japonica Group]" retrieved from NCBI Database accession No. BAG89542.1" Database Genbank, Dec. 4, 2008 (Dec. 4, 2008) (Sequence not provided).
International Search Report PCT/CN2015/081953 filed Jun. 19, 2015.
Written Opinion of the International Searching Authority PCT/CN2015/081953 filed Jun. 19, 2015.
Singh et al. "Genome-wide expressional and functional analysis of calcium transport elements during abiotic stress and development in rice" FEBS Journal, 281: 894-915 (2014).

* cited by examiner

Primary Examiner — Charles Logsdon

(57) ABSTRACT

Isolated polynucleotides and polypeptides, and recombinant DNA constructs are useful for conferring drought tolerance and/or improved nitrogen use efficiency. Compositions (such as plants or seeds) comprise these recombinant DNA constructs; and methods utilize these recombinant DNA constructs. The recombinant DNA constructs comprise a polynucleotide operably linked to a promoter that is functional in a plant, wherein said polynucleotides encode glutamate receptor polypeptides.

3 Claims, 11 Drawing Sheets
Specification includes a Sequence Listing.

SEQUENCE LISTING

```
<160> NUMBER OF SEQ ID NOS: 48

<210> SEQ ID NO 1
<211> LENGTH: 11934
<212> TYPE: DNA
<213> ORGANISM: Artificial Sequence
<220> FEATURE:
<223> OTHER INFORMATION: vector DP0005

<400> SEQUENCE: 1
gaattctcta gtcccgatct agtaacatag atgacaccgc gcgcgataat ttatcctagt      60
ttgcgcgcta tattttgttt tctatcgcgt attaaatgta taattgcggg actctaatca     120
taaaaaccca tctcataaat aacgtcatgc attacatgtt aattattaca tgcttaacgt     180
aattcaacag aaattatatg ataatcatcg caagaccggc aacaggattc aatcttaaga     240
aacgcggccg cttcagttgt ggcccagctt ggaggtcgac tcgcgaggat ctctgcagag     300
agatagattt gtagagagag actggtgatt tcagcgtgtc ctctccaaat gaaatgaact     360
tccttatata gaggaagggt cttgcgaagg atagtgggat tgtgcgtcat cccttacgtc     420
agtggagata tcacatcaat ccacttgctt tgaagacgtg gttggaacgt cttcttttc      480 cacgatgctc ctcgtgggtg ggggtccatc tttgggacca ctgtcggcag aggcatcttg     540
aacgatagcc tttcctttat cgcaatgatg gcatttgtag gtgccacctt cctttttctac    600 tgtccttttg atgaagtgac agatagctgg gcaatggaat ccgaggaggt ttcccgatat     660 tacccttgt tgaaaagtct caatagccct ttggtcttct gagactgtat cttttgatatt     720 cttggagtag acgagagtgt cgtgctccac catgttcaca tcaatccact tgctttgaag     780
acgtggttgg aacgtcttct ttttccacga tgctcctcgt gggtggggt ccatctttgg      840 gaccactgtc ggcagaggca tcttgaacga tagcctttcc tttatcgcaa tgatggcatt     900
tgtaggtgcc accttccttt tctactgtcc ttttgatgaa gtgacagata gctgggcaat     960
ggaatccgag gaggtttccc gatattaccc tttgttgaaa agtctcaata gccctttggt    1020
cttctgagac tgtatctttg atattcttgg agtagacgag agtgtcgtgc tccaccatgt    1080
tgccaagctg ctctaagctt tggcggccgc attcgcaaaa cacacctaga ctagatttgt    1140
tttgctaacc caattgatat taattatata tgattaatat ttatatgtat atggatttgg    1200
ttaatgaaat gcatctggtt catcaaagaa ttataaagac acgtgacatt catttaggat    1260
aagaaatatg gatgatctct ttctctttta ttcagataac tagtaattac acataacaca    1320
caactttgat gcccacatta tagtgattag catgtcacta tgtgtgcatc cttttatttc    1380
atacattaat taagttggcc aatccagaag atggacaagt ctaggttaac catgtggtac    1440
ctacgcgttc gaatatccat gggccgctac aggaacaggt ggtggcggcc ctcggtgcgc    1500
tcgtactgct ccacgatggt gtagtcctcg ttgtgggagg tgatgtccag cttggcgtcc    1560
acgtagtagt agccgggcag ctgcacgggc ttcttggcca tgtagatgga cttgaactcc    1620
```

```
accaggtagt ggccgccgtc cttcagcttc agggccttgt gggtctcgcc cttcagcacg      1680
ccgtcgcggg ggtacaggcg ctcggtggag gcctcccagc ccatggtctt cttctgcatc      1740
acggggccgt cggaggggaa gttcacgccg atgaacttca ccttgtagat gaagcagccg      1800
tcctgcaggg aggagtcctg ggtcacggtc gccacgccgc cgtcctcgaa gttcatcacg      1860
cgctcccact tgaagccctc ggggaaggac agcttcttgt agtcgggat gtcggcgggg       1920 tgcttcacgt acaccttgga gccgtactgg aactgggggg acaggatgtc ccaggcgaag      1980 ggcaggggc cgcccttcgt caccttcagc ttcacggtgt tgtggccctc gtaggggcgg       2040
ccctcgccct cgccctcgat ctcgaactcg tggccgttca cggtgccctc catgcgcacc      2100
ttgaagcgca tgaactcggt gatgacgttc tcggaggagg ccatggtggc gaggatctac      2160
tcggctacac tcacacgctc gctctcgcag ttgcaggtgt aagtttctag ctagggcact      2220
cacggggtac gtatttgtag ccagccacgc acggtctgag ctcgccatgt gccgccatgc      2280
atgcgggggc acgtcgccag cgtacgcggc catcgtcgct gacgaaggta gcgcattcaa      2340
gtccggtcgg tagaggtcag ctgggtcgtt cgccgatggt agttgccgcc cggactcagt      2400
gggcggtagg cgaaggctag caagcagacg actccattca tgcgcatcat ccaaaggtga      2460
tgcaaagcct tccaaacgcg attgtctcat gatgtttccg tctcttgtta cgaggagtac      2520
aattttttct tatacacgaa cgttacttta tgtcacattt ccatgccatg aacaccttgg      2580
cttcaaataa gtgagtgttt ttttcacat tctgtggcat aaacagaatt tctagagtgg       2640
catttgtgat acattgtgaa agctaagagt ggtaaaagta aaataaaatt gttttgcttt      2700
tgccgcggaa tggaaattat ttgtcaaaac ctaagagtgg caaaactgaa atgtcaaaac      2760
ctagagtgac ataaacaaaa tttacccatc actaaatgag cacaaaatat ttcaccacaa      2820
tggaggtatg tgaggtccga tgtactacta gagctcatcg gaaaagcatc ctcttgatga      2880
gtaaacctct tgaagtactg taccaccaca ttttatttat cctcatcggc ttatttttag      2940
gccacggtta ttctcacgaa gagacggtta acccttctcg tagactacac atcgagatcc      3000
actagttcta gagcggccag cttcgaagct tggcactggc cgtcgtttta caacgtcgtg      3060
actgggaaaa ccctggcgtt acccaactta atcgccttgc agcacatccc ctttcgcca     3120 gctggcgtaa tagcgaagag gcccgcaccg atcgcccttc ccaacagttg cgcagcctga      3180
atggcgaatg ctagagcagc ttgagcttgg atcagattgt cgtttcccgc cttcagttta      3240
aactatcagt gtttgacagg atatattggc gggtaaacct aagagaaaag agcgtttatt      3300
agaataatcg gatatttaaa agggcgtgaa aaggtttatc cgttcgtcca tttgtatgtg      3360
catgccaacc acagggttcc cctcgggatc aaagtacttt gatccaaccc ctccgctgct      3420
atagtgcagt cggcttctga cgttcagtgc agccgtcttc tgaaaacgac atgtcgcaca      3480
agtcctaagt tacgcgacag gctgccgccc tgccctttc ctggcgtttt cttgtcgcgt       3540
gttttagtcg cataaagtag aatacttgcg actagaaccg gagacattac gccatgaaca      3600
agagcgccgc cgctggcctg ctgggctatg cccgcgtcag caccgacgac caggacttga      3660
ccaaccaacg ggccgaactg cacgcggccg gctgcaccaa gctgttttcc gagaagatca      3720
ccggcaccag gcgcgaccgc ccggagctgg ccaggatgct tgaccaccta cgccctggcg      3780
acgttgtgac agtgaccagg ctagaccgcc tggcccgcag cacccgcgac ctactggaca      3840
ttgccgagcg catccaggag gccggcgcgg gcctgcgtag cctggcagag ccgtgggccg      3900
acaccaccac gccggccggc cgcatggtgt tgaccgtgtt cgccggcatt gccgagttcg      3960
agcgttccct aatcatcgac cgcacccgga gcgggcgcga ggccgccaag gcccgaggcg      4020
```

```
tgaagtttgg cccccgccct accctcaccc cggcacagat cgcgcacgcc cgcgagctga   4080
tcgaccagga aggccgcacc gtgaaagagg cggctgcact gcttggcgtg catcgctcga   4140
ccctgtaccg cgcacttgag cgcagcgagg aagtgacgcc caccgaggcc aggcggcgcg   4200
gtgccttccg tgaggacgca ttgaccgagg ccgacgccct ggcggccgcc gagaatgaac   4260
gccaagagga acaagcatga aaccgcacca ggacggccag gacgaaccgt ttttcattac   4320
cgaagagatc gaggcggaga tgatcgcggc cgggtacgtg ttcgagccgc ccgcgcacgt   4380
ctcaaccgtg cggctgcatg aaatcctggc cggtttgtct gatgccaagc tggcggcctg   4440
gccggccagc ttggccgctg aagaaaccga gcgccgccgt ctaaaaaggt gatgtgtatt   4500
tgagtaaaac agcttgcgtc atgcggtcgc tgcgtatatg atgcgatgag taaataaaca   4560
aatacgcaag gggaacgcat gaaggttatc gctgtactta accagaaagg cgggtcaggc   4620
aagacgacca tcgcaaccca tctagcccgc gccctgcaac tcgccggggc cgatgttctg   4680
ttagtcgatt ccgatcccca gggcagtgcc cgcgattggg cggccgtgcg ggaagatcaa   4740
ccgctaaccg ttgtcggcat cgaccgcccg acgattgacc gcgacgtgaa ggccatcggc   4800
cggcgcgact tcgtagtgat cgacggagcg ccccaggcgg cggacttggc tgtgtccgcg   4860
atcaaggcag ccgacttcgt gctgattccg gtgcagccaa gcccttacga catatgggcc   4920
accgccgacc tggtggagct ggttaagcag cgcattgagg tcacggatgg aaggctacaa   4980
gcggcctttg tcgtgtcgcg ggcgatcaaa ggcacgcgca tcggcggtga ggttgccgag   5040
gcgctggccg ggtacgagct gcccattctt gagtcccgta tcacgcagcg cgtgagctac   5100
ccaggcactg ccgccgccgg cacaaccgtt cttgaatcag aacccgaggg cgacgctgcc   5160
cgcgaggtcc aggcgctggc cgctgaaatt aaatcaaaac tcatttgagt taatgaggta   5220
aagagaaaat gagcaaaagc acaaacacgc taagtgccgg ccgtccgagc gcacgcagca   5280
gcaaggctgc aacgttggcc agcctggcag acacgccagc catgaagcgg gtcaactttc   5340
agttgccggc ggaggatcac accaagctga agatgtacgc ggtacgccaa gcaagacca   5400
ttaccgagct gctatctgaa tacatcgcgc agctaccaga gtaaatgagc aaatgaataa   5460
atgagtagat gaattttagc ggctaaagga ggcggcatgg aaaatcaaga acaaccaggc   5520
accgacgccg tggaatgccc catgtgtgga ggaacgggcg gttggccagg cgtaagcggc   5580
tgggttgtct gccggccctg caatggcact ggaaccccca gcccgaggga tcggcgtga   5640
cggtcgcaaa ccatccggcc cggtacaaat cggcgcggcg ctgggtgatg acctggtgga   5700
gaagttgaag gccgcgcagg ccgcccagcg gcaacgcatc gaggcagaag cacgcccgg   5760
tgaatcgtgg caagcggccg ctgatcgaat ccgcaaagaa tcccggcaac gccggcagc   5820
cggtgcgccg tcgattagga agccgcccaa gggcgacgag caaccagatt ttttcgttcc   5880
gatgctctat gacgtgggca cccgcgatag tcgcagcatc atggacgtgg ccgttttccg   5940
tctgtcgaag cgtgaccgac gagctggcga ggtgatccgc tacagcttc agacgggca   6000
cgtagaggtt ccgcagggc cggccggcat ggccagtgtg tgggattacg acctggtact   6060
gatggcggtt tcccatctaa ccgaatccat gaaccgatac cgggaaggga agggagacaa   6120
gcccggccgc gtgttccgtc cacacgttgc ggacgtactc aagttctgcc ggcgagccga   6180
tggcggaaag cagaaagacg acctggtaga aacctgcatt cggttaaaca ccacgcacgt   6240
tgccatgcag cgtacgaaga aggccaagaa cggccgcctg gtgacggtat ccagggtga   6300
agccttgatt agccgctaca agatcgtaaa gagcgaaacc gggcggccgg agtacatcga   6360
```

```
gatcgagcta gctgattgga tgtaccgcga gatcacagaa ggcaagaacc cggacgtgct   6420
gacggttcac cccgattact tttttgatcga tcccggcatc ggccgttttc tctaccgcct   6480
ggcacgccgc gccgcaggca aggcagaagc cagatggttg ttcaagacga tctacgaacg   6540
cagtggcagc gccggagagt tcaagaagtt ctgtttcacc gtgcgcaagc tgatcgggtc   6600
aaatgacctg ccggagtacg atttgaagga ggaggcgggg caggctggcc cgatcctagt   6660
catgcgctac cgcaacctga tcgagggcga agcatccgcc ggttcctaat gtacggagca   6720
gatgctaggg caaattgccc tagcagggga aaaggtcga aaaggtctct ttcctgtgga    6780
tagcacgtac attgggaacc caaagccgta cattgggaac cggaacccgt acattgggaa   6840
cccaaagccg tacattggga accggtcaca catgtaagtg actgatataa aagagaaaaa   6900
aggcgatttt tccgcctaaa actctttaaa acttattaaa actcttaaaa cccgcctggc   6960
ctgtgcataa ctgtctggcc agcgcacagc cgaagagctg caaaaagcgc ctacccttcg   7020
gtcgctgcgc tccctacgcc ccgccgcttc gcgtcggcct atcgcggccg ctggccgctc   7080
aaaaatggct ggcctacggc caggcaatct accaggcgc ggacaagccg cgccgtcgcc    7140
actcgaccgc cggcgcccac atcaaggcac cctgcctcgc gcgtttcggt gatgacggtg   7200
aaaacctctg acacatgcag ctcccggaga cggtcacagc ttgtctgtaa gcggatgccg   7260
ggagcagaca agcccgtcag ggccgcgtcag cgggtgttgg cgggtgtcgg ggcgcagcca   7320
tgacccagtc acgtagcgat agcggagtgt atactggctt aactatgcgg catcagagca   7380
gattgtactg agagtgcacc atatgcggtg tgaaataccg cacagatgcg taaggagaaa   7440
ataccgcatc aggcgctctt ccgcttcctc gctcactgac tcgctgcgct cggtcgttcg   7500
gctgcggcga gcggtatcag ctcactcaaa ggcggtaata cggttatcca cagaatcagg   7560
ggataacgca ggaaagaaca tgtgagcaaa aggccagcaa aaggccagga accgtaaaaa   7620
ggccgcgttg ctggcgtttt tccataggct ccgcccccct gacgagcatc acaaaaatcg   7680
acgctcaagt cagaggtggc gaaacccgac aggactataa agataccagg cgtttccccc   7740
tggaagctcc ctcgtgcgct ctcctgttcc gaccctgccg cttaccggat acctgtccgc   7800
ctttctccct tcgggaagcg tggcgctttc tcatagctca cgctgtaggt atctcagttc   7860
ggtgtaggtc gttcgctcca agctgggctg tgtgcacgaa ccccccgttc agcccgaccg   7920
ctgcgcctta tccggtaact atcgtcttga gtccaacccg gtaagacacg acttatcgcc   7980
actggcagca gccactggta acaggattag cagagcgagg tatgtaggcg gtgctacaga   8040
gttcttgaag tggtggccta actacggcta cactagaagg acagtatttg gtatctgcgc   8100
tctgctgaag ccagttacct tcggaaaaag agttggtagc tcttgatccg gcaaacaaac   8160
caccgctggt agcggtggtt tttttgtttg caagcagcag attacgcgca gaaaaaaagg   8220
atctcaagaa gatcctttga tcttttctac ggggtctgac gctcagtgga acgaaaactc   8280
acgttaaggg attttggtca tgcattctag gtactaaaac aattcatcca gtaaaatata   8340
atatttattt ttctcccaat caggcttgat ccccagtaag tcaaaaaata gctcgacata   8400
ctgttcttcc ccgatatcct ccctgatcga ccggacgcag aaggcaatgt cataccactt   8460
gtccgccctg ccgcttctcc caagatcaat aaagccactt actttgccat ctttcacaaa   8520
gatgttgctg tctcccaggt cgccgtggga aaagacaagt tcctcttcgg cttttccgt    8580 ctttaaaaaa tcatacagct cgcgcggatc tttaaatgga gtgtcttctt cccagttttc   8640
gcaatccaca tcggccagat cgttattcag taagtaatcc aattcggcta agcggctgtc   8700
taagctattc gtatagggac aatccgatat gtcgatggag tgaaagagcc tgatgcactc   8760
```

```
cgcatacagc tcgataatct tttcagggct tgttcatct tcatactctt ccgagcaaag    8820
gacgccatcg gcctcactca tgagcagatt gctccagcca tcatgccgtt caaagtgcag    8880
gacctttgga acaggcagct ttccttccag ccatagcatc atgtcctttt cccgttccac    8940
atcataggtg gtccctttat accggctgtc cgtcattttt aaatataggt tttcattttc    9000
tcccaccagc ttatatacct tagcaggaga cattccttcc gtatctttta cgcagcggta    9060
tttttcgatc agtttttca attccggtga tattctcatt ttagccattt attatttcct    9120
tcctcttttc tacagtattt aaagatacccc aagaagcta attataacaa gacgaactcc    9180
aattcactgt tccttgcatt ctaaaacctt aaataccaga aaacagcttt ttcaaagttg    9240
ttttcaaagt tggcgtataa catagtatcg acggagccga ttttgaaacc gcggtgatca    9300
caggcagcaa cgctctgtca tcgttacaat caacatgcta ccctccgcga gatcatccgt    9360
gtttcaaacc cggcagctta gttgccgttc ttccgaatag catcggtaac atgagcaaag    9420
tctgccgcct tacaacggct ctcccgctga cgccgtcccg gactgatggg ctgcctgtat    9480
cgagtggtga ttttgtgccg agctgccggt cggggagctg ttggctggct ggtggcagga    9540
tatattgtgg tgtaaacaaa ttgacgctta gacaacttaa taacacattg cggacgtttt    9600
taatgtactg aattaacgcc gaattaattc gggggatctg gattttagta ctggattttg    9660
gttttaggaa ttagaaattt tattgataga agtattttac aaatacaaat acatactaag    9720
ggtttcttat atgctcaaca catgagcgaa accctatagg aaccctaatt cccttatctg    9780
ggaactactc acacattatt atggagaaac tcgagcttgt cgatcgacag atccggtcgg    9840
catctactct atttctttgc cctcggacga gtgctggggc gtcggtttcc actatcggcg    9900
agtacttcta cacagccatc ggtccagacg gccgcgcttc tgcgggcgat ttgtgtacgc    9960
ccgacagtcc cggctccgga tcggacgatt gcgtcgcatc gaccctgcgc ccaagctgca   10020
tcatcgaaat tgccgtcaac caagctctga tagagttggt caagaccaat gcggagcata   10080
tacgcccgga gtcgtggcga tcctgcaagc tccggatgcc tccgctcgaa gtagcgcgtc   10140
tgctgctcca tacaagccaa ccacggcctc cagaagaaga tgttggcgac ctcgtattgg   10200
gaatccccga acatcgcctc gctccagtca atgaccgctg ttatgcggcc attgtccgtc   10260
aggacattgt tggagccgaa atccgcgtgc acgaggtgcc ggacttcggg gcagtcctcg   10320
gcccaaagca tcagctcatc gagagcctgc gcgacgacg cactgacggt gtcgtccatc   10380
acagtttgcc agtgatacac atggggatca gcaatcgcgc atatgaaatc acgccatgta   10440
gtgtattgac cgattccttg cggtccgaat gggccgaacc cgctcgtctg gctaagatcg   10500
gccgcagcga tcgcatccat agcctccgcg accggttgta aacagcggg cagttcggtt   10560 tcaggcaggt cttgcaacgt gacaccctgt gcacggcggg agatgcaata ggtcaggctc   10620
tcgctaaact ccccaatgtc aagcacttcc ggaatcggga gcgcggccga tgcaaagtgc   10680
cgataaacat aacgatcttt gtagaaacca tcggcgcagc tatttacccg caggacatat   10740
ccacgccctc ctacatcgaa gctgaaagca cgagattctt cgccctccga gagctgcatc   10800
aggtcggaga cgctgtcgaa cttttcgatc agaaacttct cgacagacgt cgcggtgagt   10860
tcaggctttt tcatatctca ttgccccccg ggatctgcga aagctcgaga gagatagatt   10920
tgtagagaga gactggtgat ttcagcgtgt cctctccaaa tgaaatgaac ttccttatat   10980
agaggaaggt cttgcgaagg atagtgggat tgtgcgtcat cccttacgtc agtggagata   11040
tcacatcaat ccacttgctt tgaagacgtg gttggaacgt cttctttttc cacgatgctc   11100
```

| | |
|---|---|
| ctcgtgggtg ggggtccatc tttgggacca ctgtcggcag aggcatcttg aacgatagcc | 11160 |
| tttcctttat cgcaatgatg gcatttgtag gtgccacctt cctttctac tgtccttttg | 11220 |
| atgaagtgac agatagctgg gcaatggaat ccgaggaggt ttcccgatat tacccttttgt | 11280 |
| tgaaaagtct caatagccct ttggtcttct gagactgtat ctttgatatt cttggagtag | 11340 |
| acgagagtgt cgtgctccac catgttatca catcaatcca cttgctttga agacgtggtt | 11400 |
| ggaacgtctt cttttccac gatgctcctc gtgggtgggg gtccatcttt gggaccactg | 11460 |
| tcggcagagg catcttgaac gatagccttt cctttatcgc aatgatggca tttgtaggtg | 11520 |
| ccaccttcct tttctactgt ccttttgatg aagtgacaga tagctgggca atggaatccg | 11580 |
| aggaggtttc ccgatattac cctttgttga aaagtctcaa tagccctttg gtcttctgag | 11640 |
| actgtatctt tgatattctt ggagtagacg agagtgtcgt gctccaccat gttggcaagc | 11700 |
| tgctctagcc aatacgcaaa ccgcctctcc ccgcgcgttg gccgattcat taatgcagct | 11760 |
| ggcacgacag gtttcccgac tggaaagcgg gcagtgagcg caacgcaatt aatgtgagtt | 11820 |
| agctcactca ttaggcaccc caggctttac actttatgct tccggctcgt atgttgtgtg | 11880 |
| gaattgtgag cggataacaa tttcacacag gaaacagcta tgaccatgat tacg | 11934 |

<210> SEQ ID NO 2
<211> LENGTH: 18828
<212> TYPE: DNA
<213> ORGANISM: Artificial Sequence
<220> FEATURE:
<223> OTHER INFORMATION: PHP64464

<400> SEQUENCE: 2

| | |
|---|---|
| gtttacccgc caatatatcc tgtcaaacac tgatagttta aactgaaggc gggaaacgac | 60 |
| aatctgatca tgagcggaga attaagggag tcacgttatg accccgccg atgacgcggg | 120 |
| acaagccgtt ttacgtttgg aactgacaga accgcaacgt tgaaggagcc actcagcaag | 180 |
| ctggtacgat tgtaatacga ctcactatag ggcgaattga cgctgtttta aacgctcttc | 240 |
| aactggaaga gcggttacgc tgtttaaacg ctcttcaact ggaagagcgg ttactaccgg | 300 |
| ttcactagct agctgctaag gttaccgagc tggtcacctt tgtccacca acttattaag | 360 |
| tatctagttg aagacacgtt cttcttcacg taagaagaca ctcagtagtc ttcggccaga | 420 |
| atggcctctt gattcagcgg gcctagaagg ccggatcact gactagctaa tttaaatcct | 480 |
| gaggatatcg ctatcaactt tgtatagaaa agttgggccg aattcgagct cggtacggcc | 540 |
| agaatggccc ggaccgggtt acccggaccg aagcttgcat gcctgcagtg cagcgtgacc | 600 |
| cggtcgtgcc cctctctaga gataatgagc attgcatgtc taagttataa aaaattacca | 660 |
| catatttttt ttgtcacact tgtttgaagt gcagtttatc tatctttata catatattta | 720 |
| aactttactc tacgaataat ataatctata gtactacaat aatatcagtg ttttagagaa | 780 |
| tcatataaat gaacagttag acatggtcta aaggacaatt gagtatttg acaacaggac | 840 |
| tctacagttt tatcttttta gtgtgcatgt gttctccttt ttttttgcaa atagcttcac | 900 |
| ctatataata cttcatccat tttattagta catccattta gggtttaggg ttaatggttt | 960 |
| ttatagacta attttttag tacatctatt ttattctatt ttagcctcta aattaagaaa | 1020 |
| actaaaactc tattttagtt tttttattta ataatttaga tataaaatag aataaaataa | 1080 |
| agtgactaaa aattaaacaa ataccctta agaaattaaa aaaactaagg aaacatttt | 1140 |
| cttgtttcga gtagataatg ccagcctgtt aaacgccgtc gacgagtcta acggacacca | 1200 |
| accagcgaac cagcagcgtc gcgtcgggcc aagcgaagca gacggcacgg catctctgtc | 1260 |

```
gctgcctctg gaccctctc gagagttccg ctccaccgtt ggacttgctc cgctgtcggc    1320
atccagaaat tgcgtggcgg agcggcagac gtgagccggc acggcaggcg gcctcctcct    1380
cctctcacgg caccggcagc tacggggat tcctttccca ccgctccttc gctttccctt    1440
cctcgcccgc cgtaataaat agacaccccc tccacaccct ctttcccaa cctcgtgttg    1500 ttcggagcgc acacacac aaccagatct cccccaaatc cacccgtcgg cacctccgct    1560
tcaaggtacg ccgctcgtcc tccccccccc ccctctctac cttctctaga tcggcgttcc    1620
ggtccatgca tggttagggc ccggtagttc tacttctgtt catgtttgtg ttagatccgt    1680
gtttgtgtta gatccgtgct gctagcgttc gtacacggat gcgacctgta cgtcagacac    1740
gttctgattg ctaacttgcc agtgtttctc tttggggaat cctgggatgg ctctagccgt    1800
tccgcagacg ggatcgattt catgattttt tttgtttcgt tgcatagggt ttggtttgcc    1860
cttttccttt atttcaatat atgccgtgca cttgtttgtc gggtcatctt ttcatgcttt    1920
tttttgtctt ggttgtgatg atgtggtctg gttgggcggt cgttctagat cggagtagaa    1980
ttctgtttca aactacctgg tggatttatt aattttggat ctgtatgtgt gtgccataca    2040
tattcatagt tacgaattga agatgatgga tggaaatatc gatctaggat aggtatacat    2100
gttgatgcgg gttttactga tgcatataca gagatgcttt ttgttcgctt ggttgtgatg    2160
atgtggtgtg gttgggcggt cgttcattcg ttctagatcg gagtagaata ctgtttcaaa    2220
ctacctggtg tatttattaa ttttggaact gtatgtgtgt gtcatacatc ttcatagtta    2280
cgagtttaag atggatggaa atatcgatct aggataggta tacatgttga tgtgggtttt    2340
actgatgcat atacatgatg gcatatgcag catctattca tatgctctaa ccttgagtac    2400
ctatctatta taataaacaa gtatgtttta taattatttt gatcttgata tacttggatg    2460
atggcatatg cagcagctat atgtggattt ttttagccct gccttcatac gctatttatt    2520
tgcttggtac tgtttctttt gtcgatgctc accctgttgt ttggtgttac ttctgcaggt    2580
cgactctaga ggatcccggt ccgggcctag aaggccagct tcaagtttgt acaaaaaagc    2640
aggccacgat tccgttctgc cttccctgct tattcccca ataaccatat agatgtggaa    2700
ctatacaagc tcatgaccat gcagacgcgt gtcttcattg tccacatgtt gccagcccgt    2760
gcttcccgcc tctttgcaag ggcaaaagca ctcggtatga tgactaaagg gtatgtctgg    2820
attgtcacag atagcattgg tattgtcctt gatgtgcttc cccaacattc cattgaaagc    2880
atggagggaa ttgttggttt ccggccatat attgcagaat ctacaaggat cactgatttc    2940
agctctcgat ttaccacctt attcagaact aagtaccatc caaatactga tattaggatg    3000
gcaaaaccca ctatctttca attatgggct tatgatgtgg catggcagt cgcaacagca    3060 actgagaagg ttcataggac cagatctttg aacccaactt ttcatcctcc gggaaacata    3120
ggcaagaact tagtagatga tctcccagca ttgcctgctg gtccagaact cctcaattcc    3180
attttgcaag gagagtttga tggattggct ggacaattca ggcttatcga tagacatctg    3240
caggttccca catatgagat tgtcaatgtt attggagaga aaactagagt tatcgggttt    3300
tatagtcctg attctggact cacaatgtct gtgaactcta gaattatcca tggtgatgct    3360
aaatttagca caagttcttc tgatctggaa aatatcgttt ggcctggaga ttcaacaaca    3420
gtgcccaaag ctgggactt cccagtgaat gctaagatac tccagattgg tgtgccagtg    3480
agacgtgatt ttaaaacttt tgtgaatgtt gagactaatc cgaacacgaa tagatcaact    3540
gtcagtggct acagcattga tatgtttgag gcagctgtca agaaattacc gtatgctcta    3600
```

```
cgctacgagt acattcccta tgattgtgct gtttcatatg acctgctagt atcccaggtc    3660
ttttacaagg tgagctctgc ttattttgta ttcttaacta attttcccct gtgaataaac    3720
tcattattac taatttactt gttgcctttc cgtttccctg ggtgcaacag aagtttgatg    3780
cagcagtcgg tgatgtgaca attattgcta accgaactag atatgtagat ttcacaatgc    3840
catacacaga gtctggtgtt tcgatgcttg ttctatctaa gagtgacgat gaaccaacca    3900
catggatctt cctacagcca ctagcaaagg acctatggat tgccactatg atctttatct    3960
tcttcacagg cctagttgta tgggtgattg aaagacctat aaatcgcgat ttccaagggt    4020
caaaatggaa acagtgcatc actgctttct actttgcatt ctccactttg acttttcac     4080 atggtatgtc attacagacc tagctattga atagataaaa tacataacta catacatctt    4140
cgtacattca acttattaat ttctaaggat gcttttttt attgtttttt gtcgggtcag     4200
ctgaaagact cttaaggatg ctatcatatg ctactgtgat tcagtatttg ctgtaatttg    4260
ttttgatact actatgattt tgataatct attttttttta atcctatgga caggtcaaaa    4320
gatccaaagc attcagtcaa aaattgttgt ggtaatttgg tgcttagttt tgatgattct    4380
ggtgcagagc tatacagcaa gtttgtcatc aatgctaacg gcagagaggc tccaaccttc    4440
agtgactgat ctaaaacaac ttttggccaa tggtgattct gttggacacc aaagtggatc    4500
atttgtgcaa tcaattctga agaagcttaa atttgatgac cacaagataa aggtttatag    4560
cacgcaggag aatatgcaa aagcattaag gatgggatca aagcatggag gggtttcggc     4620
tatcttcgat gagataccct atctaaattc tttctgctcg aaatacggga gggagttcca    4680
gatggttggc cccattgaca gaacaagtgg atttggtttt gtaagcttct tgcacttgtt    4740
atttattagt ataatgcatc ttcgagcatt ctgccttggc tttacaatat atgtttactt    4800
ttcgacaggt tttacctaaa ggctctccat tggtaccaga cctttcagag gccatcttga    4860
gcttaacgga agaacctgaa aggttgaaga ttgaaaagac atggttcatg gattcgtcct    4920
tggattatta tggcagtcac agcaaaggct catcacgtat cagttttcag agcttccaag    4980 gtctttcat cattgtcggg tgccttttag gtgctgtgct gttgataaac tttagcaagt     5040
ttctatatga caaatgcaaa gagatgagag gcttcggttc agaccgtgtc catagtggcg    5100
agagagttgt ttgttacggt gaagctcaac cacaaccacc gcagattgtc atggtcgatc    5160
gacgatcctg tgcctgctga taccctccag attaggactg aaaacaaata aagagtgtga    5220
acagttatct gcaccaacta tcccaactcc caagaatctt ggcagctttc ttgtacaaag    5280
tggccgttaa cggatcggcc agaatggccc ggacccggtg accaagctta ctaactatct    5340
atactgtaat aatgttgtat agccgccgga tagctagcta gtttagtcat tcagcggcga    5400
tgggtaataa taaagtgtca tccatccatc accatgggtg gcaacgtgag caatgacctg    5460
attgaacaaa ttgaaatgaa aagaagaaat atgttatatg tcaacgagat ttcctcataa    5520
tgccactgac gacgtgtgtc caagaaatgt atcagtgata cgtatattca caatttttt    5580 atgacttata ctcacaattt gttttttttac tacttatact cacaatttgt tgtgggtacc    5640
ataacaattt cgatcgaata tatatcagaa agttgacgaa agtaagctca ctcaaaaagt    5700
taaatgggct gcggaagctg cgtcaggccc aagttttggc tattctatcc ggtatccacg    5760
attttgatgg ctgagggaca tatgttcgct tcatcgatat cagacggacc gaagctggcc    5820
gctctagaac tagtggatct cgatgtgtag tctacgagaa gggttaaccg tctcttcgtg    5880
agaataaccg tggcctaaaa ataagccgat gaggataaat aaaatgtggt ggtacagtac    5940
ttcaagaggt ttactcatca agaggatgct tttccgatga gctctagtag tacatcggac    6000
```

```
ctcacatacc tccattgtgg tgaaatattt tgtgctcatt tagtgatggg taaattttgt    6060
ttatgtcact ctaggttttg acatttcagt tttgccactc ttaggttttg acaaataatt    6120
tccattccgc ggcaaaagca aaacaatttt attttacttt taccactctt agctttcaca    6180
atgtatcaca aatgccactc tagaaattct gtttatgcca cagaatgtga aaaaaaacac    6240
tcacttattt gaagccaagg tgttcatggc atggaaatgt gacataaagt aacgttcgtg    6300
tataagaaaa aattgtactc ctcgtaacaa gagacggaaa catcatgaga caatcgcgtt    6360
tggaaggctt tgcatcacct ttggatgatg cgcatgaatg gagtcgtctg cttgctagcc    6420
ttcgcctacc gcccactgag tccgggcggc aactaccatc ggcgaacgac ccagctgacc    6480
tctaccgacc ggacttgaat gcgctacctt cgtcagcgac gatggccgcg tacgctggcg    6540
acgtgccccc gcatgcatgg cggcacatgg cgagctcaga ccgtgcgtgg ctggctacaa    6600
atacgtaccc cgtgagtgcc ctagctagaa acttacacct gcaactgcga gagcgagcgt    6660
gtgagtgtag ccgagtagat cccccggtcg ccaccatggc ctcctccgag aacgtcatca    6720
ccgagttcat gcgcttcaag gtgcgcatgg agggcaccgt gaacggccac gagttcgaga    6780
tcgagggcga gggcgagggc cgcccctacg agggccacaa caccgtgaag ctgaaggtga    6840
ccaagggcgg ccccctgccc ttcgcctggg acatcctgtc ccccagttc cagtacggct    6900 ccaaggtgta cgtgaagcac cccgccgaca tccccgacta caagaagctg tccttccccg    6960
agggcttcaa gtgggagcgc gtgatgaact tcgaggacgg cggcgtggcg accgtgaccc    7020
aggactcctc cctgcaggac ggctgcttca tctacaaggt gaagttcatc ggcgtgaact    7080
tcccctccga cggccccgtg atgcagaaga agaccatggg ctgggaggcc tccaccgagc    7140
gcctgtaccc ccgcgacggc gtgctgaagg gcgagaccca caaggccctg aagctgaagg    7200
acggcggcca ctacctggtg gagttcaagt ccatctacat ggccaagaag cccgtgcagc    7260
tgcccggcta ctactacgtg gacgccaagc tggacatcac ctcccacaac gaggactaca    7320
ccatcgtgga gcagtacgag cgcaccgagg ccgccacca cctgttcctg tagcggccca    7380
tggatattcg aacgcgtagg taccacatgg ttaacctaga cttgtccatc ttctggattg    7440
gccaacttaa ttaatgtatg aaataaaagg atgcacacat agtgacatgc taatcactat    7500
aatgtgggca tcaaagttgt gtgttatgtg taattactag ttatctgaat aaaagagaaa    7560
gagatcatcc atatttctta tcctaaatga atgtcacgtg tctttataat tctttgatga    7620
accagatgca tttcattaac caaatccata tacatataaa tattaatcat atataattaa    7680
tatcaattgg gttagcaaaa caaatctagt ctaggtgtgt tttgcgaatg cggccgccac    7740
cgcggtggag ctcgaattcc ggtccgggcc tagaaggcca gcttcggccg ccccgggcaa    7800
ctttattata caaagttgat agatatctgg tctaactaac tagtcctaag gacccggcgg    7860
accgattaaa ctgattcggt ccgaagcttg catgcctgca gtgcagcgtg acccggtcgt    7920 gccctctct agagataatg agcattgcat gtctaagtta taaaaaatta ccacatattt    7980
tttttgtcac acttgtttga agtgcagttt atctatcttt atacatatat ttaaacttta    8040
ctctacgaat aatataatct atagtactac aataatatca gtgttttaga gaatcatata    8100
aatgaacagt tagacatggt ctaaggaca attgagtatt ttgacaacag gactctacag    8160
ttttatcttt ttagtgtgca tgtgttctcc ttttttttg caaatagctt cacctatata    8220
atacttcatc cattttatta gtacatccat ttagggttta gggttaatgg ttttataga    8280 ctaatttttt tagtacatct attttattct attttagcct ctaaattaag aaaactaaaa    8340
```

```
ctctatttta gttttttat ttaataattt agatataaaa tagaataaaa taaagtgact    8400
aaaaattaaa caaatacct ttaagaaatt aaaaaaacta aggaaacatt tttcttgttt    8460
cgagtagata atgccagcct gttaaacgcc gtcgacgagt ctaacggaca ccaaccagcg   8520
aaccagcagc gtcgcgtcgg gccaagcgaa gcagacggca cggcatctct gtcgctgcct   8580
ctggacccct ctcgagagtt ccgctccacc gttggacttg ctccgctgtc ggcatccaga   8640
aattgcgtgg cggagcggca gacgtgagcc ggcacggcag gcggcctcct cctcctctca   8700
cggcaccggc agctacgggg gattccttc ccaccgctcc ttcgctttcc cttcctcgcc    8760
cgccgtaata aatagacacc ccctccacac cctctttccc caacctcgtg ttgttcggag   8820
cgcacacaca cacaaccaga tctcccccaa atccacccgt cggcacctcc gcttcaaggt   8880
acgccgctcg tcctccccc ccccctctc taccttctct agatcggcgt tccggtccat     8940
ggttagggcc cggtagttct acttctgttc atgtttgtgt tagatccgtg tttgtgttag   9000
atccgtgctg ctagcgttcg tacacggatg cgacctgtac gtcagacacg ttctgattgc   9060
taacttgcca gtgtttctct ttggggaatc ctggatggc tctagccgtt ccgcagacgg    9120
gatcgatttc atgatttttt ttgtttcgtt gcatagggtt tggtttgccc ttttcctta   9180
tttcaatata tgccgtgcac ttgtttgtcg ggtcatcttt tcatgctttt ttttgtcttg  9240
gttgtgatga tgtggtctgg ttgggcggtc gttctagatc ggagtagaat tctgtttcaa   9300
actacctggt ggatttatta attttggatc tgtatgtgtg tgccatacat attcatagtt   9360
acgaattgaa gatgatggat ggaaatatcg atctaggata ggtatacatg ttgatgcggg   9420
ttttactgat gcatatacag agatgctttt tgttcgcttg gttgtgatga tgtggtgtgg   9480
ttgggcggtc gttcattcgt tctagatcgg agtagaatac tgtttcaaac tacctggtgt   9540
atttattaat tttggaactg tatgtgtgtg tcatacatct tcatagttac gagtttaaga   9600
tggatggaaa tatcgatcta ggataggtat acatgttgat gtgggtttta ctgatgcata   9660
tacatgatgg catatgcagc atcattcat atgctctaac cttgagtacc tatctattat    9720
aataaacaag tatgttttat aattattttg atcttgatat acttggatga tggcatatgc   9780
agcagctata tgtggatttt tttagccctg ccttcatacg ctatttattt gcttggtact   9840
gtttcttttg tcgatgctca ccctgttgtt tggtgttact tctgcaggtc gaccgccggg   9900
gatccacacg acaccatggc tattgaggtt aagcctatca acgcagagga tacctatgac   9960
cttaggcata gagtgctcag accaaaccag cctatcgaag cctgcatgtt tgagtctgac   10020
cttactagga gtgcatttca ccttggtgga ttctacggag gtaaactgat ttccgtggct   10080
tcattccacc aagctgagca ctctgaactt caaggtaaga agcagtacca gcttagaggt   10140
gtggctacct tggaaggtta tagagagcag aaggctggtt ccagtctcgt gaaacacgct   10200
gaagagattc tcagaaagag aggtgctgac atgatctggt gtaatgccag gacatctgct   10260
tcaggatact acaggaagtt gggattcagt gagcaaggag aggtgttcga tactcctcca   10320
gttggacctc acatcctgat gtataagagg atcacataac tagctagtca gttaacctag   10380
acttgtccat cttctggatt ggccaactta attaatgtat gaaataaaag gatgcacaca   10440
tagtgacatg ctaatcacta taatgtgggc atcaaagttg tgtgttatgt gtaattacta   10500
gttatctgaa taaaagagaa agagatcatc catatttctt atcctaaatg aatgtcacgt   10560
gtctttataa ttctttgatg aaccagatgc atttcattaa ccaaatccat atacatataa   10620
atattaatca tatataatta atatcaattg ggttagcaaa acaaatctag tctaggtgtg   10680
ttttgcgaat tatcgatggg ccccggccga agcttaagcc atggcccggg aatcttagcg   10740
```

```
gccgcctgca gagttaacgg cgcgccgact agctagctaa ggtaccgagc tcgaattcat   10800
tccgattaat cgtggcctct tgctcttcag gatgaagagc tatgtttaaa cgtgcaagcg   10860
ctactagaca attcagtaca ttaaaaacgt ccgcaatgtg ttattaagtt gtctaagcgt   10920
caatttgttt acaccacaat atatcctgcc accagccagc caacagctcc ccgaccggca   10980
gctcggcaca aaatcaccac tcgatacagg cagcccatca gtccgggacg gcgtcagcgg   11040
gagagccgtt gtaaggcggc agactttgct catgttaccg atgctattcg gaagaacggc   11100
aactaagctg ccgggtttga aacacggatg atctcgcgga gggtagcatg ttgattgtaa   11160
cgatgacaga gcgttgctgc ctgtgatcaa atatcatctc cctcgcagag atccgaatta   11220
tcagccttct tattcatttc tcgcttaacc gtgacaggct gtcgatcttg agaactatgc   11280
cgacataata ggaaatcgct ggataaagcc gctgaggaag ctgagtggcg ctatttcttt   11340
agaagtgaac gttgacgatc gtcgggccca gtagaatcc gcctgagtcg caagggtgac   11400
ttcgcctata ttggacgacg gcgcgcagag ggcgacctct ttttgggtta cgattgtagg   11460
attatcacta aacaataca tgaacatatt caaatggcaa tctctctaag gcattggaaa   11520
taaatacaaa taacagttgg gtggagtttt tcgacctgtg ggcgttaacc ttctgttaac   11580
ctaaaagctc ttgcccaaac agcagaatcg gcgctaattg ccagcggcgg aacttttcca   11640
gtttcgcgaa aaatatcgcc actggcaagg aatgggtttg agatggcgaa gtctgtccta   11700
aaagcagcgc ctgtagttgt agggttgacg gccttgatgg agcgtcatgc cgatgccctc   11760
tcgagccaac ttcaagcaca tcatcttaag gtttttcccgc cgcattccga aagggcatt   11820 cgaacattcg ggccatcgga ggcgtccaag ctgctcggcg ttggcgagtc atatttacgg   11880
cagaccgcgt ctgagatgcc agagttgaat gttagcatga gcccgggtgg caggcgaatg   11940
ttctcaattg aagatatcca tgtgattcgg aagtatatgg atcaggtcgg ccgcgggaac   12000
cggcgctacc tgccacatcg tcgaggcggc gagcagcttc aggttatctc tgtgatgaat   12060
ttcaaaggtg ggtcgggtaa gaccaccacc gccgcgcatc tggcgcagta cctcgctatg   12120
cgcggatatc gagtcttggc cattgatctc gatcctcaag cgagccttt tgcactcttt   12180 gggagccaac cggagacgga cgttggcccg aacgaaacgc tctacggcgc tataaggtat   12240
gatgatgagc aggtggcaat cgaacgagtc gtccgaggga cttacattcc cgacctccac   12300
ctgattcctg gtaatcttga gctgatggag tttgaacacg atacgccacg cgcgctgatg   12360
aaccgcaaag agggcgacac gctcttttat ggtcgcatca gccaagtaat tgaagatatc   12420
gcggataact atgacgtcgt ggtcatcgac tgccctcccc agcttgggta tctcacgcta   12480
tccgcattga ctgcggcgac gtccattctt gtcacggtcc atccgcagat gctggatgtg   12540
atgtcgatga accagtttct ggcaatgaca tcgaaccttt tgcgtgaaat cgagaatgct   12600
ggcgccaagt tcaagtttaa ttggatgcgc tatctgataa cccgtttcga accgagcgac   12660
ggaccacaga accaaatggt aggttatctg cggtcgattt ttggcgaaaa tgtcctcaat   12720
tttccgatgc ttaaaaccac cgcggtttcg acgctggcc tgacaaacca gactctattc   12780
gaagtggagc gtggcctgtt cacgcgctcg acctatgatc gagccttgga ggcgatgaac   12840
gccgtcaacg acgagatcga aacactgatc aaaaaagcat ggggtaggcc cacatgagcc   12900
ggaagcacat ccttggcgtc tcaactgacg cccctgagac gtcgcccgcc gacaatagga   12960
cggcaaagaa ccgctccatg ccgctcctcg gcgtaacaag gaaggagcgc gatccggcaa   13020
cgaagctcac agcgaacatt ggtaacgcac tgcgagagca aaacgatcgt cttagccgtg   13080
```

```
ccgaagagat cgagcggcgt ctcgctgaag gtcaggcagt gatagagttg gatgcctcgt    13140
caatagaacc gtctttcgtg caggatcgta tgcgagggga cattgacggg ctccttactt    13200
cgatccggga acaaggacag caagtcccaa tccttgtgcg accgcatccg agccagccgg    13260
gccgatatca ggttgccttc ggccaccgcc ggctacgcgc cgtttcagaa ctcggacttc    13320
cggtcagagc ggtcgttcgc gaactgacgg acgagcaagt ggtcgtagca cagggtcagg    13380
aaaacaatga gcgcgaagat cttaccttca tcgaaaaggc gcgcttcgca catcgcctga    13440
acaggcagtt ttctcgagag attgtcatcg ccgcgatgtc gatcgacaag agcaatttgt    13500
ccaagatgct tctgctcgtt gacgccctcc cctctgaact gaccgatgct attggtgccg    13560
ctcctggtgt tggacggccg agttggcaac aacttgccga gctgattgag aaagtttctt    13620
caccggccga cgtggctaaa tatgctatgt cggaggaagt tcaagcgctg ccatcggcag    13680
aacgattcaa ggcggtgatc gctagtctga agcccagtcg ggttgcgcgt ggacttcccg    13740
aggtcatggc cacccagac ggcaccagaa ttgcacaggt gacgcagagc aaggccaaac    13800
tggaaatcac gattgacagg aaggcgacgc ccgattttgc gaccttcgtg ctcgatcatg    13860
tgccagcgct gtatcaagcg taccacgctg agaaccaacg gaaacgggga gagtaaaccg    13920
caaaagaaaa gagcccccctc aacgtcgccg tcgcggaagc ccttctgtct ctctagcgcg    13980
aacagaatcg catttcctcg aatcctcgtc aagagttttt agcgccgttt tggtgagctg    14040
atttcctttg cctgctgaaa ggtgaaagat gatgcagaca ggaagtgtaa cgacgccatt    14100
cgggcggcgg ccaatgacgc ttgcgcttgt gcggcgccag acggcgctgg ccgatatcaa    14160
acaaggcaag acagcggaca agtggaaggt ctttagagac gcgtccgcgg ctatggaact    14220
acttggaatc cagtccaaca gtcttgccgt ccttgatgcg ctattgagct ttcacccgga    14280 aacgagttg cgtcaggagg cacagctgat cgtcttcccg tcgaatgctc agcttgccct    14340
tcgggcgcat gggatggctg gcgcgacttt gcgtaggcac atcgccatgc tcgtggagtc    14400
aggcttgatc gtccggaagg atagcgccaa cggaaagcgt tacgctcgta aggatggcgc    14460
tggtcagatc gagcgcgcgt ttggcttcga tttgtctccg cttctcgcgc ggtcggaaga    14520
gctagcgatg atggcacagc aggtgatggc cgatcgagca gcattcagga tggccaaaga    14580
aagtctgacg atttgccgac gggacgttcg gaagctaatt acggcagcta tggaagaggg    14640
agcggagggc gactggcaag ctgtcgagga agtctatgtg gaacttgtgg gtagaattcc    14700
acgcgccccg acgcttgctg atgtagagtc aattctcgaa gagatgtgga tgctccagga    14760
agagataatc aaccggttgg aaattagaga caattcagaa aataatagca ccaatgctgc    14820
ccagagcgag cagcacatac agaattcaaa acccgaatcc gttaatgaac ttgaacctcg    14880
ctctgaaaag gagcagggcg ctaagccgag tgaaatagac cgggcaagga gcgagccgat    14940
aaaagcgttc cccctcggga tgatcctgaa agcatgcccg accattggca actatgggcc    15000
gagcggtgcg gttgctagct ggcgtgacct catgtcggct gcggtggtgg ttcggtctat    15060
gctgggggtc agcccgtcgg cttaccaaga cgcgtgtgag gcaatgggac cggagaatgc    15120
ggcagcagcg atggcgtgca ttttggagcg agcgaacttc atcaattcgc ccgggggcta    15180
tctccgagat ctgacacggc ggagcgagct tgggaagttt tcacttggcc cgatgataat    15240
ggcgctcttg aaggctagcg ggcaggggac gttgcggttt ggctagaatt agcgagtatg    15300
gagcaggatg gtctgtggtc agctgaccac agacctaata ggttgaaaac atgagcgttt    15360
tttggatgat cgacagacca tccgattccc ggagtaccaa gcgtgctctg atgggagcga    15420
taacattact caacaagcac gaaggcccca tgccgatcgt tgatcgtgaa ggagagcctg    15480
```

```
ctctacatgc ggcggtattt tgccggccga ggcatgtagt cgcggagcac tgcctattta    15540
ctgccctagg cacaaacgtt gactcttgga tcgagctggc agacaaagca ataacccaca    15600
cagaggacga ttaatggctg acgaagagat ccagaatccg ccggacggta ctgctgctgc    15660
cgaagttgag ccggctgctc ctagaggtag aagagcaaag aaagcaccag ccgaaacagc    15720
ccgcacggga tcgttcaaat ccgtgaagcc gaaaacccgc ggcctcagca accgagaaaa    15780
actggagaag atcggtcaaa tcgaagctca ggtcgctggc ggcgcaacct tgaaggacgc    15840
cgttaagatc gtgggtattt ccgttcagac ctattatcaa tggaagagag ctgcggttca    15900
acctgtctca cagaatccgg ccgtgtctgt ttcagttgac gatgaactcg gcgagttcat    15960
ccaactcgag gaggaaaata tgcatggcat gcccgttcca tacagaagct gggcgaacaa    16020
acgatgctcg ccttccagaa aaccgaggat gcgaaccact tcatccgggg tcagcaccac    16080
cggcaagcgc cgcgacggcc gaggtcttcc gatctcctga agccagggca gatccgtgca    16140
cagcaccttg ccgtagaaga acagcaaggc cgccaatgcc tgacgatgcg tggagaccga    16200
aaccttgcgc tcgttcgcca gccaggacag aaatgcctcg acttcgctgc tgcccaaggt    16260
tgccgggtga cgcacaccgt ggaaacggat gaaggcacga acccagtgga cataagcctg    16320
ttcggttcgt aagctgtaat gcaagtagcg tatgcgctca cgcaactggt ccagaacctt    16380
gaccgaacgc agcggtggta acggcgcagt ggcggttttc atggcttgtt atgactgttt    16440
ttttggggta cagtctatgc ctcgggcatc caagcagcaa gcgcgttacg ccgtgggtcg    16500
atgtttgatg ttatggagca gcaacgatgt tacgcagcag ggcagtcgcc ctaaaacaaa    16560
gttaaacatc atgagggaag cggtgatcgc cgaagtatcg actcaactat cagaggtagt    16620
tggcgtcatc gagcgccatc tcgaaccgac gttgctggcc gtacatttgt acggctccgc    16680
agtggatggc ggcctgaagc cacacagtga tattgatttg ctggttacgg tgacggtaag    16740
gcttgatgaa acaacgcggc gagctttgat caacgacctt ttggaaactt cggcttcccc    16800
tggagagagc gagattctcc gcgctgtaga agtcaccatt gttgtgcacg acgacatcat    16860
tccgtggcgt tatccagcta agcgcgaact gcaatttgga gaatggcagc gcaatgacat    16920
tcttgcaggt atcttcgagc cagccacgat cgacattgat ctggctatct tgctgacaaa    16980
agcaagagaa catagcgttg ccttggtagg tccagcggcg gaggaactct ttgatccggt    17040
tcctgaacag gatctatttg aggcgctaaa tgaaacctta cgctatgga actgccgcc     17100 cgactgggct ggcgatgagc gaaatgtagt gcttacgttg tcccgcattt ggtacagcgc    17160
agtaaccggc aaaatcgcgc cgaaggatgt cgctgccgac tggcaatgg agcgcctgcc    17220 ggcccagtat cagcccgtca tacttgaagc tagacaggct tatcttggac aagaagaaga    17280
tcgcttggcc tcgcgcgcag atcagttgga agaatttgtc cactacgtga aaggcagat     17340 caccaaggta gtcggcaaat aatgtctaac aattcgttca agccgacgcc gcttcgcggc    17400
gcggcttaac tcaagcgtta gatgcactat acgtaaccaa ctagtgcgct cttccgcttc    17460
ctcgctcact gactcgctgc gctcggtcgt tcggctgcgg cgagcggtat cagctcactc    17520
aaaggcggta atacggttat ccacagaatc aggggataac gcaggaaaga acatgtgagc    17580
aaaaggccag caaaaggcca ggaaccgtaa aaaggccgcg ttgctggcgt ttttccatag    17640
gctccgcccc cctgacgagc atcacaaaaa tcgacgctca agtcagaggt ggcgaaaccc    17700
gacaggacta taaagatacc aggcgtttcc ccctggaagc tccctcgtgc gctctcctgt    17760
tccgaccctg ccgcttaccg gatacctgtc cgcctttctc ccttcgggaa gcgtggcgct    17820
```

```
ttctcatagc tcacgctgta ggtatctcag ttcggtgtag gtcgttcgct ccaagctggg    17880
ctgtgtgcac gaaccccccg ttcagcccga ccgctgcgcc ttatccggta actatcgtct    17940
tgagtccaac ccggtaagac acgacttatc gccactggca gcagccactg gtaacaggat    18000
tagcagagcg aggtatgtag gcggtgctac agagttcttg aagtggtggc ctaactacgg    18060
ctacactaga agaacagtat ttggtatctg cgctctgctg aagccagtta ccttcggaaa    18120
aagagttggt agctcttgat ccggcaaaca aaccaccgct ggtagcggtg gtttttttgt    18180
ttgcaagcag cagattacgc gcagaaaaaa aggatctcaa gaagatcctt tgatcttttc    18240
tacggggtct gacgctcagt ggaacgaaaa ctcacgttaa gggattttgg tcatgagatt    18300
atcaaaaagg atcttcacct agatcctttt aaattaaaaa tgaagcgtac cgacgatctt    18360
gctgcgttcg atatttttcg tggagttccc gccacagacc cggattgaag gcgagatcca    18420
gcaactcgcg ccagatcatc ctgtgacgga actttggcgc gtgatgactg gccaggacgt    18480
cggccgaaag agcgacaagc agatcacgct tttcgacagc gtcggatttg cgatcgagga    18540
tttttcggcg ctgcgctacg tccgcgaccg cgttgaggga tcaagccaca gcagcccact    18600
cgaccttcta gccgacccag acgagccaag ggatcttttt ggaatgctgc tccgtcgtca    18660
ggctttccga cgtttgggtg gttgaacaga agtcattatc gcacggaatg ccaagcactc    18720
ccgaggggaa ccctgtggtt ggcatgcaca tacaaatgga cgaacggata aaccttttca    18780
cgccctttta aatatccgat tattctaata acgctctttt tctcttag                18828

<210> SEQ ID NO 3
<211> LENGTH: 16843
<212> TYPE: DNA
<213> ORGANISM: Artificial Sequence
<220> FEATURE:
<223> OTHER INFORMATION: pBC-Yellow

<400> SEQUENCE: 3
ccgggctggt tgccctcgcc gctgggctgg cggccgtcta tggccctgca aacgcgccag      60
aaacgccgtc gaagccgtgt gcgagacacc gcggccgccg gcgttgtgga tacctcgcgg     120
aaaacttggc cctcactgac agatgagggg cggacgttga cacttgaggg gccgactcac     180
ccggcgcggc gttgacagat gaggggcagg ctcgatttcg gccggcgacg tggagctggc     240
cagcctcgca aatcggcgaa aacgcctgat tttacgcgag tttcccacag atgatgtgga     300
caagcctggg gataagtgcc ctgcggtatt gacacttgag gggcgcgact actgacagat     360
gaggggcgcg atccttgaca cttgaggggc agagtgctga cagatgaggg gcgcacctat     420
tgacatttga ggggctgtcc acaggcagaa aatccagcat ttgcaagggt ttccgcccgt     480
ttttcggcca ccgctaacct gtctttaac ctgcttttaa accaatattt ataaaccttg     540
tttttaacca gggctgcgcc ctgtgcgcgt gaccgcgcac gccgaagggg ggtgccccc     600 cttctcgaac cctcccggcc cgctaacgcg ggcctcccat ccccccaggg gctgcgcccc    660
tcggccgcga acgcctcac cccaaaaatg gcagcgctgg cagtccttgc cattgccggg    720
atcggggcag taacgggatg ggcgatcagc ccgagcgcga cgcccggaag cattgacgtg    780
ccgcaggtgc tggcatcgac attcagcgac caggtgccgg gcagtgaggg cggcggcctg    840
ggtggcggcc tgcccttcac ttcggccgtc ggggcattca cggacttcat ggcggggccg    900
gcaattttta ccttgggcat tcttggcata tgtgtcgcgg gtgccgtgct cgtgttcggg    960
ggtgcgataa acccagcgaa ccatttgagg tgataggtaa gattataccg aggtatgaaa   1020
acgagaattg gacctttaca gaattactct atgaagcgcc atatttaaaa agctaccaag   1080
```

```
acgaagagga tgaagaggat gaggaggcag attgccttga atatattgac aatactgata    1140
agataatata tcttttatat agaagatatc gccgtatgta aggatttcag ggggcaaggc    1200
ataggcagcg cgcttatcaa tatatctata gaatgggcaa agcataaaaa cttgcatgga    1260
ctaatgcttg aaacccagga caataacctt atagcttgta aattctatca taattgggta    1320
atgactccaa cttattgata gtgttttatg ttcagataat gcccgatgac tttgtcatgc    1380
agctccaccg attttgagaa cgacagcgac ttccgtccca gccgtgccag gtgctgcctc    1440
agattcaggt tatgccgctc aattcgctgc gtatatcgct tgctgattac gtgcagcttt    1500
cccttcaggc gggattcata cagcggccag ccatccgtca tccatatcac cacgtcaaag    1560
ggtgacagca ggctcataag acgccccagc gtcgccatag tgcgttcacc gaatacgtgc    1620
gcaacaaccg tcttccggag actgtcatac gcgtaaaaca gccagcgctg gcgcgattta    1680
gccccgacat agccccactg ttcgtccatt ccgcgcaga cgatgacgtc actgcccggc    1740
tgtatgcgcg aggttaccga ctgcggcctg agttttttaa gtgacgtaaa atcgtgttga    1800
ggccaacgcc cataatgcgg gctgttgccc ggcatccaac gccattcatg gccatatcaa    1860
tgattttctg gtgcgtaccg ggttgagaag cggtgtaagt gaactgcagt tgccatgttt    1920
tacggcagtg agagcagaga tagcgctgat gtccggcggt gcttttgccg ttacgcacca    1980
ccccgtcagt agctgaacag gagggacagc tgatagacac agaagccact ggagcacctc    2040
aaaaacacca tcatacacta atcagtaagt tggcagcat cacccataat tgtggtttca     2100
aaatcggctc cgtcgatact atgttatacg ccaactttga aaacaacttt gaaaaagctg    2160
ttttctggta tttaaggttt tagaatgcaa ggaacagtga attggagttc gtcttgttat    2220
aattagcttc ttggggtatc tttaaatact gtagaaaaga ggaaggaaat aataaatggc    2280
taaaatgaga atatcaccgg aattgaaaaa actgatcgaa aaataccgct gcgtaaaaga    2340
tacggaagga atgtctcctg ctaaggtata taagctggtg ggagaaaatg aaaacctata    2400
tttaaaaatg acggacagcc ggtataaagg gaccacctat gatgtggaac gggaaaagga    2460
catgatgcta tggctggaag gaaagctgcc tgttccaaag gtcctgcact ttgaacggca    2520
tgatggctgg agcaatctgc tcatgagtga ggccgatggc gtccttgct cggaagagta     2580
tgaagatgaa caaagccctg aaaagattat cgagctgtat gcggagtgca tcaggctctt    2640
tcactccatc gacatatcgg attgtcccta tacgaatagc ttagacagcc gcttagccga    2700
attggattac ttactgaata acgatctggc cgatgtggat tgcgaaaact gggaagaaga    2760
cactccattt aaagatccgc gcgagctgta tgattttta aagacggaaa agcccgaaga    2820
ggaacttgtc ttttcccacg gcgacctggg agacagcaac atctttgtga agatggcaa    2880
agtaagtggc tttattgatc ttgggagaag cggcagggcg acaagtggt atgacattgc     2940
cttctgcgtc cggtcgatca gggaggatat cggggaagaa cagtatgtcg agctatttt     3000
tgacttactg gggatcaagc ctgattggga gaaaataaaa tattatattt tactggatga    3060
attgttttag tacctagatg tggcgcaacg atgccggcga caagcaggag cgcaccgact    3120
tcttccgcat caagtgtttt ggctctcagg ccgaggccca cggcaagtat ttgggcaagg    3180
ggtcgctggt attcgtgcag ggcaagattc ggaataccaa gtacgagaag gacggccaga    3240
cggtctacgg gaccgacttc attgccgata aggtggatta tctggacacc aaggcaccag    3300
gcgggtcaaa tcaggaataa gggcacattg ccccggcgtg agtcggggca atcccgcaag    3360
gagggtgaat gaatcggacg tttgaccgga aggcatacag gcaagaactg atcgacgcgg    3420
```

```
ggttttccgc cgaggatgcc gaaaccatcg caagccgcac cgtcatgcgt gcgcccgcg    3480
aaaccttcca gtccgtcggc tcgatggtcc agcaagctac ggccaagatc gagcgcgaca    3540
gcgtgcaact ggctccccct gccctgcccg cgccatcggc cgccgtggag cgttcgcgtc    3600
gtctcgaaca ggaggcggca ggtttggcga agtcgatgac catcgacacg cgaggaacta    3660
tgacgaccaa gaagcgaaaa accgccggcg aggacctggc aaaacaggtc agcgaggcca    3720
agcaggccgc gttgctgaaa cacacgaagc agcagatcaa ggaaatgcag ctttccttgt    3780
tcgatattgc gccgtggccg gacacgatgc gagcgatgcc aaacgacacg gcccgctctg    3840
ccctgttcac cacgcgcaac aagaaaatcc cgcgcgaggc gctgcaaaac aaggtcattt    3900
tccacgtcaa caaggacgtg aagatcacct acaccggcgt cgagctgcgg gccgacgatg    3960
acgaactggt gtggcagcag gtgttggagt acgcgaagcg caccccatc ggcgagccga     4020
tcaccttcac gttctacgag cttgccagg acctgggctg gtcgatcaat ggccggtatt      4080
acacgaaggc cgaggaatgc ctgtcgcgcc tacaggcgac ggcgatgggc ttcacgtccg    4140
accgcgttgg gcacctggaa tcggtgtcgc tgctgcaccg cttccgcgtc ctggaccgtg    4200
gcaagaaaac gtcccgttgc caggtcctga tcgacgagga aatcgtcgtg ctgtttgctg    4260
gcgaccacta cacgaaattc atatgggaga agtaccgcaa gctgtcgccg acggcccgac    4320
ggatgttcga ctatttcagc tcgcaccggg agccgtaccc gctcaagctg gaaaccttcc    4380
gcctcatgtg cggatcggat tccacccgcg tgaagaagtg gcgcgagcag gtcggcgaag    4440
cctgcgaaga gttgcgaggc agcggcctgg tggaacacgc ctgggtcaat gatgacctgg    4500
tgcattgcaa acgctagggc cttgtggggt cagttccggc tgggggttca gcagccagcg    4560
ctttactggc atttcaggaa caagcgggca ctgctcgacg cacttgcttc gctcagtatc    4620
gctcgggacg cacggcgcgc tctacgaact gccgataaac agaggattaa aattgacaat    4680
tgtgattaag gctcagattc gacggcttgg agcggccgac gtgcaggatt ccgcgagat     4740
ccgattgtcg gccctgaaga aagctccaga gatgttcggg tccgtttacg agcacgagga    4800
gaaaaagccc atggaggcgt tcgctgaacg gttgcgagat gccgtggcat tcggcgccta    4860
catcgacggc gagatcattg ggctgtcggt cttcaaacag gaggacggcc ccaaggacgc    4920
tcacaaggcg catctgtccg gcgttttcgt ggagcccgaa cagcgaggcc gagggtcgc     4980
cggtatgctg ctgcgggcgt tgccggcggg tttattgctc gtgatgatcg tccgacagat    5040
tccaacggga atctggtgga tgcgcatctt catcctcggc gcacttaata tttcgctatt    5100
ctggagcttg ttgtttattt cggtctaccg cctgccgggc ggggtcgcgg cgacggtagg    5160
cgctgtgcag ccgctgatgg tcgtgttcat ctctgccgct ctgctaggta gcccgatacg    5220
attgatggcg gtcctggggg ctatttgcgg aactgcgggc gtggcgctgt tggtgttgac    5280
accaaacgca gcgctagatc ctgtcggcgt cgcagcgggc ctggcggggg cggtttccat    5340
ggcgttcgga accgtgctga cccgcaagtg gcaacctccc gtgcctctgc tcacctttac    5400
cgcctggcaa ctggcggccg gaggacttct gctcgttcca gtagctttag tgtttgatcc    5460
gccaatcccg atgcctacag gaaccaatgt tctcggcctg gcgtggctcg gcctgatcgg    5520
agcgggttta acctacttcc tttggttccg ggggatctcg cgactcgaac ctacagttgt    5580
ttccttactg ggctttctca gccccagatc tggggtcgat cagccgggga tgcatcaggc    5640
cgacagtcgg aacttcgggt ccccgacctg taccattcgg tgagcaatgg ataggggagt    5700
tgatatcgtc aacgttcact tctaaagaaa tagcgccact cagcttcctc agcggcttta    5760
tccagcgatt tcctattatg tcggcatagt tctcaagatc gacagcctgt cacggttaag    5820
```

```
cgagaaatga ataagaaggc tgataattcg gatctctgcg agggagatga tatttgatca    5880
caggcagcaa cgctctgtca tcgttacaat caacatgcta ccctccgcga gatcatccgt    5940
gtttcaaacc cggcagctta gttgccgttc ttccgaatag catcggtaac atgagcaaag    6000
tctgccgcct tacaacggct ctcccgctga cgccgtcccg gactgatggg ctgcctgtat    6060
cgagtggtga ttttgtgccg agctgccggt cggggagctg ttggctggct ggtggcagga    6120
tatattgtgg tgtaaacaaa ttgacgctta gacaacttaa taacacattg cggacgtttt    6180
taatgtactg gggtggtttt tcttttcacc agtgagacgg gcaacagctg attgcccttc    6240
accgcctggc cctgagagag ttgcagcaag cggtccacgc tggtttgccc cagcaggcga    6300
aaatcctgtt tgatggtggt tccgaaatcg gcaaaatccc ttataaatca aagaatagc    6360 ccgagatagg gttgagtgtt gttccagttt ggaacaagag tccactatta aagaacgtgg    6420
actccaacgt caagggcga aaaccgtct atcagggcga tggcccacta cctgtatggc    6480
cgcattcgca aaacacacct agactagatt tgttttgcta acccaattga tattaattat    6540
atatgattaa tatttatatg tatatggatt tggttaatga aatgcatctg gttcatcaaa    6600
gaattataaa gacacgtgac attcatttag gataagaaat atggatgatc tctttctctt    6660
ttattcagat aactagtaat tacacataac acacaacttt gatgcccaca ttatagtgat    6720
tagcatgtca ctatgtgtgc atcctttat ttcatacatt aattaagttg gccaatccag    6780
aagatggaca agtctaggtt aaccatgtgg tacctacgcg ttcgaatatc catgggccgc    6840
ttcaggccag ggcgctgggg aaggcgatgg cgtgctcggt cagctgccac ttctggttct    6900
tggcgtcgct ccggtcctcc cgcagcagct tgtgctggat gaagtgccac tcgggcatct    6960
tgctgggcac gctcttggcc ttgtacacgg tgtcgaactg gcaccggtac cggccgccgt    7020
ccttcagcag caggtacatg ctcacgtcgc ccttcaggat gccctgctta ggcacgggca    7080
tgatcttctc gcagctggcc tcccagtcgg tggtcatctt cttcatcacg gggccgtcgg    7140
cggggaagtt cacgccgttg aagatgctct tgtggtagat gcagttctcc ttcacgctca    7200
cggtgatgtc cacgttacag atgcacacgg cgccgtcctc gaacaggaag ctccggcccc    7260
aggtgtagcc ggcggggcag ctgttcttga agtagtccac gatgtcctgg gggtactcgg    7320
tgaagatccg gtcgccgtac ttgaagccgg cgctcaggat gtcctcgctg aagggcaggg    7380
ggccgccctc gatcacgcac aggttgatgg tctgcttgcc cttgaagggg tagccgatgc    7440
cctcgccggt gatcacgaac ttgtggccgt tcacgcagcc ctccatgtgg tacttcatgg    7500
tcatctcctc cttcaggccg tgcttgctgt gggccatggt ggcgaccggt gaattcgagc    7560
tcggtacccg gggatcctga gtaaaacaga ggagggtctc actaagttta tagagagact    7620
gagagagata aagggacacg tatgaagcgt ctgttttcgt ggtgtgacgt caaagtcatt    7680
ttgctctcta cgcgtgtctg tgtcggcttg atctttttt ttgcttttg gaactcatgt    7740 cggtagtata tcttttattt attttttctt ttttcccctt ttctttcaaa ctgatgtcgg    7800
tatgatattt attccatcct aaaatgtaac ttactattat tagtagtcgg tccatgtcta    7860
ttggcccatc atgtggtcat tttacgttta cgtcgtgtgg ctgtttatta taacaaacgg    7920
cacatccttc tcattcgaat tgtatttctc cttaatcgtt ctaataggta tgatctttta    7980
ttttatacgt aaaattaaaa ttgaatgatg tcaagaacga aaattaattt gtatttacaa    8040
aggagctaaa tattgtttat tcctctactg gtagaagata aagaagtag atgaaataat    8100 gatcttacta gagaatattc ctcatttaca ctagtcaaat ggaaatcttg taaactttta    8160
```

```
caataattta tcctgaaaat atgaaaaaat agaagaaaat gtttacctcc tctctcctct   8220
taattcacct acgatcggtg cgggcctctt cgctattacg ccagctggcg aaaggggggat  8280
gtgctgcaag gcgattaagt tgggtaacgc cagggttttc ccagtcacga cgttgtaaaa   8340
cgacggccag tgaattcgag ctcggtaccc ggggatcctc tagagtcgac ctgcaggcat   8400
gcaagcttgt tgaaacatcc ctgaagtgtc tcattttatt ttatttattc tttgctgata   8460
aaaaaataaa ataaagaag ctaagcacac ggtcaaccat tgctctactg ctaaagggt    8520
tatgtgtagt gttttactgc ataaattatg cagcaaacaa gacaactcaa attaaaaaat   8580
ttcctttgct tgtttttttg ttgtctctga cttgactttc ttgtggaagt tggttgtata   8640
aggattggga cacaccattg tccttcttaa tttaattta tttctttgct gataaaaaaa   8700
aaaaatttca tatagtgtta aataataatt tgttaaataa ccaaaaagtc aaatatgttt   8760
actctcgttt aaataattga gagtcgtcca gcaaggctaa acgattgtat agatttatga   8820
caatatttac ttttttatag ataaatgtta tattataata aatttatata catatattat   8880
atgttattta ttatttatta ttattttaaa tccttcaata ttttatcaaa ccaactcata   8940
atttttttt tatctgtaag aagcaataaa attaaataga cccactttaa ggatgatcca   9000
acctttatac agagtaagag agttcaaata gtaccctttc atatacatat caactaaaat   9060
attagaaata tcatggatca aaccttataa agacattaaa taagtggata agtataatat   9120
ataaatgggt agtatataat ataaatgg atacaaactt ctctctttat aattgttatg    9180
tctccttaac atcctaatat aatacataag tgggtaatat ataatatata aatggagaca   9240
aacttcttcc attataattg ttatgtcttc ttaacactta tgtctcgttc acaatgctaa   9300
agttagaatt gtttagaaag tcttatagta cacatttgtt tttgtactat ttgaagcatt   9360
ccataagccg tcacgattca gatgatttat aataataaga ggaaatttat catagaacaa   9420
taaggtgcat agatagagtg ttaatatatc ataacatcct ttgtttattc atagaagaag   9480
tgagatggag ctcagttatt atactgttac atggtcggat acaatattcc atgctctcca   9540
tgagctctta cacctacatg catttagtt catacttcat gcacgtggcc atcacagcta   9600
gctgcagcta catatttaca ttttacaaca ccaggagaac tgccctgtta gtgcataaca   9660
atcagaagat ggccgtggct actcgagtta tcgaaccact ttgtacaaga agctgaacg    9720
agaaacgtaa aatgatataa atatcaatat attaaattag attttgcata aaaaacagac   9780
tacataatac tgtaaaacac aacatatcca gtcactatgg tcgacctgca gactggctgt   9840
gtataaggga gcctgacatt tatattcccc agaacatcag gttaatggcg ttttttgatgt  9900
cattttcgcg gtggctgaga tcagccactt cttccccgat aacggagacc ggcacactgg   9960
ccatatcggt ggtcatcatg cgccagcttt catccccgat atgcaccacc gggtaaagtt   10020
cacgggagac tttatctgac agcagacgtg cactggccag ggggatcacc atccgtcgcc   10080
cgggcgtgtc aataatatca ctctgtacat ccacaaacag acgataacgg ctctctcttt   10140
tataggtgta aaccttaaac tgcatttcac cagtccctgt tctcgtcagc aaaagagccg   10200
ttcatttcaa taaaccgggc gacctcagcc atcccttcct gattttccgc tttccagcgt   10260
tcggcacgca gacgacgggc ttcattctgc atggttgtgc ttaccagacc ggagatattg   10320
acatcatata tgccttgagc aactgatagc tgtcgctgtc aactgtcact gtaatacgct   10380
gcttcatagc acacctcttt ttgacatact tcgggtatac atatcagtat atattcttat   10440
accgcaaaaa tcagcgcgca aatacgcata ctgttatctg gcttttagta agccggatcc   10500
tctagattac gccccgccct gccactcatc gcagtactgt tgtaattcat taagcattct   10560
```

```
gccgacatgg aagccatcac agacggcatg atgaacctga atcgccagcg gcatcagcac   10620
cttgtcgcct tgcgtataat atttgcccat ggtgaaaacg ggggcgaaga agttgtccat   10680
attggccacg tttaaatcaa aactggtgaa actcacccag ggattggctg agacgaaaaa   10740
catattctca ataaaccctt tagggaaata ggccaggttt tcaccgtaac acgccacatc   10800
ttgcgaatat atgtgtagaa actgccggaa atcgtcgtgg tattcactcc agagcgatga   10860
aaacgtttca gtttgctcat ggaaaacggt gtaacaaggg tgaacactat cccatatcac   10920
cagctcaccg tctttcattg ccatacggaa ttccggatga gcattcatca ggcgggcaag   10980
aatgtgaata aaggccggat aaaacttgtg cttattttc tttacggtct ttaaaaaggc    11040
cgtaatatcc agctgaacgg tctggttata ggtacattga gcaactgact gaaatgcctc   11100
aaaatgttct ttacgatgcc attgggatat atcaacggtg gtatatccag tgattttttt   11160
ctccatttta gcttccttag ctcctgaaaa tctcgccgga tcctaactca aaatccacac   11220
attatacgag ccggaagcat aaagtgtaaa gcctggggtg cctaatgcgg ccgccatagt   11280
gactggatat gttgtgtttt acagtattat gtagtctgtt ttttatgcaa aatctaattt   11340
aatatattga tatttatatc attttacgtt tctcgttcag cttttttgta caaacttgtt   11400
tgataaccgg tactagtgtg cacgtcgagc gtgtcctctc caaatgaaat gaacttcctt   11460
atatagagga agggtcttgc gaaggatagt gggattgtgc gtcatccctt acgtcagtgg   11520
agatgtcaca tcaatccact tgctttgaag acgtggttgg aacgtcttct ttttccacga   11580
tgctcctcgt gggtgggggt ccatctttgg gaccactgtc ggcagaggca tcttgaatga   11640 tagccttttcc tttatcgcaa tgatggcatt tgtaggagcc accttccttt tctactgtcc    11700
tttcgatgaa gtgacagata gctgggcaat ggaatccgag gaggtttccc gaaattatcc   11760
tttgttgaaa agtctcaata gcccttggt cttctgagac tgtatctttg acattttgg     11820 agtagaccag agtgtcgtgc tccaccatgt tgacgaagat tttcttcttg tcattgagtc   11880
gtaaaagact ctgtatgaac tgttcgccag tcttcacggc gagttctgtt agatcctcga   11940
tttgaatctt agactccatg catggcctta gattcagtag gaactaccct tttagagact   12000
ccaatctcta ttacttgcct tggtttatga agcaagcctt gaatcgtcca tactggaata   12060
gtacttctga tcttgagaaa tatgtctttc tctgtgttct tgatgcaatt agtcctgaat   12120
cttttgactg catctttaac cttcttggga aggtatttga tctcctggag attgttactc   12180
gggtagatcg tcttgatgag acctgctgcg taggcctctc taaccatctg tgggtcagca   12240
ttctttctga aattgaagag gctaaccttc tcattatcag tggtgaacat agtgtcgtca   12300
ccttcacctt cgaacttcct tcctagatcg taaagataga ggaaatcgtc cattgtaatc   12360
tccggggcaa aggagatctc ttttgggct ggatcactgc tgggccttt ggttcctagc     12420 gtgagccagt gggcttttg ctttggtggg cttgttaggg ccttagcaaa gctcttgggc    12480
ttgagttgag cttctccttt ggggatgaag ttcaacctgt ctgtttgctg acttgttgtg   12540
tacgcgtcag ctgctgctct tgcctctgta atagtggcaa atttcttgtg tgcaactccg   12600
ggaacgccgt tgttgccgc ctttgtacaa ccccagtcat cgtatatacc ggcatgtgga    12660
ccgttataca caacgtagta gttgatatga gggtgttgaa tacccgattc tgctctgaga   12720
ggagcaactg tgctgttaag ctcagatttt tgtgggattg gaattggatc ctctagagca   12780
aagcttggcg taatcatggt catagctgtt tcctgtgtga attgttatc cgctcacaat    12840 tccacacaac atacgagccg gaagcataaa gtgtaaagcc tggggtgcct aatgagtgag   12900
```

```
ctaactcaca ttaattgcgt tgcgctcact gcccgctttc cagtcgggaa acctgtcgtg    12960
ccagctgcat taatgaatcg gccaacgcgc ggggagaggc ggtttgcgta ttgggccaaa    13020
gacaaaaggg cgacattcaa ccgattgagg gagggaaggt aaatattgac ggaaattatt    13080
cattaaaggt gaattatcac cgtcaccgac ttgagccatt tgggaattag agccagcaaa    13140
atcaccagta gcaccattac cattagcaag gccggaaacg tcaccaatga aaccatcatc    13200
tagtaacata gatgacaccg cgcgcgataa tttatcctag tttgcgcgct atattttgtt    13260
ttctatcgcg tattaaatgt ataattgcgg gactctaatc ataaaaaccc atctcataaa    13320
taacgtcatg cattacatgt taattattac atgcttaacg taattcaaca gaaattatat    13380
gataatcatc gcaagaccgg caacaggatt caatcttaag aaactttatt gccaaatgtt    13440
tgaacgatct gcttcgacgc actccttctt taggtacgga ctagatctcg gtgacgggca    13500
ggaccggacg gggcggtacc ggcaggctga agtccagctg ccagaaaccc acgtcatgcc    13560
agttcccgtg cttgaagccg ccgcccgca gcatgccgcg ggggcatat ccgagcgcct    13620 cgtgcatgcg cacgctcggg tcgttgggca gcccgatgac agcgaccacg ctcttgaagc    13680
cctgtgcctc cagggacttc agcaggtggg tgtagagcgt ggagcccagt cccgtccgct    13740
ggtggcgggg ggagacgtac acggtcgact cggccgtcca gtcgtaggcg ttgcgtgcct    13800
tccaggggcc cgcgtaggcg atgccggcga cctcgccgtc cacctcggcg acgagccagg    13860
gatagcgctc ccgcagacgg acgaggtcgt ccgtccactc ctgcggttcc tgcggctcgg    13920
tacggaagtt gaccgtgctt gtctcgatgt agtggttgac gatggtgcag accgccggca    13980
tgtccgcctc ggtggcacgg cggatgtcgg ccgggcgtcg ttctgggctc atggatctgg    14040
attgagagtg aatatgagac tctaattgga taccgagggg aatttatgga acgtcagtgg    14100 agcattttg acaagaaata tttgctagct gatagtgacc ttaggcgact tttgaacgcg    14160
caataatggt ttctgacgta tgtgcttagc tcattaaact ccagaaaccc gcggctgagt    14220
ggctccttca acgttgcggt tctgtcagtt ccaaacgtaa aacggcttgt cccgcgtcat    14280 cggcggggt cataacgtga ctcccttaat tctccgctca tgatcagatt gtcgtttccc    14340
gccttcagtt taaactatca gtgtttgaca ggatatattg gcgggtaaac ctaagagaaa    14400
agagcgttta ttagaataat cggatattta aaagggcgtg aaaaggttta tccgttcgtc    14460
catttgtatg tgcatgccaa ccacagggtt ccccagatct ggcgccggcc agcgagacga    14520
gcaagattgg ccgccgcccg aaacgatccg acagcgcgcc cagcacaggt gcgcaggcaa    14580
attgcaccaa cgcatacagc gccagcagaa tgccatagtg ggcggtgacg tcgttcgagt    14640
gaaccagatc gcgcaggagg cccggcagca ccggcataat caggccgatg ccgacagcgt    14700
cgagcgcgac agtgctcaga attacgatca ggggtatgtt gggtttcacg tctggcctcc    14760
ggaccagcct ccgctggtcc gattgaacgc gcggattctt tatcactgat aagttggtgg    14820
acatattatg tttatcagtg ataaagtgtc aagcatgaca aagttgcagc cgaatacagt    14880
gatccgtgcc gccctggacc tgttaacga ggtcggcgta gacggtctga cgacacgcaa    14940
actggcggaa cggttggggg ttcagcagcc ggcgctttac tggcacttca ggaacaagcg    15000
ggcgctgctc gacgcactgg ccgaagccat gctggcggag aatcatacgc attcggtgcc    15060
gagagccgac gacgactggc gctcatttct gatcgggaat gcccgcagct tcaggcaggc    15120
gctgctcgcc taccgcgatg gcgcgcgcat ccatgccggc acgcgaccgg gcgcaccgca    15180
gatggaaacg gccgacgcgc agcttcgctt cctctgcgag gcgggttttt cggcggga    15240 cgccgtcaat gcgctgatga caatcagcta cttcactgtt ggggccgtgc ttgaggagca    15300
```

-continued

```
ggccggcgac agcgatgccg gcgagcgcgg cggcaccgtt gaacaggctc cgctctcgcc      15360
gctgttgcgg gccgcgatag acgccttcga cgaagccggt ccggacgcag cgttcgagca      15420
gggactcgcg gtgattgtcg atggattggc gaaaaggagg ctcgttgtca ggaacgttga      15480
aggaccgaga aagggtgacg attgatcagg accgctgccg gagcgcaacc cactcactac      15540
agcagagcca tgtagacaac atcccctccc cctttccacc gcgtcagacg cccgtagcag      15600
cccgctacgg gcttttcat gccctgccct agcgtccaag cctcacggcc gcgctcggcc       15660
tctctggcgg ccttctggcg ctcttccgct tcctcgctca ctgactcgct gcgctcggtc      15720
gttcggctgc ggcgagcggt atcagctcac tcaaaggcgg taatacggtt atccacagaa      15780 tcagggata acgcaggaaa gaacatgtga gcaaaaggcc agcaaaaggc caggaaccgt       15840
aaaaaggccg cgttgctggc gttttttccat aggctccgcc cccctgacga gcatcacaaa    15900
aatcgacgct caagtcagag gtggcgaaac ccgacaggac tataaagata ccaggcgttt     15960 cccctggaa gctccctcgt gcgctctcct gttccgaccc tgccgcttac cggatacctg      16020
tccgcctttc tcccttcggg aagcgtggcg ctttccgct gcataaccct gcttcggggt      16080
cattatagcg attttttcgg tatatccatc ctttttcgca cgatatacag gattttgcca     16140
aagggttcgt gtagactttc cttggtgtat ccaacggcgt cagccgggca ggataggtga     16200
agtaggccca cccgcgagcg ggtgttcctt cttcactgtc ccttattcgc acctggcggt     16260
gctcaacggg aatcctgctc tgcgaggctg gccggctacc gccggcgtaa cagatgaggg     16320
caagcggatg gctgatgaaa ccaagccaac caggaagggc agcccaccta tcaaggtgta     16380
ctgccttcca gacgaacgaa gagcgattga ggaaaaggcg gcggcggccg gcatgagcct     16440
gtcggcctac ctgctggccg tcggccaggg ctacaaaatc acgggcgtcg tggactatga     16500
gcacgtccgc gagctggccc gcatcaatgg cgacctgggc cgcctgggcg gctgctgaa      16560 actctggctc accgacgacc cgcgcacggc gcggttcggt gatgccacga tcctcgccct     16620
gctggcgaag atcgaagaga agcaggacga gcttggcaag gtcatgatgg gcgtggtccg     16680
cccgagggca gagccatgac ttttttagcc gctaaaacgg ccggggggtg cgcgtgattg     16740
ccaagcacgt ccccatgcgc tccatcaaga agagcgactt cgcggagctg gtgaagtaca     16800
tcaccgacga gcaaggcaag accgagcgcc tttgcgacgc tca                       16843
```

<210> SEQ ID NO 4
<211> LENGTH: 5749
<212> TYPE: DNA
<213> ORGANISM: Oryza sativa

<400> SEQUENCE: 4

```
ccatacattc agtaaccagt agaaccatcc gggatgggga gagcagttgg gagggctgca         60
ttcttattct tgttcctcag tctgacagtt gctcaaaata tcaccaaaaa tggagcaggc        120
acactggatg ttggggtgat cctccacctg aagtcgctgg tgggcaaaat agcacgtacc        180
agcgttttga tggctgtcga agatttctac tcggtccaca ggaacttcaa gacaaagctg       240
gttctccaca ttagagattc caatggagat gatgtccaag ctgcatcaga aggtacgtta       300
tacaattgta agctgtcact aaaaatcatc aaagtttggg tcatcatcgc atcataatgt       360
ggcaagatcc tatgcaatag ttatttcttt gaagttaagg gaacttcaca aattttagaa       420
cttcaatttc attatatttta aatgtaatgg agggaaaatg atacaaaaaa ggcactgaaa      480
cacatgtttt tcatttatac agtttttatt ttcgcgtttc tcttttctac aattgctgca       540
```

```
aatcttcaaa gcattatgtg catttagaac ttaatcctaa aaatgaaaat tttaagcaaa      600
ataaaaaact agaatcccgt gacacctcca cagatctgta tgcaggttaa aatccagtgt      660
cttcacagtt cacacttgtc ttatcgaatt taagttttg ccattgtatt ttaaaaatac      720
aacctttgtg tagtcttctc tatctttagc aactccttca attttggagc aaaaagagag      780
ctccgtatca aatatagcta tgctatgtag aatgagctca ctattttgct ctgatgtgcc      840
caatgtcgtg atgaacacct aataagaggt gattatacag cctagccatt atattctaag      900
ttataacacc gctacttcca gctgcctaac acctcaagtt gcactaagat tcttatgtgt      960
gcaaccacaa tgtatgcacg tcttacatgt tcttcaaatt aactgatttc ctattccatt     1020
gcaaagcaat tgacctgctg gaaaattaca acgtgagagc tatcgttggc ccacaaaaat     1080
cttcagaggt tacgtttgtg tctaatcttg ggaacaagag ccaagtccca gtaatctcct     1140
tcacagcaac aaaccctgct cttcatcca tcaatgtgcc atattttttg cgtggaacgt     1200
taagtgatgt tgctcaagtg aataccattg ctgctctcat taaggcatat gactggaggg     1260
aagtggtacc catttatgag gatacggact atggtagggg catcatacca tacctggctg     1320
atgctctcca agaatttgga gcttttatgc catatcgcag tgcaatatct gaatcagcaa     1380
ctactgacca acttgagaga gaactctaca agctaatgac aatgcagact agagtctatg     1440
ttgttcatat gtcattgaac attgcctcca ttctcttcgc aaaggctaag gacttaggaa     1500
tgatgagcga agattatgca tggattttga cagatggcat ttcaaatatt gttaattctc     1560
taaacacttc aattctagag aaaatgaatg gtgcaattgg tgtcaggttc tatgtgcctg     1620
catcaaagga acttgatgac ttcactacaa gatggaataa gaggttcaaa gaagacaacc     1680
caaatgatcc accatcacaa ctaagcactt tcggtctttg gggttatgat actatctggg     1740
ccttagcaca ggcagcagaa aaagtaagaa tggctgatgc tatatttcga aagcagaaag     1800
acggaaagaa ctcaacaagt ttgggaactc tgggaatttc tacaattggt ccagaactct     1860
tagactcgat cttacatagt aagtttcaag gcctaagtgg tgaatttgac cttggaaaca     1920
ggcagctgga atttccaca ttccagataa ttaatgtggt tggaggcagg tcaaaagaaa     1980
taggcttttg gataacaaag catggaatat tcaggcaaat aaacgaaaat atatcaaaaa     2040
caacaaacgt gaactctatg cctggtctta atcgagtgat gtggccagga gaagtatata     2100
cggtgcctaa aggatggcaa attcccacta atggaaagaa gctccgtgta ggtgtacgga     2160
caagtggata tcccgagttt atgaaggtgg aaaggaatac tgccaccaat gaaataactg     2220
cttctggata tgcaatcgat gtatttgaag aggcgttaaa gagacttccg tatgcaatac     2280
cttatgaata tgtagcattt gatgacggac aaggagtaaa ctctgggagc tataatgatt     2340
ttgtctacca agttcatctt ggggtaagga attttggttc tcactttgtc aaaaactgtt     2400
ctatagattg gtatacccac atgaaaattt taatcaagat aatttagtta ttcccttgct     2460
tttgctaatt tttttagtt atatgttgt caataatata taaaacataa tgatgtgaaa     2520
gtgcttttga caaaaagtct actatagcat tccctttaac aaatctaaat tattttgtgt     2580
gtattagtgg tcagagtttt taaacttaac aattcacatt ccgaaatgaa acttatagta     2640
gatgggtata caaaaaaaat gagcaaacta tgtgaaaact aagggagtaa cttttccttg     2700
ttttatgtat aataagtaca gattgattag atgtatgctc aagcatagat tgcagtactg     2760 ttccttcag attaagtctg tctatgttgt ctagtgtgga acttcttggt atcccctcaa     2820 gggagtaaa aagtctttca tcagataagg atagattggc acggtgtaac tattgccatt     2880
tttctatgat tttcccaaat catcatagag taactgaagt taaaaaagaa aaggcattgc     2940
```

```
aggtatatga tgcagcaatt ggggatataa ccatcaggta caatagaact tcatatgtcg    3000
atttcacact accttatact gaatcagggg tggcaatgat tgtgccagtt aaggacgaca    3060
gggataagaa tacatgggtt ttcttgaagc cattaactac tggcttgtgg tttggaagca    3120
ttgctttctt catctacaca gcagttgtaa tatggctgtt ggagcgaaga attaacaatg    3180
ctgaactgac tggttcattt tttcgccagc ttgggattgc aatatatttc tcattctttg    3240
cagatagtaa gtgattatat taggttttct tatttacatg caaaatacta catttttgac    3300
atttaattct gtgatttagg aatttcttgg tgacagattc tactggggtt aaaggcaaga    3360
taaacctgaa ctatcactac aaaattagag cgaaaaagag ctgacaaaaa taattttatt    3420
ctgcaatctc agtctttaac taacaaaaga tacgctgtac taagagtaaa ttcagcatta    3480
atgtttattt gaatttctaa aaaatgaagg tttgtcattt tgcaggggaa agggtggaca    3540
gtattttgtc tagattggtt gtcatcgtat gggtctttgt gcttcttgtg attacatcaa    3600
gctatacagc caatttatct tcaatgctaa cggtgcaaca gcttcaacct accgtgactg    3660
acattcatga actccttaaa agtggagaat atgtagggta tcgtaatggc tcttatttgt    3720
ccgatttact agaaggactt ggttttgaca ggacgaaaat gagggcatat gaaaatccag    3780
atgagtttgc tgatgcactt gctaaaggga gccaaaatgg aggtattgca gcagtcgtac    3840
atgaagttcc atacatcaaa atatttcttg caaagcattg caaagggtac acaatggtcg    3900
gaccaattta caaatctgaa ggctttggct ttgtaagtta aactgctaaa tatttctttg    3960
cacagaacat acctctaaag tacaaaaatc cttgtaaata tatgttcgag agctgctcat    4020
acttatcaaa acatacagaa catttggaga cagaggcaca cataataaat ttaagataat    4080
aacaaacctg ggactctaac agagctattc gtggtatgga acccatcatt ctccataatc    4140
atttactaca ataagcagtc tgtgactagt aaagtcatac tgtaactctt ttgttctgct    4200
agccgcctat agtgagtaac attcactgtt ggataatgtt gtacgcggta cgtacttatg    4260
atttgtagta atttgtgatt aactcacatt tcttcttgtt gcaaattgaa ttgccatgga    4320
ggatgtaacc tcgaaaatta ttttatgtgc tcaaatagtt ctgagtaaaa acaagaatta    4380
ccgaagtttc acttccgacc accctctatc caatcttttt tactttggac taggtttttt    4440
ttcccctttg tttcactttg gaccacccta actcttttt ctagccaacc tctcctccag    4500
caaagatgtg agctgaacgt aaaaggggag accatcggaa tgagggtgcc gatgtgcttg    4560
aggctgttga tgtgatcacg aagagagttt gagtggtcca aaatgaaaaa atgacaaaaa    4620
tacctagtcc aaagtgagaa gattaagtaa agggtggccc aaagagcaat tcactcaaaa    4680
aagtataagc agcgttttga tgtattatca atacaaagtt tcatatttgt gatcttatca    4740
atacaaggac aagaaaataa ttcttttctc aaaaagataa cataggaagg ctattatcct    4800
tggtgttttt ctgttccttg caatgccagt cgaatttaaa acaggcgttc tataacactg    4860
ctgtggacaa ttttcctttt ttttcattga ataaatttct cttgtttgat attgccccta    4920
cttgtgtggt aactttagtt catggagaaa aactttaaac cacagtgcat aggcatgtct    4980
ttggtaacac taactgcaca tatgtaccat gcaatttatt tagctctatt tcagacacca    5040
atttatttgt cttaaacata ttttttcttgt attatggaga atcctagaat gttcaccttt    5100
aaaataatat tagctatatt tcagacctat agttgagtgt gcatttgctg ttttttctgat   5160 gagcaagcga ttcattacct atcagtttgt acataactga atcagttcaa cttcttgtgt    5220
aggcatttcc caaacgatcc ccactagttt atgacttctc aagggcaatc ctcaacataa    5280
```

| | |
|---|---|
| cagagggaga ttctataatt catatagaaa agaaatggat tgaggaccag catgcctgtc | 5340 |
| agaatgatgg caccatgatc ggctcaagca gtctaaactt caacagcttt tcaggacttt | 5400 |
| ttctagtcac aggagttgct tcaacctcag ccctttaat agccctgatg atgactctct | 5460 |
| acaagaataa gcacaggata agggacagca tacgtcgtgg gcagactcag aaagaatatg | 5520 |
| aaagagagac aataaatgaa caaaatcaag aaaggacaat agactccaac caggtccaga | 5580 |
| acctgcaact gacagtgcca gatgattcaa atgaatatac ctgccaacaa gagggagaaa | 5640 |
| tatccataga gataagccca gcttcaggga tccaaacaag tcaggatatt gcatctcaca | 5700 |
| gaacatcgag aaacggctaa tagaggaatg gtaactcggc taattcagc | 5749 |

<210> SEQ ID NO 5
<211> LENGTH: 2850
<212> TYPE: DNA
<213> ORGANISM: Oryza sativa

<400> SEQUENCE: 5

| | |
|---|---|
| atggggagag cagttgggag ggctgcattc ttattcttgt tcctcagtct gacagttgct | 60 |
| caaaatatca ccaaaaatgg agcaggcaca ctggatgttg gggtgatcct ccacctgaag | 120 |
| tcgctggtgg gcaaaatagc acgtaccagc gttttgatgg ctgtcgaaga tttctactcg | 180 |
| gtccacagga acttcaagac aaagctggtt ctccacatta gagattccaa tggagatgat | 240 |
| gtccaagctg catcagaagc aattgacctg ctggaaaatt acaacgtgag agctatcgtt | 300 |
| ggcccacaaa atcttcaga ggttacgttt gtgtctaatc ttgggaacaa gagccaagtc | 360 |
| ccagtaatct ccttcacagc aacaaaccct gctctttcat ccatcaatgt gccatatttt | 420 |
| ttgcgtggaa cgttaagtga tgttgctcaa gtgaatacca ttgctgctct cattaaggca | 480 |
| tatgactgga gggaagtggt acccatttat gaggatacgg actatggtag ggcatcata | 540 |
| ccatacctgg ctgatgctct ccaagaattt ggagctttta tgccatatcg cagtgcaata | 600 |
| tctgaatcag caactactga ccaacttgag agagaactct acaagctaat gacaatgcag | 660 |
| actagagtct atgttgttca tatgtcattg acattgcct ccattctctt cgcaaaggct | 720 |
| aaggacttag gaatgatgag cgaagattat gcatggattt tgacagatgg catttcaaat | 780 |
| attgttaatt ctctaaacac ttcaattcta gagaaatga atggtgcaat ggtgtcagg | 840 |
| ttctatgtgc ctgcatcaaa ggaacttgat gacttcacta caagatggaa taagaggttc | 900 |
| aaagaagaca acccaaatga tccaccatca caactaagca ctttcggtct ttggggttat | 960 |
| gatactatct gggccttagc acaggcagca gaaaaagtaa gaatggctga tgctatattt | 1020 |
| cgaaagcaga agacggaaa gaactcaaca agtttgggaa ctctgggaat ttctacaatt | 1080 |
| ggtccagaac tcttagactc gatcttacat agtaagtttc aaggcctaag tggtgaattt | 1140 |
| gaccttggaa acaggcagct ggaattttcc acattccaga taattaatgt ggttggaggc | 1200 |
| aggtcaaaag aaataggctt ttggataaca aagcatggaa tattcaggca aataaacgaa | 1260 |
| aatatatcaa aaacaacaaa cgtgaactct atgcctggtc ttaatcgagt gatgtggcca | 1320 |
| ggagaagtat atacggtgcc taaggatgg caaattccca ctaatggaaa gaagctccgt | 1380 |
| gtaggtgtac ggacaagtgg atatcccgag tttatgaagg tggaaaggaa tactgccacc | 1440 |
| aatgaaataa ctgcttctgg atatgcaatc gatgtatttg aagaggcgtt aaagagactt | 1500 |
| ccgtatgcaa taccttatga atatgtagca tttgatgacg gacaaggagt aaactctggg | 1560 |
| agctataatg atttgtcta ccaagttcat cttggggtat atgatgcagc aattggggat | 1620 |
| ataaccatca ggtacaatag aacttcatat gtcgatttca cactacctta tactgaatca | 1680 |

-continued

```
ggggtggcaa tgattgtgcc agttaaggac gacagggata agaatacatg ggttttcttg    1740
aagccattaa ctactggctt gtggtttgga agcattgctt tcttcatcta cacagcagtt    1800
gtaatatggc tgttggagcg aagaattaac aatgctgaac tgactggttc atttttccgc    1860
cagcttggga ttgcaatata tttctcattc tttgcagata gggaaagggt ggacagtatt    1920
ttgtctagat tggttgtcat cgtatgggtc tttgtgcttc ttgtgattac atcaagctat    1980
acagccaatt tatcttcaat gctaacggtg caacagcttc aacctaccgt gactgacatt    2040
catgaactcc ttaaaagtgg agaatatgta gggtatcgta atggctctta tttgtccgat    2100
ttactagaag gacttggttt tgacaggacg aaaatgaggg catatgaaaa tccagatgag    2160
tttgctgatg cacttgctaa agggagccaa atggaggta ttgcagcagt cgtacatgaa    2220
gttccataca tcaaaatatt tcttgcaaag cattgcaaag ggtacacaat ggtcggacca    2280
atttacaaat ctgaaggctt tggctttccg cctatagtga gtaacattca ctgttggata    2340
atgttgtacg cggcatttcc caaacgatcc ccactagttt atgacttctc aagggcaatc    2400
ctcaacataa cagagggaga ttctataatt catatagaaa agaaatggat tgaggaccag    2460
catgcctgtc agaatgatgg caccatgatc ggctcaagca gtctaaactt caacagcttt    2520
tcaggacttt ttctagtcac aggagttgct tcaacctcag cccttttaat agccctgatg    2580
atgactctct acaagaataa gcacaggata agggacagca tacgtcgtgg gcagactcag    2640
aaagaatatg aaagagagac aataaatgaa caaaatcaag aaaggacaat agactccaac    2700
caggtccaga acctgcaact gacagtgcca gatgattcaa atgaatatac ctgccaacaa    2760
gagggagaaa tatccataga gataagccca gcttcaggga tccaaacaag tcaggatatt    2820
gcatctcaca gaacatcgag aaacggctaa                                      2850
```

<210> SEQ ID NO 6
<211> LENGTH: 949
<212> TYPE: PRT
<213> ORGANISM: Oryza sativa

<400> SEQUENCE: 6

```
Met Gly Arg Ala Val Gly Arg Ala Ala Phe Leu Phe Leu Phe Leu Ser
1               5                   10                  15

Leu Thr Val Ala Gln Asn Ile Thr Lys Asn Gly Ala Gly Thr Leu Asp
            20                  25                  30

Val Gly Val Ile Leu His Leu Lys Ser Leu Val Gly Lys Ile Ala Arg
        35                  40                  45

Thr Ser Val Leu Met Ala Val Glu Asp Phe Tyr Ser Val His Arg Asn
    50                  55                  60

Phe Lys Thr Lys Leu Val Leu His Ile Arg Asp Ser Asn Gly Asp Asp
65                  70                  75                  80

Val Gln Ala Ala Ser Glu Ala Ile Asp Leu Leu Glu Asn Tyr Asn Val
                85                  90                  95

Arg Ala Ile Val Gly Pro Gln Lys Ser Ser Glu Val Thr Phe Val Ser
            100                 105                 110

Asn Leu Gly Asn Lys Ser Gln Val Pro Val Ile Ser Phe Thr Ala Thr
        115                 120                 125

Asn Pro Ala Leu Ser Ser Ile Asn Val Pro Tyr Phe Leu Arg Gly Thr
    130                 135                 140

Leu Ser Asp Val Ala Gln Val Asn Thr Ile Ala Ala Leu Ile Lys Ala
145                 150                 155                 160
```

```
Tyr Asp Trp Arg Glu Val Val Pro Ile Tyr Glu Asp Thr Asp Tyr Gly
            165                 170                 175
Arg Gly Ile Ile Pro Tyr Leu Ala Asp Ala Leu Gln Glu Phe Gly Ala
        180                 185                 190
Phe Met Pro Tyr Arg Ser Ala Ile Ser Glu Ser Ala Thr Thr Asp Gln
    195                 200                 205
Leu Glu Arg Glu Leu Tyr Lys Leu Met Thr Met Gln Thr Arg Val Tyr
210                 215                 220
Val Val His Met Ser Leu Asn Ile Ala Ser Ile Leu Phe Ala Lys Ala
225                 230                 235                 240
Lys Asp Leu Gly Met Met Ser Glu Asp Tyr Ala Trp Ile Leu Thr Asp
                245                 250                 255
Gly Ile Ser Asn Ile Val Asn Ser Leu Asn Thr Ser Ile Leu Glu Lys
            260                 265                 270
Met Asn Gly Ala Ile Gly Val Arg Phe Tyr Val Pro Ala Ser Lys Glu
        275                 280                 285
Leu Asp Asp Phe Thr Thr Arg Trp Asn Lys Arg Phe Lys Glu Asp Asn
    290                 295                 300
Pro Asn Asp Pro Pro Ser Gln Leu Ser Thr Phe Gly Leu Trp Gly Tyr
305                 310                 315                 320
Asp Thr Ile Trp Ala Leu Ala Gln Ala Ala Glu Lys Val Arg Met Ala
                325                 330                 335
Asp Ala Ile Phe Arg Lys Gln Lys Asp Gly Lys Asn Ser Thr Ser Leu
            340                 345                 350
Gly Thr Leu Gly Ile Ser Thr Ile Gly Pro Glu Leu Leu Asp Ser Ile
        355                 360                 365
Leu His Ser Lys Phe Gln Gly Leu Ser Gly Glu Phe Asp Leu Gly Asn
    370                 375                 380
Arg Gln Leu Glu Phe Ser Thr Phe Gln Ile Ile Asn Val Val Gly Gly
385                 390                 395                 400
Arg Ser Lys Glu Ile Gly Phe Trp Ile Thr Lys His Gly Ile Phe Arg
                405                 410                 415
Gln Ile Asn Glu Asn Ile Ser Lys Thr Thr Asn Val Asn Ser Met Pro
            420                 425                 430
Gly Leu Asn Arg Val Met Trp Pro Gly Glu Val Tyr Thr Val Pro Lys
        435                 440                 445
Gly Trp Gln Ile Pro Thr Asn Gly Lys Lys Leu Arg Val Gly Val Arg
    450                 455                 460
Thr Ser Gly Tyr Pro Glu Phe Met Lys Val Glu Arg Asn Thr Ala Thr
465                 470                 475                 480
Asn Glu Ile Thr Ala Ser Gly Tyr Ala Ile Asp Val Phe Glu Glu Ala
                485                 490                 495
Leu Lys Arg Leu Pro Tyr Ala Ile Pro Tyr Glu Tyr Val Ala Phe Asp
            500                 505                 510
Asp Gly Gln Gly Val Asn Ser Gly Ser Tyr Asn Asp Phe Val Tyr Gln
        515                 520                 525
Val His Leu Gly Val Tyr Asp Ala Ala Ile Gly Asp Ile Thr Ile Arg
    530                 535                 540
Tyr Asn Arg Thr Ser Tyr Val Asp Phe Thr Leu Pro Tyr Thr Glu Ser
545                 550                 555                 560
Gly Val Ala Met Ile Val Pro Val Lys Asp Asp Arg Asp Lys Asn Thr
                565                 570                 575
Trp Val Phe Leu Lys Pro Leu Thr Thr Gly Leu Trp Phe Gly Ser Ile
```

```
                580                 585                 590
Ala Phe Phe Ile Tyr Thr Ala Val Val Ile Trp Leu Leu Glu Arg Arg
            595                 600                 605

Ile Asn Asn Ala Glu Leu Thr Gly Ser Phe Phe Arg Gln Leu Gly Ile
        610                 615                 620

Ala Ile Tyr Phe Ser Phe Ala Asp Arg Glu Arg Val Asp Ser Ile
625                 630                 635                 640

Leu Ser Arg Leu Val Val Ile Val Trp Val Phe Val Leu Leu Val Ile
                645                 650                 655

Thr Ser Ser Tyr Thr Ala Asn Leu Ser Ser Met Leu Thr Val Gln Gln
            660                 665                 670

Leu Gln Pro Thr Val Thr Asp Ile His Glu Leu Leu Lys Ser Gly Glu
        675                 680                 685

Tyr Val Gly Tyr Arg Asn Gly Ser Tyr Leu Ser Asp Leu Leu Glu Gly
    690                 695                 700

Leu Gly Phe Asp Arg Thr Lys Met Arg Ala Tyr Glu Asn Pro Asp Glu
705                 710                 715                 720

Phe Ala Asp Ala Leu Ala Lys Gly Ser Gln Asn Gly Gly Ile Ala Ala
                725                 730                 735

Val Val His Glu Val Pro Tyr Ile Lys Ile Phe Leu Ala Lys His Cys
            740                 745                 750

Lys Gly Tyr Thr Met Val Gly Pro Ile Tyr Lys Ser Glu Gly Phe Gly
        755                 760                 765

Phe Pro Pro Ile Val Ser Asn Ile His Cys Trp Ile Met Leu Tyr Ala
    770                 775                 780

Ala Phe Pro Lys Arg Ser Pro Leu Val Tyr Asp Phe Ser Arg Ala Ile
785                 790                 795                 800

Leu Asn Ile Thr Glu Gly Asp Ser Ile Ile His Ile Glu Lys Lys Trp
                805                 810                 815

Ile Glu Asp Gln His Ala Cys Gln Asn Asp Gly Thr Met Ile Gly Ser
            820                 825                 830

Ser Ser Leu Asn Phe Asn Ser Phe Ser Gly Leu Phe Leu Val Thr Gly
        835                 840                 845

Val Ala Ser Thr Ser Ala Leu Leu Ile Ala Leu Met Met Thr Leu Tyr
    850                 855                 860

Lys Asn Lys His Arg Ile Arg Asp Ser Ile Arg Arg Gly Gln Thr Gln
865                 870                 875                 880

Lys Glu Tyr Glu Arg Glu Thr Ile Asn Glu Gln Asn Gln Glu Arg Thr
                885                 890                 895

Ile Asp Ser Asn Gln Val Gln Asn Leu Gln Leu Thr Val Pro Asp Asp
            900                 905                 910

Ser Asn Glu Tyr Thr Cys Gln Gln Glu Gly Glu Ile Ser Ile Glu Ile
        915                 920                 925

Ser Pro Ala Ser Gly Ile Gln Thr Ser Gln Asp Ile Ala Ser His Arg
    930                 935                 940

Thr Ser Arg Asn Gly
945
```

<210> SEQ ID NO 7
<211> LENGTH: 3848
<212> TYPE: DNA
<213> ORGANISM: Oryza sativa

<400> SEQUENCE: 7

-continued

```
cttctttgtg gcaggagttc tccaactcat caataatctg caagatgtga ataagtctca      60
agtagacttt gcaccatttg agacacaatg aagataggtc tgctcatgtt gcttgttctc     120
ttcctggtca tgtcccctga tgggatccgc aggagcttag ccgcgaggcc ttctattgtg     180
aatattgggg ccattcttcg atttaactcc accattggag gtgtttcgat gattgctatc     240
caggcagcct tggaggatat taattctgat tcaacaattc taaatggaac aactttaaaa     300
gttgacatga gggatacaaa ttgtgatgat ggtttccttg gatggttga aggtaggcta      360
gctgttacac tcctttcatt ttgtttgcat tgttaaatag aatgtgcttt gtgttgtgga     420
gttctgatga tactacattc tttgtatcag ctttgcagtt catggagact gatgtgattg     480
caattattgg cccacagtgc tcaacaattg cacatatcgt ttcatatgta gcaaatgagc     540
tccgagtccc tcttatgtcc tttgcatctg atgcaacttt gtcatcaatt cagttcccat     600
tctttgttcg aactgctccc agtgatctct atcaaatgga tgctgtagct gcaatagttg     660
actactaccg ttggaagata gtgactgcta tatatattga tgatgattat ggccgaaatg     720
gaatagccac attggatgat gcacttactc aaaggcgctg caaaatctcc tacaagattg     780
catttcctgc aaatgctaga aagagcgacc tcataaattt attggtcagc gttagttata     840
tggagtctcg tgttatcatc ctccatactg gtgctggacc tggactcaag attttctctc     900
tggcgaacca actaagcatg atgggcaatg gctatgtatg gattgcaact gattggcttt     960
ctgcttatct cgatgctaat tcatcggttc ctgatgagac tatgtatggc atgcaaggag    1020
ttctcacttt acgcccacac attcctgaat caaagatgaa gagtaatttg atctccaagt    1080
ggagcaggtt aagcaagaag tacagttata gttatctccg cacaagttca tatgcttttt    1140
atgtttatga tagtgtatgg gcagtagctc gggctttgga tgctttcttt gatgatggtg    1200
ggaagatttc cttttcaaat gattcaaggc tgcgtgatga aactggaggt actcttcacc    1260
ttgaagcaat gagtattttt gatatgggaa ataacttgtt ggagaagatt agaaaggcaa    1320
acttcactgg ggtgtctggg caagtgcaat ttgatgctac tggtgacctc attcatcctg    1380
cttatgatgt cataaatata attggaaatg gcatgcggac agttggctat tggtcaaatt    1440
attctagctt gctgtcgact gtccttccgg aggttctcta ttcagagcct cctaacaatt    1500
ctctagctaa tcaacatcta tatgatgtta tttggcctgg gcagactgca caaacgcctc    1560
gaggctgggt ttttccttct aatgctaagg agttgaaaat tggtgtcccc aacagattta    1620
gcttcagaga atttgtcaca aaagataatg ttactggatc aatgaagggc tattgcattg    1680
atgtctttac tcaggcattg gctttgcttc cttatcctgt tacatacaag tttataccat    1740
ttgggggtgg taatgaaaat ccacattatg acaaactcgt acaaatggtt gaggataacg    1800
taagtatgga caagtgatgc ttttcttctt ctgcactttc tatcacaggt gatattgatc    1860
agaattttcc tatcctgcag gagtttgacg cagcaatagg ggatattgca attacaatga    1920
gcaggactgt aactactgat ttcacccagc ccttcattga atctggcttg gttatcttgg    1980
ctccagttaa aaaacatatt gttaattcct gggcattctt gcagccattc actcttcaga    2040
tgtggtgtgt tactggatta ttctttcttg ttgtgggtgc agttgtttgg gttcttgaac    2100
atcgaataaa tgacgaattc cgtggctcac cgcgagaaca aataattact attttctggt    2160
atggagctga tttgaacatt ttgtatcatc tgcccacttg tcaatcaatc tacagatatt    2220
aagatacaaa aaaaccttttt ttgcaataca ttgcacatag ctagcacctt aaaaatcctg    2280
tttctatatt tctacacagc caagtcctcc aatttgcatg tgtaaatgag gtattgatga    2340
gcaatgcacc taaaccttgt tttacgtatt ctctgcatat gcagaatcta ttgcatatga    2400
```

```
tagtatgatg cattacttgc acattgcttg cttgatggtg tgcatctttg ctaccaaatt    2460 tgtgaccttaa atctcaattt ttatattcta caggttcagc ttttcaacct tgttttttgc    2520
acacagtgag taaaccaacc ttctattata tgttttttgg ggcaaaagta atatttcagt    2580 ctgcacatt gctttcatct ctatctgctc caggagaaaa taccatgagt accttaggac     2640
gtggtgtctt gatcatatgg ctatttgttg ttttaatcat tcaatccagc tatactgcaa    2700
gtcttacttc catcctgact gttcaacaac tcgatacttc tataagagga attgatgacc    2760
tgaaaaatag tgatggtcct attggttttcc aagttggttc ttttgcagaa gaatacatgg   2820
tcagggagct gaacatctca cggtcgaggc tgagagctct tggttctcca gaagaatacg    2880
ctgaagcgct taagcatggc cctaagagag gaggtgtcat ggccattgta gatgagcgcc    2940
cctacgttga actgttttg tcaacttatt gcaagattgc agttgctggt tcggatttca     3000
ccagcagagg atggggcttt gtaagtacat ttaaacttga ttttctttaa catggattag    3060
aaaaacaaag agaaaacaac tagacacaaa atataacaac ttagcttatg aagtactact    3120
tgtttctcat cattaaaaca tagtgcttaa taaagttcac tcttatcagg catttccaag    3180
agactcccct ttgcaaattg acctatcgac tgcgatcctg tcactgtcgg agaacgggga   3240
actgcagagg atccatgaca aatggctcaa gactagcgag tgctcagccg acaacaccga   3300
gtttgtcgac tcggatcagc tccgccttga gagcttctgg ggcctgttcc tcatttgtgg   3360
tatcgcatgt gtcatcgcgc tgctcatcta cttttttcacc accgtacgca aattcctcag   3420
gcatgaacct ccagaagatc caacacctcg tccaggcgga tcaacaactc ttccagacga   3480 acgaacacccc ccaaagaacg gacaagagaa atgcaactgc agaaatttca tctcatttct   3540
tgatcacaag gagccaccaa agaagaagcg gtccttgagt ttgacgccga caacgccatt   3600
gagcaacttt actgcccttg aaatagaagg acctgtgagg acagtcagga atggtagtgt   3660
cgttgacata tagaactagt gtgtgtaaaa agctgagatg ttatatattt tggatctgag   3720
atatgccatc tttcggtcaa tctcctcaat tttagttgag agaaaatata atcagaggct   3780
gcataagatg ctatctgtag atttcaagca aatccggtga tgggaaaaat tcatttgagg   3840
ccagtttg                                                             3848

<210> SEQ ID NO 8
<211> LENGTH: 2835
<212> TYPE: DNA
<213> ORGANISM: Oryza sativa

<400> SEQUENCE: 8
atgaagatag gtctgctcat gttgcttgtt ctcttcctgg tcatgtcccc tgatgggatc      60
cgcaggagct tagccgcgag gccttctatt gtgaatattg gggccattct tcgatttaac    120
tccaccattg gaggtgtttc gatgattgct atccaggcag ccttggagga tattaattct    180
gattcaacaa ttctaaatgg aacaacttta aaagttgaca tgagggatac aaattgtgat    240
gatggtttcc ttgggatggt tgaagctttg cagttcatgg agactgatgt gattgcaatt    300
attggcccac agtgctcaac aattgcacat atcgtttcat atgtagcaaa tgagctccga    360
gtccctctta tgtcctttgc atctgatgca actttgtcat caattcagtt cccattcttt    420
gttcgaactg ctcccagtga tctctatcaa atggatgctg tagctgcaat agttgactac    480
taccgttgga agatagtgac tgctatatat attgatgatg attatggccg aaatggaata    540
gccacattgg atgatgcact tactcaaagg cgctgcaaaa tctcctacaa gattgcatttt   600
```

```
cctgcaaatg ctagaaagag cgacctcata aatttattgg tcagcgttag ttatatggag    660
tctcgtgtta tcatcctcca tactggtgct ggacctggac tcaagatttt ctctctggcg    720
aaccaactaa gcatgatggg caatggctat gtatggattg caactgattg ctttctgct    780
tatctcgatg ctaattcatc ggttcctgat gagactatgt atggcatgca aggagttctc    840
actttacgcc cacacattcc tgaatcaaag atgaagagta atttgatctc caagtggagc    900
aggttaagca agaagtacag ttatagttat ctccgcacaa gttcatatgc tttttatgtt    960
tatgatagtg tatgggcagt agctcgggct ttggatgctt tctttgatga tggtgggaag   1020
atttccttt caaatgattc aaggctgcgt gatgaaactg gaggtactct tcaccttgaa   1080
gcaatgagta tttttgatat gggaaataac ttgttggaga agattagaaa ggcaaacttc   1140
actggggtgt ctgggcaagt gcaatttgat gctactggtg acctcattca tcctgcttat   1200
gatgtcataa atataattgg aaatggcatg cggacagttg gctattggtc aaattattct   1260
agcttgctgt cgactgtcct tccggaggtt ctctattcag agcctcctaa caattctcta   1320
gctaatcaac atctatatga tgttatttgg cctgggcaga ctgcacaaac gcctcgaggc   1380
tgggttttc cttctaatgc taaggagttg aaaattggtg tccccaacag atttagcttc   1440
agagaatttg tcacaaaaga taatgttact ggatcaatga agggctattg cattgatgtc   1500
tttactcagg cattggcttt gcttccttat cctgttacat acaagtttat accatttggg   1560
ggtggtaatg aaaatccaca ttatgacaaa ctcgtacaaa tggttgagga taacgagttt   1620
gacgcagcaa tagggatat tgcaattaca atgagcagga ctgtaactac tgatttcacc   1680
cagcccttca ttgaatctgg cttggttatc ttggctccag ttaaaaaaca tattgttaat   1740
tcctgggcat tcttgcagcc attcactctt cagatgtggt gtgttactgg attattcttt   1800
cttgttgtgg gtgcagttgt ttgggttctt gaacatcgaa taaatgacga attccgtggc   1860
tcaccgcgag aacaaataat tactattttc tggttcagct tttcaacctt gttttttgca   1920
cacagagaaa ataccatgag taccttagga cgtggtgtct tgatcatatg gctatttgtt   1980
gtttttaatca ttcaatccag ctatactgca agtcttactt ccatcctgac tgttcaacaa   2040
ctcgatactt ctataagagg aattgatgac ctgaaaaata gtgatggtcc tattggtttc   2100
caagttggtt cttttgcaga agaatacatg gtcagggagc tgaacatctc acggtcgagg   2160
ctgagagctc ttggttctcc agaagaatac gctgaagcgc ttaagcatgg ccctaagaga   2220
ggaggtgtca tggccattgt agatgagcgc ccctacgttg aactgttttt gtcaacttat   2280
tgcaagattg cagttgctgg ttcggatttc accagcagag gatggggctt tgcatttcca   2340
agagactccc ctttgcaaat tgacctatcg actgcgatcc tgtcactgtc ggagaacggg   2400
gaactgcaga ggatccatga caaatggctc aagactagcg agtgctcagc cgacaacacc   2460
gagtttgtcg actcggatca gctccgcctt gagagcttct ggggcctgtt cctcatttgt   2520
ggtatcgcat gtgtcatcgc gctgctcatc tactttttca ccaccgtacg caaattcctc   2580
aggcatgaac ctccagaaga tccaacacct cgtccaggcg atcaacaac tcttccagac   2640
gaacgaacac ccccaaagaa cggacaagag aaatgcaact gcagaaattt catctcattt   2700
cttgatcaca aggagccacc aaagaagaag cggtccttga gtttgacgcc gacaacgcca   2760
ttgagcaact ttactgccct tgaaatagaa ggacctgtga ggacagtcag gaatggtagt   2820
gtcgttgaca tatag                                                   2835

<210> SEQ ID NO 9
<211> LENGTH: 944
```

<212> TYPE: PRT
<213> ORGANISM: Oryza sativa

<400> SEQUENCE: 9

```
Met Lys Ile Gly Leu Leu Met Leu Leu Val Leu Phe Leu Val Met Ser
1               5                   10                  15

Pro Asp Gly Ile Arg Arg Ser Leu Ala Ala Arg Pro Ser Ile Val Asn
            20                  25                  30

Ile Gly Ala Ile Leu Arg Phe Asn Ser Thr Ile Gly Gly Val Ser Met
        35                  40                  45

Ile Ala Ile Gln Ala Ala Leu Glu Asp Ile Asn Ser Asp Ser Thr Ile
    50                  55                  60

Leu Asn Gly Thr Thr Leu Lys Val Asp Met Arg Asp Thr Asn Cys Asp
65                  70                  75                  80

Asp Gly Phe Leu Gly Met Val Glu Ala Leu Gln Phe Met Glu Thr Asp
                85                  90                  95

Val Ile Ala Ile Ile Gly Pro Gln Cys Ser Thr Ile Ala His Ile Val
            100                 105                 110

Ser Tyr Val Ala Asn Glu Leu Arg Val Pro Leu Met Ser Phe Ala Ser
        115                 120                 125

Asp Ala Thr Leu Ser Ser Ile Gln Phe Pro Phe Phe Val Arg Thr Ala
    130                 135                 140

Pro Ser Asp Leu Tyr Gln Met Asp Ala Val Ala Ala Ile Val Asp Tyr
145                 150                 155                 160

Tyr Arg Trp Lys Ile Val Thr Ala Ile Tyr Ile Asp Asp Tyr Gly
                165                 170                 175

Arg Asn Gly Ile Ala Thr Leu Asp Asp Ala Leu Thr Gln Arg Arg Cys
            180                 185                 190

Lys Ile Ser Tyr Lys Ile Ala Phe Pro Ala Asn Ala Arg Lys Ser Asp
        195                 200                 205

Leu Ile Asn Leu Leu Val Ser Val Ser Tyr Met Glu Ser Arg Val Ile
    210                 215                 220

Ile Leu His Thr Gly Ala Gly Pro Gly Leu Lys Ile Phe Ser Leu Ala
225                 230                 235                 240

Asn Gln Leu Ser Met Met Gly Asn Gly Tyr Val Trp Ile Ala Thr Asp
                245                 250                 255

Trp Leu Ser Ala Tyr Leu Asp Ala Asn Ser Ser Val Pro Asp Glu Thr
            260                 265                 270

Met Tyr Gly Met Gln Gly Val Leu Thr Leu Arg Pro His Ile Pro Glu
        275                 280                 285

Ser Lys Met Lys Ser Asn Leu Ile Ser Lys Trp Ser Arg Leu Ser Lys
    290                 295                 300

Lys Tyr Ser Tyr Ser Tyr Leu Arg Thr Ser Tyr Ala Phe Tyr Val
305                 310                 315                 320

Tyr Asp Ser Val Trp Ala Val Ala Arg Ala Leu Asp Ala Phe Asp
                325                 330                 335

Asp Gly Gly Lys Ile Ser Phe Ser Asn Asp Ser Arg Leu Arg Asp Glu
            340                 345                 350

Thr Gly Gly Thr Leu His Leu Glu Ala Met Ser Ile Phe Asp Met Gly
        355                 360                 365

Asn Asn Leu Leu Glu Lys Ile Arg Lys Ala Asn Phe Thr Gly Val Ser
    370                 375                 380

Gly Gln Val Gln Phe Asp Ala Thr Gly Asp Leu Ile His Pro Ala Tyr
385                 390                 395                 400
```

-continued

Asp Val Ile Asn Ile Ile Gly Asn Gly Met Arg Thr Val Gly Tyr Trp
            405                 410                 415

Ser Asn Tyr Ser Ser Leu Leu Ser Thr Val Leu Pro Glu Val Leu Tyr
            420                 425                 430

Ser Glu Pro Pro Asn Asn Ser Leu Ala Asn Gln His Leu Tyr Asp Val
            435                 440                 445

Ile Trp Pro Gly Gln Thr Ala Gln Thr Pro Arg Gly Trp Val Phe Pro
450                 455                 460

Ser Asn Ala Lys Glu Leu Lys Ile Gly Val Pro Asn Arg Phe Ser Phe
465                 470                 475                 480

Arg Glu Phe Val Thr Lys Asp Asn Val Thr Gly Ser Met Lys Gly Tyr
            485                 490                 495

Cys Ile Asp Val Phe Thr Gln Ala Leu Ala Leu Leu Pro Tyr Pro Val
            500                 505                 510

Thr Tyr Lys Phe Ile Pro Phe Gly Gly Gly Asn Glu Asn Pro His Tyr
            515                 520                 525

Asp Lys Leu Val Gln Met Val Glu Asp Asn Glu Phe Asp Ala Ala Ile
            530                 535                 540

Gly Asp Ile Ala Ile Thr Met Ser Arg Thr Val Thr Thr Asp Phe Thr
545                 550                 555                 560

Gln Pro Phe Ile Glu Ser Gly Leu Val Ile Leu Ala Pro Val Lys Lys
            565                 570                 575

His Ile Val Asn Ser Trp Ala Phe Leu Gln Pro Phe Thr Leu Gln Met
            580                 585                 590

Trp Cys Val Thr Gly Leu Phe Phe Leu Val Val Gly Ala Val Val Trp
            595                 600                 605

Val Leu Glu His Arg Ile Asn Asp Glu Phe Arg Gly Ser Pro Arg Glu
            610                 615                 620

Gln Ile Ile Thr Ile Phe Trp Phe Ser Phe Ser Thr Leu Phe Phe Ala
625                 630                 635                 640

His Arg Glu Asn Thr Met Ser Thr Leu Gly Arg Gly Val Leu Ile Ile
            645                 650                 655

Trp Leu Phe Val Val Leu Ile Ile Gln Ser Ser Tyr Thr Ala Ser Leu
            660                 665                 670

Thr Ser Ile Leu Thr Val Gln Gln Leu Asp Thr Ser Ile Arg Gly Ile
            675                 680                 685

Asp Asp Leu Lys Asn Ser Asp Gly Pro Ile Gly Phe Gln Val Gly Ser
            690                 695                 700

Phe Ala Glu Glu Tyr Met Val Arg Glu Leu Asn Ile Ser Arg Ser Arg
705                 710                 715                 720

Leu Arg Ala Leu Gly Ser Pro Glu Glu Tyr Ala Glu Ala Leu Lys His
            725                 730                 735

Gly Pro Lys Arg Gly Gly Val Met Ala Ile Val Asp Glu Arg Pro Tyr
            740                 745                 750

Val Glu Leu Phe Leu Ser Thr Tyr Cys Lys Ile Ala Val Ala Gly Ser
            755                 760                 765

Asp Phe Thr Ser Arg Gly Trp Gly Phe Ala Phe Pro Arg Asp Ser Pro
            770                 775                 780

Leu Gln Ile Asp Leu Ser Thr Ala Ile Leu Ser Leu Ser Glu Asn Gly
785                 790                 795                 800

Glu Leu Gln Arg Ile His Asp Lys Trp Leu Lys Thr Ser Glu Cys Ser
            805                 810                 815

```
Ala Asp Asn Thr Glu Phe Val Asp Ser Asp Gln Leu Arg Leu Glu Ser
            820                 825                 830

Phe Trp Gly Leu Phe Leu Ile Cys Gly Ile Ala Cys Val Ile Ala Leu
        835                 840                 845

Leu Ile Tyr Phe Phe Thr Thr Val Arg Lys Phe Leu Arg His Glu Pro
    850                 855                 860

Pro Glu Asp Pro Thr Pro Arg Pro Gly Gly Ser Thr Thr Leu Pro Asp
865                 870                 875                 880

Glu Arg Thr Pro Pro Lys Asn Gly Gln Glu Lys Cys Asn Cys Arg Asn
                885                 890                 895

Phe Ile Ser Phe Leu Asp His Lys Glu Pro Pro Lys Lys Lys Arg Ser
            900                 905                 910

Leu Ser Leu Thr Pro Thr Thr Pro Leu Ser Asn Phe Thr Ala Leu Glu
        915                 920                 925

Ile Glu Gly Pro Val Arg Thr Val Arg Asn Gly Ser Val Val Asp Ile
    930                 935                 940
```

<210> SEQ ID NO 10
<211> LENGTH: 1183
<212> TYPE: DNA
<213> ORGANISM: Oryza sativa

<400> SEQUENCE: 10

```
cgatcgagct agccatgtgg agttcacaat gccgtacacc gagtctggtg tttcaatgct    60
tgtgcttgcg aagaatgaat ctgaatcaaa aatcgaatgg gtattcttga agccactgac   120
aaaagaactt tggtttgcca ctgtgatctt ctttctattc accgcattag taatttggat   180
aattgaacat cccagaaaca tggagtacca aggatcgaac acaaggcagt tgagcactgc   240
tctctatttt gctttctcca ctttgacatt ttctcatggt caaattatta aaagtccttt   300
gtcaaaaatc gttgtggtaa tctggtgctt cgtggtgctg gttcttgtgc agagctacac   360
tgctagcttt tcatccattc taactgtaaa gaggttcaag ccctcagtga catatcttga   420
ccagctcctg aataatggtg attatgttgg ataccaagag ggatcctttg tgaactcatt   480
tttgacaaga cgaggtttca gtgaaagaag gctaagatcc tacacaaaga aacaggaata   540
tgctgaagct ttgaggaagg ggtccaagaa tggaggtgtg tctgctatcg ttgatgagat   600
cccatatttta accgctattg tctcagaccc tcattaccag aaagaattcc agatgcttaa   660
gcgcatatat aagactcccg gttttggttt tgtgtttcct cctggttttc cactggtgca   720
taatctttca actgccatgt tggatgtaac aagtggggat gaggggtcac gtatggaaac   780
gaaatggttt ggtgcagagg ctgtctctcc aagtaatgca attcccaaca cagattcggc   840
acctctcact ttgcggagtt tctctggtct ttttatcatc actgggtgta tctcaactct   900
catgctgatg attaggttct ccatgtcaat tcttgccaat tacacccaaa ttagagattc   960
tgatgtgcaa agtcctgatg tgggtggtcg aaacgatgca catgaagaat ctaatcaagc  1020
acagaacagc atgggttgca ttgtggttga tatacacctc catgaagtta gaattggcag  1080
ttcccaggat atccatggga gtgtcgaacg tgctagctga tggcggagag cctcgaccaa  1140
ttcagaatgg ccctgtgcct gcaaattcca tccagacagt atg                    1183
```

<210> SEQ ID NO 11
<211> LENGTH: 1092
<212> TYPE: DNA
<213> ORGANISM: Oryza sativa

<400> SEQUENCE: 11

```
atgccgtaca ccgagtctgg tgtttcaatg cttgtgcttg cgaagaatga atctgaatca     60
aaaatcgaat gggtattctt gaagccactg acaaaagaac tttggtttgc cactgtgatc    120
ttctttctat tcaccgcatt agtaatttgg ataattgaac atcccagaaa catggagtac    180
caaggatcga acacaaggca gttgagcact gctctctatt ttgctttctc cactttgaca    240
ttttctcatg gtcaaattat taaaagtcct tgtcaaaaa tcgttgtggt aatctggtgc     300
ttcgtggtgc tggttcttgt gcagagctac actgctagct tttcatccat tctaactgta    360
aagaggttca agccctcagt gacatatctt gaccagctcc tgaataatgg tgattatgtt    420
ggataccaag agggatcctt tgtgaactca tttttgacaa gacgaggttt cagtgaaaga    480
aggctaagat cctacacaaa gaaacaggaa tatgctgaag ctttgaggaa ggggtccaag    540
aatggaggtg tgtctgctat cgttgatgag atcccatatt taaccgctat tgtctcagac    600
cctcattacc agaaagaatt ccagatgctt aagcgcatat ataagactcc cggttttggt    660
tttgtgtttc ctcctggttt tccactggtg cataatcttt caactgccat gttggatgta    720
acaagtgggg atgaggggtc acgtatggaa acgaaatggt ttggtgcaga ggctgtctct    780
ccaagtaatg caattcccaa cacagattcg gcacctctca ctttgcggag tttctctggt    840 cttttatca tcactgggtg tatctcaact ctcatgctga tgattaggtt ctccatgtca    900
attcttgcca attacaccca aattagagat tctgatgtgc aaagtcctga tgtgggtggt    960
cgaaacgatg cacatgaaga atctaatcaa gcacagaaca gcatgggttg cattgtggtt   1020
gatatacacc tccatgaagt tagaattggc agttcccagg atatccatgg gagtgtcgaa   1080
cgtgctagct ga                                                       1092
```

<210> SEQ ID NO 12
<211> LENGTH: 363
<212> TYPE: PRT
<213> ORGANISM: Oryza sativa

<400> SEQUENCE: 12

```
Met Pro Tyr Thr Glu Ser Gly Val Ser Met Leu Val Leu Ala Lys Asn
1               5                   10                  15

Glu Ser Glu Ser Lys Ile Glu Trp Val Phe Leu Lys Pro Leu Thr Lys
            20                  25                  30

Glu Leu Trp Phe Ala Thr Val Ile Phe Phe Leu Phe Thr Ala Leu Val
        35                  40                  45

Ile Trp Ile Ile Glu His Pro Arg Asn Met Glu Tyr Gln Gly Ser Asn
    50                  55                  60

Thr Arg Gln Leu Ser Thr Ala Leu Tyr Phe Ala Phe Ser Thr Leu Thr
65                  70                  75                  80

Phe Ser His Gly Gln Ile Ile Lys Ser Pro Leu Ser Lys Ile Val Val
                85                  90                  95

Val Ile Trp Cys Phe Val Leu Val Leu Val Gln Ser Tyr Thr Ala
            100                 105                 110

Ser Phe Ser Ser Ile Leu Thr Val Lys Arg Phe Lys Pro Ser Val Thr
        115                 120                 125

Tyr Leu Asp Gln Leu Leu Asn Asn Gly Asp Tyr Val Gly Tyr Gln Glu
    130                 135                 140

Gly Ser Phe Val Asn Ser Phe Leu Thr Arg Arg Gly Phe Ser Glu Arg
145                 150                 155                 160

Arg Leu Arg Ser Tyr Thr Lys Lys Gln Glu Tyr Ala Glu Ala Leu Arg
                165                 170                 175
```

```
Lys Gly Ser Lys Asn Gly Gly Val Ser Ala Ile Val Asp Glu Ile Pro
            180                 185                 190

Tyr Leu Thr Ala Ile Val Ser Asp Pro His Tyr Gln Lys Glu Phe Gln
        195                 200                 205

Met Leu Lys Arg Ile Tyr Lys Thr Pro Gly Phe Gly Phe Val Phe Pro
210                 215                 220

Pro Gly Phe Pro Leu Val His Asn Leu Ser Thr Ala Met Leu Asp Val
225                 230                 235                 240

Thr Ser Gly Asp Glu Gly Ser Arg Met Glu Thr Lys Trp Phe Gly Ala
                245                 250                 255

Glu Ala Val Ser Pro Ser Asn Ala Ile Pro Asn Thr Ser Ala Pro
            260                 265                 270

Leu Thr Leu Arg Ser Phe Ser Gly Leu Phe Ile Ile Thr Gly Cys Ile
        275                 280                 285

Ser Thr Leu Met Leu Met Ile Arg Phe Ser Met Ser Ile Leu Ala Asn
        290                 295                 300

Tyr Thr Gln Ile Arg Asp Ser Asp Val Gln Ser Pro Asp Val Gly Gly
305                 310                 315                 320

Arg Asn Asp Ala His Glu Glu Ser Asn Gln Ala Gln Asn Ser Met Gly
                325                 330                 335

Cys Ile Val Val Asp Ile His Leu His Glu Val Arg Ile Gly Ser Ser
            340                 345                 350

Gln Asp Ile His Gly Ser Val Glu Arg Ala Ser
        355                 360

<210> SEQ ID NO 13
<211> LENGTH: 1596
<212> TYPE: DNA
<213> ORGANISM: Oryza sativa

<400> SEQUENCE: 13
ctattgcatt gatgtctttg aggctgccat gaagaagtta ccaaatcatc tgagttatga      60
gtttgttgtc ttcaatggtt cttatgacca gctagtacag agtgtatctt caggggtaaa    120
gccttactcc ctgtgctttg atgacattgt aacagaaccg aattcttaca ctatatctgc    180
tggttcttac tatcagatca acgatgctgc agtggggat ataaccataa ctgccgatcg    240
agctagccag gtggagttca cgatgccgta caccgagtct ggggtttcaa tgcttgtgct    300
tgcgaagaat gaatctgaat caacaaccaa atgggtattc ttgaagccac tgacaaaaga    360
actttggttt gccactatga tactttttcc tattcactgc cttggttatt tcgatgattg    420
aacgtcccag aaacatggag ttccaaggat caagaacaag acagttctgc actgctctct    480
attttgcttt ctccactttg acattttctc atggttagta tttggagctc agctttcagg    540
ctatatttga tgcagtatta agtggtttag ctattttctt acaatagttc ttcaattacc    600
cactatcttt gttttactat gcacaggtca aattattaaa agtccgttgt cgaaaattgt    660
tgtggtaagc tggtgcttcg tggtgttggt tcttgtgcag agctacggag ctagcttggc    720
atccattcta actgttaaga ggttccagcc ctcagtgaca gatcttgacc agctcctgtg    780
taatggtgat tatgttggat accaagaggg atccttcgtg cactcatttt tgacaagacg    840
aggtttcagt gaaggaaggc taagatccta ctcaaagaag caggaatatg cagaatcttt    900
gaggaagggg tccaagaatg gaggtgtgtc tgctatcgtt gatgagatcc cattttaac    960 cgctattgtc tcagaccctc attacgagaa cgaattccag atgcttaaac gtatatataa   1020
```

```
gacgcctgga tttggtttcg taagtctctc actccattgc tttggcgaat tcactcatat    1080
tcctttaaga gctatgctac aatctggcct aaattgcatc atgttttctt cccttcaggt    1140
gtttcctcct ggttttccac tggtgcataa tctttcaact gccatgttgg atgtaacgag    1200
tggggatgag ggctcacgta tggaagtgaa attggtttgg tgcagaggct gtctctccaa    1260
gtaatgcgat ccccaacaca gattcgacac ctctcacttt gcagagtttc tctggtcttt    1320
ttatcatcta tggatttatg tcagctctca tgctgatgat aagcatttca atgtcagttc    1380
ttgcccaata cacaaaaatt agagtttctg atgtgcaaag tcctggtgtg atgatggaa     1440 acggtgctca tgaaggatct aatcaagcac aaaacagcat gggcaatggc tttgtggctg    1500
atagacctct ccgtgaaatt agaattgacg acagttccca ggatatccat gggagtgtct    1560
gaacgtgctg atggcaaaga gcctcgacca attcag                              1596

<210> SEQ ID NO 14
<211> LENGTH: 1050
<212> TYPE: DNA
<213> ORGANISM: Oryza sativa

<400> SEQUENCE: 14
atgaagaagt taccaaatca tctgagttat gagtttgttg tcttcaatgg ttcttatgac      60
cagctagtac agagtgtatc ttcaggggta aagccttact ccctgtgctt tgatgacatt     120
gtaacagaac cgaattctta cactatatct gctggttctt actatcagat caacgatgct     180
gcagtggggg atataaccat aactgccgat cgagctagcc aggtggagtt cacgatgccg     240
tacaccgagt ctggggtttc aatgcttgtg cttgcgaaga atgaatctga atcaacaacc     300
aaatgggtat tcttgaagcc actgacaaaa gaactttggt ttgccactat gatactttt      360 cctattcact gccttggtca aattattaaa gtccgttgt cgaaaattgt tgtgagctac      420
ggagctagct tggcatccat tctaactgtt aagaggttcc agccctcagt gacagatctt     480
gaccagctcc tgtgtaatgg tgattatgtt ggataccaag agggatcctt cgtgcactca     540 ttttttgacaa gacgaggttt cagtgaagga aggctaagat cctactcaaa gaagcaggaa     600
tatgcagaat ctttgaggaa ggggtccaag aatggaggtg tgtctgctat cgttgatgag     660
atcccatttt taaccgctat tgtctcagac cctcattacg agaacgaatt ccagatgctt     720
aaacgtatat ataagacgcc tggatttggt ttcgtgtttc ctcctggttt tccactggtg     780
cataatcttt caactgccat gttggatgta acgagtgggg atgagggctc acctctcatg     840
ctgatgataa gcatttcaat gtcagttctt gcccaataca caaaaattag agtttctgat     900
gtgcaaagtc ctggtgtgga tgatggaaac ggtgctcatg aaggatctaa tcaagcacaa     960
aacagcatgg gcaatggctt tgtggctgat agacctctcc gtgaaattag aattgacgac    1020
agttcccagg atatccatgg gagtgtctga                                      1050

<210> SEQ ID NO 15
<211> LENGTH: 349
<212> TYPE: PRT
<213> ORGANISM: Oryza sativa

<400> SEQUENCE: 15

Met Lys Lys Leu Pro Asn His Leu Ser Tyr Glu Phe Val Val Phe Asn
1               5                   10                  15

Gly Ser Tyr Asp Gln Leu Val Gln Ser Val Ser Ser Gly Val Lys Pro
            20                  25                  30

Tyr Ser Leu Cys Phe Asp Asp Ile Val Thr Glu Pro Asn Ser Tyr Thr
```

```
                35                  40                  45
Ile Ser Ala Gly Ser Tyr Tyr Gln Ile Asn Asp Ala Ala Val Gly Asp
 50                  55                  60
Ile Thr Ile Thr Ala Asp Arg Ala Ser Gln Val Glu Phe Thr Met Pro
 65                  70                  75                  80
Tyr Thr Glu Ser Gly Val Ser Met Leu Val Leu Ala Lys Asn Glu Ser
                 85                  90                  95
Glu Ser Thr Thr Lys Trp Val Phe Leu Lys Pro Leu Thr Lys Glu Leu
                100                 105                 110
Trp Phe Ala Thr Met Ile Leu Phe Pro Ile His Cys Leu Gly Gln Ile
                115                 120                 125
Ile Lys Ser Pro Leu Ser Lys Ile Val Val Ser Tyr Gly Ala Ser Leu
                130                 135                 140
Ala Ser Ile Leu Thr Val Lys Arg Phe Gln Pro Ser Val Thr Asp Leu
145                 150                 155                 160
Asp Gln Leu Leu Cys Asn Gly Asp Tyr Val Gly Tyr Gln Glu Gly Ser
                165                 170                 175
Phe Val His Ser Phe Leu Thr Arg Arg Gly Phe Ser Glu Gly Arg Leu
                180                 185                 190
Arg Ser Tyr Ser Lys Lys Gln Glu Tyr Ala Glu Ser Leu Arg Lys Gly
                195                 200                 205
Ser Lys Asn Gly Gly Val Ser Ala Ile Val Asp Glu Ile Pro Phe Leu
210                 215                 220
Thr Ala Ile Val Ser Asp Pro His Tyr Glu Asn Glu Phe Gln Met Leu
225                 230                 235                 240
Lys Arg Ile Tyr Lys Thr Pro Gly Phe Gly Phe Val Phe Pro Pro Gly
                245                 250                 255
Phe Pro Leu Val His Asn Leu Ser Thr Ala Met Leu Asp Val Thr Ser
                260                 265                 270
Gly Asp Glu Gly Ser Pro Leu Met Leu Met Ile Ser Ile Ser Met Ser
                275                 280                 285
Val Leu Ala Gln Tyr Thr Lys Ile Arg Val Ser Asp Val Gln Ser Pro
290                 295                 300
Gly Val Asp Asp Gly Asn Gly Ala His Glu Gly Ser Asn Gln Ala Gln
305                 310                 315                 320
Asn Ser Met Gly Asn Gly Phe Val Ala Asp Arg Pro Leu Arg Glu Ile
                325                 330                 335
Arg Ile Asp Asp Ser Ser Gln Asp Ile His Gly Ser Val
                340                 345

<210> SEQ ID NO 16
<211> LENGTH: 2603
<212> TYPE: DNA
<213> ORGANISM: Oryza sativa

<400> SEQUENCE: 16
ccgttctgcc ttccctgctt attcccccaa taaccatata gatgtggaac tatacaagct      60
catgaccatg cagacgcgtg tcttcattgt ccacatgttg ccagcccgtg cttcccgcct     120
ctttgcaagg gcaaaagcac tcggtatgat gactaaaggg tatgtctgga ttgtcacaga     180
tagcattggt attgtccttg atgtgcttcc ccaacattcc attgaaagca tggagggaat     240
tgttggtttc cggccatata ttgcagaatc tacaaggatc actgatttca gctctcgatt     300
taccacctta ttcagaacta agtaccatcc aaatactgat attaggatgg caaaacccac     360
```

```
tatctttcaa ttatgggctt atgatgtggc atgggcagtc gcaacagcaa ctgagaaggt      420
tcataggacc agatctttga acccaacttt tcatcctccg ggaaacatag gcaagaactt      480
agtagatgat ctcccagcat tgcctgctgg tccagaactc ctcaattcca ttttgcaagg      540
agagtttgat ggattggctg gacaattcag gcttatcgat agacatctgc aggttcccac      600
atatgagatt gtcaatgtta ttggagagaa aactagagtt atcgggtttt atagtcctga      660
ttctggactc acaatgtctg tgaactctag aattatccat ggtgatgcta aatttagcac      720
aagttcttct gatctggaaa atatcgtttg gcctggagat tcaacaacag tgcccaaagg      780
ctgggacttc ccagtgaatg ctaagatact ccagattggt gtgccagtga gacgtgattt      840
taaaactttt gtgaatgttg agactaatcc gaacacgaat agatcaactg tcagtggcta      900
cagcattgat atgtttgagg cagctgtcaa gaaattaccg tatgctctac gctacgagta      960
cattccctat gattgtgctg tttcatatga cctgctagta tcccaggtct tttacaaggt     1020
gagctctgct tattttgtat tcttaactaa ttttcccttg tgaataaact cattattact     1080
aatttacttg ttgcctttcc gtttccctgg gtgcaacaga agtttgatgc agcagtcggt     1140
gatgtgacaa ttattgctaa ccgaactaga tatgtagatt tcacaatgcc atacacagag     1200
tctggtgttt cgatgcttgt tctatctaag agtgacgatg aaccaaccac atggatcttc     1260
ctacagccac tagcaaagga cctatggatt gccactatga tctttatctt cttcacaggc     1320
ctagttgtat gggtgattga agacctata aatcgcgatt ccaagggtc aaaatggaaa       1380
cagtgcatca ctgctttcta ctttgcattc tccactttga cttttcaca tggtatgtca      1440
ttacagacct agctattgaa tagataaat acataactac atacatcttc gtacattcaa      1500
cttattaatt tctaaggatg ctttttttta ttgttttttg tcgggtcagc tgaaagactc     1560
ttaaggatgc tatcatatgc tactgtgatt cagtatttgc tgtaatttgt tttgatacta     1620
ctatgatttt tgataatcta ttttttttaa tcctatggac aggtcaaaag atccaaagca     1680
ttcagtcaaa aattgttgtg gtaatttggt gcttagtttt gatgattctg gtgcagagct     1740
atacagcaag tttgtcatca atgctaacgg cagagaggct ccaaccttca gtgactgatc     1800
taaaacaact tttggccaat ggtgattctg ttggacacca agtggatca tttgtgcaat      1860
caattctgaa gaagcttaaa tttgatgacc acaagataaa ggtttatagc acgcaggagg     1920
aatatgcaaa agcattaagg atgggatcaa agcatggagg ggtttcggct atcttcgatg     1980
agataccta tctaaattct ttctgctcga aatacgggag ggagttccag atggttggcc      2040
ccattgacag aacaagtgga tttggttttg taagcttctt gcacttgtta tttattagta     2100
taatgcatct tcgagcattc tgccttggct ttacaatata tgtttacttt tcgacaggtt     2160
ttacctaaag gctctccatt ggtaccagac ctttcagagg ccatcttgag cttaacggaa     2220
gaacctgaaa ggttgaagat tgaaaagaca tggttcatgg attcgtcctt ggattattat     2280
ggcagtcaca gcaaaggctc atcacgtatc agttttcaga gcttccaagg tcttttcatc     2340
attgtcgggt gccttttagg tgctgtgctg ttgataaact ttagcaagtt tctatatgac     2400
aaatgcaaag agatgagagg cttcggttca gaccgtgtcc atagtggcga gagagttgtt     2460
tgttacggtg aagctcaacc acaaccaccg cagattgtca tggtcgatcg acgatcctgt     2520
gcctgctgat accctccaga ttaggactga aaacaaataa agagtgtgaa cagttatctg     2580
caccaactat cccaactccc aag                                             2603
```

<210> SEQ ID NO 17
<211> LENGTH: 2049

<212> TYPE: DNA
<213> ORGANISM: Oryza sativa

<400> SEQUENCE: 17

| | | | | | |
|---|---|---|---|---|---|
| atgaccatgc | agacgcgtgt | cttcattgtc | cacatgttgc | cagcccgtgc | ttcccgcctc | 60 |
| tttgcaaggg | caaaagcact | cggtatgatg | actaaagggt | atgtctggat | tgtcacagat | 120 |
| agcattggta | ttgtccttga | tgtgcttccc | caacattcca | ttgaaagcat | ggagggaatt | 180 |
| gttggtttcc | ggccatatat | tgcagaatct | acaaggatca | ctgatttcag | ctctcgattt | 240 |
| accaccttat | tcagaactaa | gtaccatcca | aatactgata | ttaggatggc | aaaacccact | 300 |
| atctttcaat | tatgggctta | tgatgtgcca | tgggcagtcg | caacagcaac | tgagaaggtt | 360 |
| cataggacca | gatctttgaa | cccaactttt | catcctccgg | aaacataggc | aagaactta | 420 |
| gtagatgatc | tcccagcatt | gcctgctggt | ccagaactcc | tcaattccat | tttgcaagga | 480 |
| gagtttgatg | gattggctgg | acaattcagg | cttatcgata | gacatctgca | ggttcccaca | 540 |
| tatgagattg | tcaatgttat | ggagagaaaa | actagagtta | tcgggtttta | tagtcctgat | 600 |
| tctggactca | caatgtctgt | gaactctaga | attatccatg | gtgatgctaa | atttagcaca | 660 |
| agttcttctg | atctggaaaa | tatcgtttgg | cctggagatt | caacaacagt | gcccaaaggc | 720 |
| tgggacttcc | cagtgaatgc | taagatactc | cagattggtg | tgccagtgag | acgtgatttt | 780 |
| aaaactttg | tgaatgttga | gactaatccg | aacacgaata | gatcaactgt | cagtggctac | 840 |
| agcattgata | tgtttgaggc | agctgtcaag | aaattaccgt | atgctctacg | ctacgagtac | 900 |
| attccctatg | attgtgctgt | tcatatgac | ctgctagtat | cccaggtctt | ttacaagaag | 960 |
| tttgatgcag | cagtcggtga | tgtgacaatt | attgctaacc | gaactagata | tgtagatttc | 1020 |
| acaatgccat | acacagagtc | tggtgtttcg | atgcttgttc | tatctaagag | tgacgatgaa | 1080 |
| ccaaccacat | ggatcttcct | acagccacta | gcaaaggacc | tatggattgc | cactatgatc | 1140 |
| tttatcttct | tcacaggcct | agttgtatgg | gtgattgaaa | gacctataaa | tcgcgatttc | 1200 |
| caagggtcaa | aatggaaaca | gtgcatcact | gctttctact | ttgcattctc | cactttgact | 1260 |
| ttttcacatg | gtcaaaagat | ccaaagcatt | cagtcaaaaa | ttgttgtggt | aatttggtgc | 1320 |
| ttagttttga | tgattctggt | gcagagctat | acagcaagtt | tgtcatcaat | gctaacggca | 1380 |
| gagaggctcc | aaccttcagt | gactgatcta | aaacaacttt | tggccaatgg | tgattctgtt | 1440 |
| ggacaccaaa | gtggatcatt | tgtgcaatca | attctgaaga | agcttaaatt | tgatgaccac | 1500 |
| aagataaagg | tttatagcac | gcaggaggaa | tatgcaaaag | cattaaggat | gggatcaaag | 1560 |
| catggagggg | tttcggctat | cttcgatgag | atacccatc | taaattcttt | ctgctcgaaa | 1620 |
| tacgggaggg | agttccagat | ggttggcccc | attgacagaa | caagtggatt | tggttttgtt | 1680 |
| ttacctaaag | gctctccatt | ggtaccagac | ctttcagagg | ccatcttgag | cttaacggaa | 1740 |
| gaacctgaaa | ggttgaagat | tgaaaagaca | tggttcatgg | attcgtcctt | ggattattat | 1800 |
| ggcagtcaca | gcaaaggctc | atcacgtatc | agttttcaga | gcttccaagg | tcttttcatc | 1860 |
| attgtcgggt | gccttttagg | tgctgtgctg | ttgataaact | ttagcaagtt | tctatatgac | 1920 |
| aaatgcaaag | agatgagagg | cttcggttca | gaccgtgtcc | atagtggcga | gagagttgtt | 1980 |
| tgttacggtg | aagctcaacc | acaaccaccg | cagattgtca | tggtcgatcg | acgatcctgt | 2040 |
| gcctgctga | | | | | | 2049 |

<210> SEQ ID NO 18
<211> LENGTH: 682
<212> TYPE: PRT

<213> ORGANISM: Oryza sativa

<400> SEQUENCE: 18

Met Thr Met Gln Thr Arg Val Phe Ile Val His Met Leu Pro Ala Arg
1               5                   10                  15

Ala Ser Arg Leu Phe Ala Arg Ala Lys Ala Leu Gly Met Met Thr Lys
            20                  25                  30

Gly Tyr Val Trp Ile Val Thr Asp Ser Ile Gly Ile Val Leu Asp Val
        35                  40                  45

Leu Pro Gln His Ser Ile Glu Ser Met Glu Gly Ile Val Gly Phe Arg
    50                  55                  60

Pro Tyr Ile Ala Glu Ser Thr Arg Ile Thr Asp Phe Ser Ser Arg Phe
65                  70                  75                  80

Thr Thr Leu Phe Arg Thr Lys Tyr His Pro Asn Thr Asp Ile Arg Met
                85                  90                  95

Ala Lys Pro Thr Ile Phe Gln Leu Trp Ala Tyr Asp Val Ala Trp Ala
            100                 105                 110

Val Ala Thr Ala Thr Glu Lys Val His Arg Thr Arg Ser Leu Asn Pro
        115                 120                 125

Thr Phe His Pro Pro Gly Asn Ile Gly Lys Asn Leu Val Asp Asp Leu
    130                 135                 140

Pro Ala Leu Pro Ala Gly Pro Glu Leu Leu Asn Ser Ile Leu Gln Gly
145                 150                 155                 160

Glu Phe Asp Gly Leu Ala Gly Gln Phe Arg Leu Ile Asp Arg His Leu
                165                 170                 175

Gln Val Pro Thr Tyr Glu Ile Val Asn Val Ile Gly Glu Lys Thr Arg
            180                 185                 190

Val Ile Gly Phe Tyr Ser Pro Asp Ser Gly Leu Thr Met Ser Val Asn
        195                 200                 205

Ser Arg Ile Ile His Gly Asp Ala Lys Phe Ser Thr Ser Ser Ser Asp
    210                 215                 220

Leu Glu Asn Ile Val Trp Pro Gly Asp Ser Thr Thr Val Pro Lys Gly
225                 230                 235                 240

Trp Asp Phe Pro Val Asn Ala Lys Ile Leu Gln Ile Gly Val Pro Val
                245                 250                 255

Arg Arg Asp Phe Lys Thr Phe Val Asn Val Glu Thr Asn Pro Asn Thr
            260                 265                 270

Asn Arg Ser Thr Val Ser Gly Tyr Ser Ile Asp Met Phe Glu Ala Ala
        275                 280                 285

Val Lys Lys Leu Pro Tyr Ala Leu Arg Tyr Glu Tyr Ile Pro Tyr Asp
    290                 295                 300

Cys Ala Val Ser Tyr Asp Leu Leu Val Ser Gln Val Phe Tyr Lys Lys
305                 310                 315                 320

Phe Asp Ala Ala Val Gly Asp Val Thr Ile Ile Ala Asn Arg Thr Arg
                325                 330                 335

Tyr Val Asp Phe Thr Met Pro Tyr Thr Glu Ser Gly Val Ser Met Leu
            340                 345                 350

Val Leu Ser Lys Ser Asp Asp Glu Pro Thr Thr Trp Ile Phe Leu Gln
        355                 360                 365

Pro Leu Ala Lys Asp Leu Trp Ile Ala Thr Met Ile Phe Ile Phe Phe
    370                 375                 380

Thr Gly Leu Val Val Trp Val Ile Glu Arg Pro Ile Asn Arg Asp Phe
385                 390                 395                 400

| | | | | | | | | | | |
|---|---|---|---|---|---|---|---|---|---|---|
| Gln | Gly | Ser | Lys | Trp | Lys | Gln | Cys | Ile | Thr | Ala | Phe | Tyr | Phe | Ala | Phe |
| | | | | 405 | | | | 410 | | | | | 415 | | |

Gln Gly Ser Lys Trp Lys Gln Cys Ile Thr Ala Phe Tyr Phe Ala Phe
                405                 410                 415

Ser Thr Leu Thr Phe Ser His Gly Gln Lys Ile Gln Ser Ile Gln Ser
            420                 425                 430

Lys Ile Val Val Val Ile Trp Cys Leu Val Leu Met Ile Leu Val Gln
            435                 440                 445

Ser Tyr Thr Ala Ser Leu Ser Ser Met Leu Thr Ala Glu Arg Leu Gln
        450                 455                 460

Pro Ser Val Thr Asp Leu Lys Gln Leu Leu Ala Asn Gly Asp Ser Val
465                 470                 475                 480

Gly His Gln Ser Gly Ser Phe Val Gln Ser Ile Leu Lys Lys Leu Lys
                485                 490                 495

Phe Asp Asp His Lys Ile Lys Val Tyr Ser Thr Gln Glu Glu Tyr Ala
                500                 505                 510

Lys Ala Leu Arg Met Gly Ser Lys His Gly Gly Val Ser Ala Ile Phe
            515                 520                 525

Asp Glu Ile Pro Tyr Leu Asn Ser Phe Cys Ser Lys Tyr Gly Arg Glu
        530                 535                 540

Phe Gln Met Val Gly Pro Ile Asp Arg Thr Ser Gly Phe Gly Phe Val
545                 550                 555                 560

Leu Pro Lys Gly Ser Pro Leu Val Pro Asp Leu Ser Glu Ala Ile Leu
                565                 570                 575

Ser Leu Thr Glu Glu Pro Glu Arg Leu Lys Ile Glu Lys Thr Trp Phe
            580                 585                 590

Met Asp Ser Ser Leu Asp Tyr Tyr Gly Ser His Ser Lys Gly Ser Ser
        595                 600                 605

Arg Ile Ser Phe Gln Ser Phe Gln Gly Leu Phe Ile Ile Val Gly Cys
    610                 615                 620

Leu Leu Gly Ala Val Leu Leu Ile Asn Phe Ser Lys Phe Leu Tyr Asp
625                 630                 635                 640

Lys Cys Lys Glu Met Arg Gly Phe Gly Ser Asp Arg Val His Ser Gly
                645                 650                 655

Glu Arg Val Val Cys Tyr Gly Glu Ala Gln Pro Gln Pro Gln Ile
            660                 665                 670

Val Met Val Asp Arg Arg Ser Cys Ala Cys
        675                 680

<210> SEQ ID NO 19
<211> LENGTH: 532
<212> TYPE: DNA
<213> ORGANISM: Oryza sativa

<400> SEQUENCE: 19

```
ctcacggtgc agcagctgtc cacggacatc cagggtctgg acggcctcat tgccagctcc      60
gaccccatcg gcttccaggt cggctccttc gccaagagct acctgatgca ggagctgggc     120
gtgcccgagt cccgcctctg ggagctcgcc atcaccgact actcctccac cctgcagagc     180
ggcatcgtgg cggccatcgt cgacgagctg ccatacgtgg agctcttcct ctccatcaac     240
tgccagttca ggacagtggg gcaggagttc acaaagagcg atggggatt cgtgagttct      300 tttccttgtt ggcttctttt cttcctcttt ttattctaca ctacaaccaa gtactacata     360
tgcaggcttt ccatcacgac tcccctctgg ccgtggacct tcgtcggct gccgaggagg      420 aggagggtga cgtggccgcc gaggaggagg aggccggaga gcgaggtagg tgcggaggca     480
atccgatctg atgaattggc ggaggcggcg ctccatggca gggcaatct tg              532
```

<210> SEQ ID NO 20
<211> LENGTH: 312
<212> TYPE: DNA
<213> ORGANISM: Oryza sativa

<400> SEQUENCE: 20

```
atgcaggagc tgggcgtgcc cgagtcccgc tctctgggagc tcgccatcac cgactactcc      60
tccaccctgc agagcggcat cgtggcggcc atcgtcgacg agctgccata cgtggagctc     120
ttcctctcca tcaactgcca gttcaggaca gtggggcagg agttcacaaa gagcggatgg     180
ggattcgctt tccatcacga ctcccctctg gccgtggacc tttcgtcggc tgccgaggag     240
gaggagggtg acgtggccgc cgaggaggag gaggccggag agcgaggtag gtgcggaggc     300
aatccgatct ga                                                         312
```

<210> SEQ ID NO 21
<211> LENGTH: 103
<212> TYPE: PRT
<213> ORGANISM: Oryza sativa

<400> SEQUENCE: 21

```
Met Gln Glu Leu Gly Val Pro Glu Ser Arg Leu Trp Glu Leu Ala Ile
1               5                   10                  15

Thr Asp Tyr Ser Ser Thr Leu Gln Ser Gly Ile Val Ala Ala Ile Val
            20                  25                  30

Asp Glu Leu Pro Tyr Val Glu Leu Phe Leu Ser Ile Asn Cys Gln Phe
        35                  40                  45

Arg Thr Val Gly Gln Glu Phe Thr Lys Ser Gly Trp Gly Phe Ala Phe
    50                  55                  60

His His Asp Ser Pro Leu Ala Val Asp Leu Ser Ser Ala Ala Glu Glu
65                  70                  75                  80

Glu Glu Gly Asp Val Ala Ala Glu Glu Glu Glu Ala Gly Glu Arg Gly
                85                  90                  95

Arg Cys Gly Gly Asn Pro Ile
            100
```

<210> SEQ ID NO 22
<211> LENGTH: 3065
<212> TYPE: DNA
<213> ORGANISM: Oryza sativa

<400> SEQUENCE: 22

```
ctcgttgtcc ttgcagttga ggagttgatg aacaagaacg cccaggtcga agccatcatc      60
gggcctcaaa cctcagccga agtcgagctc ttcgctggca tcgcgatccg caaccacatc     120
ccgatcctct ccttctcccc tactacctca ccggcgttga gctcaccgcc gacacgcttc     180
ttcgtgcgca ccgctgccag catcgcctcc caggccgcgc catcgccgc aatcctcgat     240 gtgttctcgt ggcgcgcggc cgtgctcctt cacgaggact cgctctacgg catcggcatc     300
ctcccggcgc tggttcacgc gttccaggtg caagggcagc tgctggcagg gtcgtacggt     360
gcgcgtggcg tggtggacag cgtgtccgtg ccggccgacg cgacggatgg ccgcctcgac     420
gcggcgctcc gtgccgtcaa gatcatgccg tggcgggtct acgtcgtgca catgctcccc     480
gccctggtcg cgcgcctctt cgccggggcc agcgtcgccg gcatgatgtc ggagggctac     540
gcgtggatcg ccaccgccgg cgtcggcgcc gggcggacg gccttagccc tgacgacatc     600
gagcacatgc agggtgtcgt cagcctacgc ccgtacgtgc agccgacggg ccaagtcagg     660
```

```
agtttcacga ggcggctcaa ggcaaggttt cgccgtgata acccgggcat cgacgacgaa    720
gacgacgacg acgacgtcgc gcacacgtcg gcgtcgctgc tctggctgta cgacacggca    780
tgggcagccg ccgccgcagc cgatcgatgt ctccaccaga gcagcaacgc gagggaagaa    840
cacaacacga cgacgtttct cgatgctctg ctcgcgacca cgtttcaagg cctggccgga    900
aggttcaggc tggtcgacgg cgagcggcag gtgtcggcgt acgaggttgt caacattatc    960
ggcagcggcg cgaggacggt gggtttctgg acgccggagc ttggggtctc ccaggacatg   1020
gcgcggcgcc gccccaagag tggcagcaat gaggagctga agcaaatcct atggccgggc   1080
gagacggcgg ccgtcccgat cgggtggagc gagtcggcga acgggcggcc gctccgcgtc   1140
gccgtcccgg tgaaggtcgg attcaaccaa ttcgtggcga tccgaaggca acaaaaccag   1200
acgagcgccg gcggggcaat gatcacaggc ttctgcatag acgtgttcca agcggtcatg   1260
gcgaagctgg cgtatccagt cgcatatcag tatgtgccag tcactgacaa catgttatct   1320
tatgacaaaa tggtgaacct ggtgcatgaa aaggttagtg tctacttacc acctccacta   1380
atttgcgttt acttggcagc attaactttt attgcttcaa ctttgatcac aaaatttatt   1440
tttaacttaa atgggtagaa taccattaat atattttaga acgaaggagg tacgaaacaa   1500
tatgtgctac aagtataggc cgataaaggg aaactattct aatccctcga ggggatgttc   1560
cctcgtttgc taaaaaacca tctaaatggt tatgaaaaat tctggaaaaa tttgacaaca   1620
ttcatacaac acatatatac aacttcacaa aatcttaagt ccaaactcaa ctcacacgtc   1680
gagatataaa aaagacaaat tcagcgtatg aatagtagcg tactgtttat atctaaattt   1740
gtcttttttg tttctcgatg tgtagatcga atttgaacat gaattttggt ggactagtag   1800
gtatcattat actctacatt gtcaattttt tttagatttt ttcacaacta tttgtatcga   1860
atttggaaga aaaatgtata cgaggggata tcctttcgag ggattagaat ccactcccgc   1920
cgataaacaa tgcatgcca ctaaaataat ttatcctgac cttgttgagg atagaattgt   1980
attaagatag aacatttaaa tatactaaaa tttaacaaat gcatccgtct caaaatatac   2040
caatctaata ctattgtatt gtagaaagcc gatgtggttg tggctgatat gacgatcacg   2100
gcagaacgga tgaaactggt ttcattcacg atgccattca ccgactcagg agtgtcgatg   2160
gttgtggcgg aagaggagaa ggcaaacaac atgtggatct tcctaaggcc actaactccg   2220
ggcctttgga tcactagcat ggcttttctt ttcttcaccg gcttcgtcgt gtgggcaatt   2280
gagcacagga tcaaccccg attccatggc acgccatgta atcagttcgg agttgtattc   2340
tactttgcat tctcgactct agtcttctcc catagtaaac cccgttcttg cccccccccc   2400
tttttttaag tactccatca ttctaaaata tagtaattta gtactccctc cttcccatat   2460
tgatcatcat ataaatttat acaccaagat caaagataat ttaaatcaca acaatcaaga   2520
taccatgcac acgttctctc acaatgcatg catcggttaa attataatgc caactacaca   2580
ccttagcata cacacattct cccgtgctgc attaataatt gtattctgat gaaatccgtg   2640
tccatgcggt tatatgatga tcaatttgag aaatttttaaa tttcattgta tgatgatcaa   2700
tttgggaagg agggagtatt gaattagaaa caatctagta ctacgatatc tgtccaagtt   2760
catagtacta tattatatca aattcaatac tcgattacta tattttaaga ttggggagta   2820
tattattata tgattgcaca attttgttac tattcccttt tgatgacgac actaatcctg   2880
atttaatttt cagaggagaa gttggagagc aacctgtcga agctcgtggt catcgtatgg   2940
gtgtttactg ttcttatcat cacgacaagc tacacggcaa acctaacatc gatgttgaca   3000
```

-continued

```
gtgggacagc tgcagccgac gataaacgaa ttaaagaagg gcgactatgt gggttatcag    3060
caggg                                                                 3065
```

<210> SEQ ID NO 23
<211> LENGTH: 1419
<212> TYPE: DNA
<213> ORGANISM: Oryza sativa

<400> SEQUENCE: 23

```
atgaacaaga acgcccaggt cgaagccatc atcgggcctc aaacctcagc cgaagtcgag      60
ctcttcgctg gcatcgcgat ccgcaaccac atcccgatcc tctccttctc ccctactacc     120
tcaccggcgt tgagctcacc gccgacacgc ttcttcgtgc gcaccgctgc cagcatcgcc     180
tcccaggccg cgcccatcgc cgcaatcctc gatgtgttct cgtggcgcgc ggccgtgctc     240
cttcacgagg actcgctcta cggcatcggc atcctcccgg cgctggttca cgcgttccag     300
gtgcaagggc agctgctggc agggtcgtac ggtgcgcgtg gcgtggtgga cagcgtgtcc     360
gtgccggccg acgcgacgga tggccgcctc gacgcggcgc tccgtgccgt caagatcatg     420
ccgtggcggg tctacgtcgt gcacatgctc cccgccctgg tcgcgcgcct cttccgccgg     480
gccagcgtcg ccggcatgat gtcggagggc tacgcgtgga tcgccaccgc cggcgtcggc     540
gccgcggcgg acggccttag ccctgacgac atcgagcaca tgcagggtgt cgtcagccta     600
cgcccgtacg tgcagccgac gggccaagtc aggagtttca cgaggcggct caaggcaagg     660
tttcgccgtg ataacccggg catcgacgac gaagacgacg acgacgacgt cgcgcacacg     720
tcggcgtcgc tgctctggct gtacgacacg gcatgggcag ccgccgccgc agccgatcga     780
tgtctccacc agagcagcaa cgcgagggaa gaacacaaca cgacgacgtt tctcgatgct     840
ctgctcgcga ccacgtttca aggcctggcc ggaaggttca ggctggtcga cggcgagcgg     900
caggtgtcgg cgtacgaggt tgtcaacatt atcggcagcg gcgcgaggac ggtgggtttc     960
tggacgccag agcttggggt ctcccaggac atggcgcggc ccgcccaa gagtggcagc      1020 aatgaggagc tgaagcaaat cctatggccg gcgagacgg cggccgtccc gatcgggtgg     1080
agcgagtcgg cgaacgggcg gccgctccgc gtcgccgtcc cggtgaaggt cggattcaac     1140
caattcgtgg cgatccgaag gcaacaaaac cagacgagcg ccggcgggc aatgatcaca      1200 ggcttctgca tagacgtgtt ccaagcggtc atggcgaagc tggcgtatcc agtcgcatat     1260
cagtatgtgc cagtcactga caacatgtta tcttatgaca aaatggtgaa cctggtgcat     1320
gaaaagagga gaagttggag agcaacctgt cgaagctcgt ggtcatcgta tgggtgttta    1380
ctgttcttat catcacgaca agctacacgg caaacctaa                           1419
```

<210> SEQ ID NO 24
<211> LENGTH: 472
<212> TYPE: PRT
<213> ORGANISM: Oryza sativa

<400> SEQUENCE: 24

```
Met Asn Lys Asn Ala Gln Val Glu Ala Ile Ile Gly Pro Gln Thr Ser
1               5                   10                  15

Ala Glu Val Glu Leu Phe Ala Gly Ile Ala Ile Arg Asn His Ile Pro
            20                  25                  30

Ile Leu Ser Phe Ser Pro Thr Thr Ser Pro Ala Leu Ser Ser Pro Pro
        35                  40                  45

Thr Arg Phe Phe Val Arg Thr Ala Ala Ser Ile Ala Ser Gln Ala Ala
    50                  55                  60
```

```
Pro Ile Ala Ala Ile Leu Asp Val Phe Ser Trp Arg Ala Val Leu
 65                  70                  75                  80

Leu His Glu Asp Ser Leu Tyr Gly Ile Gly Ile Leu Pro Ala Leu Val
                 85                  90                  95

His Ala Phe Gln Val Gln Gly Gln Leu Leu Ala Gly Ser Tyr Gly Ala
            100                 105                 110

Arg Gly Val Val Asp Ser Val Ser Val Pro Ala Asp Ala Thr Asp Gly
            115                 120                 125

Arg Leu Asp Ala Ala Leu Arg Ala Val Lys Ile Met Pro Trp Arg Val
        130                 135                 140

Tyr Val Val His Met Leu Pro Ala Leu Val Ala Arg Leu Phe Arg Arg
145                 150                 155                 160

Ala Ser Val Ala Gly Met Met Ser Glu Gly Tyr Ala Trp Ile Ala Thr
                165                 170                 175

Ala Gly Val Gly Ala Ala Ala Asp Gly Leu Ser Pro Asp Asp Ile Glu
            180                 185                 190

His Met Gln Gly Val Val Ser Leu Arg Pro Tyr Val Gln Pro Thr Gly
        195                 200                 205

Gln Val Arg Ser Phe Thr Arg Arg Leu Lys Ala Arg Phe Arg Arg Asp
210                 215                 220

Asn Pro Gly Ile Asp Asp Glu Asp Asp Asp Asp Val Ala His Thr
225                 230                 235                 240

Ser Ala Ser Leu Leu Trp Leu Tyr Asp Thr Ala Trp Ala Ala Ala
                245                 250                 255

Ala Ala Asp Arg Cys Leu His Gln Ser Ser Asn Ala Arg Glu Glu His
            260                 265                 270

Asn Thr Thr Thr Phe Leu Asp Ala Leu Leu Ala Thr Thr Phe Gln Gly
        275                 280                 285

Leu Ala Gly Arg Phe Arg Leu Val Asp Gly Glu Arg Gln Val Ser Ala
        290                 295                 300

Tyr Glu Val Val Asn Ile Ile Gly Ser Gly Ala Arg Thr Val Gly Phe
305                 310                 315                 320

Trp Thr Pro Glu Leu Gly Val Ser Gln Asp Met Ala Arg Arg Pro
                325                 330                 335

Lys Ser Gly Ser Asn Glu Glu Leu Lys Gln Ile Leu Trp Pro Gly Glu
            340                 345                 350

Thr Ala Ala Val Pro Ile Gly Trp Ser Glu Ser Ala Asn Gly Arg Pro
            355                 360                 365

Leu Arg Val Ala Val Pro Val Lys Val Gly Phe Asn Gln Phe Val Ala
        370                 375                 380

Ile Arg Arg Gln Gln Asn Gln Thr Ser Ala Gly Gly Ala Met Ile Thr
385                 390                 395                 400

Gly Phe Cys Ile Asp Val Phe Gln Ala Val Met Ala Lys Leu Ala Tyr
                405                 410                 415

Pro Val Ala Tyr Gln Tyr Val Pro Val Thr Asp Asn Met Leu Ser Tyr
            420                 425                 430

Asp Lys Met Val Asn Leu Val His Glu Lys Arg Arg Ser Trp Arg Ala
        435                 440                 445

Thr Cys Arg Ser Ser Trp Ser Ser Tyr Gly Cys Leu Leu Phe Leu Ser
        450                 455                 460

Ser Arg Gln Ala Thr Arg Gln Thr
465                 470
```

<210> SEQ ID NO 25
<211> LENGTH: 30
<212> TYPE: DNA
<213> ORGANISM: Artificial Sequence
<220> FEATURE:
<223> OTHER INFORMATION: Forward primer for cloning gDNA of OsGLR2.2

<400> SEQUENCE: 25
ccatacattc agtaaccagt agaaccatcc                                    30

<210> SEQ ID NO 26
<211> LENGTH: 27
<212> TYPE: DNA
<213> ORGANISM: Artificial Sequence
<220> FEATURE:
<223> OTHER INFORMATION: Reverse primer for cloning gDNA of OsGLR2.2

<400> SEQUENCE: 26
gctgaattag ccgagttacc attcctc                                       27

<210> SEQ ID NO 27
<211> LENGTH: 22
<212> TYPE: DNA
<213> ORGANISM: Artificial Sequence
<220> FEATURE:
<223> OTHER INFORMATION: Forward primer for cloning gDNA of OsGLR3.2

<400> SEQUENCE: 27
cttctttgtg gcaggagttc tc                                            22

<210> SEQ ID NO 28
<211> LENGTH: 27
<212> TYPE: DNA
<213> ORGANISM: Artificial Sequence
<220> FEATURE:
<223> OTHER INFORMATION: Reverse primer for cloning gDNA of OsGLR3.2

<400> SEQUENCE: 28
caaactggcc tcaaatgaat ttttccc                                       27

<210> SEQ ID NO 29
<211> LENGTH: 25
<212> TYPE: DNA
<213> ORGANISM: Artificial Sequence
<220> FEATURE:
<223> OTHER INFORMATION: Forward primer for cloning cDNA of OsGLRL1.2

<400> SEQUENCE: 29
cgatcgagct agccatgtgg agttc                                         25

<210> SEQ ID NO 30
<211> LENGTH: 26
<212> TYPE: DNA
<213> ORGANISM: Artificial Sequence
<220> FEATURE:
<223> OTHER INFORMATION: Reverse primer for cloning cDNA of OsGLRL1.2

<400> SEQUENCE: 30
catactgtct ggatggaatt tgcagg                                        26

<210> SEQ ID NO 31
<211> LENGTH: 26
<212> TYPE: DNA
<213> ORGANISM: Artificial Sequence
<220> FEATURE:
<223> OTHER INFORMATION: Forward primer for cloning gDNA of OsGLRL1.3

```
<400> SEQUENCE: 31
ctattgcatt gatgtctttg aggctg                                           26

<210> SEQ ID NO 32
<211> LENGTH: 22
<212> TYPE: DNA
<213> ORGANISM: Artificial Sequence
<220> FEATURE:
<223> OTHER INFORMATION: Reverse primer for cloning gDNA of OsGLRL1.3

<400> SEQUENCE: 32
ctgaattggt cgaggctctt tg                                               22

<210> SEQ ID NO 33
<211> LENGTH: 24
<212> TYPE: DNA
<213> ORGANISM: Artificial Sequence
<220> FEATURE:
<223> OTHER INFORMATION: Forward primer for cloning gDNA of OsGLRL1.7

<400> SEQUENCE: 33
ccgttctgcc ttccctgctt attc                                             24

<210> SEQ ID NO 34
<211> LENGTH: 26
<212> TYPE: DNA
<213> ORGANISM: Artificial Sequence
<220> FEATURE:
<223> OTHER INFORMATION: Reverse primer for cloning gDNA of OsGLRL1.7

<400> SEQUENCE: 34
cttgggagtt gggatagttg gtgcag                                           26

<210> SEQ ID NO 35
<211> LENGTH: 21
<212> TYPE: DNA
<213> ORGANISM: Artificial Sequence
<220> FEATURE:
<223> OTHER INFORMATION: Forward primer for cloning gDNA of OsGLRL2.1

<400> SEQUENCE: 35
ctcacggtgc agcagctgtc c                                                21

<210> SEQ ID NO 36
<211> LENGTH: 22
<212> TYPE: DNA
<213> ORGANISM: Artificial Sequence
<220> FEATURE:
<223> OTHER INFORMATION: Reverse primer for cloning gDNA of OsGLRL2.1

<400> SEQUENCE: 36
caagattgcc cctgccatgg ag                                               22

<210> SEQ ID NO 37
<211> LENGTH: 22
<212> TYPE: DNA
<213> ORGANISM: Artificial Sequence
<220> FEATURE:
<223> OTHER INFORMATION: Forward primer for cloning gDNA of OsGLRL3.1

<400> SEQUENCE: 37
ctcgttgtcc ttgcagttga gg                                               22

<210> SEQ ID NO 38
```

```
<211> LENGTH: 25
<212> TYPE: DNA
<213> ORGANISM: Artificial Sequence
<220> FEATURE:
<223> OTHER INFORMATION: Reverse primer for cloning gDNA of OsGLRL3.1

<400> SEQUENCE: 38
ccctgctgat aacccacata gtcgc                                        25

<210> SEQ ID NO 39
<211> LENGTH: 19
<212> TYPE: DNA
<213> ORGANISM: Artificial Sequence
<220> FEATURE:
<223> OTHER INFORMATION: Forward primer for real-time RT-PCR analysis of
      OsGLRL2.1 gene

<400> SEQUENCE: 39
ctttccatca cgactcccc                                               19

<210> SEQ ID NO 40
<211> LENGTH: 20
<212> TYPE: DNA
<213> ORGANISM: Artificial Sequence
<220> FEATURE:
<223> OTHER INFORMATION: Reverse primer for real-time RT-PCR analysis of
      OsGLRL2.1 gene

<400> SEQUENCE: 40
ctccgccaat tcatcagatc                                              20

<210> SEQ ID NO 41
<211> LENGTH: 26
<212> TYPE: DNA
<213> ORGANISM: Artificial Sequence
<220> FEATURE:
<223> OTHER INFORMATION: Forward primer for real-time RT-PCR analysis of
      OsGLRL1.3 gene

<400> SEQUENCE: 41
ggttcttact atcagatcaa cgatgc                                       26

<210> SEQ ID NO 42
<211> LENGTH: 24
<212> TYPE: DNA
<213> ORGANISM: Artificial Sequence
<220> FEATURE:
<223> OTHER INFORMATION: Reverse primer for real-time RT-PCR analysis of
      OsGLRL1.3 gene

<400> SEQUENCE: 42
ccatttggtt gttgattcag attc                                         24

<210> SEQ ID NO 43
<211> LENGTH: 21
<212> TYPE: DNA
<213> ORGANISM: Artificial Sequence
<220> FEATURE:
<223> OTHER INFORMATION: Forward primer for real-time RT-PCR analysis of
      OsGLRL1.2 gene

<400> SEQUENCE: 43
gcaattccca acacagattc g                                            21

<210> SEQ ID NO 44
<211> LENGTH: 22
<212> TYPE: DNA
```

```
<213> ORGANISM: Artificial Sequence
<220> FEATURE:
<223> OTHER INFORMATION: Reverse primer for real-time RT-PCR analysis of
      OsGLRL1.2 gene

<400> SEQUENCE: 44
gcatgagagt tgagatacac cc                                              22

<210> SEQ ID NO 45
<211> LENGTH: 21
<212> TYPE: DNA
<213> ORGANISM: Artificial Sequence
<220> FEATURE:
<223> OTHER INFORMATION: Forward primer for real-time RT-PCR analysis of
      OsGLRL3.1 gene

<400> SEQUENCE: 45
tgatcacagg cttctgcata g                                               21

<210> SEQ ID NO 46
<211> LENGTH: 24
<212> TYPE: DNA
<213> ORGANISM: Artificial Sequence
<220> FEATURE:
<223> OTHER INFORMATION: Reverse primer for real-time RT-PCR analysis of
      OsGLRL3.1 gene

<400> SEQUENCE: 46
catactgata tgcgactgga tacg                                            24

<210> SEQ ID NO 47
<211> LENGTH: 22
<212> TYPE: DNA
<213> ORGANISM: Artificial Sequence
<220> FEATURE:
<223> OTHER INFORMATION: Forward primer for real-time RT-PCR analysis of
      OsGLRL1.7 gene

<400> SEQUENCE: 47
gcaaagagat gagaggcttc gg                                              22

<210> SEQ ID NO 48
<211> LENGTH: 21
<212> TYPE: DNA
<213> ORGANISM: Artificial Sequence
<220> FEATURE:
<223> OTHER INFORMATION: Reverse primer for real-time RT-PCR analysis of
      OsGLRL1.7 gene

<400> SEQUENCE: 48
catgacaatc tgcggtggtt g                                               21
```

CONSTRUCTS AND METHOD OF USE FOR RICE GLUATAMATE RECEPTOR-LIKE GENES

FIELD

The field of the disclosure relates to plant breeding and genetics and, in particular, relates to recombinant DNA constructs useful in plants for conferring tolerance to abiotic stress, such as drought, and for improving nitrogen use efficiency.

BACKGROUND

Abiotic stress is the primary cause of crop loss worldwide, causing average yield losses more than 50% for major crops (Boyer, J. S. (1982) *Science* 218:443-448; Bray, E. A. et al. (2000) In Biochemistry and Molecular Biology of Plants, edited by Buchannan, B. B. et al., Amer. Soc. Plant Biol., pp. 1158-1249). Plants are sessile and have to adjust to the prevailing environmental conditions of their surroundings. This has led to their development of a great plasticity in gene regulation, morphogenesis, and metabolism. Adaption and defense strategies involve the activation of genes encoding proteins important in the acclimation or defense towards the different stresses.

Drought is one of the major abiotic stresses that limit crop productivity worldwide, and exposure of plants to a water-limiting environment during various developmental stages appears to activate various physiological and developmental changes. Although many reviews on molecular mechanisms of abiotic stress responses and genetic regulatory networks of drought stress tolerance have been published (Valliyodan, B., and Nguyen, H. T. (2006) *Curr. Opin. Plant Biol.* 9:189-195; Wang, W., et al. (2003) *Planta* 218:1-14; Vinocur, B., and Altman, A. (2005) *Curr. Opin. Biotechnol.* 16:123-132; Chaves, M. M., and Oliveira, M. M. (2004) *J. Exp. Bot.* 55:2365-2384; Shinozaki, K., et al. (2003) *Curr. Opin. Plant Biol.* 6:410-417; Yamaguchi-Shinozaki, K., and Shinozaki, K. (2005) *Trends Plant Sci.* 10:88-94), it remains a major challenge in biology to understand the basic biochemical and molecular mechanisms for drought stress perception, transduction and tolerance. Genetic research has shown that drought tolerance is a quantitative trait, controlled by many genes. Molecular marker-assisted breeding has led to improved drought tolerance in crops. However, marker accuracy and breeding efficiency remain problematic (Ashraf M. (2010) *Biotechnol. Adv.* 28:169-183). Transgenic approaches to engineering drought tolerance in crops have made progress (Vinocur B. and Altman A. (2005) *Curr. Opin. Biotechnol.* 16:123-132; Lawlor D W. (2013) *J. Exp. Bot.* 64:83-108).

The absorption of nitrogen by plants plays an important role in their growth (Gallais et al. (2004), *J. Exp. Bot.* 55(396):295-306). Plants synthesize amino acids from inorganic nitrogen absorbed from environment, so, nitrogen fertilization has been a powerful tool for increasing yield of cultivated plants, such as maize. Lack of sufficient plant-available nitrogen for optimum growth and development may be considered as an abiotic stress. In order to avoid pollution by nitrates and to maintain a sufficient profit margin, today farmers desire to reduce the use of nitrogen fertilizer. If a plant variety has increased nitrogen assimilation capacity, it would also be expected to have increased growth and yield. In summary, plant varieties that have better nitrogen use efficiency (NUE) are desirable.

Glutamate receptors (GLR) can bind glutamate and function through ligand gated ion channels or G-protein coupled receptors in the major excitatory neurotransmitter in mammals. GLR-like genes have been identified in plants (Davenport R. (2002) *Annals of Botany* 90:549-557).

SUMMARY

The following embodiments are among those encompassed by the disclosure:

1. An isolated polynucleotide enhancing drought tolerance of plant, comprising (a) a polynucleotide with nucleotide sequence of at least 85% sequence identity to SEQ ID NO: 4, 5, 7, 8, 10, 11, 13, 14, 16, 17, 19, 20, 22 or 23; (b) a polynucleotide encoding a polypeptide with amino acid sequence of at least 90% sequence identity to SEQ ID NO: 6, 9, 12, 15, 18, 21 or 24; or (c) the full complement of the nucleotide sequence of (a) or (b).

2. A recombinant DNA construct comprising the isolated polynucleotide of embodiment 1 operably linked to at least one regulatory sequence.

3. A transgenic plant or seed comprising a recombinant DNA construct, wherein the recombinant DNA construct comprises the polynucleotide operably linked to at least one regulatory sequence, wherein said polynucleotide encodes GLR protein having amino acid sequence of at least 90% sequence identity to SEQ ID NO: 6, SEQ ID NO: 9, SEQ ID NO: 12, SEQ ID NO: 15, SEQ ID NO: 18, SEQ ID NO: 21, or SEQ ID NO: 24.

4. A transgenic plant comprising in its genome a recombinant DNA construct comprising a polynucleotide operably linked to at least one regulatory element, wherein said polynucleotide encodes GLR protein having amino acid sequence of at least 90% sequence identity to SEQ ID NO: 6, 9, 12, 15, 18, 21 or 24, wherein said plant exhibits increased drought tolerance when compared to a control plant, and wherein said plant exhibits an increase in grain yield, biomass, or both, when compared to a control plant.

5. The transgenic plant of embodiment 4, wherein said plant exhibits said increase in grain yield, biomass, or both when compared, under water limiting conditions, to said control plant.

6. The transgenic plant of embodiment 4, wherein said plant is selected from the group consisting of rice, maize, soybean, sunflower, sorghum, canola, wheat, alfalfa, cotton, barley, millet, sugar cane and switchgrass.

7. Seed of the transgenic plant of embodiment 4, wherein said seed comprises in its genome a recombinant DNA construct comprising a polynucleotide operably linked to at least one regulatory element, wherein said polynucleotide encodes GLR protein having amino acid sequence of at least 90% sequence identity to SEQ ID NO: 6, 9, 12, 15, 18, 21 or 24, and wherein a plant produced from said seed exhibits an increase in at least one trait selected from the group consisting of drought tolerance, grain yield and biomass, when compared to a control plant.

8. A method of increasing drought tolerance in a plant, comprising: (a) introducing into a regenerable plant cell a recombinant DNA construct comprising a polynucleotide operably linked to at least one regulatory sequence, wherein the polynucleotide encodes a polypeptide having an amino acid sequence of at least 90% sequence identity to SEQ ID NO: 6, 9, 12, 15, 18, 21 or 24; (b) regenerating a transgenic plant from the regenerable plant cell after step (a), wherein the transgenic plant comprises in its genome the recombinant DNA construct; and (c) obtaining a progeny plant derived from the transgenic plant of step (b), wherein said progeny plant comprises in its genome the recombinant DNA construct and exhibits increased drought tolerance when compared to a control plant.

9. A method of evaluating drought tolerance in a plant, comprising: (a) obtaining a transgenic plant, wherein the transgenic plant comprises in its genome a recombinant DNA construct comprising a polynucleotide operably linked to at least one regulatory element, wherein the polynucleotide encodes a polypeptide having an amino acid sequence of at least 90% sequence identity to SEQ ID NO: 6, 9, 12, 15, 18, 21 or 24; (b) obtaining a progeny plant derived from the transgenic plant, wherein the progeny plant comprises in its genome the recombinant DNA construct; and (c) evaluating the progeny plant for drought tolerance compared to a control plant not comprising the recombinant DNA construct.

10. A method of determining an alteration of grain yield, biomass, or both in a plant, comprising: (a) obtaining a transgenic plant, wherein the transgenic plant comprises in its genome a recombinant DNA construct comprising a polynucleotide operably linked to at least one regulatory element, wherein the polynucleotide encodes a polypeptide having an amino acid sequence of at least 90% sequence identity to SEQ ID NO: 6, 9, 12, 15, 18, 21 or 24; (b) obtaining a progeny plant derived from the transgenic plant, wherein the progeny plant comprises in its genome the recombinant DNA construct; and (c) measuring the grain yield and/or biomass of the progeny plant and comparing said measurement to the grain yield and/or biomass of a control plant.

11. The method of embodiment 10, wherein grain yield and/or biomass of the progeny plant and control plant are measured under water-limiting conditions, and wherein said grain yield and/or biomass of the progeny plant is increased relative to that of the control plant.

12. An isolated polynucleotide enhancing nitrogen stress tolerance of plant, comprising (a) a polynucleotide with nucleotide sequence of at least 85% sequence identity to SEQ ID NO: 22 or 23; (b) a polynucleotide encoding a polypeptide with amino acid sequence of at least 90% sequence identity to SEQ ID NO: 24; or (c) the full complement of the nucleotide sequence of (a) or (b).

13. A recombinant DNA construct comprising the isolated polynucleotide of embodiment 12 operably linked to at least one regulatory sequence.

14. A transgenic plant or seed comprising a recombinant DNA construct, wherein the recombinant DNA construct comprises the polynucleotide operably linked to at least one regulatory sequence, wherein said polynucleotide encodes GLR protein having amino acid sequence of at least 90% sequence identity to SEQ ID NO: 24.

15. A transgenic plant comprising in its genome a recombinant DNA construct comprising a polynucleotide operably linked to at least one regulatory element, wherein said polynucleotide encodes GLR protein having amino acid sequence of at least 90% sequence identity to SEQ ID NO: 24, wherein said plant exhibits improved nitrogen use efficiency (NUE) when compared to a control plant, and wherein said plant exhibits an increase in grain yield, biomass, or both, when compared to a control plant.

16. The transgenic plant of embodiment 15, wherein said plant exhibits said increase in grain yield, biomass, or both when compared, under nitrogen limiting conditions, to said control plant.

17. The transgenic plant of embodiment 15, wherein said plant is selected from the group consisting of rice, maize, soybean, sunflower, sorghum, canola, wheat, alfalfa, cotton, barley, millet, sugar cane and switchgrass.

18. A method of improving nitrogen use efficiency (NUE) in a plant, comprising: (a) introducing into a regenerable plant cell a recombinant DNA construct comprising a polynucleotide operably linked to at least one regulatory sequence, wherein the polynucleotide encodes a polypeptide having an amino acid sequence of at least 90% sequence identity to SEQ ID NO: 24; (b) regenerating a transgenic plant from the regenerable plant cell after step (a), wherein the transgenic plant comprises in its genome the recombinant DNA construct; and (c) obtaining a progeny plant derived from the transgenic plant of step (b), wherein said progeny plant comprises in its genome the recombinant DNA construct and exhibits improving nitrogen use efficiency when compared to a control plant.

19. A method of evaluating NUE in a plant, comprising: (a) obtaining a transgenic plant, wherein the transgenic plant comprises in its genome a recombinant DNA construct comprising a polynucleotide operably linked to at least one regulatory element, wherein the polynucleotide encodes a polypeptide having an amino acid sequence of at least 90% sequence identity to SEQ ID NO: 24; (b) obtaining a progeny plant derived from the transgenic plant, wherein the progeny plant comprises in its genome the recombinant DNA construct; and (c) evaluating the progeny plant for NUE compared to a control plant not comprising the recombinant DNA construct.

20. A method of determining an alteration of grain yield, biomass, or both in a plant, comprising: (a) obtaining a transgenic plant, wherein the transgenic plant comprises in its genome a recombinant DNA construct comprising a polynucleotide operably linked to at least one regulatory element, wherein the polynucleotide encodes a polypeptide having an amino acid sequence of at least 90% sequence identity to SEQ ID NO: 24; (b) obtaining a progeny plant derived from the transgenic plant, wherein the progeny plant comprises in its genome the recombinant DNA construct; and (c) measuring the grain yield and/or biomass of the progeny plant and comparing said measurement to the grain yield and/or biomass of a control plant.

21. The method of embodiment 20, wherein grain yield and/or biomass of the progeny plant and control plant are measured under nitrogen-limiting conditions, and wherein said grain yield and/or biomass of the progeny plant is increased relative to that of the control plant.

In another embodiment, the present disclosure concerns a recombinant DNA construct comprising any of the isolated polynucleotides of the present disclosure operably linked to at least one regulatory sequence, and a cell, a plant, or a seed comprising the recombinant DNA construct. The cell may be eukaryotic, e.g., a yeast, insect or plant cell; or prokaryotic, e.g., a bacterial cell.

BRIEF DESCRIPTION OF THE DRAWINGS AND SEQUENCE LISTING

The disclosure can be more fully understood from the following detailed description and the accompanying drawings and Sequence Listing which form a part of this application.

Figure 4:
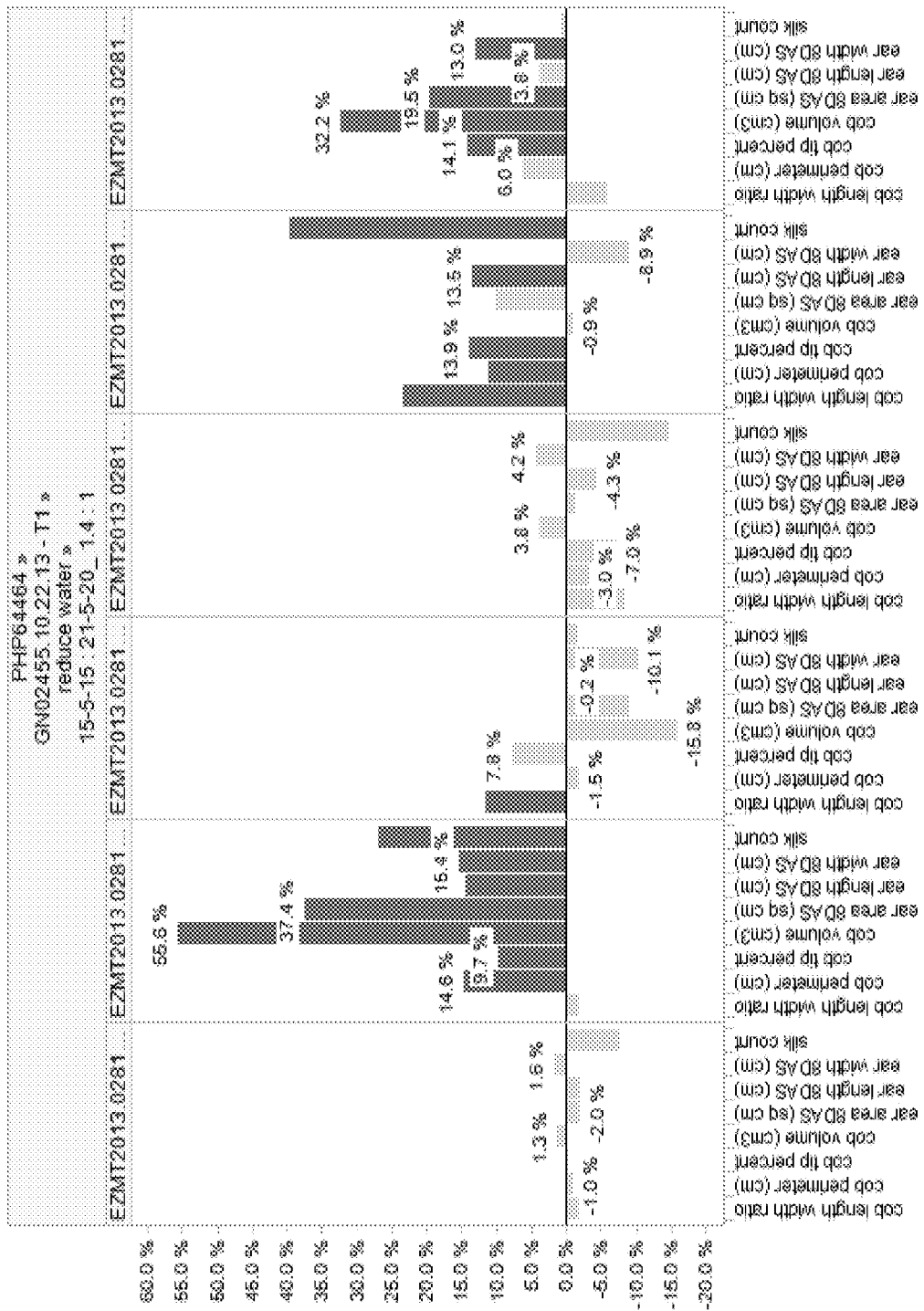

FIG. 4 shows overexpression of OsGLRL1.7 (PHP64464) under Maize Ubi promoter significantly enhanced drought tolerance in rapid-cycling Corn $T_1$ plants under greenhouse drought condition. The y-axis is % of increase or decrease of the transgenic to control. The dark gray indicates statistically significant (P<0.1, Two tailed t-test), light gray indicates not significant, for each of the ear traits indicated in the X-axis. Cob length width ratio, ratio of length to width, collected at eight days after silking; Cob tip percent, percentage of total ear area occupied by the ⅓ upper section (tip area) of the immature ear [tip area/total area*100], collected at 8 days after silking (DAS); Cob perimeter, cob volume, ear area 8DAS, ear length 8 DAS, and ear width 8DAS, collected at eight days after silking; Silk count, the number of silks.

Figure 5:
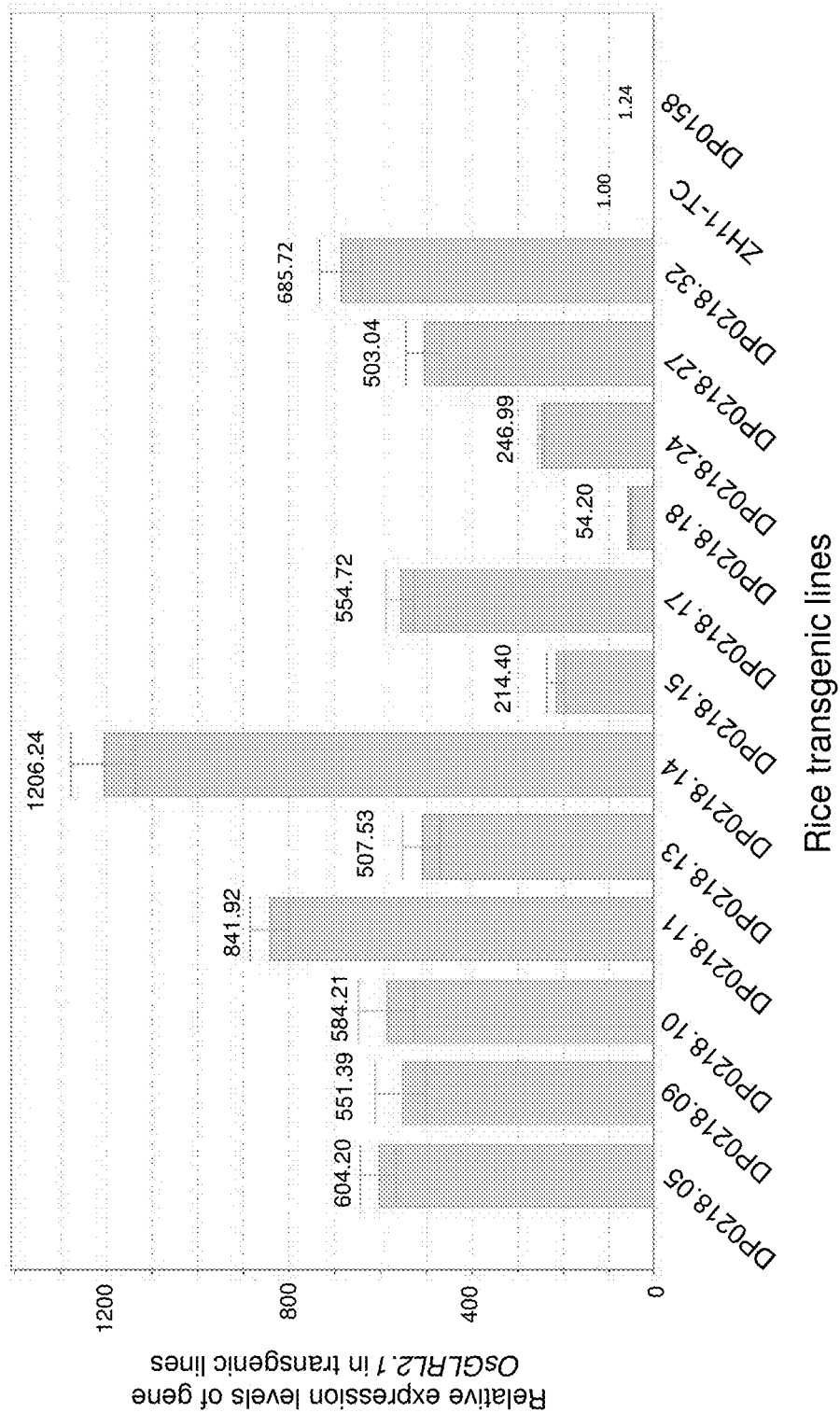

FIG. 5 shows the relative expression levels of OsGLRL2.1 gene in leaves of different transgenic rice lines by real-time PCR analyses. The base expression level in ZH11-TC is set at 1.00, the numbers on the top of the columns are fold-changes compared to ZH11-TC rice. ZH11-TC is tissue cultured ZH11 rice and DP0158 is empty vector transformed ZH11 rice plants.

Figure 6:
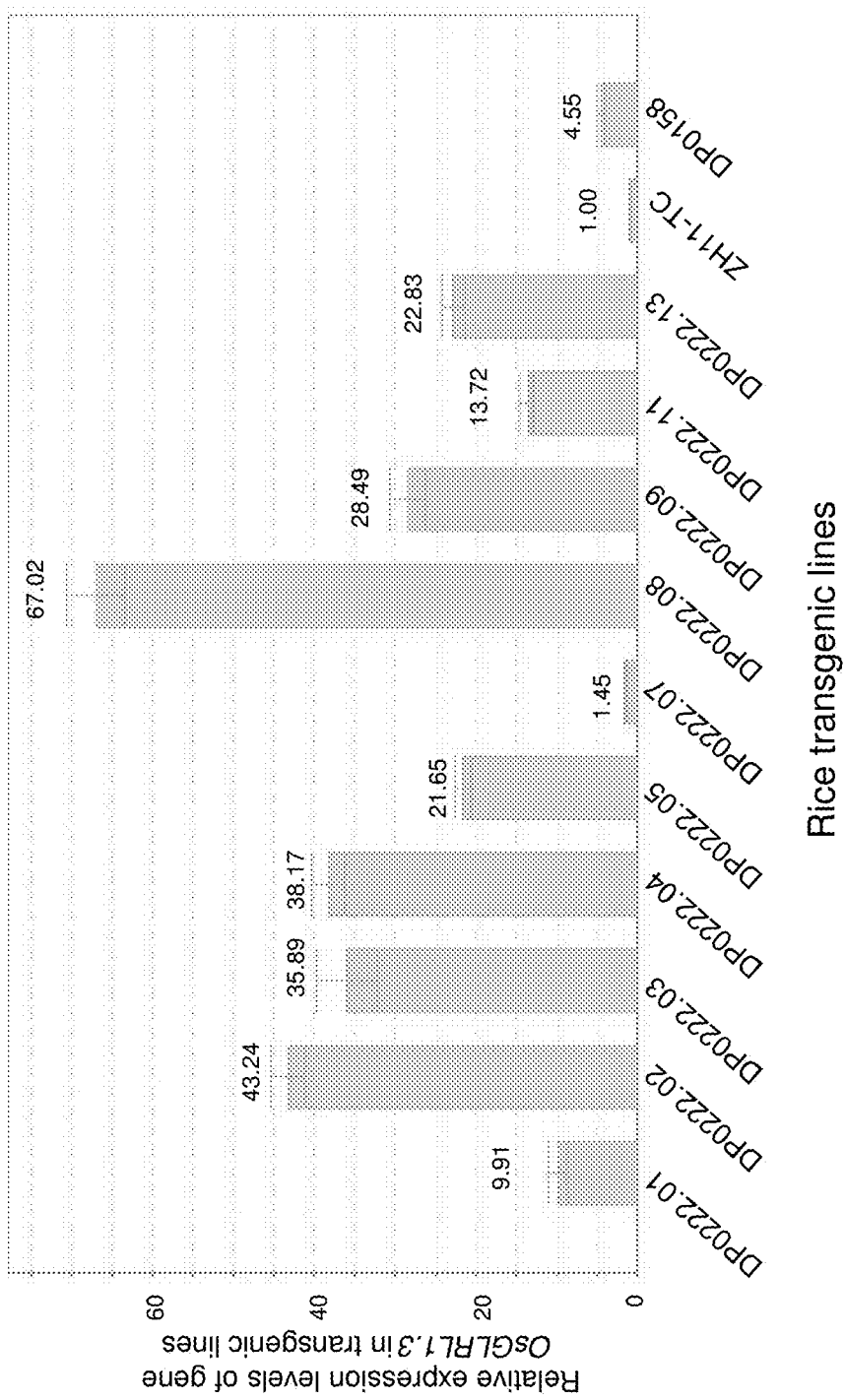

FIG. 6 shows the relative expression levels of OsGLRL1.3 gene in leaves of different transgenic rice lines by real-time PCR analyses. The base expression level in ZH11-TC is set at 1.00, the numbers on the top of the columns are fold-changes compared to ZH11-TC rice. ZH11-TC is tissue cultured ZH11 rice and DP0158 is empty vector transformed ZH11 rice plants.

Figure 7:
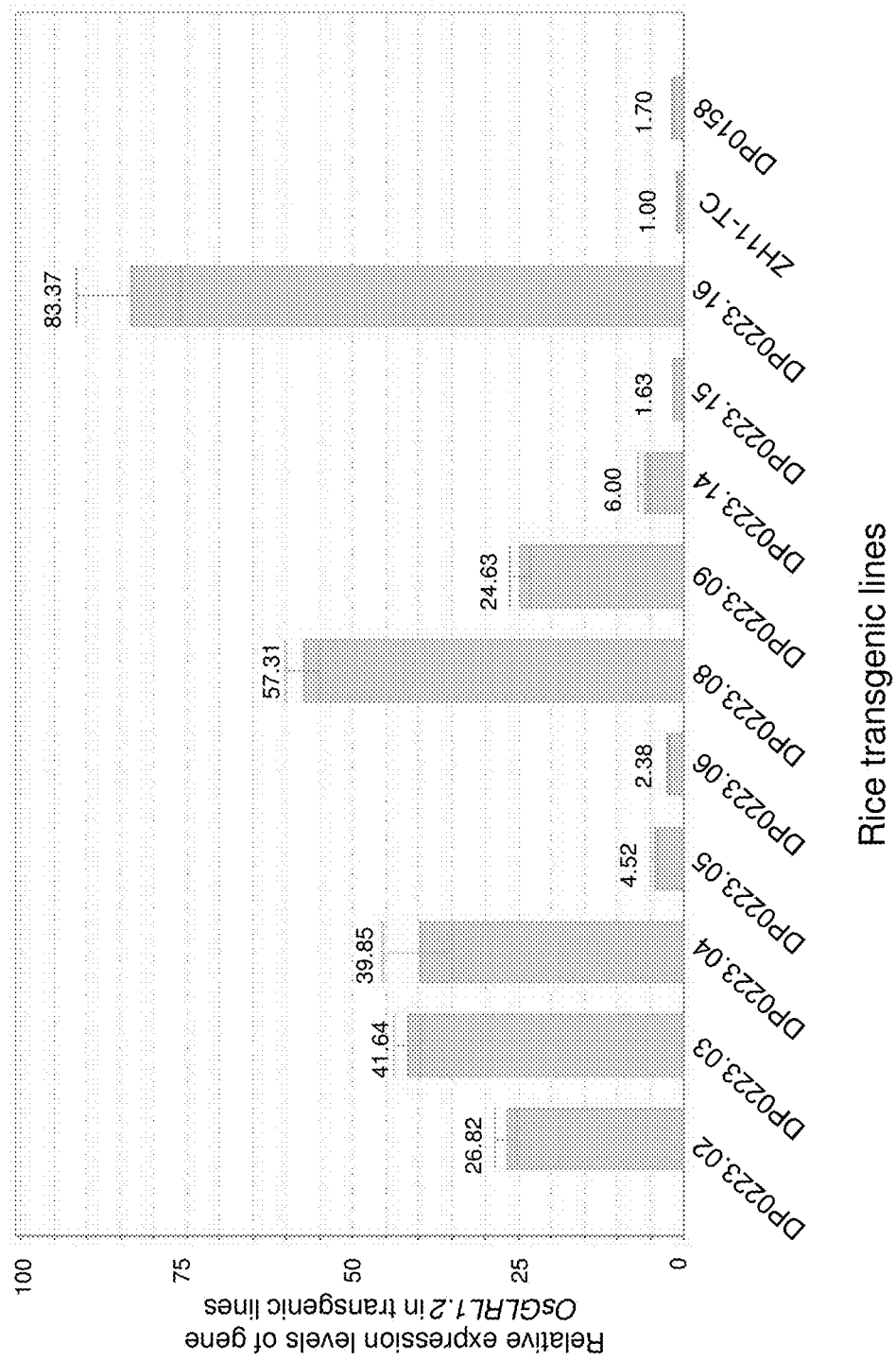

FIG. 7 shows the relative expression levels of OsGLRL1.2 gene in leaves of different transgenic rice lines by real-time PCR analyses. The base expression level in ZH11-TC is set at 1.00, the numbers on the top of the columns are fold-changes compared to ZH11-TC rice. ZH11-TC is tissue cultured ZH11 rice and DP0158 is empty vector transformed ZH11 rice plants.

Figure 8:
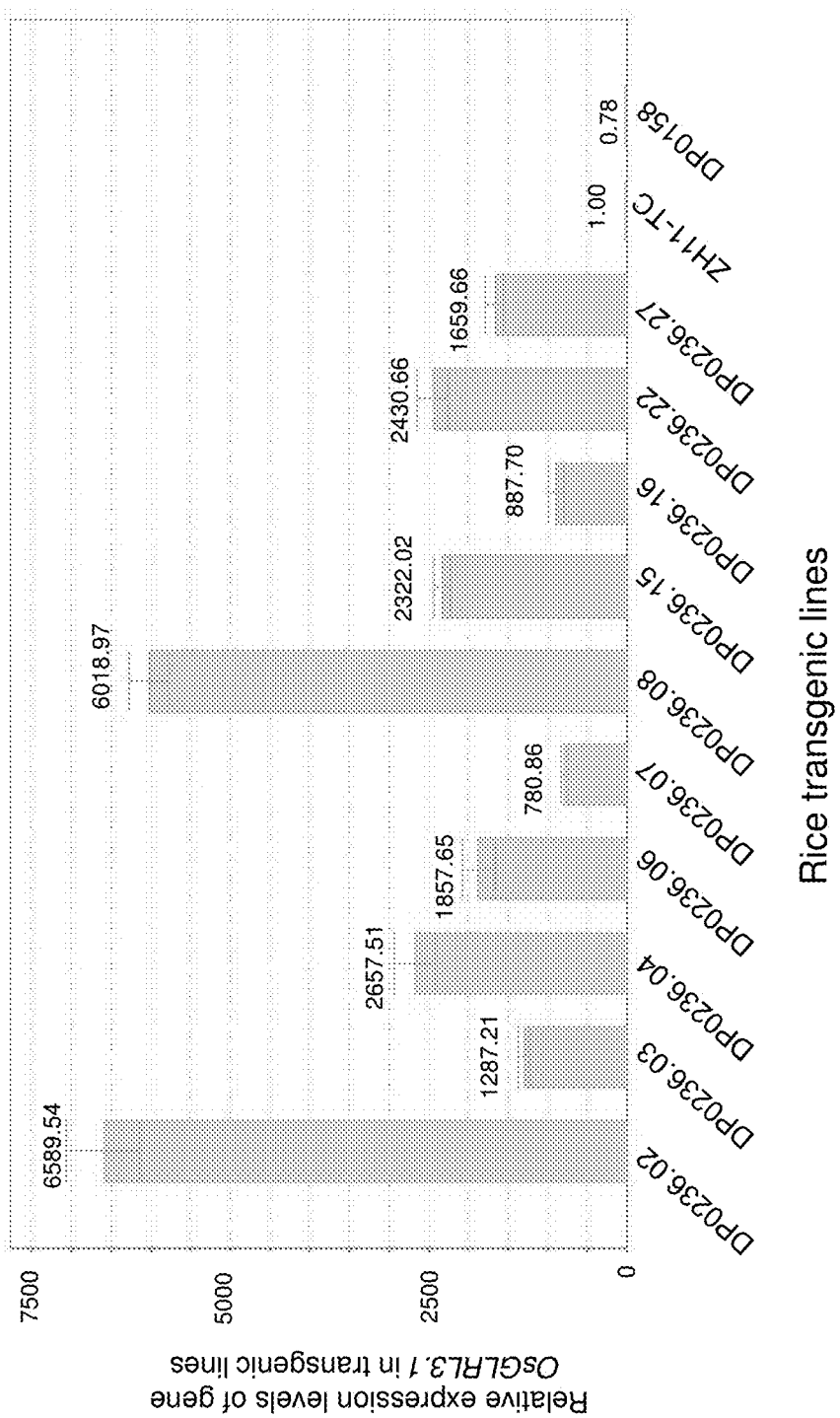

FIG. 8 shows the relative expression levels of OsGLRL3.1 gene in leaves of different transgenic rice lines by real-time PCR analyses. The base expression level in ZH11-TC is set at 1.00, the numbers on the top of the columns are fold-changes compared to ZH11-TC rice. ZH11-TC is tissue cultured ZH11 rice and DP0158 is empty vector transformed ZH11 rice plants.

Figure 9:
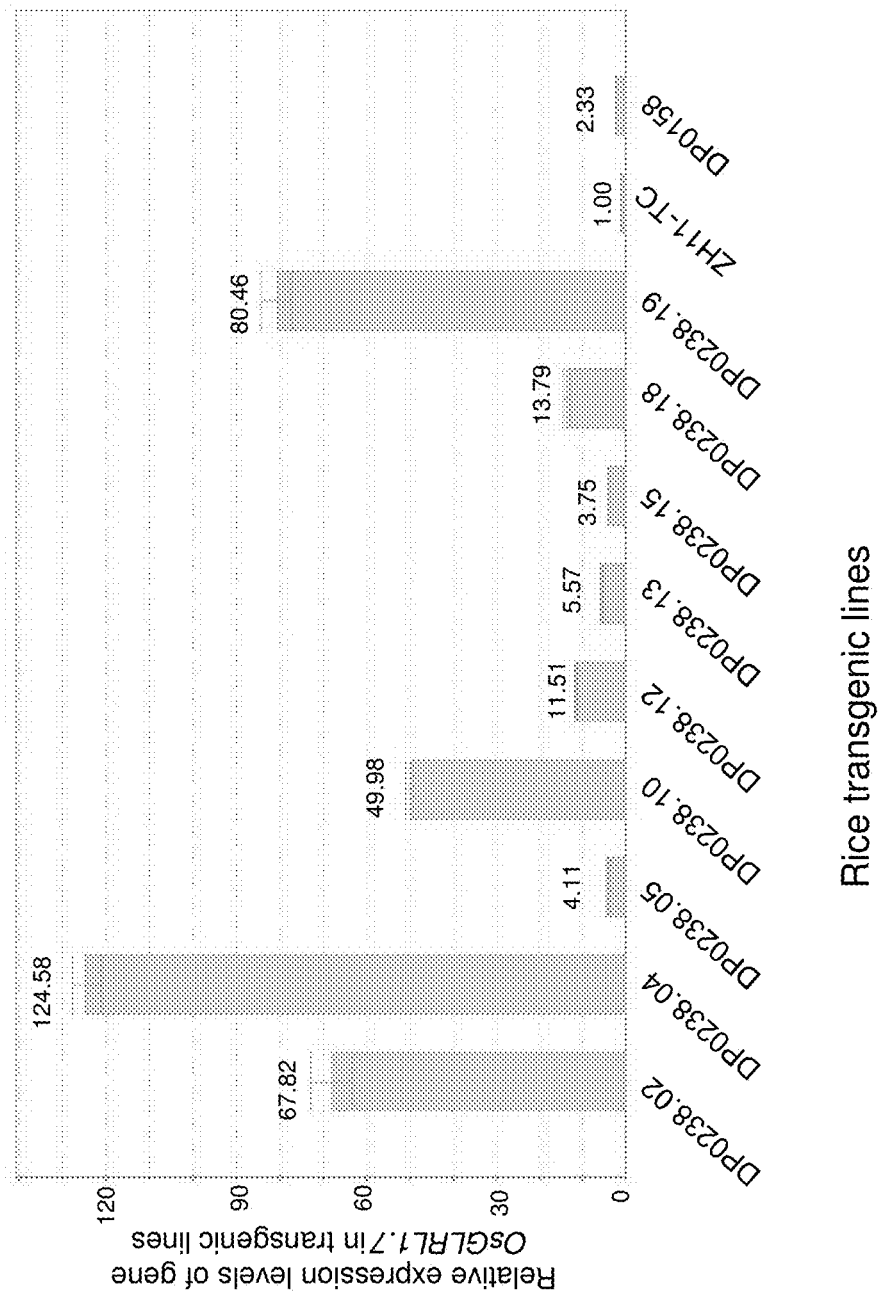

FIG. 9 shows the relative expression levels of OsGLRL1.7 gene in leaves of different transgenic rice lines by real-time PCR analyses. The base expression level in ZH11-TC is set at 1.00, the numbers on the top of the columns are fold-changes compared to ZH11-TC rice. ZH11-TC is tissue cultured ZH11 rice and DP0158 is empty vector transformed ZH11 rice plants.

Figure 10:
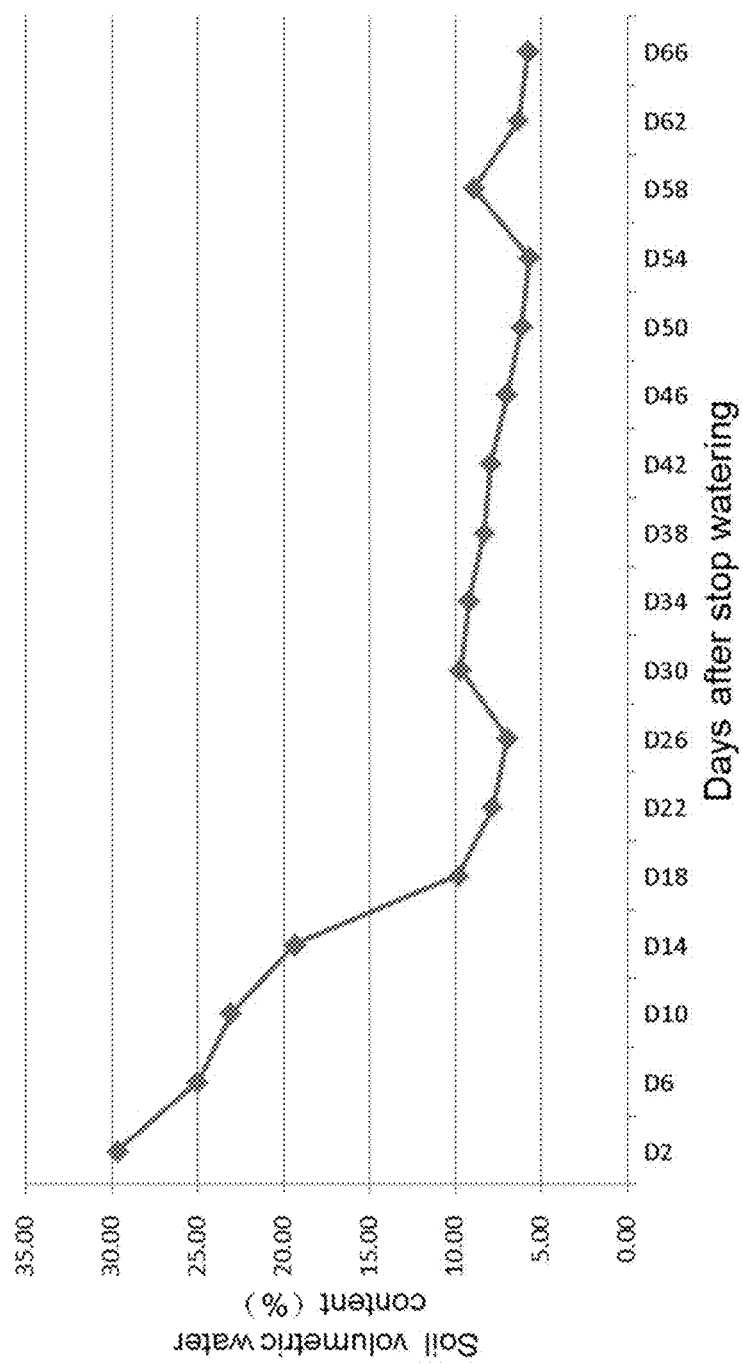

FIG. 10 shows changes of soil volumetric water content at different developmental stage for drought testing OsGLRL1.3 transgenic rice. The OsGLRL1.3 transgenic rice started heading at 45 days after stopping watering.

Figure 11:
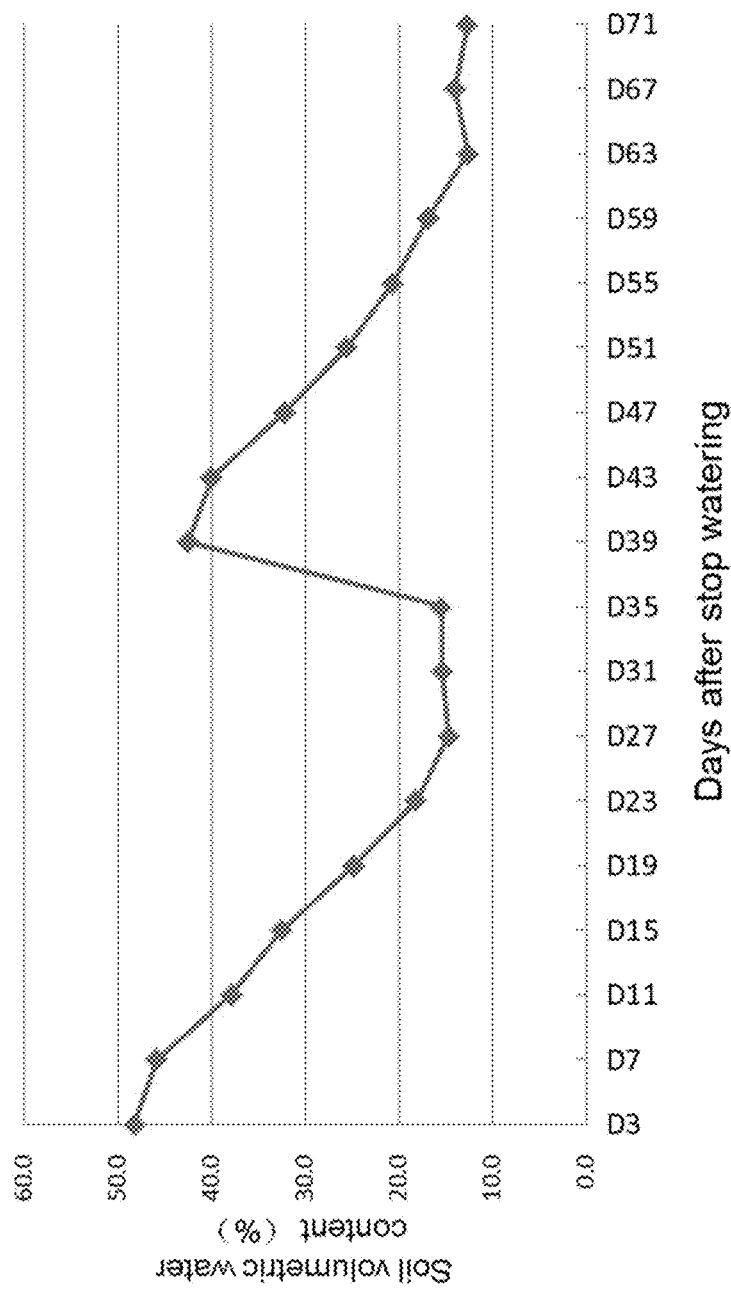

FIG. 11 shows changes of soil volumetric water content at different developmental stage for drought testing OsGLRL3.1 transgenic rice. The OsGLRL3.1 transgenic rice started heading at 31 days after stopping watering. The field is re-watered at Day 35 to avoid total loss of seed.

Table 1. SEQ ID NOs for nucleotide and amino acid sequences provided in the sequence listing Table 2. Rice GLR gene names, Gene IDs (from TIGR) and Construct IDs Table 3. Primers for cloning GLR genes Table 4. PCR reaction mixture Table 5. PCR cycle conditions for cloning GLR genes Table 6. Modified IRRI nutrient solution formula for culturing rice Table 7. Enhanced drought tolerance of OsGLRL1.2 transgenic rice plants under greenhouse conditions ($1^{st}$ experiment)

Table 8. Enhanced drought tolerance of OsGLRL1.2 transgenic rice plants under greenhouse conditions ($2^{nd}$ experiment, at construct level)

Table 9. Enhanced drought tolerance of OsGLRL1.2 transgenic rice plants under greenhouse conditions ($2^{nd}$ experiment, at line level)

Table 10. Enhanced drought tolerance of OsGLRL1.2 transgenic rice plants under greenhouse conditions ($3^{rd}$ experiment, at line level)

Table 11. Enhanced drought tolerance of OsGLRL3.1 transgenic rice plants under greenhouse conditions ($1^{st}$ experiment)

Table 12. Enhanced drought tolerance of OsGLRL3.1 transgenic rice plants under greenhouse conditions ($2^{nd}$ experiment)

Table 13. Enhanced drought tolerance of OsGLRL3.1 transgenic rice plants under greenhouse conditions ($3^{rd}$ experiment)

Table 14. Paraquat tolerance analysis of OsGLRL1.2 transgenic rice plants at transgenic line level ($1^{st}$ experiment)

Table 15. Paraquat tolerance analysis of OsGLRL1.2 transgenic rice plants at transgenic line level ($2^{nd}$ experiment)

Table 16. Paraquat tolerance analysis of OsGLRL1.3 transgenic rice plants at transgenic line level ($1^{st}$ experiment)

Table 17. Paraquat tolerance analysis of OsGLRL1.3 transgenic rice plants at transgenic line level ($2^{nd}$ experiment)

Table 18. Paraquat tolerance analysis of OsGLRL3.1 transgenic rice plant at transgenic line level ($1^{st}$ experiment)

Table 19. Paraquat tolerance analysis of OsGLRL3.1 transgenic rice plant at transgenic line level ($2^{nd}$ experiment)

Table 20. Paraquat tolerance analysis of OsGLRL2.1 transgenic rice plant at transgenic line level ($1^{st}$ experiment)

Table 21. Paraquat tolerance analysis of OsGLRL2.1 transgenic rice plant at transgenic line level ($2^{nd}$ experiment)

Table 22. Paraquat tolerance analysis of OsGLRL1.7 transgenic rice plant at transgenic line level ($1^{st}$ experiment)

Table 23. Paraquat tolerance analysis of OsGLRL1.7 transgenic rice plant at transgenic line level ($2^{nd}$ experiment)

Table 24. Paraquat tolerance analysis of OsGLR3.2 transgenic rice plant at transgenic line level ($1^{St}$ experiment)

Table 25. Paraquat tolerance analysis of OsGLR3.2 transgenic rice plant at transgenic line level ($2^{nd}$ experiment)

Table 26. Grain yield analysis of OsGLRL1.3 rice plants under field drought conditions Table 27. Grain yield analysis of OsGLRL3.1 rice plants under field drought conditions Table 28. Grain yield analysis of OsGLRL3.1 transgenic rice under field low nitrogen condition Table 29. Grain yield analysis of OsGLRL3.1 transgenic rice under field normal nitrogen condition Table 30. Biomass analysis of OsGLRL3.1 transgenic rice under low nitrogen condition Table 31. Plant height analysis of OsGLRL3.1 transgenic rice under low nitrogen condition Table 32. Plant height analysis of OsGLRL3.1 transgenic rice under normal nitrogen condition Table 33. Modified Hoagland's nutrient solution for culturing *Arabidopsis*

TABLE 1

SEQ ID NOs for nucleotide and amino acid sequences provided in the sequence listing

| Source species | Clone Designation | SEQ ID NO: (Nucleotide) | SEQ ID NO: (Amino Acid) |
|---|---|---|---|
| Artificial | DP0158 vector | 1 | n/a |
| Artificial | PHP64464 | 2 | n/a |
| Artificial | pBC-Yellow | 3 | n/a |
| Oryza sativa | OsGLR2.2 | 4, 5 | 6 |
| Oryza sativa | OsGLR3.2 | 7, 8 | 9 |
| Oryza sativa | OsGLRL1.2 | 10, 11 | 12 |
| Oryza sativa | OsGLRL1.3 | 13, 14 | 15 |
| Oryza sativa | OsGLRL1.7 | 16, 17 | 18 |
| Oryza sativa | OsGLRL2.1 | 19, 20 | 21 |
| Oryza sativa | OsGLRL3.1 | 22 23 | 24 |
| Artificial | Primers | 25-48 | n/a |

The Sequence Listing contains the one-letter code for nucleotide sequences and the three-letter code for amino acid sequences as defined in conformity with the IUPAC-IUBMB standards described in *Nucleic Acids Res.* 13:3021-3030 (1985) and in the *Biochemical J.* 219 (No. 2):345-373 (1984) which are herein incorporated by reference. The symbols and format used for nucleotide and amino acid sequence data comply with the rules set forth in 37 C.F.R. § 1.822.

Figure 1:
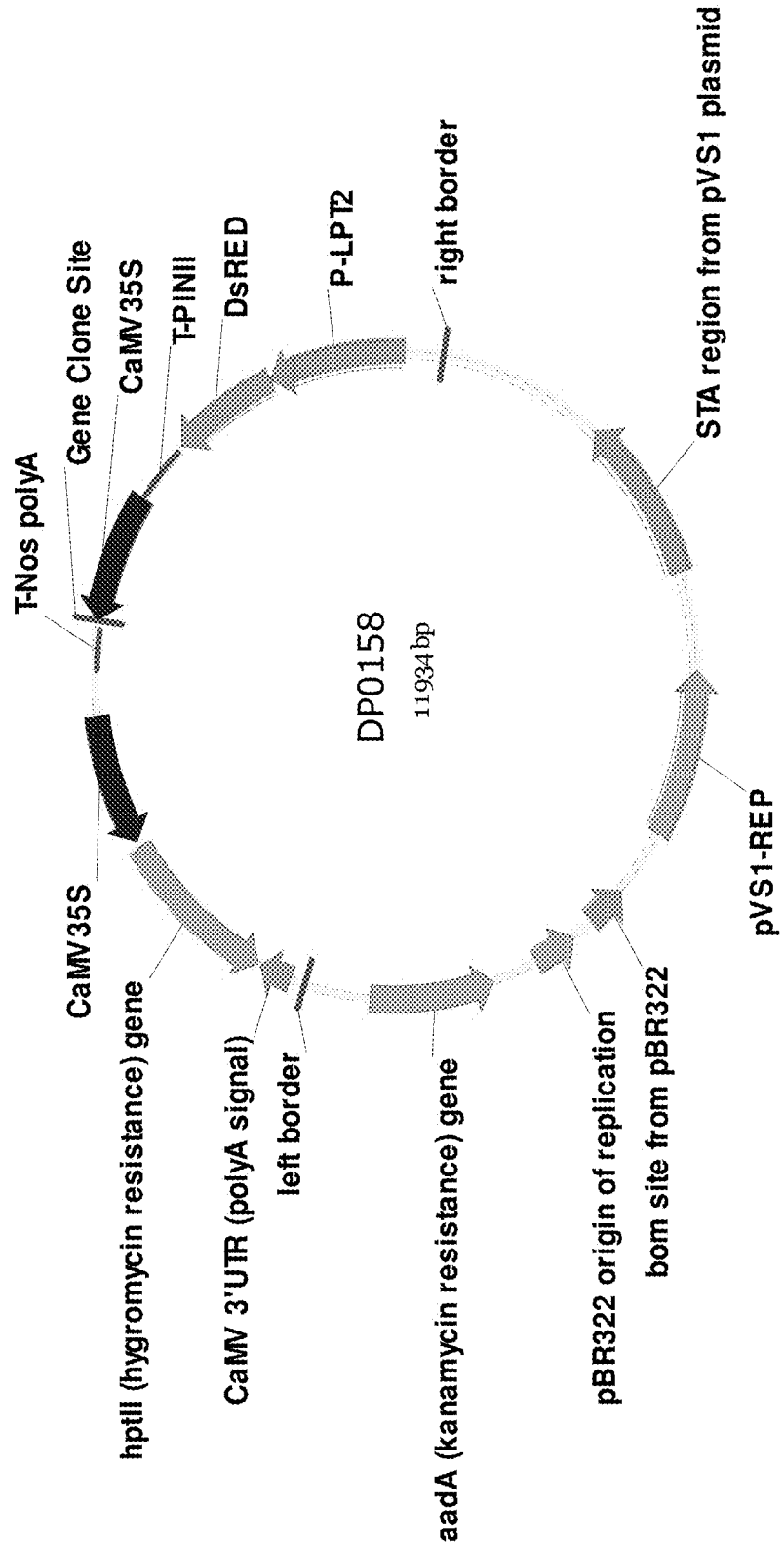
FIG. 1 shows a schematic of the vector DP0158 (pCAMBIA1300-DsRed) (SEQ ID NO: 1), a destination vector for use in construction of expression vector in rice. The CaMV 35S promoter driving the rice gene is located at nucleotide 299-1078 (complementary strand); the T-Nos polyA terminator is located at nucleotide 8-243 (complementary strand).

SEQ ID NO: 1 is the nucleotide sequence of the empty vector DP0158 (FIG. 1).

Figure 2:
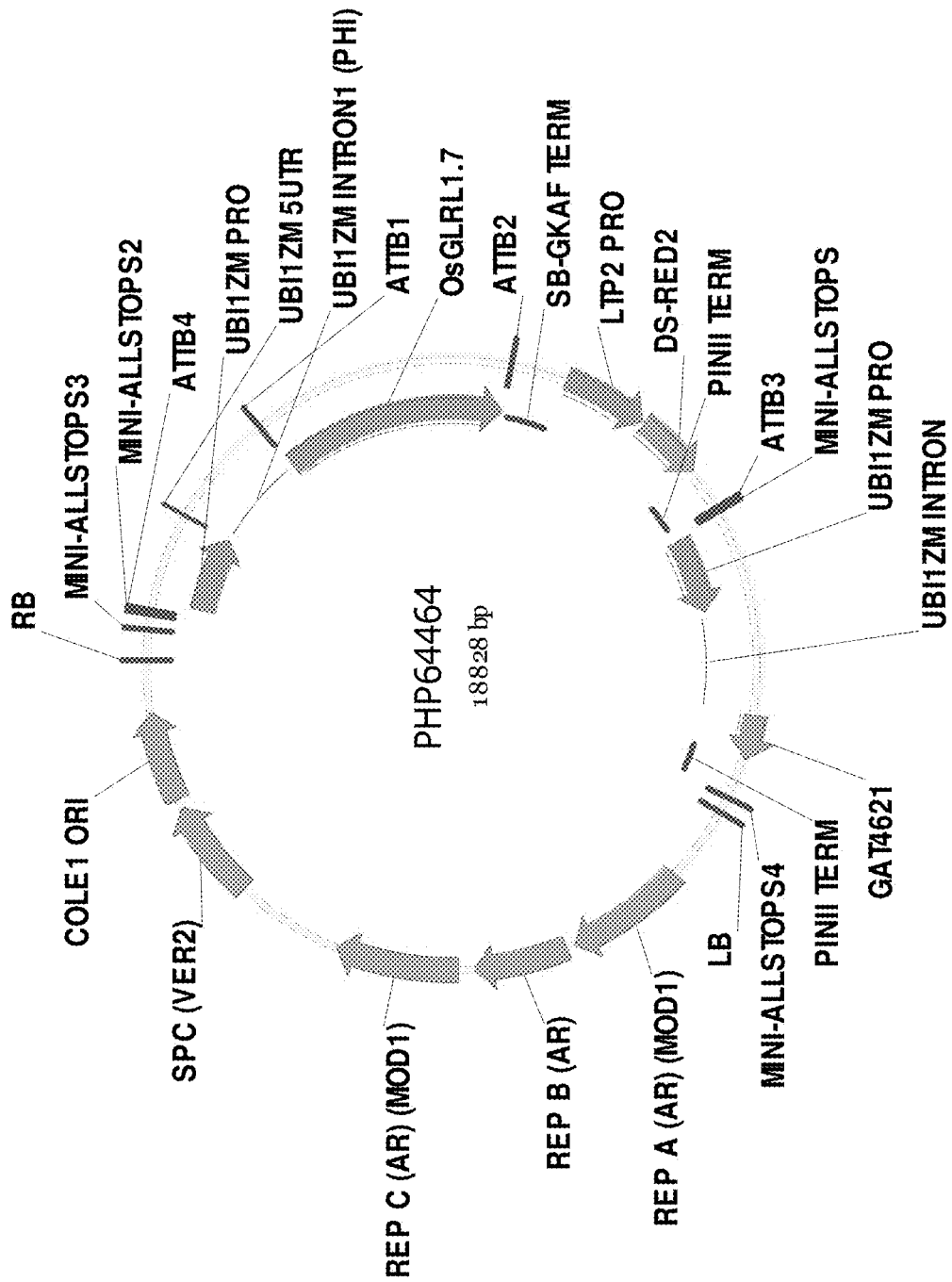
FIG. 2 shows a schematic of the vector PHP64464 (SEQ ID NO: 2)

SEQ ID NO: 2 is the nucleotide sequence of PHP64464 (FIG. 2).

Figure 3:
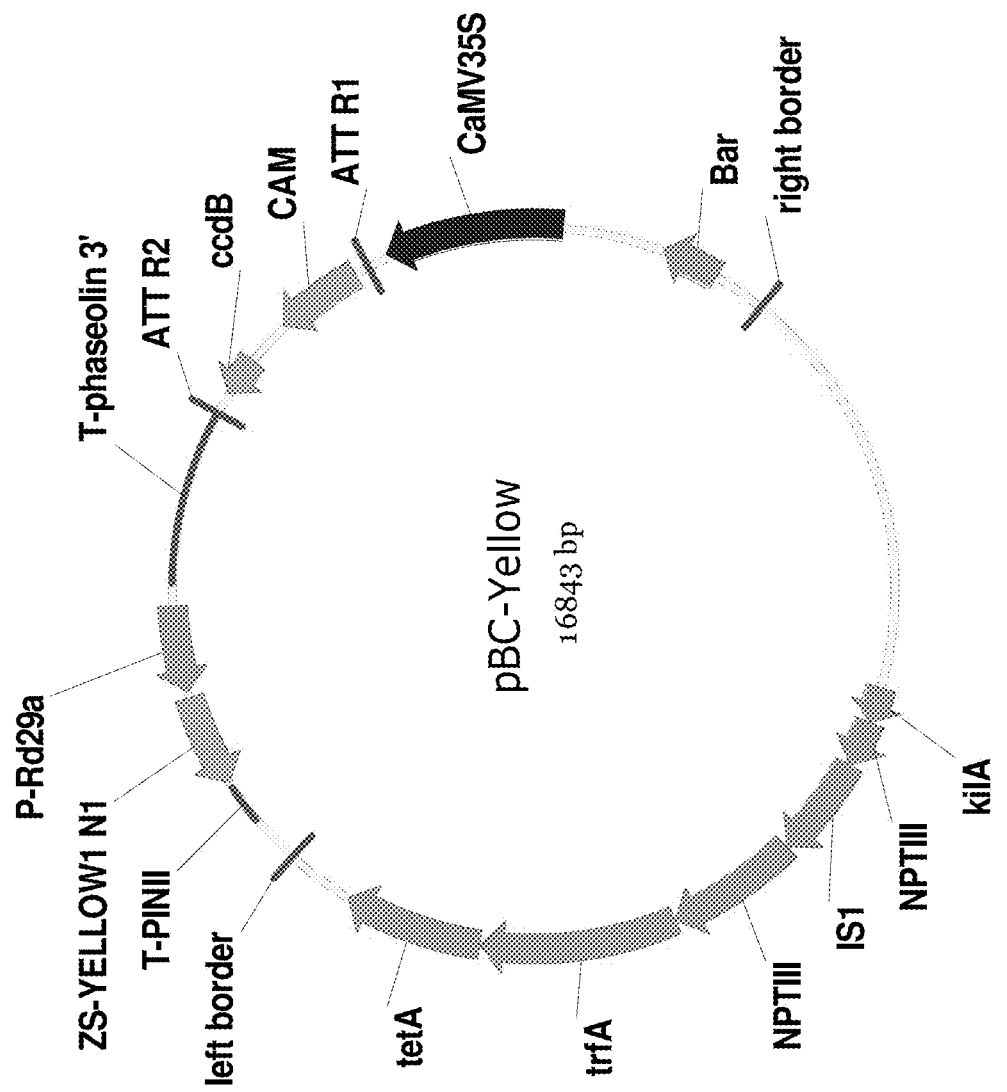
FIG. 3 shows a schematic of the vector pBC-yellow (SEQ ID NO: 3), a destination vector for use in construction of expression vectors in *Arabidopsis*. The attR1 is located at nucleotides 11276-11399 (complementary strand); the attR2 is located at nucleotides 9695-9819 (complementary strand).

SEQ ID NO: 3 is the nucleotide sequence of the pBC-yellow vector (FIG. 3).

SEQ ID NO: 4 is the nucleotide sequence of gDNA of OsGLR2.2 gene.

SEQ ID NO: 5 is the nucleotide sequence of CDS of OsGLR2.2 gene.

SEQ ID NO: 6 is the amino acid sequence of OsGLR2.2.

SEQ ID NO: 7 is the nucleotide sequence of gDNA of OsGLR3.2 gene.

SEQ ID NO: 8 is the nucleotide sequence of CDS of OsGLR3.2 gene.

SEQ ID NO: 9 is the amino acid sequence of OsGLR3.2.

SEQ ID NO: 10 is the nucleotide sequence of cDNA of OsGLRL1.2 gene.

SEQ ID NO: 11 is the nucleotide sequence of CDS of OsGLRL1.2 gene.

SEQ ID NO: 12 is the amino acid sequence of OsGLRL1.2.

SEQ ID NO: 13 is the nucleotide sequence of gDNA of OsGLRL1.3 gene.

SEQ ID NO: 14 is the nucleotide sequence of CDS of OsGLRL1.3 gene.

SEQ ID NO: 15 is the amino acid sequence of OsGLRL1.3.

SEQ ID NO: 16 is the nucleotide sequence of gDNA of OsGLRL1.7 gene.

SEQ ID NO: 17 is the nucleotide sequence of CDS of OsGLRL1.7 gene.

SEQ ID NO: 18 is the amino acid sequence of OsGLRL1.7.

SEQ ID NO: 19 is the nucleotide sequence of gDNA of OsGLRL2.1 gene.

SEQ ID NO: 20 is the nucleotide sequence of CDS of OsGLRL2.1 gene.

SEQ ID NO: 21 is the amino acid sequence of OsGLRL2.1.

SEQ ID NO: 22 is the nucleotide sequence of gDNA of OsGLRL3.1 gene.

SEQ ID NO: 23 is the nucleotide sequence of CDS of OsGLRL3.1 gene.

SEQ ID NO: 24 is the amino acid sequence of OsGLRL3.1.

SEQ ID NO: 25 is forward primer for cloning gDNA of OsGLR2.2.

SEQ ID NO: 26 is reverse primer for cloning gDNA of OsGLR2.2.

SEQ ID NO: 27 is forward primer for cloning gDNA of OsGLR3.2.

SEQ ID NO: 28 is reverse primer for cloning gDNA of OsGLR3.2.

SEQ ID NO: 29 is forward primer for cloning cDNA of OsGLRL1.2.

SEQ ID NO: 30 is reverse primer for cloning cDNA of OsGLRL1.2.

SEQ ID NO: 31 is forward primer for cloning gDNA of OsGLRL1.3.

SEQ ID NO: 32 is reverse primer for cloning gDNA of OsGLRL1.3.

SEQ ID NO: 33 is forward primer for cloning gDNA of OsGLRL1.7.

SEQ ID NO: 34 is reverse primer for cloning gDNA of OsGLRL1.7.

SEQ ID NO: 35 is forward primer for cloning gDNA of OsGLRL2.1.

SEQ ID NO: 36 is reverse primer for cloning gDNA of OsGLRL2.1.

SEQ ID NO: 37 is forward primer for cloning gDNA of OsGLRL3.1.

SEQ ID NO: 38 is reverse primer for cloning gDNA of OsGLRL3.1.

SEQ ID NO: 39 is forward primer for real-time RT-PCR analysis of OsGLRL2.1 gene.

SEQ ID NO: 40 is reverse primer for real-time RT-PCR analysis of OsGLRL2.1 gene.

SEQ ID NO: 41 is forward primer for real-time RT-PCR analysis of OsGLRL1.3 gene.

SEQ ID NO: 42 is reverse primer for real-time RT-PCR analysis of OsGLRL1.3 gene.

SEQ ID NO: 43 is forward primer for real-time RT-PCR analysis of OsGLRL1.2 gene.

SEQ ID NO: 44 is reverse primer for real-time RT-PCR analysis of OsGLRL1.2 gene.

SEQ ID NO: 45 is forward primer for real-time RT-PCR analysis of OsGLRL3.1 gene.

SEQ ID NO: 46 is reverse primer for real-time RT-PCR analysis of OsGLRL3.1 gene.

SEQ ID NO: 47 is forward primer for real-time RT-PCR analysis of OsGLRL1.7 gene.

SEQ ID NO: 48 is reverse primer for real-time RT-PCR analysis of OsGLRL1.7 gene.

DETAILED DESCRIPTION

The disclosure of each reference set forth herein is hereby incorporated by reference in its entirety.

As used herein and in the appended claims, the singular forms "a", "an", and "the" include plural reference unless the context clearly dictates otherwise. Thus, for example, reference to "a plant" includes a plurality of such plants;

reference to "a cell" includes one or more cells and equivalents thereof known to those skilled in the art, and so forth.

As used herein:

"GLR polypeptide" refers to glutamate receptor polypeptide encoded by glutamate receptor-like gene (GLR gene). 24 GLR genes were isolated from rice. Two genes, OsGLR1 and OGLR2 were included in patent application CN201210236405.6.

OsGLR2.2, OsGLR3.2, OsGLRL1.2, OsGLRL1.3, OsGLRL1.7, OsGLRL2.1, and OsGLRL3.1 are examples of GLR polypeptides. In this disclosure, OsGLR2.2 refers to the polypeptide (SEQ ID NO: 6) encoded by SEQ ID NO: 5; OsGLR3.2 refers to the polypeptide (SEQ ID NO: 9) encoded by SEQ ID NO: 8; OsGLRL1.2 refers to the polypeptide (SEQ ID NO: 12) encoded by SEQ ID NO: 11; OsGLRL1.3 refers to the polypeptide (SEQ ID NO: 15) encoded by SEQ ID NO: 14; OsGLRL1.7 refers to the polypeptide (SEQ ID NO: 18) encoded by SEQ ID NO: 17; OsGLRL2.1 refers to the polypeptide (SEQ ID NO: 21) encoded by SEQ ID NO: 20; OsGLRL3.1 refers to the polypeptide (SEQ ID NO: 24) encoded by SEQ ID NO: 23.

The terms "monocot" and "monocotyledonous plant" are used interchangeably herein. A monocot of the current disclosure includes plants of the Gramineae family.

The terms "dicot" and "dicotyledonous plant" are used interchangeably herein. A dicot of the current disclosure includes the following families: Brassicaceae, Leguminosae, and Solanaceae.

The terms "full complement" and "full-length complement" are used interchangeably herein, and refer to a complement of a given nucleotide sequence, wherein the complement and the nucleotide sequence consist of the same number of nucleotides and are 100% complementary.

An "Expressed Sequence Tag" ("EST") is a DNA sequence derived from a cDNA library and therefore represents a sequence which has been transcribed. An EST is typically obtained by a single sequencing pass of a cDNA insert. The sequence of an entire cDNA insert is termed the "Full-Insert Sequence" ("FIS"). A "Contig" sequence is a sequence assembled from two or more sequences that can be selected from, but not limited to, the group consisting of an EST, FIS and PCR sequence. A sequence encoding an entire or functional protein is termed a "Complete Gene Sequence" ("CGS") and can be derived from an FIS or a contig.

The term "trait" refers to a physiological, morphological, biochemical, or physical characteristics of a plant or particular plant material or cell. In some instances, this characteristic is visible to the human eye, such as seed or plant size, or can be measured by biochemical techniques, such as detecting the protein, starch, or oil content of seed or leaves, or by observation of a metabolic or physiological process, e.g. by measuring tolerance to water deprivation or particular salt or sugar or nitrogen concentrations, or by the observation of the expression level of a gene or genes, or by agricultural observations such as osmotic stress tolerance or yield.

"Agronomic characteristics" is a measurable parameter including but not limited to: greenness, grain yield, growth rate, total biomass or rate of accumulation, fresh weight at maturation, dry weight at maturation, fruit yield, seed yield, total plant nitrogen content, fruit nitrogen content, seed nitrogen content, nitrogen content in a vegetative tissue, total plant free amino acid content, fruit free amino acid content, seed free amino acid content, free amino acid content in a vegetative tissue, total plant protein content, fruit protein content, seed protein content, protein content in a vegetative tissue, drought tolerance, nitrogen uptake, root lodging, harvest index, stalk lodging, plant height, ear height, ear length, salt tolerance, tiller number, panicle size, early seedling vigor and seedling emergence under low temperature stress.

Increased biomass can be measured, for example, as an increase in plant height, plant total leaf area, plant fresh weight, plant dry weight or plant seed yield, as compared with control plants.

The ability to increase the biomass or size of a plant would have several important commercial applications. Crop cultivars may be developed to produce higher yield of the vegetative portion of the plant, to be used in food, feed, fiber, and/or biofuel.

Increased leaf size may be of particular interest. Increased leaf biomass can be used to increase production of plant-derived pharmaceutical or industrial products. Increased tiller number may be of particular interest and can be used to increase yield. An increase in total plant photosynthesis is typically achieved by increasing leaf area of the plant. Additional photosynthetic capacity may be used to increase the yield derived from particular plant tissue, including the leaves, roots, fruits or seed, or permit the growth of a plant under decreased light intensity or under high light intensity.

Modification of the biomass of another tissue, such as root tissue, may be useful to improve a plant's ability to grow under harsh environmental conditions, including drought or nutrient deprivation, because larger roots may better reach or take up water or nutrients.

For some ornamental plants, the ability to provide larger varieties would be highly desirable. For many plants, including fruit-bearing trees, trees that are used for lumber production, or trees and shrubs that serve as view or wind screens, increased stature provides improved benefits, such as in the forms of greater yield or improved screening.

"Transgenic" refers to any cell, cell line, callus, tissue, plant part or plant, the genome of which has been altered by the presence of a heterologous nucleic acid, such as a recombinant DNA construct, including those initial transgenic events as well as those created by sexual crosses or asexual propagation from the initial transgenic event. The term "transgenic" used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

A "control" or "control plant" or "control plant cell" provides a reference point for measuring changes in phenotype of a subject plant or plant cell in which genetic alteration, such as transformation, has been effected as to a gene of interest. A subject plant or plant cell may be descended from a plant or cell so altered and will comprise the alteration.

A control plant or plant cell may comprise, for example: (a) a wild-type plant or cell, i.e., of the same genotype as the starting material for the genetic alteration which resulted in the subject plant or cell; (b) a plant or plant cell of the same genotype as the starting material but which has been transformed with a null construct (i.e., with a construct which has no known effect on the trait of interest, such as a construct comprising a marker gene); (c) a plant or plant cell which is a non-transformed segregant among progeny of a subject plant or plant cell; (d) a plant or plant cell genetically identical to the subject plant or plant cell but which is not exposed to a condition or stimulus that would induce expression of the gene of interest; or (e) the subject plant or plant cell itself, under conditions in which the gene of interest is not expressed.

"Genome" as it applies to plant cells encompasses not only chromosomal DNA found within the nucleus, but also organelle DNA found within subcellular components (e.g., mitochondria, plastid) of the cell.

"Plant" includes reference to whole plants, plant organs, plant tissues, seeds and plant cells and progeny of the same. Plant cells include, without limitation, cells from seeds, suspension cultures, embryos, meristematic regions, callus tissues, leaves, roots, shoots, gametophytes, sporophytes, pollen, and microspores.

"Progeny" comprises any subsequent generation of a plant.

"Transgenic plant" includes reference to a plant which comprises within its genome a heterologous polynucleotide. For example, the heterologous polynucleotide is stably integrated within the genome such that the polynucleotide is passed on to successive generations. The heterologous polynucleotide may be integrated into the genome alone or as part of a recombinant DNA construct. A $T_0$ plant is directly recovered from the transformation and regeneration process. Progeny of $T_0$ plants are referred to as $T_1$ (first progeny generation), $T_2$ (second progeny generation), etc.

"Heterologous" with respect to sequence means a sequence that originates from a foreign species, or, if from the same species, is substantially modified from its native form in composition and/or genomic locus by deliberate human intervention.

"Polynucleotide", "nucleic acid sequence", "nucleotide sequence", and "nucleic acid fragment" are used interchangeably and refer to a polymer of RNA or DNA that is single- or double-stranded, optionally containing synthetic, non-natural or altered nucleotide bases. Nucleotides (usually found in their 5'-monophosphate form) are referred to by their single-letter designation as follows: "A" for adenylate or deoxyadenylate, "C" for cytidylate or deoxycytidylate, and "G" for guanylate or deoxyguanylate for RNA or DNA, respectively; "U" for uridylate; "T" for deoxythymidylate; "R" for purines (A or G); "Y" for pyrimidines (C or T); "K" for G or T; "H" for A or C or T; "I" for inosine; and "N" for any nucleotide.

"Polypeptide", "peptide", "amino acid sequence" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The terms "polypeptide", "peptide", "amino acid sequence", and "protein" are also inclusive of modifications including, but not limited to, glycosylation, lipid attachment, and sulfation, gamma-carboxylation of glutamic acid residues, hydroxylation and ADP-ribosylation.

"Messenger RNA (mRNA)" refers to the RNA which has no intron and can be translated into protein by the cell.

"cDNA" refers to a DNA that is complementary to and synthesized from an mRNA template using reverse transcriptase. The cDNA can be single-stranded or converted into the double-stranded form using the Klenow fragment of DNA polymerase I.

"Mature" protein refers to a post-translationally processed polypeptide; i.e., any pre- or pro-peptides present in the primary translation product has been removed.

"Precursor" protein refers to the primary product of translation of mRNA; i.e., with pre- and pro-peptides still present. Pre- and pro-peptides may be and are not limited to intracellular localization signals.

"Isolated" refers to materials, such as nucleic acid molecules and/or proteins, which are substantially free or otherwise removed from components that normally accompany or interact with the materials in a naturally occurring environment. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

"Recombinant" refers to an artificial combination of two otherwise separated segments of sequence, e.g., by chemical synthesis or by the manipulation of isolated segments of nucleic acids by genetic engineering techniques. "Recombinant" also includes reference to a cell or vector, that has been modified by the introduction of a heterogonous nucleic acid or a cell derived from a cell so modified, but does not encompass the alteration of the cell or vector by naturally occurring events (e.g., spontaneous mutation, natural transformation/transduction/transposition) such as those occurring without deliberate human intervention.

"Recombinant DNA construct" refers to a combination of nucleic acid fragments that are not normally found together in nature. Accordingly, a recombinant DNA construct may comprise regulatory sequences and coding sequences that are derived from different sources, or regulatory sequences and coding sequences derived from the same source, but arranged in a manner different than that normally found in nature.

The terms "entry clone" and "entry vector" are used interchangeably herein.

"Regulatory sequences" refer to nucleotide sequences located upstream (5' non-coding sequences), within, or downstream (3' non-coding sequences) of a coding sequence, and influencing the transcription, RNA processing or stability, or translation of the associated coding sequence. Regulatory sequences may include, but are not limited to, promoters, translation leader sequences, introns, and polyadenylation recognition sequences. The terms "regulatory sequence" and "regulatory element" are used interchangeably herein.

"Promoter" refers to a nucleic acid fragment capable of controlling transcription of another nucleic acid fragment.

"Promoter functional in a plant" is a promoter capable of controlling transcription of genes in plant cells whether or not its origin is from a plant cell.

"Tissue-specific promoter" and "tissue-preferred promoter" may refer to a promoter that is expressed predominantly but not necessarily exclusively in one tissue or organ, but that may also be expressed in one specific cell or cell type.

"Developmentally regulated promoter" refers to a promoter whose activity is determined by developmental events.

"Operably linked" refers to the association of nucleic acid fragments in a single fragment so that the function of one is regulated by the other. For example, a promoter is operably linked with a nucleic acid fragment when it is capable of regulating the transcription of that nucleic acid fragment.

"Expression" refers to the production of a functional product. For example, expression of a nucleic acid fragment may refer to transcription of the nucleic acid fragment (e.g., transcription resulting in mRNA or functional RNA) and/or translation of mRNA into a precursor or mature protein.

"Phenotype" means the detectable characteristics of a cell or organism.

"Introduced" in the context of inserting a nucleic acid fragment (e.g., a recombinant DNA construct) into a cell, means "transfection" or "transformation" or "transduction" and includes reference to the incorporation of a nucleic acid fragment into a eukaryotic or prokaryotic cell where the nucleic acid fragment may be incorporated into the genome of the cell (e.g., chromosome, plasmid, plastid or mitochondrial DNA), converted into an autonomous replicon, or transiently expressed (e.g., transfected mRNA).

A "transformed cell" is any cell into which a nucleic acid fragment (e.g., a recombinant DNA construct) has been introduced.

"Transformation" as used herein refers to both stable transformation and transient transformation.

"Stable transformation" refers to the introduction of a nucleic acid fragment into a genome of a host organism resulting in genetically stable inheritance. Once stably transformed, the nucleic acid fragment is stably integrated in the genome of the host organism and any subsequent generation.

"Transient transformation" refers to the introduction of a nucleic acid fragment into the nucleus, or DNA-containing organelle, of a host organism resulting in gene expression without genetically stable inheritance.

An "allele" is one of two or more alternative forms of a gene occupying a given locus on a chromosome. When the alleles present at a given locus on a pair of homologous chromosomes in a diploid plant are the same, that plant is homozygous at that locus. If the alleles present at a given locus on a pair of homologous chromosomes in a diploid plant differ, that plant is heterozygous at that locus. If a transgene is present on one of a pair of homologous chromosomes in a diploid plant, that plant is hemizygous at that locus.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels. (1991) *Ann. Rev. Plant Phys. Plant Mol. Biol.* 42:21-53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel. (1992) *Plant Phys.* 100:1627-1632). A "mitochondrial signal peptide" is an amino acid sequence which directs a precursor protein into the mitochondria (Zhang and Glaser. (2002) *Trends Plant Sci* 7:14-21).

Methods to determine the relationship of various polynucleotide and polypeptide sequences are known. As used herein, "reference sequence" is a defined sequence used as a basis for sequence comparison. A reference sequence may be a subset or the entirety of a specified sequence, such as a segment of a full-length cDNA or gene sequence, or may be the complete cDNA or gene sequence. As used herein, "comparison window" makes reference to a contiguous and specified segment of a polynucleotide or polypeptide sequence, wherein the sequence in the comparison window may comprise additions or deletions (i.e., gaps) compared to the reference sequence (which does not comprise additions or deletions) for optimal alignment of the two sequences. Generally, the comparison window is at least 20 contiguous nucleotides or amino acids in length, and optionally can be 30, 40, 50, 100 or longer. Those of skill in the art understand that to avoid a high similarity to a reference sequence due to inclusion of gaps in the sequence, a gap penalty is typically introduced and is subtracted from the number of matches.

The determination of percent sequence identity between any two sequences can be accomplished using a mathematical algorithm. Examples of such mathematical algorithms for sequence comparison include the algorithm of Myers and Miller. (1988) *CABIOS* 4:11-17; the local alignment algorithm of Smith, et al. (1981) *Adv. Appl. Math.* 2:482; the global alignment algorithm of Needleman and Wunsch. (1970) *J. Mol. Biol.* 48:443-453; the search-for-local alignment method of Pearson and Lipman. (1988) *Proc. Natl. Acad. Sci.* 85:2444-2448; the algorithm of Karlin and Altschul. (1990) *Proc. Natl. Acad. Sci. USA* 872264, modified as in Karlin and Altschul. (1993) *Proc. Natl. Acad. Sci. USA* 90:5873-5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA and TFASTA in the GCG Wisconsin Genetics Software Package, Version 10 (available from Accelrys Inc., 9685 Scranton Road, San Diego, Calif., USA); and the Megalign® program of the LASERGENE® bioinformatics computing suite (DNASTAR® Inc., Madison, Wis.).

Alignments using these programs can be performed using the default parameters. The CLUSTAL program is well described by Higgins, et al. (1988) *Gene* 73:237-244; Higgins, et al. (1989) *CABIOS* 5:151-153; Corpet, et al. (1988) *Nucleic Acids Res.* 16:10881-10890; Huang, et al. (1992) *CABIOS* 8:155-165 and Pearson, et al. (1994) *Meth. Mol. Biol.* 24:307-331. The ALIGN program is based on the algorithm of Myers and Miller, (1988) supra. A PAM120 weight residue table, a gap length penalty of 12 and a gap penalty of 4 can be used with the ALIGN program when comparing amino acid sequences. The BLAST programs of Altschul, et al. (1990) *J. Mol. Biol.* 215:403 are based on the algorithm of Karlin and Altschul. (1990) supra. BLAST nucleotide searches can be performed with the BLASTN program, score=100, wordlength=12, to obtain nucleotide sequences homologous to a nucleotide sequence encoding a protein of the disclosures. BLAST protein searches can be performed with the BLASTX program, score=50, wordlength=3, to obtain amino acid sequences homologous to a protein or polypeptide of the disclosures. To obtain gapped alignments for comparison purposes, Gapped BLAST (in BLAST 2.0) can be utilized as described in Altschul, et al. (1997) *Nucleic Acids Res.* 25:3389. Alternatively, PSI-BLAST (in BLAST 2.0) can be used to perform an iterated search that detects distant relationships between molecules (Altschul, et al. (1997) supra). When utilizing BLAST, Gapped BLAST, PSI-BLAST and the default parameters of the respective programs (e.g., BLASTN for nucleotide sequences, BLASTX for proteins) can be used (the National Center for Biotechnology Information of the National Library of Medicine of the National Institutes of Health of the U.S. government). Alignment may also be performed by manual inspection.

Paired sequence identity/similarity values can be obtained using GAP Version 10 with the following parameters: % identity and % similarity for a nucleotide sequence using GAP Weight of 50 and Length Weight of 3 and the nwsgapdna.cmp scoring matrix; % identity and % similarity for an amino acid sequence using GAP Weight of 8 and Length Weight of 2, and the BLOSUM62 scoring matrix; or any equivalent program thereof. By "equivalent program" is intended any sequence comparison program that, for any two sequences in question, generates an alignment having identical nucleotide or amino acid residue matches and an identical percent sequence identity when compared to the corresponding alignment generated by GAP Version 10.

GAP uses the algorithm of Needleman and Wunsch. (1970) *J. Mol. Biol.* 48:443-453, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the GCG Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater.

GAP presents one member of the family of best alignments. There may be many members of this family, but no other member has a better quality. GAP displays four figures of merit for alignments: Quality, Ratio, Identity and Similarity. The Quality is the metric maximized in order to align the sequences. Ratio is the Quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the GCG Wisconsin Genetics Software Package is BLOSUM62 (Henikoff and Henikoff. (1989) *Proc. Natl. Acad. Sci. USA* 89:10915).

Unless stated otherwise, multiple alignments of the sequences provided herein are performed using the Clustal V method of alignment (Higgins and Sharp. (1989) CABIOS. 5:151-153) with the default parameters (GAP PENALTY=10, GAP LENGTH PENALTY=10). Default parameters for pairwise alignments and calculation of percent identity of amino acid sequences using the Clustal V method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences, using the Clustal V program, it is possible to obtain "percent identity" and "divergence" values by viewing the "sequence distances" table on the same program; unless stated otherwise, percent identities and divergences provided and claimed herein were calculated in this manner.

As used herein, "sequence identity" or "identity" in the context of two polynucleotides or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

As used herein, "percentage of sequence identity" is calculated by determining the number of positions at which the identical nucleic acid base or amino acid residue occurs in both sequences to yield the number of matched positions, dividing the number of matched positions by the total number of positions in the window of comparison, and multiplying the result by 100.

Standard recombinant DNA and molecular cloning techniques used herein are well known in the art and are described more fully in Sambrook, J., Fritsch, E. F. and Maniatis, T. *Molecular Cloning: A Laboratory Manual*; Cold Spring Harbor Laboratory Press: Cold Spring Harbor, 1989 (hereinafter "Sambrook").

Embodiments include isolated polynucleotides and polypeptides, and recombinant DNA constructs useful for conferring drought tolerance; compositions (such as plants or seeds) comprising these recombinant DNA constructs; and methods utilizing these recombinant DNA constructs.

Isolated Polynucleotides and Polypeptides:

The present disclosure includes the following isolated polynucleotides and polypeptides:

An isolated polynucleotide comprising: (i) a nucleic acid sequence encoding a polypeptide having at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO: 6, 9, 12, 15, 18, 21 or 24; or (ii) a full complement of the nucleic acid sequence of (i), wherein the full complement and the nucleic acid sequence of (i) consist of the same number of nucleotides and are 100% complementary. Any of the foregoing isolated polynucleotides may be utilized in any recombinant DNA constructs of the present disclosure. Over-expression of the encoded polypeptide preferably increases plant drought tolerance activity, paraquat tolerance, and/or NUE.

An isolated polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO: 6, 9, 12, 15, 18, 21 or 24; The polypeptide is preferably a GLR or GLRL polypeptide. Over-expression of the polypeptide preferably increases plant drought tolerance activity, paraquat tolerance and/or NUE.

An isolated polynucleotide comprising (i) a nucleic acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO: 5, 8, 11, 14, 17, 20 or 23; (ii) a nucleic acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO: 4, 7, 10, 13, 16, 19 or 22; or (iii) a full complement of the nucleic acid sequence of (i) or (ii). Any of the foregoing isolated polynucleotides may be utilized in any recombinant DNA constructs of the present disclosure. The isolated polynucleotide preferably encodes a GLR polypeptide. Over-expression of the GLR polypeptide preferably improves plant drought tolerance activity, paraquat tolerance, and/or NUE.

Recombinant DNA Constructs:

In one aspect, the present disclosure includes recombinant DNA constructs.

In one embodiment, a recombinant DNA construct comprises a polynucleotide operably linked to at least one regulatory sequence (e.g., a promoter functional in a plant), wherein the polynucleotide comprises (i) a nucleic acid sequence encoding an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO: 6, 9, 12, 15, 18, 21 or 24; or (ii) a full complement of the nucleic acid sequence of (i).

In another embodiment, a recombinant DNA construct comprises a polynucleotide operably linked to at least one regulatory sequence (e.g., a promoter functional in a plant), wherein said polynucleotide comprises (i) a nucleic acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO: 5, 8, 11, 14, 17, 20 or 23; (ii) a nucleic acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, to SEQ ID NO: 4, 7, 10, 13, 16, 19 or 22; or (iii) a full complement of the nucleic acid sequence of (i) or (ii).

In another embodiment, a recombinant DNA construct comprises a polynucleotide operably linked to at least one regulatory sequence (e.g., a promoter functional in a plant), wherein said polynucleotide encodes a GLR polypeptide. The GLR polypeptide preferably has drought tolerance activity, paraquat tolerance, and/or improved NUE. The GLR polypeptide may be from, for example, *Oryza sativa*, *Arabidopsis thaliana*, *Zea mays*, *Glycine max*, *Glycine tabacina*, *Glycine soja* or *Glycine tomentella*.

It is understood, as those skilled in the art will appreciate, that the disclosure encompasses more than the specific exemplary sequences. Alterations in a nucleic acid fragment which result in the production of a chemically equivalent amino acid at a given site, but do not affect the functional properties of the encoded polypeptide, are well known in the art. For example, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products.

"Suppression DNA construct" is a recombinant DNA construct which when transformed or stably integrated into the genome of the plant, results in "silencing" of a target gene in the plant. The target gene may be endogenous or transgenic to the plant. "Silencing," as used herein with respect to the target gene, refers generally to the suppression of levels of mRNA or protein/enzyme expressed by the target gene, and/or the level of the enzyme activity or protein functionality. The terms "suppression", "suppressing" and "silencing", used interchangeably herein, include lowering, reducing, declining, decreasing, inhibiting, eliminating or preventing. "Silencing" or "gene silencing" does not specify mechanism and is inclusive of, and not limited to, anti-sense, cosuppression, viral-suppression, hairpin suppression, stem-loop suppression, RNAi-based approaches, and small RNA-based approaches.

A suppression DNA construct may comprise a region derived from a target gene of interest and may comprise all or part of the nucleic acid sequence of the sense strand (or antisense strand) of the target gene of interest. Depending upon the approach to be utilized, the region may be 100% identical or less than 100% identical (e.g., at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical) to all or part of the sense strand (or antisense strand) of the gene of interest.

Suppression DNA constructs are well-known in the art, are readily constructed once the target gene of interest is selected, and include, without limitation, cosuppression constructs, antisense constructs, viral-suppression constructs, hairpin suppression constructs, stem-loop suppression constructs, double-stranded RNA-producing constructs, and more generally, RNAi (RNA interference) constructs and small RNA constructs such as sRNA (short interfering RNA) constructs and miRNA (microRNA) constructs.

"Antisense inhibition" refers to the production of antisense RNA transcripts capable of suppressing the expression of the target gene or gene product. "Antisense RNA" refers to an RNA transcript that is complementary to all or part of a target primary transcript or mRNA and that blocks the expression of a target isolated nucleic acid fragment (for example, U.S. Pat. No. 5,107,065). The complementarity of an antisense RNA may be with respect to any part of the specific gene transcript, i.e., at the 5' non-coding sequence, 3' non-coding sequence, introns, or the coding sequence.

"Cosuppression" refers to the production of sense RNA transcripts capable of suppressing the expression of the target gene or gene product. "Sense" RNA refers to RNA transcript that includes the mRNA and can be translated into protein within a cell or in vitro. Cosuppression constructs in plants have been previously designed by focusing on overexpression of a nucleic acid sequence having homology to a native mRNA, in the sense orientation, which results in the reduction of all RNA having homology to the overexpressed sequence (Vaucheret et al. (1998) Plant J. 16:651-659; and Gura. (2000) Nature 404:804-808).

RNA interference (RNAi) refers to the process of sequence-specific post-transcriptional gene silencing (PTGS) in animals mediated by short interfering RNAs (siRNAs) (Fire et al. (1998) Nature 391:806). The corresponding process in plants is commonly referred to as PTGS or RNA silencing and is also referred to as quelling in fungi. The process of PTGS is thought to be an evolutionarily-conserved cellular defense mechanism used to prevent the expression of foreign genes and is commonly shared by diverse flora and phyla (Fire et al. (1999) Trends Genet. 15:358).

Small RNAs play an important role in controlling gene expression, for example, small RNAs regulate many developmental processes which include flowering. It is now possible to engineer changes in gene expression of plant genes by using transgenic constructs which produce small RNAs in the plant.

Small RNAs appear to function by base-pairing to complementary RNA or DNA target sequences. When bound to RNA, small RNAs trigger either RNA cleavage or translational inhibition of the target sequence. When bound to DNA target sequences, it is thought that small RNAs can mediate DNA methylation of the target sequence. The consequence of these events, regardless of the specific mechanism, is that gene expression is inhibited.

MicroRNAs (miRNAs) are noncoding RNAs of about 19 to 24 nucleotides (nt) in length that have been identified in both animals and plants (Lagos-Quintana et al. (2001) Science 294:853-858, Lagos-Quintana et al. (2002)Curr. Biol. 12:735-739; Lau et al. (2001) Science 294:858-862; Lee and Ambros. (2001) Science 294:862-864; Llave et al. (2002) Plant Cell 14:1605-1619; Mourelatos et al. (2002) Genes Dev. 16:720-728; Park et al. (2002)Curr. Biol. 12:1484-1495; Reinhart et al. (2002) Genes. Dev. 16:1616-1626). They are processed from longer precursor transcripts that range in size from approximately 70 to 200 nt, and these precursor transcripts have the ability to form stable hairpin structures.

miRNAs appear to regulate target genes by binding to complementary sequences located in the transcripts produced by these genes. It seems likely that miRNAs can enter at least two pathways of target gene regulation: (1) translational inhibition; and (2) RNA cleavage. miRNAs entering the RNA cleavage pathway are analogous to the 21-25 nt siRNAs generated during RNAi in animals and PTGS in plants, and likely are incorporated into an RNA-induced silencing complex (RISC) that is similar or identical to that seen for RNAi.

Regulatory Sequences:

A recombinant DNA construct (including a suppression DNA construct) of the present disclosure may comprise at least one regulatory sequence.

A regulatory sequence may be a promoter.

A number of promoters can be used in recombinant DNA constructs of the present disclosure. The promoters can be selected based on the desired outcome, and may include constitutive, tissue-specific, inducible, or other promoters for expression in the host organism.

Promoters that cause a gene to be expressed in most cell types at most times are commonly referred to as "constitutive promoters".

High-level, constitutive expression of the candidate gene under control of the 35S or UBI promoter may have pleiotropic effects, although candidate gene efficacy may be estimated when driven by a constitutive promoter. Use of tissue-specific and/or stress-induced promoters may eliminate undesirable effects but retain the ability to enhance drought tolerance. This effect has been observed in Arabidopsis (Kasuga et al. (1999) Nature Biotechnol. 17:287-91).

Suitable constitutive promoters for use in a plant host cell include, for example, the core promoter of the Rsyn7 promoter and other constitutive promoters disclosed in WO 99/43838 and U.S. Pat. No. 6,072,050; the core CaMV 35S promoter (Odell et al. (1985) Nature 313:810-812); rice actin (McElroy et al. (1990) Plant Cell 2:163-171); ubiquitin (Christensen et al. (1989) Plant Mol. Biol. 12:619-632 and Christensen et al. (1992) Plant Mol. Biol. 18:675-689); pEMU (Last et al. (1991) Theor. Appl. Genet. 81:581-588); MAS (Velten et al. (1984) EMBO J. 3:2723-2730); ALS promoter (U.S. Pat. No. 5,659,026), and the like. Other constitutive promoters include, for example, those discussed in U.S. Pat. Nos. 5,608,149; 5,608,144; 5,604,121; 5,569,597; 5,466,785; 5,399,680; 5,268,463; 5,608,142; and 6,177,611.

In choosing a promoter to use in the methods of the disclosure, it may be desirable to use a tissue-specific or developmentally regulated promoter.

A tissue-specific or developmentally-regulated promoter is a DNA sequence which regulates the expression of a DNA sequence selectively in the cells/tissues of a plant, such as in those cells/tissues critical to tassel development, seed set, or both, and which usually limits the expression of such a DNA sequence to the developmental period of interest (e.g. tassel development or seed maturation) in the plant. Any identifiable promoter which causes the desired temporal and spatial expression may be used in the methods of the present disclosure.

Many leaf-preferred promoters are known in the art (Yamamoto et al. (1997) Plant J. 12(2):255-265; Kwon et al. (1994) Plant Physiol. 105:357-367; Yamamoto et al. (1994) Plant Cell Physiol. 35(5):773-778; Gotor et al. (1993) Plant J. 3:509-518; Orozco et al. (1993) Plant Mol. Biol. 23(6): 1129-1138; and Matsuoka et al. (1993) Proc. Natl. Acad. Sci. USA 90(20):9586-9590).

Promoters which are seed or embryo-specific and may be useful in the disclosure include soybean Kunitz trypsin inhibitor (Kti3, Jofuku and Goldberg. (1989) Plant Cell 1:1079-1093), convicilin, vicilin, and legumin (pea cotyledons) (Rerie, W. G., et al. (1991) Mol. Gen. Genet. 259: 149-157; Newbigin, E. J., et al. (1990) Planta 180:461-470; Higgins, T. J. V., et al. (1988) Plant. Mol. Biol. 11:683-695), zein (maize endosperm) (Schemthaner, J. P., et al. (1988) EMBO J. 7:1249-1255), phaseolin (bean cotyledon) (Segupta-Gopalan, C., et al. (1985) Proc. Natl. Acad. Sci. 82:3320-3324), phytohemagglutinin (bean cotyledon) (Voelker, T. et al. (1987) EMBO J. 6:3571-3577), B-conglycinin and glycinin (soybean cotyledon) (Chen, Z-L, et al. (1988) EMBO J. 7:297-302), glutelin (rice endosperm), hordein (barley endosperm) (Marris, C., et al. (1988) Plant Mol. Biol. 10:359-366), glutenin and gliadin (wheat endosperm) (Colot, V., et al. (1987) *EMBO J.* 6:3559-3564). Promoters of seed-specific genes operably linked to heterologous coding regions in chimeric gene constructions maintain their temporal and spatial expression pattern in transgenic plants. Such examples include *Arabidopsis* 2S seed storage protein gene promoter to express enkephalin peptides in *Arabidopsis* and *Brassica napus* seeds (Vanderkerckhove et al. (1989) *Bio/Technology* 7:L929-932), bean lectin and bean beta-phaseolin promoters to express luciferase (Riggs et al. (1989) *Plant Sci.* 63:47-57), and wheat glutenin promoters to express chloramphenicol acetyl transferase (Colot et al. (1987) *EMBO J* 6:3559-3564).

Inducible promoters selectively express an operably linked DNA sequence in response to the presence of an endogenous or exogenous stimulus, for example by chemical compounds (chemical inducers) or in response to environmental, hormonal, chemical, and/or developmental signals. Inducible or regulated promoters include, for example, promoters regulated by light, heat, stress, flooding or drought, phytohormones, wounding, or chemicals such as ethanol, jasmonate, salicylic acid, or safeners.

Promoters for use in certain embodiments include the following: 1) the stress-inducible promoter RD29A (Kasuga et al. (1999) *Nature Biotechnol.* 17:287-291); 2) the stress-inducible promoter Rab17 (Vilardell et al. (1991) *Plant Mol. Bio.* 17:985-993; Kamp Busk et al. (1997) *Plant J* 11(6):1285-1295); 3) the barley promoter B22E whose expression is specific to the pedicel in developing maize kernels ("Primary Structure of a Novel Barley Gene Differentially Expressed in Immature Aleurone Layers". Klemsdal, S. S. et al. (1991) *Mol. Gen. Genet.* 228(1/2):9-16); and 4) maize promoter Zag2 ("Identification and molecular characterization of ZAG1, the maize homolog of the *Arabidopsis* floral homeotic gene AGAMOUS", Schmidt, R. J. et al. (1993) *Plant Cell* 5(7):729-737; "Structural characterization, chromosomal localization and phylogenetic evaluation of two pairs of AGAMOUS-like MADS-box genes from maize", Theissen et al. (1995) *Gene* 156(2):155-166; NCBI GenBank Accession No. X80206)). Zag2 transcripts can be detected 5 days prior to pollination to 7 to 8 days after pollination ("DAP"), and directs expression in the carpel of developing female inflorescences and Ciml which is specific to the nucleus of developing maize kernels. Ciml transcript is detected 4 to 5 days before pollination to 6 to 8 DAP. Other useful promoters include any promoter which can be derived from a gene whose expression is maternally associated with developing female florets.

For the expression of a polynucleotide in developing seed tissue, promoters of particular interest include seed-preferred promoters, particularly early kernel/embryo promoters and late kernel/embryo promoters. Kernel development post-pollination is divided into approximately three primary phases. The lag phase of kernel growth occurs from about 0 to 10-12 DAP. During this phase the kernel is not growing significantly in mass, but rather important events are being carried out that will determine kernel vitality (e.g., number of cells established). The linear grain fill stage begins at about 10-12 DAP and continues to about 40 DAP. During this stage of kernel development, the kernel attains almost all of its final mass, and various storage products (i.e., starch, protein, oil) are produced. Finally, the maturation phase occurs from about 40 DAP to harvest. During this phase of kernel development the kernel becomes quiescent and begins to dry down in preparation for a long period of dormancy prior to germination. As defined herein "early kernel/embryo promoters" are promoters that drive expression principally in developing seed during the lag phase of development (i.e., from about 0 to about 12 DAP). "Late kernel/embryo promoters", as defined herein, drive expression principally in developing seed from about 12 DAP through maturation. There may be some overlap in the window of expression. The choice of the promoter will depend on the ABA-associated sequence utilized and the phenotype desired.

Early kernel/embryo promoters include, for example, Cim1 that is active 5 DAP in particular tissues (WO 00/11177), which is herein incorporated by reference. Other early kernel/embryo promoters include the seed-preferred promoters end1 which is active 7-10 DAP, and end2, which is active 9-14 DAP in the whole kernel and active 10 DAP in the endosperm and pericarp. (WO 00/12733), herein incorporated by reference. Additional early kernel/embryo promoters that find use in certain methods of the present disclosure include the seed-preferred promoter ltp2 (U.S. Pat. No. 5,525,716); maize Zm40 promoter (U.S. Pat. No. 6,403,862); maize nuc1c (U.S. Pat. No. 6,407,315); maize ckx1-2 promoter (U.S. Pat. No. 6,921,815 and US Patent Application Publication Number 2006/0037103); maize led promoter (U.S. Pat. No. 7,122,658); maize ESR promoter (U.S. Pat. No. 7,276,596); maize ZAP promoter (U.S. Patent Application Publication Numbers 20040025206 and 20070136891); maize promoter eep1 (U.S. Patent Application Publication Number 20070169226); and maize promoter ADF4 (U.S. Patent Application No. 60/963,878, filed 7 Aug. 2007).

Additional promoters for regulating the expression of the nucleotide sequences of the present disclosure in plants are stalk-specific promoters, including the alfalfa S2A promoter (GenBank Accession No. EF030816; Abrahams et al. (1995) *Plant Mol. Biol.* 27:513-528) and S2B promoter (GenBank Accession No. EF030817) and the like, herein incorporated by reference.

Promoters may be derived in their entirety from a native gene, or be composed of different elements derived from different promoters found in nature, or even comprise synthetic DNA segments.

Promoters for use in certain embodiments of the current disclosure may include: RIP2, mLIP15, ZmCOR1, Rab17, CaMV 35S, RD29A, B22E, Zag2, SAM synthetase, ubiquitin, CaMV 19S, nos, Adh, sucrose synthase, R-allele, the vascular tissue preferred promoters S2A (Genbank accession number EF030816) and S2B (Genbank accession number EF030817), and the constitutive promoter GOS2 from *Zea mays*; root preferred promoters, such as the maize NAS2 promoter, the maize Cyclo promoter (US 2006/0156439, published Jul. 13, 2006), the maize ROOTMET2 promoter (WO05063998, published Jul. 14, 2005), the CR1BIO promoter (WO06055487, published May 26, 2006), the CRWAQ81 (WO05035770, published Apr. 21, 2005) and the maize ZRP2.47 promoter (NCBI accession number: U38790; GI No. 1063664).

Recombinant DNA constructs of the present disclosure may also include other regulatory sequences, including but not limited to, translation leader sequences, introns, and polyadenylation recognition sequences. In certain embodiments, a recombinant DNA construct further comprises an enhancer or silencer.

An intron sequence can be added to the 5' untranslated region, the protein-coding region or the 3' untranslated region to increase the amount of the mature message that accumulates in the cytosol. Inclusion of a spliceable intron in the transcription unit in both plant and animal expression constructs has been shown to increase gene expression at both the mRNA and protein levels up to 1000-fold (Buchman and Berg. (1988) *Mol. Cell Biol.* 8:4395-4405; Callis et al. (1987) *Genes Dev.* 1:1183-1200).

Any plant can be selected for the identification of regulatory sequences and GLR polypeptide genes to be used in recombinant DNA constructs of the present disclosure. Examples of suitable plant targets for the isolation of genes and regulatory sequences would include but are not limited to alfalfa, apple, apricot, *Arabidopsis*, artichoke, arugula, asparagus, avocado, banana, barley, beans, beet, blackberry, blueberry, broccoli, brussels sprouts, cabbage, canola, cantaloupe, carrot, cassava, castorbean, cauliflower, celery, cherry, chicory, cilantro, citrus, clementines, clover, coconut, coffee, corn, cotton, cranberry, cucumber, Douglas fir, eggplant, endive, escarole, eucalyptus, fennel, figs, garlic, gourd, grape, grapefruit, honey dew, jicama, kiwifruit, lettuce, leeks, lemon, lime, Loblolly pine, linseed, mango, melon, mushroom, nectarine, nut, oat, oil palm, oil seed rape, okra, olive, onion, orange, ornamental plant, palm, papaya, parsley, parsnip, pea, peach, peanut, pear, pepper, persimmon, pine, pineapple, plantain, plum, pomegranate, poplar, potato, pumpkin, quince, radiata pine, radicchio, radish, rapeseed, raspberry, rice, rye, sorghum, Southern pine, soybean, spinach, squash, strawberry, sugarbeet, sugarcane, sunflower, sweet potato, sweetgum, switchgrass, tangerine, tea, tobacco, tomato, triticale, turf, turnip, vine, watermelon, wheat, yams, and zucchini.

Compositions:

A composition of the present disclosure is a plant comprising in its genome any of the recombinant DNA constructs of the present disclosure (such as any of the constructs discussed above). Compositions also include any progeny of the plant, and any seed obtained from the plant or its progeny, wherein the progeny or seed comprises within its genome the recombinant DNA construct. Progeny includes subsequent generations obtained by self-pollination or out-crossing of a plant. Progeny also includes hybrids and inbreds.

In hybrid seed propagated crops, mature transgenic plants can be self-pollinated to produce a homozygous inbred plant. The inbred plant produces seed containing the newly introduced recombinant DNA construct. These seeds can be grown to produce plants that would exhibit an altered agronomic characteristic (e.g., an increased agronomic characteristic optionally under water limiting conditions), or used in a breeding program to produce hybrid seed, which can be grown to produce plants that would exhibit such an altered agronomic characteristic. The seeds may be maize seeds or rice seeds.

The plant may be a monocotyledonous or dicotyledonous plant, for example, a rice or maize or soybean plant, such as a maize hybrid plant or a maize inbred plant. The plant may also be sunflower, sorghum, canola, wheat, alfalfa, cotton, barley, millet, sugar cane or switchgrass.

The recombinant DNA construct may be stably integrated into the genome of the plant.

Particular embodiments include but are not limited to the following:

1. A plant (for example, a rice or maize or soybean plant) comprising in its genome a recombinant DNA construct comprising a polynucleotide operably linked to at least one regulatory sequence, wherein said polynucleotide encodes a polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO: 6, 9, 12, 15, 18, 21 or 24, and wherein said plant exhibits increased drought tolerance, paraquat tolerance, and/or improved NUE when compared to a control plant. The plant may further exhibit an alteration of at least one agronomic characteristic when compared to the control plant.

2. A plant (for example, a rice or maize or soybean plant) comprising in its genome a recombinant DNA construct comprising a polynucleotide operably linked to at least one regulatory sequence, wherein said polynucleotide encodes a GLR polypeptide, and wherein said plant exhibits increased drought tolerance, paraquat tolerance and/or improved NUE when compared to a control plant. The plant may further exhibit an alteration of at least one agronomic characteristic when compared to the control plant.

3. A plant (for example, a rice or maize or soybean plant) comprising in its genome a recombinant DNA construct comprising a polynucleotide operably linked to at least one regulatory sequence, wherein said polynucleotide encodes a GLR polypeptide, and wherein said plant exhibits an alteration of at least one agronomic characteristic when compared to a control plant.

4. Any progeny of the above plants in embodiments 1-3, any seeds of the above plants in embodiments 1-3, any seeds of progeny of the above plants in embodiments 1-3, and cells from any of the above plants in embodiments 1-3 and progeny thereof.

In any of the foregoing embodiments 1-4 or other embodiments, the GLR polypeptide may be from *Oryza sativa, Arabidopsis thaliana, Zea mays, Glycine max, Glycine tabacina, Glycine soja* or *Glycine tomentella*.

In any of the foregoing embodiments 1-4 or other embodiments, the recombinant DNA construct may comprise at least a promoter functional in a plant as a regulatory sequence.

In any of the foregoing embodiments 1-4 or other embodiments, the alteration of at least one agronomic characteristic is either an increase or decrease.

In any of the foregoing embodiments 1-4 or other embodiments, the at least one agronomic characteristic may be selected from the group consisting of greenness, grain yield, growth rate, biomass, fresh weight at maturation, dry weight at maturation, fruit yield, seed yield, total plant nitrogen content, fruit nitrogen content, seed nitrogen content, nitrogen content in a vegetative tissue, total plant free amino acid content, fruit free amino acid content, seed free amino acid content, free amino acid content in a vegetative tissue, total plant protein content, fruit protein content, seed protein content, protein content in a vegetative tissue, drought tolerance, nitrogen uptake, root lodging, harvest index, stalk lodging, plant height, ear height, ear length, salt tolerance, tiller number, panicle size, early seedling vigor and seedling emergence under low temperature stress. For example, the alteration of at least one agronomic characteristic may be an increase in grain yield, greenness or biomass.

In any of the foregoing embodiments 1-4 or other embodiments, the plant may exhibit the alteration of at least one agronomic characteristic when compared, under water limiting conditions, to a control plant.

In any of the foregoing embodiments 1-4 or other embodiments, the plant may exhibit the alteration of at least one agronomic characteristic when compared, under oxidative stress (paraquat) conditions, to a control plant.

In any of the foregoing embodiments 1-4 or other embodiments, the plant may exhibit the alteration of at least one agronomic characteristic when compared, under low nitrogen conditions, to a control plant.

One of ordinary skill in the art is familiar with protocols for simulating nitrogen conditions, whether limiting or non-limiting, and for evaluating plants that have been subjected to simulated or naturally-occurring nitrogen conditions, whether limiting or non-limiting. For example, one can simulate nitrogen conditions by giving plants less nitrogen than normally required or no nitrogen over a period of time, and one can evaluate such plants by looking for differences in agronomic characteristics, e.g., changes in physiological and/or physical condition, including (but not limited to) vigor, growth, size, or root length, or in particular, tiller number, fresh weight, leaf color or leaf area size. Other techniques for evaluating such plants include measuring chlorophyll fluorescence, photosynthetic rates, root growth or gas exchange rates.

"Drought" refers to a decrease in water availability to a plant that, especially when prolonged or when occurring during critical growth periods, can cause damage to the plant or prevent its successful growth (e.g., limiting plant growth or seed yield).

"Drought tolerance" reflects a plant's ability to survive under drought without exhibiting substantial physiological or physical deterioration, and/or its ability to recover when water is restored following a period of drought.

"Drought tolerance activity" of a polypeptide indicates that over-expression of the polypeptide in a transgenic plant confers increased drought tolerance of the transgenic plant relative to a reference or control plant.

"Increased drought tolerance" of a plant is measured relative to a reference or control plant, and reflects ability of the plant to survive under drought conditions with less physiological or physical deterioration than a reference or control plant grown under similar drought conditions, or ability of the plant to recover more substantially and/or more quickly than would a control plant when water is restored following a period of drought.

"Nitrogen limiting conditions", "low nitrogen conditions" and "nitrogen stress" are used interchangeably, refer to conditions where the amount of total available nitrogen (e.g., from nitrates, ammonia, or other known sources of nitrogen) is not sufficient to sustain optimal plant growth and development. Nitrogen limiting conditions will vary depending upon a number of factors, including but not limited to, the particular plant and environmental conditions.

"Nitrogen stress tolerance" is a trait of a plant and refers to the ability of the plant to survive and/or grow better under nitrogen limiting conditions/nitrogen stress.

"Increased nitrogen stress tolerance" of a polypeptide indicates that over-expression of the polypeptide in a transgenic plant confers increased nitrogen stress tolerance of the transgenic plant relative to a reference or control plant.

"Increased nitrogen stress tolerance" of a plant is measured relative to a reference or control plant, reflects ability of the plant to survive and/or grow better under nitrogen limiting conditions, and means that the nitrogen stress tolerance of the plant is increased by any amount or measure when compared to the nitrogen stress tolerance of the reference or control plant.

"Environmental conditions" refer to conditions under which the plant is grown, such as the availability of water, availability of nutrients (for example nitrogen), or the presence of insects or disease.

"NUE" is nitrogen use efficiency and refers to a plant's ability to utilize nitrogen in low or high levels of fertilizer. It reflects plant ability to uptake, assimilate, and/or otherwise utilize nitrogen.

Soil plant analyses development (SPAD) value is SPAD reading which is measured by SPAD-502 plus (a chlorophyll meter, made by KONICA MINOLTA). the SPAD value is relative content of leaf chlorophyll and an important indicator of plant health. Many studies indicated that a significant and positive correlation was observed between leaf nitrogen content and SPAD value (Swain D. K. and Sandip S. J. (2010) *Journal of Agronomy* 9 (2):38-44), and leaf SPAD value is used as index of nitrogen status diagnosis in crops (Cai H.-G. et al. (2010) *Acta metallurgica sinica* 16 (4): 866-873).

"Paraquat" (1,1-dimethyl-4,4-bipyridinium dichloride), is a foliar-applied and non-selective bipyridinium herbicides, and causes photooxidative stress which further cause damage to plant or prevent its successful growth.

"Paraquat tolerance" is a trait of a plant, reflects the ability to survive and/or grow better when treated with Paraquat solution, compared to a reference or control plant.

"Increased paraquat tolerance" of a plant is measured relative to a reference or control plant, and reflects ability of the plant to survive with less physiological or physical deterioration than a reference or control plant after treated with paraquat solution. In general, tolerance to relative low level of paraquat can be used as a marker of abiotic stress tolerance, such as drought tolerance.

"Oxidative stress" reflects an imbalance between the systemic manifestation of reactive oxygen species and a biological system's ability to readily detoxify the reactive intermediates or to repair the resulting damage. Disturbances in the normal redox state of cells can cause toxic effects through the production of peroxides and free radicals that damage all components of the cell, including proteins, lipids, and DNA.

"Chlorate" refers to a chemical compound containing chlorate anion, is salt of chloric acid. It is a nitrate analog which can be uptake by plant with same transport system like nitrate, and then reduced to chlorite by nitrate reductase which is toxic and lead to plant damage, wither, dead. Potassium chlorate is used in this disclosure.

"Chlorate sensitivity" is a trait of plant, reflects the level of damage, even dead after chlorate uptake, transport or reduction when treated with chlorate solution, compared to a reference or control plant.

"Increased Chlorate sensitivity" of a plant is measured relative to a reference or control plant, and reflects higher ability of the plant to chlorate or nitrate uptake, transport or reduction than a reference or control plant in chlorate or nitrate solution. In general, chlorate sensitivity can be used as a marker of NUE. The more sensitive of plants to chlorate, the higher NUE.

"Chlorate sensitive seedlings" are the damaged seedlings with phenotype of withered leaves in whole and without green leaf, and considered as dead after treated with chlorate solution.

The Examples below describe some representative protocols and techniques for simulating drought conditions and/or evaluating drought tolerance; simulating oxidative conditions; and simulating nitrogen limiting conditions.

One can also evaluate drought tolerance by the ability of a plant to maintain sufficient yield (at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% yield) in field testing under simulated or naturally-occurring drought conditions (e.g., by measuring for substantially equivalent yield under drought conditions compared to non-drought conditions, or by measuring for less yield loss under drought conditions compared to yield loss exhibited by a control or reference plant).

One can also evaluate nitrogen stress tolerance by the ability of a plant to maintain sufficient yield (at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% yield) in field testing under simulated or naturally-occurring low or high nitrogen conditions (e.g., by measuring for substantially equivalent yield under low or high nitrogen conditions compared to normal nitrogen conditions, or by measuring for less yield loss under low or high nitrogen conditions compared to a control or reference plant).

Parameters such as recovery degree, survival rate, paraquat tolerance rate, tiller number, SPAD value, fresh weight, chlorate sensitive rate, gene expression level, water use efficiency, level or activity of an encoded protein, and others are typically presented with reference to a control cell or control plant. A "control" or "control plant" or "control plant cell" provides a reference point for measuring changes in phenotype of a subject plant or plant cell in which genetic alteration, such as transformation, has been effected as to a gene of interest. A subject plant or plant cell may be descended from a plant or cell so altered and will comprise the alteration. One of ordinary skill in the art would readily recognize a suitable control or reference plant to be utilized when assessing or measuring an agronomic characteristic or phenotype of a transgenic plant using compositions or methods as described herein. For example, by way of non-limiting illustrations:

1. Progeny of a transformed plant which is hemizygous with respect to a recombinant DNA construct, such that the progeny are segregating into plants either comprising or not comprising the recombinant DNA construct: the progeny comprising the recombinant DNA construct would be typically measured relative to the progeny not comprising the recombinant DNA construct. The progeny not comprising the recombinant DNA construct is the control or reference plant.

2. Introgression of a recombinant DNA construct into an inbred line, such as in rice and maize, or into a variety, such as in soybean: the introgressed line would typically be measured relative to the parent inbred or variety line (i.e., the parent inbred or variety line is the control or reference plant).

3. Two hybrid lines, wherein the first hybrid line is produced from two parent inbred lines, and the second hybrid line is produced from the same two parent inbred lines except that one of the parent inbred lines contains a recombinant DNA construct: the second hybrid line would typically be measured relative to the first hybrid line (i.e., the first hybrid line is the control or reference plant).

4. A plant comprising a recombinant DNA construct: the plant may be assessed or measured relative to a control plant not comprising the recombinant DNA construct but otherwise having a comparable genetic background to the plant (e.g., sharing at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity of nuclear genetic material compared to the plant comprising the recombinant DNA construct). There are many laboratory-based techniques available for the analysis, comparison and characterization of plant genetic backgrounds; among these are Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLP®s), and Simple Sequence Repeats (SSRs) which are also referred to as Microsatellites.

A control plant or plant cell may comprise, for example: (a) a wild-type (WT) plant or cell, i.e., of the same genotype as the starting material for the genetic alteration which resulted in the subject plant or cell; (b) a plant or plant cell of the same genotype as the starting material but which has been transformed with a null construct (i.e., with a construct which has no known effect on the trait of interest, such as a construct comprising a marker gene); (c) a plant or plant cell which is a non-transformed segregant among progeny of a subject plant or plant cell; (d) a plant or plant cell genetically identical to the subject plant or plant cell but which is not exposed to conditions or stimulus that would induce expression of the gene of interest or (e) the subject plant or plant cell itself, under conditions in which the gene of interest is not expressed. A control may comprise numerous individuals representing one or more of the categories above; for example, a collection of the non-transformed segregants of category "c" is often referred to as a bulk null.

In this disclosure, WT, ZH11-TC, and DP0158 indicate control plants. WT represents wild-type rice or *Arabidopsis* plants, ZH11-TC represents rice plants generated from tissue cultured Zhonghua 11, and DP0158 represents plants transformed with empty vector of DP0158.

Methods:

Methods include but are not limited to methods for increasing drought tolerance in a plant, methods for evaluating drought tolerance in a plant, methods for increasing nitrogen stress tolerance in a plant, methods for evaluating nitrogen stress tolerance in a plant, methods for increasing paraquat tolerance, methods for increasing chlorate tolerance in a plant, methods for altering an agronomic characteristic in a plant, methods for determining an alteration of an agronomic characteristic in a plant, methods for increasing NUE in a plant, and methods for producing seed. The plant may be a monocotyledonous or dicotyledonous plant, for example, rice, maize or soybean plant. The plant may also be sunflower, canola, wheat, alfalfa, cotton, rice, barley, millet, sugar cane or sorghum. The seed may be a maize or soybean seed, for example, a maize hybrid seed or maize inbred seed.

Methods include but are not limited to the following:

A method for transforming a cell comprising transforming a cell with any one or more of the isolated polynucleotides of the present disclosure, wherein, in particular embodiments, the cell is eukaryotic cell, e.g., a yeast, insect or plant cell; or prokaryotic cell, e.g., a bacterial cell.

A method for producing a transgenic plant comprising transforming a plant cell with any of the isolated polynucleotides or recombinant DNA constructs of the present disclosure and regenerating a transgenic plant from the transformed plant cell, wherein, the transgenic plant and the transgenic seed obtained by this method may be used in other methods of the present disclosure.

A method for isolating a polypeptide of the disclosure from a cell or culture medium of the cell, wherein the cell comprises a recombinant DNA construct comprising a polynucleotide of the disclosure operably linked to at least one regulatory sequence, and wherein the transformed host cell is grown under conditions that are suitable for expression of the recombinant DNA construct.

A method for altering the level of expression of a polypeptide of the disclosure in a host cell comprising: (a) transforming a host cell with a recombinant DNA construct of the present disclosure; and (b) growing the transformed host cell under conditions that are suitable for the expression of the recombinant DNA construct, wherein the expression of the recombinant DNA construct results in production of altered levels of the polypeptide of the disclosure in the transformed host cell.

A method of increasing drought tolerance, paraquat tolerance and/or nitrogen stress tolerance in a plant, comprising: (a) introducing into a regenerable plant cell a recombinant DNA construct comprising a polynucleotide operably linked to at least one regulatory sequence (for example, a promoter functional in a plant), wherein the polynucleotide encodes a polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO: 6, 9, 12, 15, 18, 21 or 24; (b) regenerating a transgenic plant from the regenerable plant cell after step (a), wherein the transgenic plant comprises in its genome the recombinant DNA construct and exhibits increased drought tolerance when compared to a control plant; and further (c) obtaining a progeny plant derived from the transgenic plant, wherein said progeny plant comprises in its genome the recombinant DNA construct and exhibits increased drought tolerance, paraquat tolerance, nitrogen stress tolerance, and/or chlorate sensitivity when compared to a control plant.

A method of evaluating drought tolerance, paraquat tolerance, and/or nitrogen stress tolerance in a plant comprising (a) obtaining a transgenic plant, which comprises in its genome a recombinant DNA construct comprising a polynucleotide operably linked to at least one regulatory sequence (for example, a promoter functional in a plant), wherein said polynucleotide encodes a polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO: 6, 9, 12, 15, 18, 21 or 24; (b) obtaining a progeny plant derived from said transgenic plant, wherein the progeny plant comprises in its genome the recombinant DNA construct; and (c) evaluating the progeny plant for drought tolerance, paraquat tolerance, and/or nitrogen stress tolerance compared to a control plant.

A method of determining an alteration of an agronomic characteristic in a plant comprising (a) obtaining a transgenic plant which comprises in its genome a recombinant DNA construct comprising a polynucleotide operably linked to at least one regulatory sequence (for example, a promoter functional in a plant), wherein said polynucleotide encodes a polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity when compared to SEQ ID NO: 6, 9, 12, 15, 18, 21 or 24; (b) obtaining a progeny plant derived from said transgenic plant, wherein the progeny plant comprises in its genome the recombinant DNA construct; and (c) determining whether the progeny plant exhibits an alteration in at least one agronomic characteristic when compared, optionally under water limiting conditions and/or nitrogen stress, to a control plant.

A method of producing seed (for example, seed that can be sold as a drought tolerant product, or as a nitrogen stress tolerant product offering) comprising any of the preceding methods, and further comprising obtaining seeds from said progeny plant, wherein said seeds comprise in their genome said recombinant DNA construct.

In any of the preceding methods or any other embodiments of methods of the present disclosure, in said introducing step, the said regenerable plant cell may comprise a callus cell, an embryogenic callus cell, a gametic cell, a meristematic cell, or a cell of an immature embryo. The regenerable plant cells may derive from an inbred maize plant.

In any of the preceding methods or any other embodiments of methods of the present disclosure, said regenerating step may comprise the following: (i) culturing said transformed plant cells in a medium comprising an embryogenic promoting hormone until callus organization is observed; (ii) transferring said transformed plant cells of step (i) to a first media which includes a tissue organization promoting hormone; and (iii) subculturing said transformed plant cells after step (ii) onto a second media, to allow for shoot elongation, root development or both.

In any of the preceding methods or any other embodiments of methods of the present disclosure, the step of determining an alteration of an agronomic characteristic in a transgenic plant, if applicable, may comprise determining whether the transgenic plant exhibits an alteration of at least one agronomic characteristic when compared, under varying environmental conditions, to a control plant not comprising the recombinant DNA construct.

In any of the preceding methods or any other embodiments of methods of the present disclosure, the step of determining an alteration of an agronomic characteristic in a progeny plant, if applicable, may comprise determining whether the progeny plant exhibits an alteration of at least one agronomic characteristic when compared, under varying environmental conditions, to a control plant not comprising the recombinant DNA construct.

In any of the preceding methods or any other embodiments of methods of the present disclosure, the plant may exhibit the alteration of at least one agronomic characteristic when compared, under water limiting conditions and/or nitrogen stress conditions, to a control plant.

In any of the preceding methods or any other embodiments of methods of the present disclosure, alternatives exist for introducing into a regenerable plant cell a recombinant DNA construct comprising a polynucleotide operably linked to at least one regulatory sequence. For example, one may introduce into a regenerable plant cell a regulatory sequence (such as one or more enhancers, optionally as part of a transposable element), and then screen for an event in which the regulatory sequence is operably linked to an endogenous gene encoding a polypeptide of the instant disclosure.

The introduction of recombinant DNA constructs of the present disclosure into plants may be carried out by any suitable technique, including but not limited to direct DNA uptake, chemical treatment, electroporation, microinjection, cell fusion, infection, vector-mediated DNA transfer, bombardment, or *Agrobacterium*-mediated transformation.

Techniques for plant transformation and regeneration have been described in International Patent Publication WO 2009/006276, the contents of which are herein incorporated by reference.

In addition, methods to modify or alter the host endogenous genomic DNA are available. This includes altering the host native DNA sequence or a pre-existing transgenic sequence including regulatory elements, coding and non-coding sequences. These methods are also useful in targeting nucleic acids to pre-engineered target recognition sequences in the genome. As an example, the genetically modified cell or plant described herein, is generated using "custom" meganucleases produced to modify plant genomes (e.g., WO 2009/114321; Gao et al. (2010) Plant Journal 1:176-187). Another site-directed engineering is through the use of zinc finger domain recognition coupled with the restriction properties of restriction enzyme (e.g., Urnov, et al. (2010) *Nat Rev Genet*. 11(9):636-46; Shukla, et al. (2009) *Nature* 459 (7245):437-41). A transcription activator-like (TAL) effector-DNA modifying enzyme (TALE or TALEN) is also used to engineer changes in plant genome. See e.g., US20110145940, Cermak et al., (2011) Nucleic Acids Res. 39(12) and Boch et al., (2009), Science 326 (5959): 1509-12. Site-specific modification of plant genomes can also be performed using the bacterial type II CRISPR (clustered regularly interspaced short palindromic repeats)/Cas (CRISPR-associated) system. See e.g., Belhaj et al., (2013), Plant Methods 9: 39; The CRISPR/Cas system allows targeted cleavage of genomic DNA guided by a customizable small noncoding RNA.

The development or regeneration of plants containing the foreign, exogenous isolated nucleic acid fragment that encodes a protein of interest is well known in the art. The regenerated plants may be self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant containing a desired polypeptide is cultivated using methods well known to one skilled in the art.

EXAMPLES

Certain embodiments of the present disclosure are further illustrated in the following examples, in which parts and percentages are by weight and degrees are Celsius, unless otherwise stated. It should be understood that these examples, while indicating embodiments of the disclosure, are given by way of illustration only. From the above discussion and these examples, one skilled in the art can ascertain the essential characteristics of this disclosure, and without departing from the spirit and scope thereof, can make various changes and modifications of the disclosure to adapt it to various usages and conditions. Thus, various modifications of the disclosure in addition to those shown and described herein will be apparent to those skilled in the art from the foregoing description. Such modifications are also intended to fall within the scope of the appended claims.

Example 1

GLR Genes Cloning and Over-Expression Vector Construction

Based on the sequences information of gene ID shown in the Table 2, primers were designed for cloning rice GLR genes. The primers are shown in Table 3, and also the expected-lengths of the amplified GLR genes are displayed.

For OsGLRL1.2, cDNA was cloned, and pooled cDNA from leaf, stem and root tissues of Zhonghua 11 plant was used as the template. For OsGLR2.2, OsGLR3.2, OsGLRL1.3, OsGLRL1.7, OsGLRL2.1 and OsGLRL3.1, their gDNAs were cloned, and amplified using genomic DNA of Zhonghua 11 as the template. The PCR reaction mixtures and PCR procedures are shown in Table 4 and Table 5.

TABLE 2

Rice GLR gene names, Gene IDs (from TIGR) and Construct IDs

| Gene name | Gene ID | Construct ID |
|---|---|---|
| OsGLR2.2 | LOC_Os09g25990 | DP0239 |
| OsGLR3.2 | LOC_Os02g02540 | DP0260 |
| OsGLRL1.2 | LOC_Os06g09090 | DP0223 |
| OsGLRL1.3 | LOC_Os06g09050 | DP0222 |
| OsGLRL1.7 | LOC_Os06g09130 | DP0238 |
| OsGLRL2.1 | LOC_Os06g13730 | DP0218 |
| OsGLRL3.1 | LOC_Os06g08880 | DP0236 |

TABLE 3

Primers for cloning GLR genes

| Primer | Sequence | SEQ ID NO: | Gene name | Length of amplified fragment (bp) |
|---|---|---|---|---|
| gc-3083 | 5'-CCATACATTCAGTAACCAGTAGAACCATCC-3' | 25 | OsGLR2. | 5749 |
| gc-3084 | 5'-GCTGAATTAGCCGAGTTACCATTCCTC-3 | 26 | 2 | |
| gc-2988 | 5'-CTTCTTTGTGGCAGGAGTTCTC-3' | 27 | OsGLR3. | 3848 |
| gc-2989 | 5'-CAAACTGGCCTCAAATGAATTTTTCCC-3' | 28 | 2 | |
| gc-3038 | 5'-CGATCGAGCTAGCCATGTGGAGTTC-3' | 29 | OsGLRL | 1183 |
| gc-3039 | 5'-CATACTGTCTGGATGGAATTTGCAGG-3' | 30 | 1.2 | |
| gc-3033 | 5'-CTATTGCATTGATGTCTTTGAGGCTG-3' | 31 | OsGLRL | 1596 |
| gc-3034 | 5'-CTGAATTGGTCGAGGCTCTTTG-3' | 32 | 1.3 | |
| gc-3048 | 5'-CCGTTCTGCCTTCCCTGCTTATTC-3' | 33 | OsGLRL | 2603 |
| gc-3049 | 5'-CTTGGGAGTTGGGATAGTTGGTGCAG-3' | 34 | 1.7 | |

TABLE 3-continued

Primers for cloning GLR genes

| Primer | Sequence | SEQ ID NO: | Gene name | Length of amplified fragment (bp) |
|---|---|---|---|---|
| gc-3053 | 5'-CTCACGGTGCAGCAGCTGTCC-3' | 35 | OsGLRL 2.1 | 532 |
| gc-3054 | 5'-CAAGATTGCCCCTGCCATGGAG-3' | 36 | | |
| gc-3008 | 5'-CTCGTTGTCCTTGCAGTTGAGG-3' | 37 | OsGLRL 3.1 | 3065 |
| gc-3009 | 5'-CCCTGCTGATAACCCACATAGTCGC-3' | 38 | | |

TABLE 4

PCR reaction mixture

| Reaction mix | 50 µL |
|---|---|
| Template | 1 µL |
| TOYOBO KOD-FX (1.0 U/µL) | 1 µL |
| 2 × PCR buffer for KOD-FX | 25 µL |
| 2 mM dNTPs (0.4 mM each) | 10 µL |
| Primer-F/R (10 µM) | 2 µL each |
| ddH$_2$O | 9 µL |

TABLE 5

PCR cycle conditions for cloning GLR genes

| 94° C. | 3 min | |
|---|---|---|
| 98° C. | 10 s | |
| 58° C. | 30 s | ×30 |
| 68° C. | (1 Kb/min) min | |
| 68° C. | 5 min | |

The PCR amplified products were extracted after the agarose gel electrophoresis using a column kit and then ligated with TA cloning vectors. The sequences and orientation in these constructs were confirmed by sequencing. Then the GLR genes were cloned into plant binary construct DP0158 (pCAMBIA1300-DsRed) (FIG. 1). The generated over-expression vectors were listed in Table 2. The cloned nucleotide sequence in construct of DP0239 and coding sequence of OsGLR2.2 are provided as SEQ ID NO: 4 and 5, the encoded amino acid sequence of OsGLR2.2 is SEQ ID NO: 6; the cloned nucleotide sequence in construct of DP0260 and coding sequence of OsGLR3.2 are provided as SEQ ID NO: 7 and 8, the encoded amino acid sequence of OsGLR3.2 is SEQ ID NO: 9; the cloned nucleotide sequence in construct of DP0223 and coding sequence of OsGLRL1.2 are provided as SEQ ID NO: 10 and 11, the encoded amino acid sequence of OsGLRL1.2 is SEQ ID NO: 12; the cloned nucleotide sequence in construct of DP0222 and coding sequence of OsGLRL1.3 are provided as SEQ ID NO: 13 and 14, the encoded amino acid sequence of OsGLRL1.3 is SEQ ID NO: 15; the cloned nucleotide sequence in construct of DP0238 and coding sequence of OsGLRL1.7 are provided as SEQ ID NO: 16 and 17, the encoded amino acid sequence of OsGLRL1.7 is SEQ ID NO: 18; the cloned nucleotide sequence in construct of DP0218 and coding sequence of OsGLRL2.1 are provided as SEQ ID NO: 19 and 20, the encoded amino acid sequence of OsGLRL2.1 is SEQ ID NO: 21; the cloned nucleotide sequence in construct of DP0236 and coding sequence of OsGLRL3.1 are provided as SEQ ID NO: 22 and 23, the encoded amino acid sequence of OsGLRL3.1 is SEQ ID NO: 24.

Example 2

Transformation to Get Transgenic Rice Lines

In this research, all of the over-expression vectors and DP0158 (empty vector) were transformed into the Zhonghua 11 (*Oryza sativa* L.) by *Agrobacteria*-mediated method as described by Lin and Zhang ((2005) *Plant Cell Rep.* 23:540-547). Zhonghua 11 was cultivated by institute of crop sciences, Chinese Academy of Agricultural Sciences. The first batch of seeds used in this research was provided by Beijing Weiming Kaituo Agriculture Biotech Co., Ltd. Calli induced from embryos was transformed with *Agrobacteria* with the vector. The transgenic seedlings ($T_0$) generated in transformation laboratory are transplanted in the field to get $T_1$ seeds. The $T_1$ and $T_2$ seeds are stored at cold room (4° C.), and $T_2$ seeds were used for following trait screening.

Example 3

Gene Expression Analysis

The gene expression levels in the GLR genes transgenic rice plants were analyzed. A standard RT-PCR or a real-time PCR procedure, such as the QuantiTect® Reverse Transcription Kit from Qiagen® and Real Time-PCR(SYBR®Premix Ex Taq™, TaKaRa), was used. EF1α gene was used as an internal control to show that the amplification and loading of samples from the transgenic rice and wild-type were similar. Gene expression was normalized based on the EF1α mRNA levels.

As shown in FIG. 5, the expression level of OsGLRL2.1 gene in ZH11-TC rice is set at 1.00, OsGLRL2.1 over-expressed in all the ten transgenic rice lines. The primers used for the real-time PCR are as below:

```
DP0218-F1:
                                   (SEQ ID NO: 39)
5'-CTTTCCATCACGACTCCCC-3'

DP0218-R1:
                                   (SEQ ID NO: 40)
5'-CTCCGCCAATTCATCAGATC-3'
```

As shown in FIG. 6, the expression level of OsGLRL1.3 gene in ZH11-TC rice is set at 1.00, OsGLRL1.3 over-expressed in almost all the transgenic lines.

```
DP0222-F1:
                                   (SEQ ID NO: 41)
5'-GGTTCTTACTATCAGATCAACGATGC-3'
```

-continued

```
DP0222-R1:
                                      (SEQ ID NO: 42)
5'-CCATTTGGTTGTTGATTCAGATTCG-3'
```

As shown in FIG. 7, the expression level of OsGLRL1.2 gene in ZH11-TC rice is set at 1.00, OsGLRL1.2 over-expressed in almost all the transgenic lines, while the expression levels of OsGLRL1.2 were very low in both ZH11-TC and DP0158 controls.

```
DP0223-F1:
                                      (SEQ ID NO: 43)
5'-GCAATTCCCAACACAGATTCG-3'

DP0223-R1:
                                      (SEQ ID NO: 44)
5'-GCATGAGAGTTGAGATACACCC-3'
```

As shown in FIG. 8, the expression level of OsGLRL3.1 gene in ZH11-TC rice is set at 1.00, OsGLRL3.1 over-expressed in all the ten transgenic lines.

```
DP0236-F1:
                                      (SEQ ID NO: 45)
5'-TGATCACAGGCTTCTGCATAG-3'

DP0236-R1:
                                      (SEQ ID NO: 46)
5'-CATACTGATATGCGACTGGATACG-3'
```

OsGLRL1.7 over-expressed in all the transgenic lines, while the expression levels were low in both ZH11-TC and DP0158 (FIG. 9). The primers for OsGLRL1.7 gene are as below:

```
DP0238-F1:
                                      (SEQ ID NO: 47)
5'-GCAAAGAGATGAGAGGCTTCGG-3'

DP0238-R1:
                                      (SEQ ID NO: 48)
5'-CATGACAATCTGCGGTGGTTG-3'
```

Example 4

Drought Tolerance Assay of GLR Gene Transgenic Rice Plants Under Greenhouse Condition In order to investigate whether GLR genes could improve drought tolerance in rice plants, the GLR gene transgenic rice plants were screened in greenhouse drought assays. In the greenhouse, two types of lamps are provided as light source, i.e. sodium lamp and metal halide lamp, the ratio is 1:1. Lamps provide the 16 h/8 h period of day/night, and are placed approximately 1.5 m above the seedbed. The light intensity 30 cm above the seedbed is measured as 10,000-20,000 lx in sunny day, while 6,000-10,000 lx in cloudy day, the relative humidity ranges from 30% to 90%, and the temperature ranges from 20 to 35° C.

Drought Tolerance Assay Method:

GLR genes transgenic $T_2$ seeds which showed red color under green fluorescent light were used for greenhouse drought tolerance screens. Seeds were sterilized by 800 ppm carbendazol for 8 h at 32° C. and washed 3-5 times, then soaked in water for 16 h at 32° C., germinated for 18 h at 35-37° C. in an incubator. The germinated seeds were sowed in trays filled with mixture of organic soil, vermiculite and sand (V:V:V=3:3:2). Latin Square design was used in the drought screen experiments, and the total 16 plants for each line grew in different positions of the tray. After thinning the seedlings, 16 uniform seedlings from each GLR gene transgenic line, wild-type control (Zhonghua 11) from tissue culture procedure (ZH11-TC) and/or empty vector (DP0158) transgenic control were used for the drought tolerance screens. Several positive control (a drought tolerant variety, Mianhui 501) and negative control (a drought sensitive variety, Dongbeiyin 2) seedlings also were planted in the same tray. The seedlings were grown under normal greenhouse condition and watered by modified IRRI solution for rice culture (see Table 6). When the seedlings grew to 3-leaf stage, watering was stopped and the trays were kept in a dry place until the leaves became dry and curved (approximately 9-15 days depending on the seasons). The trays were transferred into water pool to recover the seedlings for 5-7 days, and then plants were scored for the degree of recovery. The following scoring system was used: more than half green stem=1, more than two third green leaf=1, less than two third but more than one third green leaf=0.5, less than one third green leaf=0.2, no green leaf or less than half green stem=0. The recovery degree was the sum of the score of the green tissues, and the data were statistically analyzed using Mixed Model. The lines which showed significant better than controls (P<0.05) were considered as positive ones. Survival rate (percentage of survived plants over the total plant number) was also used as a parameter for drought screening.

Also further, randomized block design was used for confirming the observation of GLR gene transformed rice from construct level. Nine transgenic lines from the same construct were planted in one experimental unit to evaluate the transgene at construct level by Mixed Model considering construct, line and environment effects. The construct which recovery degree was significantly greater than that of the controls P<0.05) was considered as the gene in this construct has drought tolerance function.

TABLE 6

Modified IRRI nutrient solution formula for culturing rice

| Molecular formula | Mass concentration (g/L) |
|---|---|
| $NH_4NO_3$ | 114.36 |
| $NaH_2PO_4 \cdot 2H_2O$ | 50.33 |
| $K_2SO_4$ | 89.37 |
| $MgSO_4 \cdot 7H_2O$ | 405.73 |
| $CaCl_2 \cdot 2H_2O$ | 210.22 |
| $H_3BO_3$ | 11.42 |
| $MnCl_2 \cdot 4H_2O$ | 18.01 |
| $ZnSO_4 \cdot 7H_2O$ | 0.44 |
| $(NH_4)_6MoO_{24} \cdot 2H_2O$ | 0.89 |
| $CuSO_4 \cdot 5H_2O$ | 0.39 |
| $Na_2SiO_3 \cdot 9H_2O$ | 284.20 |
| EDTA-2Na | 7.45 |
| $FeSO_4 \cdot 7H_2O$ | 5.57 |

GH Drought Tolerance Assay Results:
1) GH DRT Validation Results of OsGLRL1.2 (DP0223) Transgenic Rice For gene OsGLRL1.2, twelve transgenic rice lines were planted on different trays, and the ZH11-TC and DP0158 seedlings on the same tray were used as control. As shown in Table 7, five transgenic lines had higher survival rates and significantly higher average recovery degrees than that of ZH11-TC, respectively. When compared to DP0158 seedlings, eight lines showed higher survival rates and average recovery degree. These results indicate that the OsGLRL1.2 transgenic rice plants had improved drought tolerance at seedling stage.

Further screening demonstrated that after drought stressed for 19 days and recovered for four days, 75 of 107 OsGLRL1.2 transgenic plants (70.1%) from nine different transgenic lines survived, while only 11 of 24 (45.8%) ZH11-TC plants survived. The average recovery degree of transgenic plants was significantly greater than that of ZH11-TC (Table 8). Analysis at transgenic line level showed that all the nine lines exhibited greater survival rates and average recovery degrees than ZH11-TC seedlings (Table 9). These results further indicate that the over-expression of OsGLRL1.2 can enhanced drought tolerance in transgenic rice at seedling stage.

TABLE 7

Enhanced drought tolerance of OsGLRL1.2 transgenic rice plants under greenhouse conditions (1$^{st}$ experiment)

| Line ID | Number of survived plants | Number of total plants | Survival rate (%) | Average recovery degree | P value | P ≤ 0.05 |
| --- | --- | --- | --- | --- | --- | --- |
| DP0223.02 | 12 | 16 | 75.0 | 2.24 | 0.1506 | |
| ZH11-TC | 6 | 15 | 40.0 | 1.44 | | |
| DP0223.03 | 14 | 16 | 87.5 | 3.11 | 0.0011 | Y |
| ZH11-TC | 8 | 16 | 50 | 1.21 | | |
| DP0223.04 | 12 | 16 | 75 | 3.20 | 0.0000 | Y |
| ZH11-TC | 2 | 16 | 12.5 | 0.73 | | |
| DP0223.05 | 5 | 16 | 31.3 | 0.44 | 1.0000 | |
| ZH11-TC | 6 | 16 | 37.5 | 0.44 | | |
| DP0223.06 | 12 | 16 | 75.0 | 0.94 | 0.3710 | |
| ZH11-TC | 7 | 16 | 43.8 | 0.69 | | |
| DP0223.08 | 2 | 16 | 12.5 | 0.13 | 0.6479 | |
| ZH11-TC | 1 | 16 | 6.3 | 0.06 | | |
| DP0223.09 | 6 | 16 | 37.5 | 0.50 | 0.2917 | |
| ZH11-TC | 9 | 16 | 56.3 | 0.74 | | |
| DP0223.13 | 2 | 16 | 12.5 | 0.13 | 0.6376 | |
| ZH11-TC | 1 | 16 | 6.3 | 0.06 | | |
| DP0223.14 | 9 | 16 | 56.3 | 0.56 | 0.0099 | Y |
| ZH11-TC | 2 | 16 | 12.5 | 0.13 | | |
| DP0223.15 | 15 | 16 | 93.8 | 1.26 | 0.0028 | Y |
| ZH11-TC | 8 | 16 | 50 | 0.56 | | |
| DP0223.16 | 8 | 16 | 50 | 0.56 | 0.0133 | Y |
| ZH11-TC | 2 | 16 | 12.5 | 0.13 | | |
| DP0223.19 | 10 | 16 | 62.5 | 1.00 | 0.8083 | |
| ZH11-TC | 10 | 16 | 62.5 | 0.94 | | |

TABLE 8

Enhanced drought tolerance of OsGLRL1.2 transgenic rice plants under greenhouse conditions (2$^{nd}$ experiment, at construct level)

| Material | Number of survived plants | Number of total plants | Survival rate (%) | Average recovery degree | P value | P ≤ 0.1 |
| --- | --- | --- | --- | --- | --- | --- |
| DP0223 | 75 | 107 | 70.1 | 0.72 | 0.0443 | Y |
| ZH11-TC | 11 | 24 | 45.8 | 0.50 | | |

TABLE 9

Enhanced drought tolerance of OsGLRL1.2 transgenic rice plants under greenhouse conditions (2$^{nd}$ experiment, at line level)

| Line ID | Number of survived plants | Number of total plants | Survival rate (%) | Average recovery degree | P value | P ≤ 0.05 |
| --- | --- | --- | --- | --- | --- | --- |
| DP0223.02 | 8 | 12 | 66.7 | 0.71 | 0.0682 | |
| DP0223.03 | 9 | 12 | 75.0 | 0.73 | 0.0454 | Y |
| DP0223.04 | 11 | 12 | 91.7 | 0.74 | 0.0358 | Y |
| DP0223.06 | 7 | 12 | 58.3 | 0.70 | 0.0881 | |
| DP0223.08 | 9 | 11 | 81.8 | 0.73 | 0.0434 | Y |
| DP0223.14 | 10 | 12 | 83.3 | 0.73 | 0.0454 | Y |
| DP0223.15 | 7 | 12 | 58.3 | 0.70 | 0.0881 | |
| DP0223.16 | 8 | 12 | 66.7 | 0.71 | 0.0713 | |
| DP0223.19 | 6 | 12 | 50.0 | 0.69 | 0.1079 | |
| ZH11-TC | 11 | 24 | 45.8 | 0.50 | | |

The third experiments were performed to further confirm the observation. After drought stressed for 17 days and recovered for seven days, 83 of 108 OsGLRL1.2 transgenic rice plants (77%) survived, and 12 of 24 ZH11-TC seedlings survived. The average recovery degree of OsGLRL1.2 transgenic rice was 1.45, which was significantly greater than that of ZH11-TC seedlings at construct level. Analysis at transgenic line level was shown in Table 10. Eight transgenic lines exhibited greater survival rates and average recovery degrees than ZH11-TC seedlings. These results further demonstrate that OsGLRL1.2 transgenic rice plants had enhanced drought tolerance.

TABLE 10

Enhanced drought tolerance of OsGLRL1.2 transgenic rice plants under greenhouse conditions ($3^{rd}$ experiment, at line level)

| Line ID | Number of survived plants | Number of total plants | Survival rate (%) | Average recovery degree | P value | P ≤ 0.05 |
|---|---|---|---|---|---|---|
| DP0223.02 | 9 | 12 | 75 | 1.42 | 0.0858 | |
| DP0223.03 | 9 | 12 | 75 | 1.41 | 0.0981 | |
| DP0223.04 | 11 | 12 | 92 | 1.67 | 0.0066 | Y |
| DP0223.06 | 10 | 12 | 83 | 1.44 | 0.0749 | |
| DP0223.08 | 4 | 12 | 33 | 1.12 | 0.6197 | |
| DP0223.14 | 9 | 12 | 75 | 1.40 | 0.1013 | |
| DP0223.15 | 10 | 12 | 83 | 1.51 | 0.0373 | Y |
| DP0223.16 | 11 | 12 | 92 | 1.60 | 0.0144 | Y |
| DP0223.19 | 10 | 12 | 83 | 1.52 | 0.0331 | Y |
| ZH11-TC | 12 | 24 | 50 | 1.00 | | |

These three experiments consistently demonstrate that OsGLRL1.2 transgenic rice plants had enhanced drought tolerance; OsGLRL1.2 plays a role of improving drought tolerance of transgenic plants.

2) GH DRT Validation Results of OsGLRL3.1 (DP0236) Transgenic Tice

Twelve OsGLRL3.1 transgenic rice lines were planted on different trays, and the ZH11-TC and DP0158 seedlings on the same tray were used as control. As shown in Table 11, eleven lines exhibited higher survival rate and average recovery degree and three transgenic lines had significantly higher average recovery degrees ZH11-TC plants. When compared to DP0158 seedlings, nine lines showed higher survival rates and average recovery degree. These results indicated that the OsGLRL3.1 transgenic rice plants had improved drought tolerance at seedling stage.

TABLE 11

Enhanced drought tolerance of OsGLRL3.1 transgenic rice plants under greenhouse conditions ($1^{st}$ experiment)

| Line ID | Number of survived plants | Number of total plants | Survival rate (%) | Average recovery degree | P value | P ≤ 0.05 |
|---|---|---|---|---|---|---|
| DP0236.04 | 7 | 16 | 43.8 | 1.48 | 0.9372 | |
| ZH11-TC | 6 | 15 | 40.0 | 1.44 | | |
| DP0236.06 | 11 | 16 | 68.8 | 2.08 | 0.1186 | |
| ZH11-TC | 8 | 16 | 50.0 | 1.21 | | |
| DP0236.07 | 7 | 16 | 43.8 | 1.69 | 0.0864 | |
| ZH11-TC | 2 | 16 | 12.5 | 0.73 | | |
| DP0236.09 | 5 | 16 | 31.3 | 0.31 | 0.4869 | |
| ZH11-TC | 6 | 16 | 37.5 | 0.44 | | |
| DP0236.15 | 14 | 16 | 87.5 | 1.44 | 0.0090 | Y |
| ZH11-TC | 7 | 16 | 43.8 | 0.69 | | |
| DP0236.16 | 4 | 16 | 25.0 | 0.25 | 0.1749 | |
| ZH11-TC | 1 | 16 | 6.3 | 0.06 | | |
| DP0236.17 | 12 | 16 | 75.0 | 1.03 | 0.2246 | |
| ZH11-TC | 9 | 16 | 56.3 | 0.74 | | |
| DP0236.20 | 8 | 16 | 50 | 0.63 | 0.0001 | Y |

TABLE 11-continued

Enhanced drought tolerance of OsGLRL3.1 transgenic rice plants under greenhouse conditions (1st experiment)

| Line ID | Number of survived plants | Number of total plants | Survival rate (%) | Average recovery degree | P value | P ≤ 0.05 |
|---|---|---|---|---|---|---|
| ZH11-TC | 1 | 16 | 6.3 | 0.06 | | |
| DP0236.22 | 5 | 16 | 31.3 | 0.31 | 0.2535 | |
| ZH11-TC | 2 | 16 | 12.5 | 0.13 | | |
| DP0236.27 | 13 | 16 | 81.3 | 1.25 | 0.0033 | Y |
| ZH11-TC | 8 | 16 | 50 | 0.56 | | |
| DP0236.34 | 3 | 16 | 18.8 | 0.19 | 0.7136 | |
| ZH11-TC | 2 | 16 | 12.5 | 0.13 | | |
| DP0236.37 | 14 | 16 | 87.5 | 1.42 | 0.0664 | |
| ZH11-TC | 10 | 16 | 62.5 | 0.94 | | |

The second experiments were carried out, and ZH11-TC and DP0158 seedlings were used as control. Nine OsGLRL3.1 transgenic lines and the controls were planted in one experiment unit. After drought stressed for 15 days and recovered for five days, 58 of the 108 OsGLRL3.1 transgenic rice plants survived, while 11 of the 24 ZH11-TC seedlings and 3 of the 12 DP0158 seedlings survived. The survival rate of OsGLRL3.1 transgenic rice was 53.7%, which was greater than that of ZH11-TC (45.8%) and DP0158 (25%) controls. The average recovery degree of OsGLRL3.1 transgenic rice was 0.54. It was greater than that of ZH11-TC and DP0158 controls.

Analysis at transgenic line level (Table 12) demonstrates that six lines exhibited greater survival rates than both of ZH11-TC and DP0158 controls, and all the nine transgenic lines showed greater average recovery degrees than both of ZH11-TC and DP0158 controls. These results indicated that OsGLRL3.1 transgenic rice had improved drought tolerance at line level at seedling stage.

TABLE 12

Enhanced drought tolerance of OsGLRL3.1 transgenic rice plants under greenhouse conditions (2nd experiment)

| Line ID | Number of survived plants | Number of total plants | Survival rate (%) | Average recovery degree | CK = ZH11-TC | | CK = DP0158 | |
|---|---|---|---|---|---|---|---|---|
| | | | | | P value | P ≤ 0.1 | P value | P ≤ 0.1 |
| DP0236.06 | 5 | 12 | 41.7 | 0.54 | 0.4474 | | 0.0523 | Y |
| DP0236.07 | 5 | 12 | 41.7 | 0.54 | 0.4474 | | 0.0523 | Y |
| DP0236.15 | 5 | 12 | 41.7 | 0.54 | 0.4474 | | 0.0523 | Y |
| DP0236.16 | 7 | 12 | 58.3 | 0.54 | 0.4474 | | 0.0523 | Y |
| DP0236.17 | 9 | 12 | 75.0 | 0.54 | 0.4474 | | 0.0523 | Y |
| DP0236.20 | 7 | 12 | 58.3 | 0.54 | 0.4474 | | 0.0523 | Y |
| DP0236.22 | 6 | 12 | 50.0 | 0.54 | 0.4474 | | 0.0523 | Y |
| DP0236.27 | 6 | 12 | 50.0 | 0.54 | 0.4474 | | 0.0523 | Y |
| DP0236.37 | 8 | 12 | 66.7 | 0.54 | 0.4474 | | 0.0523 | Y |
| ZH11-TC | 11 | 24 | 45.8 | 0.46 | | | | |
| DP0158 | 3 | 12 | 25.0 | 0.25 | | | | |

The third experiments were carried out to confirm the observation, and ZH11-TC and DP0158 seedlings were used as control. The rice seedlings were first drought stressed for 14 days and recovered for seven days, and then drought stressed for 25 days for the second times and recovered five days. 81 of the 108 OsGLRL3.1 transgenic rice plants survived, while 6 of the 12 ZH11-TC seedlings and 5 of the 12 DP0158 seedlings survived. The survival rate of OsGLRL3.1 transgenic rice was 75%, which was greater than that of ZH11-TC (50%) and DP0158 (41.7%) controls. The average recovery degree of OsGLRL3.1 transgenic rice was 1.77. It was greater than that of ZH11-TC and DP0158 controls.

Analysis at transgenic line level (Table 13) demonstrates that eight lines exhibited greater survival rates than both of ZH11-TC and DP0158 controls, and all the nine transgenic lines showed greater average recovery degrees than both of ZH11-TC and DP0158 controls. These results further indicated that OsGLRL3.1 transgenic rice had improved drought tolerance at line level at seedling stage.

TABLE 13

Enhanced drought tolerance of OsGLRL3.1 transgenic rice plants under greenhouse conditions (3rd experiment)

| Line ID | Number of survived plants | Number of total plants | Survival rate (%) | Average recovery degree | CK = ZH11-TC P value | P ≤ 0.05 | CK = DP0158 P value | P ≤ 0.05 |
|---|---|---|---|---|---|---|---|---|
| DP0236.06 | 9 | 12 | 75.0 | 1.85 | 0.0045 | Y | 0.0080 | Y |
| DP0236.07 | 9 | 12 | 75.0 | 1.81 | 0.0069 | Y | 0.0110 | Y |
| DP0236.15 | 10 | 12 | 83.3 | 1.80 | 0.0079 | Y | 0.0122 | Y |
| DP0236.16 | 9 | 12 | 75.0 | 1.75 | 0.0123 | Y | 0.0171 | Y |
| DP0236.17 | 5 | 12 | 41.7 | 1.56 | 0.0681 |  | 0.0657 |  |
| DP0236.20 | 12 | 12 | 100.0 | 1.88 | 0.0031 | Y | 0.0060 | Y |
| DP0236.22 | 9 | 12 | 75.0 | 1.75 | 0.0129 | Y | 0.0178 | Y |
| DP0236.27 | 7 | 12 | 58.3 | 1.64 | 0.0345 | Y | 0.0382 | Y |
| DP0236.37 | 11 | 12 | 91.7 | 1.92 | 0.0020 | Y | 0.0043 | Y |
| ZH11-TC | 6 | 12 | 45.8 | 1.03 |  |  |  |  |
| DP0158 | 5 | 12 | 41.7 | 0.89 |  |  |  |  |

These three experiments consistently demonstrate that OsGLRL3.1 transgenic rice plants had enhanced drought tolerance; OsGLRL3.1 plays a role of improving drought tolerance of transgenic plants.

Example 5

Laboratory Paraquat Screening of GLR Gene Transgenic Rice Plants

Paraquat (1,1-dimethyl-4,4-bipyridinium dichloride), is a foliar-applied and non-selective bipyridinium herbicides, and it is one of the most widely used herbicides in the world, controlling weeds in a huge variety of crops like corn, rice, soybean etc. In plant cells, paraquat mainly targets chloroplasts by accepting electrons from photosystem I and then reacting with oxygen to produce superoxide and hydrogen peroxide, which cause photooxidative stress. Drought stress usually leads to increased reactive oxygen species (ROS) in plants and sometimes, the drought tolerance of plant is associated with enhanced antioxidative ability. Paraquat is a potent oxidative stress inducer; it greatly increases the ROS production and inhibits the regeneration of reducing equivalents and compounds necessary for the activity of the antioxidant system. The ROS generation is enhanced under abiotic stress conditions, and the plant responses range from tolerance to death depending on the stress intensity and its associated –ROS levels. Relative low level of paraquat can mimic the stress-associated ROS production and used as a stress tolerance marker in plant stress biology (Hasaneen M. N. A. (2012) Herbicide-Properties, Synthesis and Control of Weeds book). Therefore, we tested the paraquat tolerance of the GLR gene transgenic rice plants to further understand GLR genes' role in drought tolerance.

Laboratory Paraquat Screening Method:

Transgenic rice plants from 8-10 transgenic lines of each GLR gene over-expression rice were screened by paraquat assay. Tissue-cultured Zhonghua 11 plants (ZH11-TC) and transgenic plants from empty vector (DP0158) were used as controls. $T_2$ GLR transgenic seeds were sterilized and germinated as description in Example 4, and this assay was carried out in growth room with temperature at 28-30° C. and humidity ~30%. The germinated seeds were placed in a tube with a hole at the bottom, and water cultured at 30° C. for 5 days till one-leaf and one-terminal bud stage. Uniform seedlings about 3.5-4 cm in height were selected for paraquat screening. Randomized block design was used in this experiment. There were five blocks, each of which has 16*12 holes. Each transgenic line was placed in one row (12 plants/line), and ZH11-TC and DP0158 seedlings were placed in 3 rows (3*12 plants) randomly in one block. Then the seedlings were treated with 0.8 µM paraquat in concentration for 7 days at 10 h day/14 h night, and the treated seedlings first encountered dark and uptake the paraquat solution which was changed every two days. After treated for 7 days, the green seedlings were counted. Those maintain green in whole without damage were considered to be paraquat tolerance seedling; those with bleached leaves or stem were not considered to be paraquat tolerance seedling.

Tolerance rate was used as a parameter for this trait screen, which is the percentage of plants which kept green and showed tolerant phenotype over the total plant number.

The data was analyzed at construct level (all transgenic plants compared with the control) and transgenic line level (different transgenic lines compared with the control) using a statistic model of "Y~seg+line (seg)+rep+error", random effect of "rep", Statistic Method of "SAS Proc Glimmix".

Laboratory Paraquat Screening Results:

1) Paraquat Validation Results of OsGLRL1.2 transgenic Rice Plants

For OsGLRL1.2, 248 of 600 transgenic seedlings (41%) kept green and showed tolerant phenotype after treated with 0.8 µM paraquat solutions for 7 days, while 58 of 180 (32%) seedlings from ZH11-TC showed tolerant phenotype and only 43 of 180 (24%) seedlings from DP0158 showed tolerant phenotype. The tolerance rate of OsGLRL1.2 transgenic seedlings was significantly higher than that of ZH11-TC (P value=0.0418) and DP0158 (P value=0.0001) seedlings. These results indicate that the OsGLRL1.2 transgenic seedling exhibited enhanced paraquat tolerance compared to both controls of ZH11-TC and DP0158 seedlings at construct level.

Further analysis at transgenic line level is displayed in Table 14, ten transgenic lines were screened. The tolerance rates of eight transgenic lines were higher than ZH11-TC control, and the tolerance rates of all these ten transgenic lines were higher than DP0158 control. Five transgenic lines (DP0223.03, DP0223.04, DP0223.05, DP0223.06 and DP0223.14) had significantly higher tolerance rates than that of DP0158 seedlings; and three transgenic lines (DP0223.03, DP0223.04, and DP0223.05) had significantly higher tolerance rates than that of ZH11-TC seedlings. These results demonstrate that OsGLRL1.2 transgenic rice plants had enhanced paraquat tolerance compared to either ZH11-TC or DP0158 control at construct and transgenic line level at seedling stages. Over-expression OsGLRL1.2 under CaMV 35S promoter improved the paraquat tolerance of the transgenic plants.

seedling stages and many transgenic lines exhibited increased drought tolerance and paraquat tolerance. These cross-validations confirm that OsGLRL1.2 plays a role in increasing drought tolerance.

TABLE 14

Paraquat tolerance analysis of OsGLRL1.2 transgenic rice plants at transgenic line level ($1^{st}$ experiment)

| Line ID | Number of tolerant seedlings | Number of total seedlings | Tolerance rate (%) | CK = ZH11-TC P value | P ≤ 0.05 | CK = DP0158 P value | P ≤ 0.05 |
|---|---|---|---|---|---|---|---|
| DP0223.02 | 21 | 60 | 35 | 0.6934 | | 0.0988 | |
| DP0223.03 | 32 | 60 | 53 | 0.0053 | Y | 0.0001 | Y |
| DP0223.04 | 33 | 60 | 55 | 0.0029 | Y | 0.0000 | Y |
| DP0223.05 | 39 | 60 | 65 | 0.0000 | Y | 0.0000 | Y |
| DP0223.06 | 26 | 60 | 43 | 0.1248 | | 0.0061 | Y |
| DP0223.08 | 20 | 60 | 33 | 0.8743 | | 0.1567 | |
| DP0223.09 | 20 | 60 | 33 | 0.8743 | | 0.1567 | |
| DP0223.14 | 24 | 60 | 40 | 0.2767 | | 0.0202 | Y |
| DP0223.15 | 15 | 60 | 25 | 0.2977 | | 0.8622 | |
| DP0223.16 | 18 | 60 | 30 | 0.7497 | | 0.3510 | |
| ZH11-TC | 58 | 180 | 32 | | | | |
| DP0158 | 43 | 180 | 24 | | | | |

In the second experiment, 371 of the 600 OsGLRL1.2 transgenic seedlings (62%) kept green and showed tolerant phenotype after treated with 0.8 μM paraquat solutions for 7 days, while 45 of 180 (25%) seedlings from ZH11-TC showed tolerant phenotype and only 43 of 180 (24%) seedlings from DP0158 showed tolerant phenotype. The tolerance rate of OsGLRL1.2 transgenic seedlings was significantly higher than that of ZH11-TC (P value=0.0000) and DP0158 (Pvalue=0.0000) seedlings.

Analysis at transgenic line level (Table 15) showed that all the ten transgenic lines exhibited significantly higher tolerance rates than both of ZH11-TC and DP0158 controls. These results further demonstrate that OsGLRL1.2 transgenic rice plants had enhanced paraquat tolerance compared to either ZH11-TC or DP0158 control at construct and transgenic line level at seedling stages.

2) Paraquat Validation Results of OsGLRL1.3 Transgenic Rice

In the first experiment, 195 of the 600 OsGLRL1.3 transgenic seedlings (33%) kept green and showed tolerant phenotype after treated with paraquat solution, while only 40 of the 180 (22%) seedlings from ZH11-TC showed tolerant phenotype, and the tolerance rate of OsGLRL1.3 transgenic plants was significantly (P value=0.0230) higher than that of the ZH11-TC. These results indicate that the OsGLRL1.3 transgenic seedlings had enhanced paraquat tolerance compared to ZH11-TC at construct level.

The analysis at transgenic line level is displayed in Table 16, ten transgenic lines seedlings were screened, the tolerance rates of eight transgenic lines were higher than that of the ZH11-TC, and the tolerance rates of four transgenic lines were significantly higher than that of ZH11-TC seedlings.

TABLE 15

Paraquat tolerance analysis of OsGLRL1.2 transgenic rice plants at transgenic line level ($2^{nd}$ experiment)

| Line ID | Number of tolerant seedlings | Number of total seedlings | Tolerance rate (%) | CK = ZH11-TC P value | P ≤ 0.05 | CK = DP0158 P value | P ≤ 0.05 |
|---|---|---|---|---|---|---|---|
| DP0223.02 | 32 | 60 | 53 | 0.0002 | Y | 0.0001 | Y |
| DP0223.03 | 44 | 60 | 73 | 0.0000 | Y | 0.0000 | Y |
| DP0223.04 | 31 | 60 | 52 | 0.0004 | Y | 0.0002 | Y |
| DP0223.05 | 44 | 60 | 73 | 0.0000 | Y | 0.0000 | Y |
| DP0223.06 | 38 | 60 | 63 | 0.0000 | Y | 0.0000 | Y |
| DP0223.08 | 39 | 60 | 65 | 0.0000 | Y | 0.0000 | Y |
| DP0223.09 | 30 | 60 | 50 | 0.0008 | Y | 0.0004 | Y |
| DP0223.14 | 47 | 60 | 78 | 0.0000 | Y | 0.0000 | Y |
| DP0223.15 | 36 | 60 | 60 | 0.0000 | Y | 0.0000 | Y |
| DP0223.16 | 30 | 60 | 50 | 0.0007 | Y | 0.0004 | Y |
| ZH11-TC | 45 | 180 | 25 | | | | |
| DP0158 | 43 | 180 | 24 | | | | |

As described in Example 4, over-expression of OsGLRL1.2 increased the drought tolerance of rice plants at The tolerance rates of six transgenic lines were higher than that of DP0158 seedlings. These results demonstrate that OsGLRL1.3 transgenic rice plants had enhanced paraquat tolerance at construct and transgenic line level at seedling stages. Over-expression of OsGLRL1.3 improved the paraquat tolerance of the transgenic plants.

3) Paraquat Validation Results of OsGLRL3.1 Transgenic Rice Plants

In the first experiment, 139 of the 600 OsGLRL3.1 transgenic seedlings (23%) kept green and showed tolerant

TABLE 16

Paraquat tolerance analysis of OsGLRL1.3 transgenic rice plants at transgenic line level (1$^{st}$ experiment)

| Line ID | Number of tolerant seedlings | Number of total seedlings | Tolerance rate (%) | CK = ZH11-TC P value | P ≤ 0.05 | CK = DP0158 P value | P ≤ 0.05 |
|---|---|---|---|---|---|---|---|
| DP0222.01 | 13 | 60 | 22 | 0.9287 | | 0.1475 | |
| DP0222.02 | 24 | 60 | 40 | 0.0099 | Y | 0.2427 | |
| DP0222.03 | 7 | 60 | 12 | 0.0845 | | 0.0051 | |
| DP0222.04 | 29 | 60 | 48 | 0.0004 | Y | 0.0241 | Y |
| DP0222.05 | 21 | 60 | 35 | 0.0553 | | 0.6348 | |
| DP0222.07 | 17 | 60 | 28 | 0.3402 | | 0.6301 | |
| DP0222.08 | 25 | 60 | 42 | 0.0053 | Y | 0.1636 | |
| DP0222.09 | 17 | 60 | 28 | 0.3402 | | 0.6301 | |
| DP0222.11 | 22 | 60 | 37 | 0.0321 | Y | 0.4784 | |
| DP0222.13 | 20 | 60 | 33 | 0.0922 | | 0.8115 | |
| ZH11-TC | 40 | 180 | 22 | | | | |
| DP0158 | 57 | 180 | 32 | | | | |

In the second experiment, 337 of the 600 OsGLRL1.3 transgenic seedlings (56%) kept green and showed tolerant phenotype after treated with paraquat solution, while only 31 of the 180 (17%) seedlings from ZH11-TC showed tolerant phenotype, and 51 of the 180 (28%) DP0158 seedlings kept green. The tolerance rate of OsGLRL1.3 transgenic plants was significantly higher than that of the ZH11-TC (P value=0.0000) and DP0158 (P value=0.0000) seedlings. These results indicate that the OsGLRL1.3 transgenic seedlings had enhanced paraquat tolerance compared to either ZH11-TC or DP0158 control at construct level.

The analysis at transgenic line level is displayed in Table 17, nine transgenic exhibited significantly higher tolerance rates than ZH11-TC and DP0158 seedlings. These results clearly demonstrate that OsGLRL1.3 transgenic rice plants had enhanced paraquat tolerance at transgenic line level at seedling stages. Over-expression of OsGLRL1.3 improved the paraquat tolerance of the transgenic plants.

phenotype after treated with paraquat solution, while only 26 of the 180 (14%) ZH11-TC seedlings showed tolerant phenotype, and 35 of the 180 (19%) DP0158 seedlings showed tolerant phenotype. The tolerance rate of all the screened OsGLRL3.1 transgenic seedlings was significantly (P value=0.0355) higher than that of the ZH11-TC seedlings and higher (P value=0.4938, not significantly) than that of the DP0158 seedlings. These results indicate that the OsGLRL3.1 transgenic seedling had enhanced parauqat tolerance compared to either ZH11-TC or DP0158 control seedlings at construct level, and the OsGLRL3.1 transgenic seedlings grow better after treat by 0.8 μM paraquat solution compared to ZH11-TC.

The analysis at transgenic line level indicates that eight of the ten screened transgenic lines had higher tolerance rates compared to ZH11-TC seedlings, and the tolerance rates of two transgenic lines were significantly higher than that of the ZH11-TC seedlings (Table 18). Six transgenic lines had

TABLE 17

Paraquat tolerance analysis of OsGLRL1.3 transgenic rice plants at transgenic line level (2$^{nd}$ experiment)

| Line ID | Number of tolerant seedlings | Number of total seedlings | Tolerance rate (%) | CK = ZH11-TC P value | P ≤ 0.05 | CK = DP0158 P value | P ≤ 0.05 |
|---|---|---|---|---|---|---|---|
| DP0222.01 | 38 | 60 | 63 | 0.0000 | Y | 0.0000 | Y |
| DP0222.02 | 46 | 60 | 77 | 0.0000 | Y | 0.0000 | Y |
| DP0222.03 | 25 | 60 | 42 | 0.0004 | Y | 0.0595 | |
| DP0222.04 | 32 | 60 | 53 | 0.0000 | Y | 0.0009 | Y |
| DP0222.05 | 26 | 60 | 43 | 0.0002 | Y | 0.0355 | Y |
| DP0222.07 | 40 | 60 | 67 | 0.0000 | Y | 0.0000 | Y |
| DP0222.08 | 33 | 60 | 55 | 0.0000 | Y | 0.0005 | Y |
| DP0222.09 | 34 | 60 | 57 | 0.0000 | Y | 0.0002 | Y |
| DP0222.11 | 33 | 60 | 55 | 0.0000 | Y | 0.0005 | Y |
| DP0222.13 | 30 | 60 | 50 | 0.0000 | Y | 0.0034 | Y |
| ZH11-TC | 31 | 180 | 17 | | | | |
| DP0158 | 51 | 180 | 28 | | | | | higher tolerance rates compared to DP0158 seedlings, and the tolerance rates of two transgenic lines (DP0236.15 and DP0236.22) were also significantly higher than that of DP0158 seedlings. These results demonstrate that OsGLRL3.1 transgenic rice plants had enhanced paraquat tolerance compared to both controls of ZH11-TC and DP0158 rice plants at construct and transgenic line level at seedling stages.

TABLE 18

Paraquat tolerance analysis of OsGLRL3.1 transgenic rice plant at transgenic line level (1$^{st}$ experiment)

| Line ID | Number of tolerant seedlings | Number of total seedlings | Tolerance rate (%) | CK = ZH11-TC P value | P ≤ 0.05 | CK = DP0158 P value | P ≤ 0.05 |
| --- | --- | --- | --- | --- | --- | --- | --- |
| DP0236.02 | 9 | 60 | 15 | 0.9164 | | 0.4435 | |
| DP0236.03 | 13 | 60 | 22 | 0.1953 | | 0.7095 | |
| DP0236.04 | 14 | 60 | 23 | 0.1166 | | 0.5185 | |
| DP0236.06 | 10 | 60 | 17 | 0.6774 | | 0.6337 | |
| DP0236.07 | 12 | 60 | 20 | 0.3118 | | 0.9251 | |
| DP0236.08 | 8 | 60 | 13 | 0.8307 | | 0.2903 | |
| DP0236.15 | 28 | 60 | 47 | 0.0000 | Y | 0.0001 | Y |
| DP0236.16 | 8 | 60 | 13 | 0.8307 | | 0.2903 | |
| DP0236.22 | 23 | 60 | 38 | 0.0003 | Y | 0.0049 | Y |
| DP0236.27 | 14 | 60 | 23 | 0.1170 | | 0.5197 | |
| ZH11-TC | 26 | 180 | 14 | | | | |
| DP0158 | 35 | 180 | 19 | | | | |

In the second experiment, 323 of the 600 OsGLRL3.1 transgenic seedlings (54%) kept green and showed tolerant phenotype after treated with paraquat solution, while 47 of the 180 (26%) ZH11-TC seedlings showed tolerant phenotype, and 52 of the 180 (29%) DP0158 seedlings showed tolerant phenotype. The tolerance rate of OsGLRL3.1 transgenic seedlings was significantly higher than both controls of the ZH11-TC (P value=0.0000) and DP0158 (P value=0.0000) seedlings. These results further indicate that the OsGLRL3.1 transgenic seedlings exhibited enhanced paraquat tolerance compared to both controls of ZH11-TC and DP0158 seedlings at construct level.

The analysis at transgenic line level is shown in Table 19, all the ten screened transgenic lines had significantly higher tolerance rates than both of ZH11-TC and DP0158 controls. These results clearly demonstrate that OsGLRL3.1 transgenic rice plants had enhanced paraquat tolerance compared to both DP0158 and ZH11-TC control at construct and transgenic line level at seedling stages. OsGLRL3.1 plays a role in the improvement of paraquat tolerance of transgenic plants.

TABLE 19

Paraquat tolerance analysis of OsGLRL3.1 transgenic rice plant at transgenic line level (2$^{nd}$ experiment)

| Line ID | Number of tolerant seedlings | Number of total seedlings | Tolerance rate (%) | CK = ZH11-TC P value | P ≤ 0.05 | CK = DP0158 P value | P ≤ 0.05 |
| --- | --- | --- | --- | --- | --- | --- | --- |
| DP0236.02 | 33 | 60 | 55 | 0.0002 | Y | 0.0007 | Y |
| DP0236.03 | 36 | 60 | 60 | 0.0000 | Y | 0.0000 | Y |
| DP0236.04 | 29 | 60 | 48 | 0.0025 | Y | 0.0083 | Y |
| DP0236.06 | 32 | 60 | 53 | 0.0003 | Y | 0.0013 | Y |
| DP0236.07 | 26 | 60 | 43 | 0.0157 | Y | 0.0441 | Y |
| DP0236.08 | 29 | 60 | 48 | 0.0025 | Y | 0.0083 | Y |
| DP0236.15 | 42 | 60 | 70 | 0.0000 | Y | 0.0000 | Y |
| DP0236.16 | 29 | 60 | 48 | 0.0025 | Y | 0.0083 | Y |
| DP0236.22 | 39 | 60 | 65 | 0.0000 | Y | 0.0000 | Y |
| DP0236.27 | 28 | 60 | 47 | 0.0047 | Y | 0.0149 | Y |
| ZH11-TC | 47 | 180 | 26 | | | | |
| DP0158 | 52 | 180 | 29 | | | | |

Over-expression of OsGLRL3.1 increased the paraquat tolerance of transgenic plants. Over-expression of OsGLRL3.1 also increased the drought tolerance of transgenic rice plants, these cross-validation by two different assays further indicate the function of OsGLRL3.1 in increasing drought tolerance.

4) Paraquat Validation Results of OsGLRL2.1 Transgenic Rice

In the first experiment, 311 of the 600 OsGLRL2.1 transgenic seedlings (52%) kept green and showed tolerant phenotype after treated with paraquat solutions, while only 39 of the 180 (22%) ZH11-TC seedlings showed tolerant phenotype, and 66 of 180 (37%) DP0158 seedlings showed tolerant phenotype. The tolerance rate of OsGLRL2.1 transgenic seedlings was significantly higher than ZH11-TC (P value=0.0000) and DP0158 (P value=0.0007) seedlings. These results indicate that the OsGLRL2.1 transgenic seedlings exhibited enhanced paraquat tolerance rate compared to both controls of ZH11-TC and DP0158 seedlings at construct level.

Further analysis at transgenic line level is shown in Table 20, eight transgenic lines had higher tolerance rates than both of ZH11-TC and DP0158 controls, and the tolerance rates of eight transgenic lines were significantly higher than that of ZH11-TC control, and six transgenic lines had significantly higher tolerance rates than DP0158 seedlings. These results demonstrate that OsGLRL2.1 transgenic rice plants had enhanced paraquat tolerance compared to both DP0158 and ZH11-TC control at construct and transgenic line level at seedling stages. OsGLRL2.1 plays a role in the improvement of paraquat tolerance of transgenic plants.

TABLE 20

Paraquat tolerance analysis of OsGLRL2.1 transgenic rice plant at transgenic line level (1$^{st}$ experiment)

| Line ID | Number of tolerant seedlings | Number of total seedlings | Tolerance rate (%) | CK = ZH11-TC P value | P ≤ 0.05 | CK = DP0158 P value | P ≤ 0.05 |
| --- | --- | --- | --- | --- | --- | --- | --- |
| DP0218.05 | 19 | 60 | 32 | 0.1228 | | 0.4857 | |
| DP0218.09 | 31 | 60 | 52 | 0.0000 | Y | 0.0451 | Y |
| DP0218.10 | 27 | 60 | 45 | 0.0010 | Y | 0.2544 | |
| DP0218.11 | 36 | 60 | 60 | 0.0000 | Y | 0.0027 | Y |
| DP0218.13 | 38 | 60 | 63 | 0.0000 | Y | 0.0007 | Y |
| DP0218.14 | 16 | 60 | 27 | 0.4266 | | 0.1630 | |
| DP0218.15 | 25 | 60 | 42 | 0.0039 | Y | 0.4898 | |
| DP0218.17 | 31 | 60 | 52 | 0.0000 | Y | 0.0451 | Y |
| DP0218.18 | 48 | 60 | 80 | 0.0000 | Y | 0.0000 | Y |

TABLE 20-continued

Paraquat tolerance analysis of OsGLRL2.1 transgenic
rice plant at transgenic line level (1st experiment)

| Line ID | Number of tolerant seedlings | Number of total seedlings | Tolerance rate (%) | CK = ZH11-TC P value | CK = ZH11-TC P ≤ 0.05 | CK = DP0158 P value | CK = DP0158 P ≤ 0.05 |
|---|---|---|---|---|---|---|---|
| DP0218.32 | 40 | 60 | 67 | 0.0000 | Y | 0.0002 | Y |
| ZH11-TC | 39 | 180 | 22 | | | | |
| DP0158 | 66 | 180 | 37 | | | | |

In the second experiment, 344 of the 600 OsGLRL2.1 transgenic seedlings (60%) kept green and showed tolerant phenotype after treated with paraquat solution, while 105 of the 240 (51%) ZH11-TC seedlings showed tolerant phenotype, and 79 of the 180 (44%) DP0158 seedlings showed tolerant phenotype. The tolerance rate of all the screened OsGLRL2.1 seedlings was significantly higher than DP0158 seedlings (P value=0.0006) and higher than ZH11-TC seedlings (P value=0.0555, not significantly). These results further indicate that the OsGLRL2.1 transgenic seedling had enhanced parauqat tolerance compared to either ZH11-TC or DP0158 control seedlings at construct level.

The analysis at transgenic line level indicates that seven transgenic lines had higher tolerance rates compared to ZH11-TC seedlings and DP0158 seedlings (Table 21). Four lines exhibited significantly higher tolerance rates than ZH11-TC seedlings, and six lines exhibited significantly higher tolerance rates than DP0158 seedlings. These results demonstrate that OsGLRL2.1 transgenic rice plants had enhanced paraquat tolerance compared to both controls of ZH11-TC and DP0158 rice plants at construct and transgenic line level at seedling stages.

TABLE 21

Paraquat tolerance analysis of OsGLRL2.1 transgenic
rice plant at transgenic line level (2nd experiment)

| Line ID | Number of tolerant seedlings | Number of total seedlings | Tolerance rate (%) | CK = ZH11-TC P value | CK = ZH11-TC P ≤ 0.05 | CK = DP0158 P value | CK = DP0158 P ≤ 0.05 |
|---|---|---|---|---|---|---|---|
| DP0218.05 | 27 | 60 | 45 | 0.3821 | | 0.8812 | |
| DP0218.09 | 41 | 60 | 68 | 0.0257 | Y | 0.0020 | Y |
| DP0218.10 | 36 | 60 | 60 | 0.2498 | | 0.0356 | Y |
| DP0218.11 | 42 | 60 | 70 | 0.0148 | Y | 0.0011 | Y |
| DP0218.13 | 28 | 60 | 47 | 0.5156 | | 0.7091 | |
| DP0218.14 | 14 | 36 | 39 | 0.1716 | | 0.5825 | |
| DP0218.15 | 32 | 60 | 53 | 0.8004 | | 0.2096 | |
| DP0218.17 | 37 | 60 | 62 | 0.1701 | | 0.0211 | Y |
| DP0218.18 | 47 | 60 | 78 | 0.0007 | Y | 0.0000 | Y |
| DP0218.32 | 40 | 60 | 67 | 0.0433 | Y | 0.0038 | Y |
| ZH11-TC | 105 | 180 | 51 | | | | |
| DP0158 | 79 | 180 | 44 | | | | |

5) Paraquat Validation Results of OsGLRL1.7 transgenic Rice

In the first experiment, 279 of the 600 OsGLRL1.7 transgenic seedlings (47%) kept green and showed tolerant phenotype after treated with paraquat solutions, while only 52 of the 180 (29%) ZH11-TC seedlings showed tolerant phenotype, and 57 of the 180 (32%) DP0158 seedlings showed tolerant phenotype. The tolerance rate of OsGLRL1.7 transgenic seedlings was significantly higher than ZH11-TC (P value=0.0002) and DP0158 (P value=0.0015) seedlings. These results indicate that the OsGLRL1.7 transgenic seedlings exhibited enhanced paraquat tolerance rate compared to both controls of ZH11-TC and DP0158 seedlings at construct level.

Further analysis at transgenic line level is shown in Table 22, seven transgenic lines had higher tolerance rates than both of ZH11-TC and DP0158 controls, six lines exhibited significantly higher tolerance rates than ZH11-TC seedlings, and five transgenic lines had significantly higher tolerance rates than DP0158 seedlings. These results demonstrate that OsGLRL1.7 transgenic rice plants had enhanced paraquat tolerance compared to both DP0158 and ZH11-TC control at construct and transgenic line level at seedling stages. OsGLRL1.7 plays a role in the improvement of paraquat tolerance of transgenic plants.

TABLE 22

Paraquat tolerance analysis of OsGLRL1.7 transgenic
rice plant at transgenic line level (1st experiment)

| Line ID | Number of tolerant seedlings | Number of total seedlings | Tolerance rate (%) | CK = ZH11-TC P value | CK = ZH11-TC P ≤ 0.05 | CK = DP0158 P value | CK = DP0158 P ≤ 0.05 |
|---|---|---|---|---|---|---|---|
| DP0238.02 | 34 | 60 | 57 | 0.0003 | Y | 0.0011 | Y |
| DP0238.04 | 14 | 60 | 23 | 0.4064 | | 0.2254 | |
| DP0238.05 | 32 | 60 | 53 | 0.0012 | Y | 0.0041 | Y |
| DP0238.07 | 40 | 60 | 67 | 0.0000 | Y | 0.0000 | Y |
| DP0238.10 | 18 | 60 | 30 | 0.8694 | | 0.8098 | |
| DP0238.12 | 13 | 60 | 22 | 0.2796 | | 0.1459 | |
| DP0238.13 | 23 | 60 | 38 | 0.1764 | | 0.3454 | |
| DP0238.15 | 38 | 60 | 63 | 0.0000 | Y | 0.0000 | Y |
| DP0238.18 | 26 | 60 | 43 | 0.0434 | Y | 0.1050 | |
| DP0238.19 | 41 | 60 | 68 | 0.0000 | Y | 0.0000 | Y |
| ZH11-TC | 52 | 180 | 29 | | | | |
| DP0158 | 57 | 180 | 32 | | | | |

In the second experiment, 397 of the 600 OsGLRL1.7 transgenic seedlings (66%) kept green and showed tolerant phenotype after treated with paraquat solution, while 91 of the 180 (51%) ZH11-TC seedlings showed tolerant phenotype, and 56 of the 180 (31%) DP0158 seedlings showed tolerant phenotype. The tolerance rate of all the screened OsGLRL1.7 seedlings was significantly higher than ZH11-TC (P value=0.0002) and DP0158 (P value=0.0000) seedlings. These results further indicate that the OsGLRL1.7 transgenic seedling had enhanced parauqat tolerance compared to either ZH11-TC or DP0158 control seedlings at construct level.

The analysis at transgenic line level indicates that nine transgenic lines had higher tolerance rates compared to ZH11-TC seedlings and DP0158 seedlings (Table 23). Six lines exhibited significantly higher tolerance rates than ZH11-TC seedlings, and ten lines exhibited significantly higher tolerance rates than DP0158 seedlings. These results clearly demonstrate that OsGLRL1.7 transgenic rice plants had enhanced paraquat tolerance compared to both controls of ZH11-TC and DP0158 rice plants at construct and transgenic line level at seedling stages.

TABLE 23

Paraquat tolerance analysis of OsGLRL1.7 transgenic rice plant at transgenic line level (2$^{nd}$ experiment)

| Line ID | Number of tolerant seedlings | Number of total seedlings | Tolerance rate (%) | CK = ZH11-TC P value | P ≤ 0.05 | CK = DP0158 P value | P ≤ 0.05 |
|---|---|---|---|---|---|---|---|
| DP0238.02 | 28 | 60 | 47 | 0.6038 |   | 0.0337 | Y |
| DP0238.04 | 31 | 60 | 52 | 0.8819 |   | 0.0062 | Y |
| DP0238.05 | 49 | 60 | 82 | 0.0002 | Y | 0.0000 | Y |
| DP0238.07 | 38 | 60 | 63 | 0.0921 |   | 0.0000 | Y |
| DP0238.10 | 32 | 60 | 53 | 0.7105 |   | 0.0034 | Y |
| DP0238.12 | 43 | 60 | 72 | 0.0067 | Y | 0.0000 | Y |
| DP0238.13 | 45 | 60 | 75 | 0.0020 | Y | 0.0000 | Y |
| DP0238.15 | 44 | 60 | 73 | 0.0036 | Y | 0.0000 | Y |
| DP0238.18 | 41 | 60 | 68 | 0.0208 | Y | 0.0000 | Y |
| DP0238.19 | 46 | 60 | 77 | 0.0010 | Y | 0.0000 | Y |
| ZH11-TC | 91 | 180 | 51 |   |   |   |   |
| DP0158 | 56 | 180 | 31 |   |   |   |   |

6) Paraquat Validation Results of OsGLR3.2 Transgenic Rice Plants

In the first experiment, 300 of the 600 OsGLR3.2 transgenic seedlings (50%) kept green and showed tolerant phenotype after treated with paraquat solution, whereas 71 of the 180 (39%) ZH11-TC seedlings showed tolerant phenotype, and only 39 of the 180 (22%) DP0158 seedlings showed tolerant phenotype. The tolerance rate of all the screened OsGLR3.2 seedlings was significantly higher than ZH11-TC seedlings (P value=0.0128) and DP0158 seedlings (P value=0.0000). These results indicate that the OsGLR3.2 transgenic seedling had enhanced parauqat tolerance compared to either ZH11-TC or DP0158 control seedlings at construct level.

The analysis at transgenic line level indicates that seven transgenic lines had higher tolerance rates compared to ZH11-TC seedlings, and the tolerance rates of three transgenic lines were significantly higher than ZH11-TC seedlings (Table 24). All the ten transgenic lines had higher tolerance rates compared to DP0158 seedlings, and the tolerance rates of nine transgenic lines were also significantly higher than DP0158 seedlings. These results demonstrate that OsGLR3.2 transgenic rice plants had enhanced paraquat tolerance compared to both controls of ZH11-TC and DP0158 rice plants at construct and transgenic line level at seedling stages.

TABLE 24

Paraquat tolerance analysis of OsGLR3.2 transgenic rice plant at transgenic line level (1$^{st}$ experiment)

| Line ID | Number of tolerant seedlings | Number of total seedlings | Tolerance rate (%) | CK = ZH11-TC P value | P ≤ 0.05 | CK = DP0158 P value | P ≤ 0.05 |
|---|---|---|---|---|---|---|---|
| DP0260.09 | 22 | 60 | 37 | 0.9385 |   | 0.0041 | Y |
| DP0260.10 | 25 | 60 | 42 | 0.9385 |   | 0.0041 | Y |
| DP0260.11 | 34 | 60 | 57 | 0.0223 | Y | 0.0000 | Y |
| DP0260.12 | 49 | 60 | 82 | 0.0000 | Y | 0.0000 | Y |
| DP0260.13 | 34 | 60 | 57 | 0.0621 |   | 0.0000 | Y |
| DP0260.16 | 27 | 60 | 45 | 0.4450 |   | 0.0005 | Y |
| DP0260.17 | 15 | 60 | 25 | 0.0467 |   | 0.4676 |   |
| DP0260.18 | 24 | 60 | 40 | 0.5917 |   | 0.0010 | Y |
| DP0260.19 | 48 | 60 | 80 | 0.0000 | Y | 0.0000 | Y |
| DP0260.22 | 22 | 60 | 37 | 0.7586 |   | 0.0021 | Y |
| ZH11-TC | 71 | 180 | 39 |   |   |   |   |
| DP0158 | 39 | 180 | 22 |   |   |   |   |

In the second experiment, 377 of the 600 OsGLR3.2 transgenic seedlings (63%) kept green and showed tolerant phenotype after treated with paraquat solution, while 95 of the 180 (53%) ZH11-TC seedlings showed tolerant phenotype, and 71 of the 180 (39%) DP0158 seedlings showed tolerant phenotype. The tolerance rate of OsGLR3.2 transgenic seedlings was significantly higher than both controls of the ZH11-TC (P value=0.0125) and DP0158 (P value=0.0000) seedlings. These results further indicate that the OsGLR3.2 transgenic seedlings exhibited enhanced paraquat tolerance compared to both controls of ZH11-TC and DP0158 seedlings at construct level.

The analysis at transgenic line level is shown in Table 25, nine transgenic lines had higher tolerance rates than both of ZH11-TC and DP0158 controls, three lines exhibited significantly higher tolerance rates than ZH11-TC seedlings, and nine lines exhibited significantly higher tolerance rates than DP0158 seedlings. These results demonstrate that OsGLR3.2 transgenic rice plants had enhanced paraquat tolerance compared to both DP0158 and ZH11-TC control at construct and transgenic line level at seedling stages. OsGLR3.2 plays a role in the improvement of paraquat tolerance of transgenic plants.

TABLE 25

Paraquat tolerance analysis of OsGLR3.2 transgenic rice plant at transgenic line level (2$^{nd}$ experiment)

| Line ID | Number of tolerant seedlings | Number of total seedlings | Tolerance rate (%) | CK = ZH11-TC P value | P ≤ 0.05 | CK = DP0158 P value | P ≤ 0.05 |
|---|---|---|---|---|---|---|---|
| DP0260.09 | 40 | 60 | 67 | 0.0648 |   | 0.0006 | Y |
| DP0260.10 | 22 | 60 | 37 | 0.0345 |   | 0.7015 |   |
| DP0260.11 | 41 | 60 | 68 | 0.0394 | Y | 0.0003 | Y |
| DP0260.12 | 50 | 60 | 83 | 0.0002 | Y | 0.0000 | Y |
| DP0260.13 | 38 | 60 | 63 | 0.1577 |   | 0.0022 | Y |
| DP0260.14 | 37 | 60 | 62 | 0.2330 |   | 0.0041 | Y |
| DP0260.17 | 37 | 60 | 62 | 0.2330 |   | 0.0041 | Y |
| DP0260.18 | 35 | 60 | 58 | 0.4545 |   | 0.0134 | Y |
| DP0260.20 | 41 | 60 | 68 | 0.0394 | Y | 0.0003 | Y |
| DP0260.22 | 36 | 60 | 60 | 0.3299 |   | 0.0075 | Y |
| ZH11-TC | 95 | 180 | 53 |   |   |   |   |
| DP0158 | 71 | 180 | 39 |   |   |   |   |

Example 6

Field Drought Tolerance Assay of GLR Gene Transgenic Rice Plants

Flowering stage drought stress is an important problem in agriculture practice. The transgenic rice plants were further tested under field drought conditions. For the field drought assay, 9-12 transgenic lines of each gene were screened. The T₂ seeds were first sterilized as described in Example 4. The germinated seeds were planted in a seedbed field. At 3-leaf stage, the seedlings were transplanted into the testing field, with 4 replicates and 10 plants per replicate for each transgenic line, and the 4 replicates were planted in the same block. ZH11-TC and DP0158 plants nearby the transgenic lines in the same block were used as controls in the statistical analysis.

The rice plants were managed by normal practice using pesticides and fertilizers. Watering was stopped at the tillering stage, so as to give drought stress at flowering stage depending on the weather conditions (temperature and humidity). The soil water content was measured every 4 days at about 10 sites per block using TDR30 (Spectrum Technologies, Inc.).

Plant phenotypes were observed and recorded during the experiments. The phenotypes include heading date, leaf rolling degree, drought sensitivity and/or drought tolerance. Special attention was paid to leaf rolling degree at noontime. At the end of the planting season, 6 representative plants of each transgenic line were harvested from the middle of the row per line, and grain weight per plant was measured. The grain weight data were statistically analyzed using mixed linear model. Positive transgenic lines were selected based on the analysis (P<0.1).

Field Drought Assay Results:

1) Field DRT Validation Results of OsGLRL1.3 (DP0222) Transgenic Rice

Twelve OsGLRL1.3 transgenic lines were tested in Hainan Province in the first experiment, ZH11-TC and DP0158 rice plants planted nearby were used as controls. Watering was stopped from panicle initiation stage I to seed maturity to produce moderate drought stress. The soil volumetric moisture content was about 6% during heading and maturation stage (FIG. 10). During drought stress, the plants began to show leaf roll phenotype at 23 days and started heading at 45 days after stopping watering. Six rice lines DP0222.01, DP0222.05, DP0222.07, DP0222.12, DP0222.13 and DP0222.16 showed better seed setting rates at maturation stage.

At the end of the planting season, about six representative plants of each transgenic line were harvested from the middle of the row per line, and grain weight per plant was measured. As shown in Table 26, the grain yield per plant of OsGLRL1.3 transgenic rice was less than that of ZH11-TC and DP0158 controls at construct level; four lines exhibited greater grain yield per plant than ZH11-TC and three lines exhibited greater grain yield per plants than DP0158 control at transgenic line level. These results show that OsGLRL1.3 transgenic rice plant obtained drought tolerance at vegetative stage in field after drought stress.

TABLE 26

Grain yield analysis of OsGLRL1.3 rice plants under field drought conditions

| Line ID | Number of survival plants | Number of harvested plants | Yield per plant (g) | CK = ZH11-TC P value | CK = ZH11-TC P ≤ 0.1 | CK = DP0158 P value | CK = DP0158 P ≤ 0.1 |
|---|---|---|---|---|---|---|---|
| DP0222.01 | 24 | 18 | 9.67 | 0.162 | | 0.250 | |
| DP0222.02 | 24 | 18 | 6.93 | 0.081 | | 0.050 | |
| DP0222.04 | 24 | 17 | 7.56 | 0.311 | | 0.216 | |
| DP0222.05 | 24 | 16 | 8.49 | 0.968 | | 0.844 | |
| DP0222.07 | 24 | 18 | 9.50 | 0.228 | | 0.337 | |
| DP0222.08 | 24 | 16 | 5.81 | 0.002 | | 0.001 | |
| DP0222.09 | 24 | 18 | 6.89 | 0.072 | | 0.044 | |
| DP0222.11 | 24 | 12 | 6.15 | 0.008 | | 0.005 | |
| DP0222.12 | 24 | 18 | 8.19 | 0.758 | | 0.588 | |
| DP0222.13 | 24 | 18 | 8.14 | 0.717 | | 0.552 | |
| DP0222.16 | 24 | 17 | 8.68 | 0.792 | | 0.981 | |
| DP0222.28 | 24 | 18 | 7.94 | 0.558 | | 0.414 | |
| ZH11-TC | 24 | 17 | 8.45 | | | | |
| DP0158 | 24 | 18 | 8.66 | | | | |
| DP0222 (construct) | | | 7.83 | 0.298 | | 0.173 | |

2) Field DRT Validation Results of OsGLRL3.1 (DP0236) Transgenic Rice

Nine OsGLRL3.1 transgenic lines were tested in Beijing field, ZH11-TC and DP0158 rice plants planted nearby were used as control. Watering was stopped from panicle initiation stage I to seed maturity to produce heavier drought stress. The rice plants began to show leaf roll phenotype at 17 days after stopping watering. Water was provided at 35 days after first stopping water, and the rice plants started heading at 31 days after first stopping water. The soil volumetric moisture content decreased from 40% to 10% during heading and maturation stage (FIG. 11).

At the end of the planting season, six representative plants of each transgenic line were harvested from the middle of the row per line, and grain weight per plant was measured. As shown in Table 27, the grain yield of OsGLRL3.1 transgenic rice was 6.45 g per plant, was more than that of DP0158 and less than that of ZH11-TC at construct level; four lines exhibited higher grain yield per plant than that of ZH11-TC control and all the lines exhibited higher grain yield per plant than DP0158 control. These results demonstrate that OsGLRL3.1 rice plant exhibited better grain yield per plant than control after drought stress, and OsGLRL3.1 may play a role in enhancing drought tolerance and may improve the grain yield at maturation stage.

Over-expression of OsGLRL3.1 improved the paraquat tolerance and drought tolerance at seedlings and maturation stage, these cross-validations indicated that OsGLRL3.1 plays a role in enhancing drought tolerance.

TABLE 27

Grain yield analysis of OsGLRL3.1 rice plants under field drought conditions

| Line ID | Number of survival plants | Number of harvested plants | Yield per plant (g) | CK = ZH11-TC P value | CK = ZH11-TC P ≤ 0.1 | CK = DP0158 P value | CK = DP0158 P ≤ 0.1 |
|---|---|---|---|---|---|---|---|
| DP0236.04 | 23 | 10 | 6.34 | 0.873 | | 0.248 | |
| DP0236.06 | 24 | 10 | 7.17 | 0.597 | | 0.042 | Y |
| DP0236.07 | 24 | 16 | 5.99 | 0.578 | | 0.237 | |
| DP0236.09 | 23 | 7 | 6.99 | 0.717 | | 0.072 | Y |
| DP0236.15 | 24 | 15 | 6.03 | 0.627 | | 0.260 | |
| DP0236.16 | 24 | 17 | 5.78 | 0.505 | | 0.402 | |
| DP0236.17 | 24 | 15 | 6.20 | 0.743 | | 0.198 | |
| DP0236.20 | 23 | 12 | 6.94 | 0.731 | | 0.061 | Y |
| DP0236.34 | 16 | 10 | 6.64 | 0.937 | | 0.113 | |

TABLE 27-continued

Grain yield analysis of OsGLRL3.1 rice plants under field drought conditions

| Line ID | Number of survival plants | Number of harvested plants | Yield per plant (g) | CK = ZH11-TC P value | CK = ZH11-TC P ≤ 0.1 | CK = DP0158 P value | CK = DP0158 P ≤ 0.1 |
|---|---|---|---|---|---|---|---|
| ZH11-TC | 24 | 11 | 6.55 | | | | |
| DP0158 | 24 | 17 | 4.81 | | | | |
| DP0236 (construct) | | | 6.45 | 0.406 | | 0.087 | Y |

Example 7

Field Low Nitrogen Screens of Mature Transgenic Rice Plants

Field low nitrogen screens were carried out in Beijing. Two nitrogen levels: N-0 (using fertilizer without nitrogen) and N-1 (with normal fertilizer at 180 kg Nitrogen/ha) were set in this experiment. Seed germination and seedling culturing were performed as described in Example 6. At 3-leaf stage, the seedlings were transplanted into two testing fields, with 4 replicates and 10 plants per replicate for each transgenic line, and the 4 replicates were planted in the same block. The ZH11-TC and DP0158 plants nearby the transgenic lines in the same block were used as controls in the statistical analysis.

The rice plants were managed by normal practice using pesticides, but applying phosphor fertilizer and potassium fertilizer for N-0 treatment and normal fertilizers for N-1.

The SPAD value of the fully expanded flag leaf and top second leaf were measured by SPAD-502 chlorophyll meter at about 10 day after heading. The SPAD value of each transgenic rice plant is the arithmetic mean of SPAD values from three rice plants in the middle of one rice row.

The plant height, which is the length from the rice stem base to the end of panicle or the end of the highest leaf, was measured at 20 day after heading. Six rice plants in the middle of one rice row were measured and the arithmetic mean of these three values is the plant height of the transgenic rice plant.

At the end of the season, six representative plants of each transgenic line were harvested from the middle of the row per line. The panicles which have five seeds are considered as effective panicles, and the effective panicle number is the total of the effective panicle per plant. The biomass per plant is the dry weight of the rice plant without root and panicle. The SPAD value, plant height, effective number, biomass and grain weight data were statistically analyzed using mixed linear model by ASReml program. Positive transgenic lines are selected based on the analysis (P≤0.1).

Field NUE Validation Results of OsGLRL3.1 (DP0236) Transgenic Rice

The grain yield, biomass, effective panicle number, plant height and SPAD value of OsGLRL3.1 transgenic rice plants were measured.

Table 28 shows that the grain yield of the OsGLRL3.1 transgenic rice was more than ZH11-TC and DP0158 controls under field low nitrogen conditions at construct level. Ten lines showed more grain yield than ZH11-TC controls and eleven lines showed more grain yield than DP0158 control at transgenic line level. Table 29 shows the grain yield results under field normal nitrogen conditions. The grain yield of OsGLRL3.1 transgenic rice was higher than that of DP0158 control and less than that of ZH11-TC control at construct level, only one lines exhibited more grain yield than that of ZH11-TC control, and eleven lines exhibited higher grain yields than DP0158 control. OsGLRL3.1 transgenic rice exhibited 4% and 9% grain yield increase than ZH11-TC and DP0158 control under low nitrogen conditions, respectively; and exhibited 7% grain yield decrease than ZH11-TC control and 3% grain yield increase than DP0158 control under field normal nitrogen conditions. These results demonstrate that OsGLRL3.1 transgenic rice obtained low nitrogen tolerance, and over-expression of OsGLRL3.1 improves the grain yield of transgenic plants under low nitrogen conditions.

The biomass of the OsGLRL3.1 transgenic rice was significantly higher than ZH11-TC and DP0158 controls under low nitrogen conditions at the construct level as indicated in Table 30. All the transgenic rice lines exhibited higher biomass than either ZH11-TC or DP0158 control.

The plant height of OsGLRL3.1 transgenic rice under low nitrogen conditions and normal nitrogen conditions were displayed in Table 31 and 32. Under low nitrogen conditions, three lines were taller than ZH11-TC control, and nine lines were taller than DP0158 control at the transgenic line level. At construct level, the differences between the transgenic rice and controls did not reach significant level. Under normal nitrogen conditions, the plant height of OsGLRL3.1 transgenic rice was significantly lower than ZH11-TC plants at construct level. These results indicate that the plant height of the transgenic rice was not affected by the content of nitrogen.

There were no significant differences between the OsGLRL3.1 transgenic rice and the controls for the parameters of effective panicle number, flag leaf SPAD value and top second leaf SPAD value.

These results indicate that OsGLRL3.1 transgenic rice plants obtained higher grain yield and more biomass under low nitrogen conditions, over-expression of OsGLRL3.1 improves the grain yield of transgenic plants under low nitrogen conditions, OsGLRL3.1 gene plays a role in enhancing low nitrogen tolerance and/or NUE.

TABLE 28

Grain yield analysis of OsGLRL3.1 transgenic rice under field low nitrogen condition

| Line ID | Number of survival plants | Number of harvested plants | Yield per plant (g) | CK = ZH11-TC P value | CK = ZH11-TC P ≤ 0.1 | CK = DP0158 P value | CK = DP0158 P ≤ 0.1 |
|---|---|---|---|---|---|---|---|
| DP0236.02 | 40 | 24 | 31.11 | 0.401 | | 0.092 | Y |
| DP0236.03 | 39 | 24 | 31.13 | 0.395 | | 0.090 | Y |
| DP0236.04 | 40 | 23 | 30.36 | 0.653 | | 0.195 | |
| DP0236.06 | 39 | 24 | 30.87 | 0.475 | | 0.119 | |
| DP0236.07 | 40 | 23 | 31.35 | 0.335 | | 0.070 | Y |
| DP0236.08 | 40 | 24 | 30.24 | 0.698 | | 0.218 | |
| DP0236.15 | 40 | 24 | 30.73 | 0.523 | | 0.138 | |
| DP0236.16 | 40 | 24 | 32.93 | 0.074 | Y | 0.009 | Y |
| DP0236.22 | 39 | 23 | 26.64 | 0.135 | | 0.519 | |
| DP0236.23 | 40 | 25 | 30.76 | 0.509 | | 0.132 | |
| DP0236.27 | 40 | 24 | 28.90 | 0.751 | | 0.595 | |
| DP0236.38 | 40 | 24 | 31.84 | 0.221 | | 0.039 | Y |
| ZH11-TC | 40 | 24 | 29.50 | | | | |
| DP0158 | 40 | 24 | 27.88 | | | | |
| DP0236 (construct) | | | 30.57 | 0.430 | | 0.047 | Y |

TABLE 29

Grain yield analysis of OsGLRL3.1 transgenic rice under field normal nitrogen condition

| Line ID | Number of survival plants | Number of harvested plants | Yield per plant (g) | CK = ZH11-TC P value | CK = ZH11-TC P ≤ 0.1 | CK = DP0158 P value | CK = DP0158 P ≤ 0.1 |
|---|---|---|---|---|---|---|---|
| DP0236.02 | 40 | 24 | 41.39 | 0.366 | | 0.419 | |
| DP0236.03 | 40 | 22 | 40.78 | 0.249 | | 0.576 | |
| DP0236.04 | 40 | 21 | 43.23 | 0.875 | | 0.120 | |
| DP0236.06 | 40 | 24 | 42.13 | 0.547 | | 0.267 | |
| DP0236.07 | 40 | 23 | 40.67 | 0.231 | | 0.606 | |
| DP0236.08 | 40 | 24 | 41.91 | 0.488 | | 0.309 | |
| DP0236.15 | 39 | 24 | 40.89 | 0.267 | | 0.546 | |
| DP0236.16 | 40 | 24 | 39.51 | 0.096 | | 0.964 | |
| DP0236.22 | 40 | 21 | 34.24 | 0.000 | | 0.035 | |
| DP0236.23 | 40 | 24 | 40.27 | 0.174 | | 0.726 | |
| DP0236.27 | 39 | 24 | 40.09 | 0.153 | | 0.781 | |
| DP0236.38 | 40 | 24 | 44.44 | 0.738 | | 0.041 | Y |
| ZH11-TC | 40 | 24 | 43.62 | | | | |
| DP0158 | 40 | 24 | 39.40 | | | | |
| DP0236 (construct) | | | 40.80 | 0.430 | | 0.377 | |

TABLE 30

Biomass analysis of OsGLRL3.1 transgenic rice under low nitrogen condition

| Line ID | Number of survival plants | Number of harvested plants | Biomass (g) | CK = ZH11-TC P value | CK = ZH11-TC P ≤ 0.1 | CK = DP0158 P value | CK = DP0158 P ≤ 0.1 |
|---|---|---|---|---|---|---|---|
| DP0236.02 | 40 | 24 | 22.75 | 0.061 | Y | 0.171 | |
| DP0236.03 | 39 | 24 | 22.73 | 0.063 | Y | 0.177 | |
| DP0236.04 | 40 | 23 | 22.81 | 0.055 | Y | 0.158 | |
| DP0236.06 | 39 | 24 | 22.73 | 0.064 | Y | 0.177 | |
| DP0236.07 | 40 | 23 | 22.88 | 0.049 | Y | 0.142 | |
| DP0236.08 | 40 | 24 | 23.09 | 0.033 | Y | 0.103 | |
| DP0236.15 | 40 | 24 | 22.94 | 0.043 | Y | 0.129 | |
| DP0236.16 | 40 | 24 | 23.32 | 0.021 | Y | 0.070 | Y |
| DP0236.22 | 39 | 23 | 24.89 | 0.000 | Y | 0.002 | Y |
| DP0236.23 | 40 | 25 | 23.25 | 0.023 | Y | 0.078 | Y |
| DP0236.27 | 40 | 24 | 22.41 | 0.108 | | 0.269 | |
| DP0236.38 | 40 | 24 | 22.86 | 0.050 | Y | 0.146 | |
| ZH11-TC | 40 | 24 | 20.36 | | | | |
| DP0158 | 40 | 24 | 21.00 | | | | |
| DP0236 (construct) | | | 23.05 | 0.006 | Y | 0.038 | Y |

TABLE 31

Plant height analysis of OsGLRL3.1 transgenic rice under low nitrogen condition

| Line ID | Number of survival plants | Number of harvested plants | Plant Height (cm) | CK = ZH11-TC P value | CK = ZH11-TC P ≤ 0.1 | CK = DP0158 P value | CK = DP0158 P ≤ 0.1 |
|---|---|---|---|---|---|---|---|
| DP0236.02 | 40 | 24 | 106.35 | 0.010 | | 0.292 | |
| DP0236.03 | 39 | 24 | 107.49 | 0.106 | | 0.943 | |
| DP0236.04 | 40 | 23 | 107.68 | 0.143 | | 0.925 | |
| DP0236.06 | 39 | 24 | 109.89 | 0.639 | | 0.038 | Y |
| DP0236.07 | 40 | 23 | 108.20 | 0.304 | | 0.579 | |
| DP0236.08 | 40 | 24 | 110.85 | 0.185 | | 0.003 | Y |
| DP0236.15 | 40 | 24 | 108.42 | 0.394 | | 0.443 | |
| DP0236.16 | 40 | 24 | 107.89 | 0.174 | | 0.777 | |
| DP0236.22 | 39 | 23 | 108.03 | 0.245 | | 0.696 | |
| DP0236.23 | 40 | 25 | 110.84 | 0.193 | | 0.004 | Y |
| DP0236.27 | 40 | 24 | 105.48 | 0.001 | | 0.069 | Y |
| DP0236.38 | 40 | 24 | 111.57 | 0.054 | Y | 0.000 | Y |
| ZH11-TC | 40 | 24 | 109.36 | | | | |
| DP0158 | 40 | 24 | 107.58 | | | | |
| DP0236 (construct) | | | 108.56 | 0.453 | | 0.360 | |

TABLE 32

Plant height analysis of OsGLRL3.1 transgenic rice under normal nitrogen condition

| Line ID | Number of survival plants | Number of harvested plants | Plant Height (cm) | CK = ZH11-TC P value | CK = ZH11-TC P ≤ 0.1 | CK = DP0158 P value | CK = DP0158 P ≤ 0.1 |
|---|---|---|---|---|---|---|---|
| DP0236.02 | 40 | 24 | 125.48 | 0.015 | | 0.901 | |
| DP0236.03 | 40 | 22 | 125.38 | 0.016 | | 0.852 | |
| DP0236.04 | 40 | 21 | 125.17 | 0.006 | | 0.729 | |
| DP0236.06 | 40 | 24 | 127.08 | 0.187 | | 0.324 | |
| DP0236.07 | 40 | 23 | 124.26 | 0.002 | | 0.354 | |
| DP0236.08 | 40 | 24 | 128.45 | 0.703 | | 0.042 | Y |
| DP0236.15 | 39 | 24 | 124.05 | 0.001 | | 0.281 | |
| DP0236.16 | 40 | 24 | 125.44 | 0.019 | | 0.887 | |
| DP0236.22 | 40 | 21 | 122.54 | 0.000 | | 0.035 | |
| DP0236.23 | 40 | 24 | 125.87 | 0.029 | | 0.877 | |
| DP0236.27 | 39 | 24 | 123.69 | 0.000 | | 0.175 | |
| DP0236.38 | 40 | 24 | 130.03 | 0.471 | | 0.003 | Y |
| ZH11-TC | 40 | 24 | 128.98 | | | | |
| DP0158 | 40 | 24 | 125.65 | | | | |
| DP0236 (construct) | | | 125.62 | 0.009 | | 0.979 | |

Example 8

Transformation and Evaluation of Rice GLR Genes in FAST Corn

Vector Construction:

The full-length GLR genes were cloned as described in Example 1, and then were cloned into pENTR GATEWAY compatible vector (Invitrogen). Using the INVITROGEN-™GATEWAY® technology, a LR recombination Reaction was performed, and OsGLRL1.7 sequence was transferred to a destination vector to generate the PHP64464 vector (SEQ ID NO: 2, FIG. 2).

The PHP64464 vector were introduced into *Agrobacterium* strain LBA4404 and used to transform embryos of FAST Corn from Pioneer as described previously (Unger et al., (2001) *Transgenic Research* 10:409-422; Cigan et al., (2005) *The Plant Journal* 43: 929-940).

FAST Corn Drought Assay Method:

Transgenic plants with GS3/GF3/GF3 background will segregate 1:1 in $T_1$ for a transgene (OsGLRL1.7). $T_1$ seeds were sown in a 50% Turface and 50% SB300 soil mixture at a uniform depth of 2" from the surface and a planting density of 8.5" between plants (~72K plants/acre). Each $T_1$ plant was grown in a classic 200 size pot (volume equivalent to 1.7 L) and tagged with a bar code label that contains information about the plant's genetic identity, planting date and greenhouse location. Transgenic plants and their non-transgenic segregants were distinguished using DsRED fluorescence screening or ELISA strip tests that detect the presence of a marker gene linked with a gene of interest.

Drought stress was applied by delivering a minimal amount of liquid fertilizer daily for an extended period of time. A split block design with stationary blocks was used to minimize spatial variation. Six lines from each constructs were chosen for the $T_1$ assay. For each line 15 transgene positive and 15 transgene negative plants were used. Positives and negatives were randomly paired within each line block.

Ear shoots were covered with a shoot bag to prevent pollination and were monitored for $1^{st}$ day of silk-exertion. Immature (un-pollinated) ears were then harvested at 8 days after initial silking and placed in a shoot-bag or other suitable container, labeled with a bar-code tag containing the sample-identification-number and any other info needed for sampled recognition.

Immature ears were hand harvested and a digital image taken. Digital image analysis of immature ear photographs can be conducted using image processing software to extract data. Various image processing operations may be performed, e.g. techniques or algorithms to delineate image pixels associated with the immature ear object of interest from the general image background and\or extraneous debris. Data information can be recorded for each whole or subsection of immature ear objects including, without limitation, object area, minor axis length, major axis length, perimeter, ear color, and/or other information regarding ear size, shape, morphology, location, or color. Results are analyzed for statistical significance. Significant increase in immature ear parameters or vegetative parameters indicates increased drought tolerance.

FAST Corn Drought Assay Results:

The Multivariate Desirability Indexes at construct level and line level of PHP64464 were 1.15 and 2.08, respectively, showing its significant effects in increasing drought tolerance in FAST corn $T_1$ plants under drought conditions.

Constitutive overexpression of OsGLRL1.7 (PHP64464) under Maize Ubi promoter significantly enhanced drought tolerance in FAST corn $T_1$ plants as further illustrated in FIG. 4. Three (EZMT2013.0281.1.11, EZMT2013.0281.1.9 and EZMT2013.0281.2.1) of the 6 lines which significantly over express OsGLRL1.7 and also significantly increased most of the ear parameters compared to the corresponding nulls.

Example 9

Transformation and Evaluation of Maize with Rice GLR Genes

Maize plants can be transformed to over-express *Oryza sativa* GLR genes or a corresponding homolog from maize, *Arabidopsis*, or other species. Expression of the gene in the maize transformation vector can be under control of a constitutive promoter such as the maize ubiquitin promoter (Christensen et al. (1989) *Plant Mol. Biol.* 12:619-632 and Christensen et al. (1992) *Plant Mol. Biol.* 18:675-689) or under control of another promoter, such as a stress-responsive promoter. The recombinant DNA construct can be introduced into maize cells by particle bombardment substantially as described in International Patent Publication WO 2009/006276. Alternatively, maize plants can be transformed with the recombinant DNA construct by *Agrobacterium*-mediated transformation substantially as described by Zhao et al. in *Meth. Mol. Biol.* 318:315-323 (2006) and in Zhao et al., *Mol. Breed.* 8:323-333 (2001) and U.S. Pat. No. 5,981,840 issued Nov. 9, 1999. The *Agrobacterium*-mediated transformation process involves bacterium inoculation, co-cultivation, resting, selection and plant regeneration.

Progeny of the regenerated plants, such as $T_1$ plants, can be subjected to a soil-based drought stress. Using image analysis, plant area, volume, growth rate and color can be measured at multiple times before and during drought stress. Significant delay in wilting or leaf area reduction, a reduced yellow-color accumulation, and/or an increased growth rate during drought stress, relative to a control, will be considered evidence that the GLR functions in maize to enhance drought tolerance and NUE.

Example 10

Transformation and Evaluation of Gaspe Flint Derived Maize Lines

As described in Example 8, maize plants can be transformed to over-express the rice GLR genes, or corresponding homologs from another species. In certain circumstances, recipient plant cells can be from a uniform maize line having a short life cycle ("fast cycling"), a reduced size, and high transformation potential, e.g. as disclosed in Tomes et al. U.S. Pat. No. 7,928,287.

The population of transgenic ($T_0$) plants resulting from the transformed maize embryos can be grown in a controlled greenhouse environment using a modified randomized block design to reduce or eliminate environmental error. For example, a group of 30 plants, comprising 24 transformed experimental plants and 6 control plants (collectively, a "replicate group"), are placed in pots which are arranged in an array (a.k.a. a replicate group or block) on a table located inside a greenhouse. Each plant, control or experimental, is randomly assigned to a location with the block which is mapped to a unique, physical greenhouse location as well as to the replicate group. Multiple replicate groups of 30 plants each may be grown in the same greenhouse in a single experiment. The layout (arrangement) of the replicate groups should be determined to minimize space requirements as well as environmental effects within the greenhouse. Such a layout may be referred to as a compressed greenhouse layout.

Each plant in the line population is identified and tracked throughout the evaluation process, and the data gathered from that plant are automatically associated with that plant so that the gathered data can be associated with the transgene carried by the plant. For example, each plant container can have a machine readable label (such as a Universal Product Code (UPC) bar code) which includes information about the plant identity, which in turn is correlated to a greenhouse location so that data obtained from the plant can be automatically associated with that plant.

Alternatively any efficient, machine readable, plant identification system can be used, such as two-dimensional matrix codes or even radio frequency identification tags (RFID) in which the data is received and interpreted by a radio frequency receiver/processor (U.S. Pat. Nos. 7,403,855 and 7,702,462).

Each greenhouse plant in the $T_0$ line population, including any control plants, is analyzed for agronomic characteristics of interest, and the agronomic data for each plant are recorded or stored in a manner so as to be associated with the identifying data for that plant. Confirmation of a phenotype (gene effect) can be accomplished in the $T_1$ generation with a similar experimental design to that described above.

Example 11

Laboratory Drought Screening of Rice GLR Genes in *Arabidopsis*

To understand whether rice GLR genes can improve dicot plants' drought tolerance, or other traits, rice GLR gene over-expression vectors were transformed into *Arabidopsis* (Columbia) using floral dip method by *Agrobacterium* mediated transformation procedure and transgenic plants were identified (Clough, S. T. and Bent, A. F. (1998) The Plant Journal 16, 735-743; Zhang, X. et al. (2006) *Nature Protocols* 1: 641-646).

A 16.8-kb T-DNA based binary vector (FIG. 3) which is called pBC-yellow was used in this experiment. This vector contains the RD29a promoter driving expression of the gene for ZS-Yellow, which confers yellow fluorescence to transformed seed. The GLR genes, OsGLR2.2, OsGLR3.2, and OsGLRL2.1 were cloned as described in Example 1, and constructed in the Gateway vector. Then using the INVITROGEN™ GATEWAY® technology, an LR Recombination Reaction was performed on the entry clone containing the directionally cloned PCR product and the pBC-yellow vector, and GWD0239, GWD0260, and GWD0218 were obtained vectors. In these vectors, OsGLR2.2, OsGLR3.2, and OsGLRL2.1 were driven by constitutive promoter CaMV 35S.

$T_2$ seeds were used for lab drought assay. *Arabidopsis* drought screening is a soil-based water withdrawal assay performed in a growth chamber with conditions of light intensity 145 μMol, temperature 22° C. day/20° C. night and humidity ~60%. The transgenic seeds were sorted by Copas (Complex Object Parametric Analyzer and Sorter, a seed sorter), and were stratified by putting in 0.1% agarose solution, and placing at 4° C. for 3 days. Wild-type *Arabidopsis* were used as control and stratified as above. 36 plants each for over-expression transgenic *Arabidopsis* and wild-type were planted equidistantly and alternatively to each other in a zig-zag fashion. The soil composition was 3 parts peat moss, 2 parts vermiculite and 1 part perlite. Apart from these, fertilizers and fungicides were added to the soil in the following concentrations: NPK (Nitrogen, Phosphorus, Potassium)-1 gm/kg soil, Micronutrients—0.5 gm/kg soil, Fungicide—0.5 gm/kg soil. Plants were thinned to 9 plants per pot (72 plants per flat), and were well watered for the first 12 days, then saturated with 1 L of deionized water for 30 min with excess water drained off completely. The plants were imaged between days 28 and 36 after germination using LemnaTec equipment (LemnaTec GmbH, Germany) and data analyzed. The flats were rotated each day from the second day after sowing till the last day of imaging. The files generated in LemnaTec Scanalyzer were converted into XLS files and put in a Stan's format and sent to ESL for generating Stan's score for the experimental lines. Rate of decay or wilting under drought conditions is used as tested parameter. And the cut-off Score=1.5.

After drought stress treated as above, the transgenic lines were compared against the control (wild-type *Arabidopsis*) for the rate of decay under drought conditions. The images captured by LemnaTec Scanalyzer were analyzed to generate a score. Those lines that exceeded the cut-off of 1.5 indicate to have slower decay or wilting as compared to control. Scores for OsGLR2.2 transgenic (GWD239) *Arabidopsis*, OsGLR3.2 transgenic (GWD 260) *Arabidopsis* and OsGLRL2.1 transgenic (GWD0218) *Arabidopsis* were 2.379, 1.547, and 1.601, respectively, which indicate that transgenic *Arabidopsis* of these three had slower decay or wilting rate. During drought treatment, the wilting levels of wild-type plants were more apparent than those of the OsGLR2.2, OsGLR3.2 and OsGLRL2.1 transgenic lines. These results indicate that over-expression of rice OsGLR2.2, OsGLR3.2 or OsGLRL2.1 gene under constitutive promoter CaMV 35S significantly enhanced drought tolerance in *Arabidopsis*.

Example 12

Laboratory NUE Screening of Rice GLR Genes in *Arabidopsis*

To understand whether rice GLR genes can improve dicot plants' low nitrogen tolerance, or other traits, transgenic *Arabidopsis* which over-express rice GLR genes are validated at low nitrogen condition.

The $T_1$ fluorescent seeds are selected, surface sterilized and stratified in the dark at 4° C. for three days. Then 32 $T_2$ individuals are sown next to 32 empty vector control (pB-Cyellow-empty vector) individuals on one low nitrogen media containing 0.5×N-Free Hoagland's, 0.4 mM potassium nitrate, 0.1% sucrose, 1 mM MES and 0.25% Phytagel™ as shown in Table 33. Two repeats are prepared. The plates are horizontally placed in the growth chamber and cultured for a period of 10 days at 22° C., 60% relative humidity and a 16 hour day cycle. Seedling status is evaluated by imaging the entire plate from 10-13 days after stratifications.

After masking the plate image to remove background color, two different measurements are collected for each individual: total rosette area, and the percentage of color that falls into a green color bin. Using hue, saturation and intensity data (HSI), the green color bin consists of hues 50 to 66. Total rosette area is used as a measure of plant biomass, whereas the green color bin was shown by dose-response studies to be an indicator of nitrogen assimilation (patent application US20110209245).

The images are analyzed using Nitrosight software and the number of Pixel (for size of the plants) and the intensity of Bin2 (for green color of leaves) for each of the 32/64 transgenic seedlings are compared with 32/64 seedlings of empty vector control for similar parameters. The green color and better growth of the seedling as compared to the empty vector control seedling signifies improved NUE. The data was statistically analyzed and a gene was considered as a weak validation with a P value less than $10^{-4}$ and a strong validation at $10^{-5}$ for Bin2 and Area in replicates and multiple days (Day 10 to Day 13 of assay). In this experiment the statement regarding a positive response being less than $10^{-3}$ holds.

TABLE 33

Modified Hoagland's nutrient solution for culturing *Arabidopsis*

| Molecular formula | Molecular weight | Concentration (mM) |
| --- | --- | --- |
| KNO$_3$ | 101.1 | 0.4 |
| MgSO$_4$•7H$_2$O | 246.49 | 1.0 |
| CaCl$_2$ | 110.98 | 2.5 |
| Na$_2$HPO$_4$ | 141.96 | 1.0 |
| K$_2$SO$_4$ | 174.26 | 1.3 |
| Fe-EDTA | 367.1 | $4.6 \times 10^{-3}$ |

TABLE 33-continued

Modified Hoagland's nutrient solution for culturing *Arabidopsis*

| Molecular formula | Molecular weight | Concentration (mM) |
|---|---|---|
| MES | 195.2 | 1.0 |
| $H_3BO_3$ | 61.84 | $12.5 \times 10^{-3}$ |
| $MnSO_4 \cdot H_2O$ | 169.01 | $1.0 \times 10^{-3}$ |
| $ZnSO_4 \cdot 7H_2O$ | 287.5 | $1.0 \times 10^{-3}$ |
| $CuSO_4 \cdot 5H_2O$ | 249.71 | $0.25 \times 10^{-3}$ |
| $Na_2MoO_4 \cdot 2H_2O$ | 241.95 | $0.25 \times 10^{-3}$ |

What is claimed is:

1. A method of increasing drought tolerance in a plant, comprising:
   (a) expressing in a plant, a polynucleotide operably linked to at least one heterologous regulatory element, wherein the polynucleotide encodes a polypeptide having an amino acid sequence of at least 97% sequence identity to SEQ ID NO: 24 and the expression level of the polynucleotide is increased compared to that of a control plant; and
   (b) selecting a plant of part (a) comprising the polynucleotide operably linked to the heterologous regulatory element for increased drought tolerance as compared to a control plant not comprising the polynucleotide operably linked to the heterologous regulatory element.

2. The method of claim 1, wherein the plant is maize or rice.

3. The method of claim 1, wherein the polypeptide comprises SEQ ID NO: 24.

* * * * *